(12) United States Patent
Anthony et al.

(10) Patent No.: US 8,956,850 B2
(45) Date of Patent: Feb. 17, 2015

(54) ENHANCED PYRUVATE TO ACETOLACTATE CONVERSION IN YEAST

(75) Inventors: Larry Cameron Anthony, Aston, PA (US); Lori Ann Maggio-Hall, Wilmington, DE (US)

(73) Assignee: Butamax Advanced Biofuels LLC DE (US)

( * ) Notice: Subject to any disclaimer, the term of this patent is extended or adjusted under 35 U.S.C. 154(b) by 620 days.

(21) Appl. No.: 12/477,942

(22) Filed: Jun. 4, 2009

(65) Prior Publication Data

US 2009/0305363 A1 Dec. 10, 2009

Related U.S. Application Data

(60) Provisional application No. 61/058,970, filed on Jun. 5, 2008.

(51) Int. Cl.
*C12N 1/19* (2006.01)
*C12P 7/04* (2006.01)
*C12P 7/16* (2006.01)
*C12N 9/88* (2006.01)

(52) U.S. Cl.
CPC ... *C12P 7/16* (2013.01); *C12N 9/88* (2013.01); *C12P 7/04* (2013.01); *C12Y 202/01006* (2013.01); *Y02E 50/10* (2013.01)
USPC ........ 435/254.2; 435/115; 435/116; 435/160; 435/255.1

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,643,779 A | 7/1997 | Ehrlich et al. | |
| 6,514,733 B1 | 2/2003 | Emptage et al. | |
| 6,660,507 B2 | 12/2003 | Cheng et al. | |
| 7,067,300 B2 | 6/2006 | Emptage et al. | |
| 7,504,250 B2 | 3/2009 | Emptage et al. | |
| 7,851,188 B2 | 12/2010 | Donaldson et al. | |
| 7,993,889 B1 | 8/2011 | Donaldson et al. | |
| 8,017,375 B2 | 9/2011 | Feldman et al. | |
| 8,178,328 B2 | 5/2012 | Donaldson et al. | |
| 8,188,250 B2 | 5/2012 | Bramucci et al. | |
| 8,273,558 B2 | 9/2012 | Donaldson et al. | |
| 8,283,144 B2 | 10/2012 | Donaldson et al. | |
| 2003/0166179 A1 | 9/2003 | Rajgarhia et al. | |
| 2004/0146996 A1 | 7/2004 | Yocum et al. | |
| 2004/0157305 A1 | 8/2004 | Stampfer et al. | |
| 2005/0059136 A1 | 3/2005 | van Maris et al. | |
| 2007/0031950 A1 | 2/2007 | Winkler | |
| 2007/0092957 A1* | 4/2007 | Donaldson et al. ........... 435/157 |
| 2007/0259410 A1 | 11/2007 | Donaldson et al. | |
| 2007/0292927 A1 | 12/2007 | Donaldson et al. | |
| 2008/0182308 A1 | 7/2008 | Donaldson et al. | |
| 2008/0261230 A1 | 10/2008 | Liao et al. | |
| 2009/0155870 A1 | 6/2009 | Donaldson et al. | |
| 2009/0269823 A1 | 10/2009 | Bramucci et al. | |
| 2009/0305370 A1 | 12/2009 | Grady et al. | |
| 2010/0081154 A1 | 4/2010 | Flint et al. | |
| 2010/0129886 A1 | 5/2010 | Anthony et al. | |
| 2010/0143997 A1 | 6/2010 | Buelter et al. | |
| 2011/0020889 A1 | 1/2011 | Feldman et al. | |
| 2011/0053235 A1 | 3/2011 | Festel et al. | |
| 2011/0076733 A1 | 3/2011 | Urano et al. | |
| 2011/0124060 A1 | 5/2011 | Anthony et al. | |
| 2011/0136193 A1 | 6/2011 | Grady et al. | |
| 2011/0159558 A1 | 6/2011 | Grady et al. | |
| 2011/0183392 A1 | 7/2011 | Feldman et al. | |
| 2011/0244536 A1 | 10/2011 | Nagarajan et al. | |
| 2012/0064585 A1 | 3/2012 | Anthony et al. | |
| 2012/0252084 A1 | 10/2012 | Anthony et al. | |

FOREIGN PATENT DOCUMENTS

| WO | 2007050671 | 5/2007 |
|---|---|---|
| WO | 2007061590 | 5/2007 |
| WO | WO 2007/106524 A2 | 9/2007 |
| WO | WO 2008/052991 A2 | 5/2008 |
| WO | 2008072920 | 6/2008 |
| WO | 2008072921 | 6/2008 |
| WO | 2009086423 | 7/2009 |
| WO | 2010151525 | 12/2010 |
| WO | WO 2011/040901 A2 | 1/2011 |

OTHER PUBLICATIONS van Maris et al. (Applied and Environmental Microbiology 70(1): 159-166, 2004.*
Methods in Enzymology, Eds. C. Guthrie and G. Fink, Academic Press, Inc., 194:281-301 (1991) (Providing a reference cited in IDS efiled on Nov. 12, 2009).
Bellion et al., Microb. Growth C1 Compd., [Int. Symp.], 7th (1993), 415-32. Editors: Murrell, J. Collin; Kelly, Don P. Publisher: Intercept; Andover, UK (Providing a reference cited in IDS efiled on Nov. 12, 2009).
Methods in Yeast Genetics, 2005, pp. 201-202, Cold Spring Harbor Laboratory Press, Cold Spring Harbor, NY ((Providing a reference cited in IDS efiled on Nov. 12, 2009).
Voloch et al. Fermentation Derived 2,3-Butanediol, in Comprehensive Biotechnology, Pergamon Press Ltd, England vol. 2, Section 3:933-947 (1986) (Providing a reference cited in IDS efiled on Nov. 12, 2009).
Rychlik, W., In Methods in Molecular Biology, White, B. A. Ed., (1993) vol. 15, pp. 31-39, PCR Protocols: Current Methods and Applications. Humania: Totowa, NJ (Providing a reference cited in IDS efiled on Nov. 12, 2009).

(Continued)

*Primary Examiner* — Tekchand Saidha
*Assistant Examiner* — Md. Younus Meah

(57) ABSTRACT

A high flux in conversion of pyruvate to acetolactate was achieved in yeast through expression of acetolactate synthase in the cytosol in conjunction with reduction in pyruvate decarboxylase activity. Additional manipulations to improve flux to acetolactate are reduced pyruvate dehydrogenase activity and reduced glycerol-3-phosphate dehydrogenase activity. Production of compounds having acetolactate as an upstream intermediate benefit from the increased conversion of pruvate to acetolactate in the described strains.

22 Claims, 7 Drawing Sheets

(56) References Cited

OTHER PUBLICATIONS

Sambrook, J., Fritsch, E. F. and Maniatis, T. Molecular Cloning: A Laboratory Manual, 2nd ed., pp. 11.7-11.8, Table 11.1 and pp. 9.50-9.51 Cold Spring Harbor Laboratory: Cold Spring Harbor, NY (1989) (Providing a reference cited in IDS efiled on Nov. 12, 2009).
Kiers et al., "Regulation of alcoholic fermentation in batch and chemostat cultures of *Kluyveromyces lactis* CBS 2359", Yeast, vol. 14 (1998) pp. 459-469.
Bianchi et al., "Efficient homolactic fermentation by *Kluyveromyces lactis* strains defective in pyruvate utilization and transformed with the heterologous LDH gene", Applied and Environmental Microbiology, vol. 67, No. 12, (2001) pp. 5621-5625.
van Mans et al., "Directed Evolution of Pyruvate Decarboxylase-Negative *Saccharomyces cerevisiae*, Yielding a C2-Independent, Glucose-Tolerant, and Pyruvate-Hyperproducing Yeast", Applied and Environmental Microbiology, Jan. 2004, vol. 70, No. 1, pp. 159-166.
Valadi et al., "Improved ethanol production by glycerol-3-phosphate dehydrogenase mutants of *Saccharomyces cerevisiae*", Appl. Microbiol. Biotechol. (1998) vol. 50, pp. 434-439.
International Search Report and Written Opinion of corresponding PCT/US2009/046226 patent application mailed Apr. 8, 2011.
Altschul et al., J. Mol. Biol. 215:403 410 (1990).
Bianchi et al., Mol. Microbiol. (1996) 19(1):27-36.
Deshpande, Appl. Biochem. Biotechnol. 36:227 (1992).
Flikweert et al., Yeast (1996) 12:247-257.
Frohman et al., PNAS USA 85:8998 (1988).
Gollop et al., J. Bacteriol. 172(6):3444-3449 (1990).
Guo et al., J. Membr. Sci. 245, 199-210 (2004).
Higgins, CABIOS 5:151-153 (1989).
Higgins et al., Comput. Appl. Biosci. 8:189-191 (1992).
Hohmann, (Mol. Gen. Genet. (1993) 241:657-666.
Holtzclaw et al., J. Bacteriol. 121(3):917-922 (1975).
Ishida et al., Biosci. Biotech. and Biochem. 70:1148-1153 (2006).
Loh et al., Science 243:217 (1989).
Neveling et al., J. Bacteriol. 180(6):1540-8 (1998).
Nevoigt et al., Yeast 12:1331-1337 (1996).
Nystrom et al., J. Am. Chem. Soc. (1947) 69:1198.
Ohara et al., PNAS USA 86:5673 (1989).
Sulter et al., Arch. Microbiol. 153:485 489 (1990).
Tabor et al., Proc. Acad. Sci. USA 82:1074 (1985).
Van Ness et al., Nucl. Acids Res. 19:5143 5151 (1991).
Wach et al. (1994) Yeast 10:1793-1808.
Walker et al., Proc. Natl. Acad. Sci. U.S.A., 89:392 (1992).
Methods in Enzymology, Eds. C. Guthrie and G. Fink, Academic Press, Inc., 194:281-301 (1991).
Ausubel, et al., Current Protocols in Molecular Biology, published by Greene Publishing Assoc. and Wiley Interscience (1987).
Biocomputing: Informatics and Genome Projects (Smith, D. W., Ed.) Academic: NY (1993).
Bellion et al., Microb. Growth C1 Compd., [Int. Symp.], 7th (1993), 415-32. Editors: Murrell, J. Collin; Kelly, Don P. Publisher: Intercept; Andover, UK.
Thomas D. Brock in Biotechnology: A Textbook of Industrial Microbiology, Second Edition (1989) Sinauer Associates, Inc., Sunderland, MA.
Aden et al. Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Computer Analysis of Sequence Data, Part I (Griffin, A. M., and Griffin, H. G., Eds.) Humania: NJ (1994).
Doherty and Malone, Conceptual Design of Distillation Systems, McGraw Hill, New York, 2001.
Human Genetic Diseases: A Practical Approach, K. E. Davis Ed., (1986) pp. 33-50, IRL: Herndon, VA.
Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC (1994).
Methods in Enzymology, vol. 194, Guide to Yeast Genetics and Molecular and Cell Biology (Part A, 2004, Christine Guthrie and Gerald R. Fink (Eds.), Elsevier Academic Press, San Diego, CA.
Methods in Yeast Genetics, 2005, pp. 201-202, Cold Spring Harbor Laboratory Press, Cold Spring Harbor, NY.
Rychlik, W., In Methods in Molecular Biology, White, B. A. Ed., (1993) vol. 15, pp. 31-39, PCR Protocols: Current Methods and Applications. Humania: Totowa, NJ.
Sambrook, J., Fritsch, E. F. and Maniatis, T. Molecular Cloning: A Laboratory Manual, 2nd ed., pp. 11.7-11.8, Table 11.1 and pp. 9.50-9.51 Cold Spring Harbor Laboratory: Cold Spring Harbor, NY (1989).
Sequence Analysis in Molecular Biology (von Heinje, G., Ed.) Academic (1987).
Sequence Analysis Primer (Gribskov, M. and Devereux, J., Eds.) Stockton: NY (1991).
Silhavy, T. J., Bennan, M. L. and Enquist, L. W., Experiments with Gene Fusions, Cold Spring Harbor Laboratory Press, Cold Spring Harbor, NY (1984).
Spencer et al (Mutagenesis in Yeast, 1996, Yeast Protocols: Methods in Cell and Molecular Biology. Humana Press, Totowa, NJ).
Voloch et al. Fermentation Derived 2,3-Butanediol, in Comprehensive Biotechnology, Pergamon Press Ltd, England vol. 2, Section 3:933-947 (1986).
Enzyme Nomenclature 1992, Academic Press, San Diego.
Computational Molecular Biology (Lesk, A. M., Ed.) Oxford University: NY (1988).
Ishida, et al., "The Effect of Pyruvate Decarboxylase Gene Knockout in *Saccharomyces cerevisiae* on L-lactic Acid Production", Biosci. Biotechnol. Biochem, 70(5), 1148-1153, 2006.
Skory, "Lactic acid producion by *Saccharomyces cerevisiae* expressing a *Rhizopus oryzae* lactate dehydrogenase gene", J Ind Microbiol Biotechnol (2003) 30: 22-27.
Adachi, et al., "Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value.", J of Fermentation and Bioengineering vol. 86, No. 3, 284-289, 1998.
Bjorkqvist, et al., "Physiological Response to Anaerobicity of Glycerol-3-Phosphase Dehydrogenase Mutants of *Saccharomyces cerevisae*", Appl. and Environmental Microbiology, Jan. 1997, p. 128-132.
Nissen, et al., "Anaerobic and aerobic batch cultivations of *Saccharomyces cerevisiae* mutants impaired in glycerol synthesis", Yeast 2000; 16; 463-474.
Abbott, et al., "Metabolic engineering of *Saccharomyces cerevisiae* for production of carboxylic acids: current status and challenges", FEMS Yeast Res 9 (2009) 1123-1136.
Zelle, et al., "Malic Acid production by *Saccharomyces cerevisiae*: Engineering of Pyruvate Carboxylation, Oxaloacetate Reduction, and Malate Export", Applied and Environmental Microbiology, May 2008, p. 2766-2777.
"Acetolactate Synthase" in *Springer Handbook of Enzymes*, vol. 29, Transferases II, $2^{nd}$ Ed., Schomburg, D., et al., Eds., pp. 202-216, Springer-Verlag, Germany (2006).
Chen, E. C-H., "Formation and Analysis of Fusel Alcohols in Beer," Submitted to the Faculty of Graduate Studies and Research, Department of Agricultural Chemistry, McGill University, Montreal, Canada (1978).
Chen, S., et al., "Role of NifS in Maturation of Glutamine Phosphoribosylpyrophosphate Amidotransferase," *Journal of Bacteriology* 179(23):7587-7590, American Society of Microbiology, United States (1997).
Chica, R.A., et al. "Semi-rational approaches to engineering enzyme activity: combining the benefits of directed evolution and rational design," *Current Opinion Biotechnology* 16:378-384, Elsevier Ltd., England (2005).
"Dihydroxy-Acid Dehydratase" in *Springer Handbook of Enzymes*, vol. 4, Class 4, Lyases II, $2^{nd}$ Ed., Schomburg, D., et al., Eds., pp. 296-303, Springer-Verlag, Germany (2002).

(56) References Cited

OTHER PUBLICATIONS

Flint, D.H., "*Escherichia coli* Contains a Protein that is Homologous in Function and N-terminal Sequence to the Protein Encoded by the *nifS* Gene of *Azotobacter vinelandii* and That Can Participate in the Synthesis of the Fe—S Cluster of Dihydroxy-acid Dehydratase," *The Journal of Biological Chemistry 271*(27):16068-16074, The American Society for Biochemistry and Molecular Biology, Inc., United States (1996).
Gellissen, G., et al., "Heterologous protein production in yeast," *Antonie van Leeuwenhoek 62*:79-93, Kluwer Academic Publishers, Netherlands (1992).
Godon, J-J., et al., "Branched-Chain Amino Acid Biosynthesis Genes in *Lactococcus lactis* subsp. *lactis*," *Journal of Bacteriology 174*(20):6580-6589, American Society for Microbiology, United States (1992).
González, E., et al., "Characterization and functional role of *Saccharomyces cerevisiae* 2,3-butanediol dehydrogenase," *Chemico-Biological Interactions 130-132*:425-434, Elsevier Science Ireland Ltd., Ireland (2001).
Harashima, S., "Heterologous Protein Production by Yeast Host-Vector Systems," *Bioprocess Technol. 19*:137-158. Marcel Dekker, Inc., New York, United States (1994).
Henriksen, C.M. and Nilsson, D., "Redirection of pyruvate catabolism in *Lactococcus lactis* by selection of mutants with additional growth requirements," *Appl Microbiol Biotechnol 56*:767-775, Springer-Verlag, Germany (2001).
Johnson, D.C., et al., "Structure, Function, and Formation of Biological Iron-Sulfur Clusters," *Annu. Rev. Biochem. 74*:247-281, Annual Reviews, United States (2005).
Karlin, S., et al., "Comparative analysis of gene expression among low G+C gram-positive genomes," *PNAS 101*(16):6182-6187, The National Academy of Sciences of the USA, United States (2004).
Kong, Q-X., et al., "Overexpressing *GLT1* in *gpd1*Δmutant to improve the production of ethanol of *Saccharomyces cerevisiae*," *Appl Microbiol Biotechnol 73*:1382-1386, Springer-Verlag, Germany (2007).
Maiorella, B., et al., "By-Product Inhibition Effects on Ethanolic Fermentation by *Saccharomyces cerevisiae*," *Biotechnology and Bioengineering XXV*:103-121, John Wiley & Sons, Inc., England (1983).
Mendoza-Vega, O., et al., "Industrial production of heterologous proteins by fed-batch cultures of the yeast *Saccharomyces cerevisiae*," *FEMS Microbiology Reviews 15*:369-410, Elsevier, England (1994).
Michnick, S., et al., "Modulation of Glycerol and Ethanol Yields During Alcoholic Fermentation in *Saccharomyces cerevisiae* Strains Overexpressed or Disrupted for *GPD1* Encoding Glycerol 3-Phosphate Dehydrogenase," *Yeast 13*:783-793, John Wiley & Sons, Ltd, England (1997).
Neves, A.R., et al., "Metabolic characterization of *Lactococcus lactis* deficient in lactate dehydrogenase using in vivo $^{13}$C-NMR," *Eur. J. Biochem. 267*:3859-3868, FEBS, England (2000).
Pronk, J.T., et al., "Pyruvate Metabolism in *Saccharomyces cerevisiae*," *Yeast 12*:1607-1633, John Wiley & Sons, Ltd., England (1996).
Remize, F., et al., "Glycerol Overproduction by Engineered *Saccharomyces cerevisiae* Wine Yeast Strains Leads to Substantial Changes in By-Product Formation and to a Stimulation of Fermentation Rate in Stationary Phase," *Applied and Environmental Microbiology 65*(1):143-149, American Society for Microbioloy, United States (1999).
Roggenkamp, R., et al., "Expression and processing of bacterial β-lactamase in the yeast *Saccharomyces cerevisiae*," *Proc. Natl. Acad. Sci. USA 78*(7):4466-4470, National Academy of Sciences, United States (1981).
Romano, P. and Suzzi, G., "Origin and Production of Acetoin during Wine Yeast Fermentation," *Applied and Environmental Microbiology 62*(2):309-315, American Society for Microbiology, United States (1996).
Romanos, M.A., et al., "Foreign Gene Expression in Yeast: a Review," *Yeast* vol. 8:423-488, John Wiley & Sons Ltd, England (1992).
Russell, C., et al., "Production of Recombinant Products in Yeasts: A Review," *Australian Journal of Biotechnology 5*(1):48-55, Australian Industrial Publishers for the Australian Biotechnology Association, Australia (1991).
Ui, S., et al., "Production of L-2,3-butanediol by a new pathway constructed in *Escherichia coli*," *Letters in Applied Microbiology 39*:533-537, The Society for Applied Microbiology, England (2004).
GenBank Accession No. ADA64951, Siezen, R.J., et al., NCBI Database, accessed at www.ncbi.nlm.nih.gov/protein/ADA64951, on Jul. 12, 2013.
UniProtKB, Entry Name ILVD_STRMU, Accession No. Q8DRT7, Integrated Date Apr. 4, 2003.
UniProtKB, Entry Name E1TL94_LACPS, Accession No. E1TL94, Integrated Date Nov. 30, 2010.
UniProtKB, Entry Name E1TPR8_LACPS, Accession No. E1TPR8, Integrated Date Nov. 30, 2010.
O'Brien et al. "Insight into the Mechanism of the B12-Independent Glycerol Dehydratase from *Clostridium butyricum*: Preliminary Biochemical and Structural Characterization", Biochemistry. 43(16) 4635-4645 (2004).
Scott et al. "Whole-Genome Transcription Profiling Reveals Genes Up-Regulated by Growth on Fucose in the Human Gut Bacterium "*Roseburia inulinivorans*"", Journal of Bacteriology, 188(12) 4340-4349 (2006).
Seyfried, et al. "Cloning, sequencing, and overexpression of the genes encoding coenzyme B12-dependent glycerol dehydratase of *Citrobacter freundii*", Journal of Bacteriology, 178(19): 5793-5796 (1996).
Tobimatsu, et al. "Molecular Cloning, Sequencing, and Expression of the Genes Encoding Adenosylcobalamin-dependent Diol Dehydrase of *Klebsiella oxytoca*", Journal of Biological Chemistry, 270(13): 7142-7148 (1995).
Voloch, et al. "Reduction of Acetoin to 2,3-Butanediol in *Klebsiella pneumoniae*: A New Model" Biotechnology and Bioengineering, vol. XXV: 173-183 (1983).
Pang, et al., "The Crystal Structures of *Klebsiella pneumonia* Acetolactate Synthase with Enzyme-bound Cofactor and with an Unsual Intermediate", J. Biol. Chem., 279(3): 2242-2253, (2004).
Stewart, "A Chemist's Perspective on the Use of Genetically Engineered Microbes as Reagents for Organic Synthesis" biotechnology and Genetic Engineering Reviews, vol. 14, Apr. 1997, pp. 67-143.
Overkamp, K.M., et al., "Metabolic Engineering of Glycerol Production in *Saccharomyces cerevisiae*," *AEM 68*(6):2814-2821, American Society for Microbiology, United States (2002).
Final Judgment of U.S. District Court Judge Robinson, in *Gevo, Inc. v. Butamax™ Advanced Biofuels LLC*, Case 1:13-cv-00576-SLR, United States District Court for the District of Delaware, issued Aug. 8, 2013; 2 pages.
Memorandum Opinion and Order of U.S. District Court Judge Robinson, in *Gevo, Inc. v. Butamax™ Advanced Biofuels LLC*, Case 1:13-cv-00576-SLR, United States District Court for the District of Delaware, issued Jul. 16, 2013; 48 pages.
U.S. Control No. 95/001,735, filed Sep. 1, 2011.
U.S. Control No. 95/001,857, filed Dec. 19, 2011.
U.S. Control No. 95/001,998, filed Jun. 21, 2012.
U.S. Control No. 95/002,158, filed Sep. 7, 2012.
U.S. Control No. 90/012,503, filed Sep. 12, 2012.
U.S. Control No. 95/002,167, filed Sep. 10, 2012.
U.S. Control No. 95/002,227, filed Sep. 14, 2012.

* cited by examiner

| | |
|---|---|
| 1 | Bacillus cereus E33L |
| 2 | Bacillus thuringiensis serovar konkukian str. 97-27 |
| 3 | Bacillus cereus G9241 |
| 4 | Bacillus cereus B4264 |
| 5 | Bacillus cereus AH1134 |
| 6 | Bacillus cereus ATCC 14579 |
| 7 | Bacillus cereus G9842 |
| 8 | Bacillus thuringiensis serovar israelensis ATCC 35646 |
| 9 | Bacillus cereus 03BB108 |
| 10 | Bacillus cereus NVH0597-99 |
| 11 | Bacillus thuringiensis str. Al Hakam |
| 12 | Bacillus anthracis str. Ames |
| 13 | Bacillus cereus W |
| 14 | Bacillus cereus AH187 |
| 15 | Bacillus cereus ATCC 10987 |
| 16 | Bacillus weihenstephanensis KBAB4 |
| 17 | Listeria monocytogenes F5L JI-208 |
| 18 | Listeria welshimeri serovar 6b str. SLCC5334 |
| 19 | Listeria innocua clip 11262 |
| 20 | Listeria monocytogenes F5L JI-175 |
| 21 | Listeria monocytogenes str. 4b H7858 |
| 22 | Listeria monocytogenes str. 4b F2365 |
| 23 | Listeria monocytogenes HP B2262 |
| 24 | Listeria monocytogenes F5L N1-017 |
| 25 | Listeria monocytogenes str. 1/2a F6854 |
| 26 | Listeria monocytogenes EDG-e |
| 27 | Exiguobacterium sibiricum 255-15 |
| 28 | Bacillus coagulans 36D1 |
| 29 | Bacillus licheniformis ATCC 14580 |
| 30 | Bacillus pumilus 5A FR-032 |
| 31 | Bacillus amyloliquefaciens FZB42 |
| 32 | Unknown |
| 33 | Bacillus subtilis subsp. subtilis str. 168 |
| 34 | Bacillus subtilis |
| 35 | Staphylococcus haemolyticus JC5C1435 |
| 36 | Staphylococcus epidermidis ATCC 12228 |
| 37 | Staphylococcus saprophyticus subsp. saprophyticus ATCC 15305 |
| 38 | Staphylococcus aureus subsp. aureus Mu 50 |
| 39 | Staphylococcus aureus subsp. aureus MR5A252 |
| 40 | Staphylococcus aureus subsp. aureus NCTC 8325 |
| 41 | Staphylococcus aureus |
| 42 | Staphylococcus aureus subsp. aureus MW2 |
| 43 | Staphylococcus aureus RF122 |
| 44 | Lactococcus lactis subsp. lactis il1403 |
| 45 | Lactococcus lactis subsp. cremoris MG 1363 |

FIG. 4B

| | |
|---|---|
| 46 | Lactococcus lactis subsp. cremoris 5K11 |
| 47 | Streptococcus infantarius subsp. infantarius ATCC BAA-102 |
| 48 | Streptococcus agalactiae COHI |
| 49 | Streptococcus agalactiae 2603V/R |
| 50 | Streptococcus agalactiae NEM316 |
| 51 | Streptococcus mutans UA 159 |
| 52 | Streptococcus thermophilus LMD-9 |
| 53 | Streptococcus thermophilus LMG 18311 |
| 54 | Streptococcus thermophilus CNRZ1066 |
| 55 | Streptococcus thermophilus |
| 56 | Enterococcus faecium DO |
| 57 | Enterococcus faecalis V583 |
| 58 | Lactobacillus brevis ATCC 367 |
| 59 | Oenococcus oeni |
| 60 | Oenococcus oeni P 5U-1 |
| 61 | Oenococcus oeni ATCC BAA-1163 |
| 62 | Lactobacillus reuteri F275 |
| 63 | Lactobacillus reuteri |
| 64 | Lactobacillus reuteri 100-23 |
| 65 | Leuconostoc mesenteroides subsp. mesenteroides ATCC 8293 |
| 66 | Leuconostoc lactis |
| 67 | Leuconostoc citreum KM20 |
| 68 | Lactobacillus casei ATCC 334 |
| 69 | Pediococcus pentosaceus ATCC 25745 |
| 70 | Lactobacillus fermentum IFO 3956 |
| 71 | Lactobacillus plantarum WCF51 |
| 72 | Lactobacillus sakei subsp. sakei 23K |
| 73 | Lactobacillus salivarius UCC118 |
| 74 | Lactobacillus johnsonii NCC 533 |
| 75 | Mycobacterium marinum |
| 76 | Mycobacterium ulcerans Agy99 |
| 77 | Magnaporthe grisea 70-15 |
| 78 | Phaeosphaeria nodorum SN15 |
| 79 | Methylococcus capsulatus str. Bath |
| 80 | Vibrio angustum S14 |
| 81 | Synechococcus sp. CC9605 |
| 82 | Vibrio cholerae 1587 |
| 83 | Vibrio cholerae AM-19226 |
| 84 | Vibrio cholerae 623-39 |
| 85 | Vibrio cholerae O 1 biovar eltor str. N1... |
| 86 | Vibrio cholerae V51 |
| 87 | Vibrio cholerae 2740-80 |
| 88 | Vibrio cholerae V52 |
| 89 | Vibrio alginolyticus 12G01 |
| 90 | Vibrio sp. Ex25 |

FIG. 4C

| | |
|---|---|
| 91 | Serratia prataemacuans 568 |
| 92 | Aeromanas hydrophila subsp. hydrophila ATCC 7966 |
| 93 | Enterobacter sp. 638 |
| 94 | Enterobacter sakazakii ATCC 8AA-894 |
| 95 | Raoultello terrigena |
| 96 | Klebsiella pneumoniae subsp. pneumoniae MGH 78578 |
| 97 | Klebsiella pneumoniae |
| 98 | Klebsiella pneumoniae |
| 99 | Pectobacterium atrosepticum 5CRI1043 |
| 100 | Yersinia intermedia ATCC 29909 |
| 101 | Yersinia enterocolitica subsp. enterocolitica 8081 |

FIG. 4D

```
                        SEQUENCE LISTING

<160> NUMBER OF SEQ ID NOS: 208

<210> SEQ ID NO 1
<211> LENGTH: 1680
<212> TYPE: DNA
<213> ORGANISM: K. pneumoniae

<400> SEQUENCE: 1
atggacaaac agtatccggt acgccagtgg gcgcacggcg ccgatctcgt cgtcagtcag      60
ctggaagctc agggagtacg ccaggtgttc ggcatcccg gcgccaaaat cgacaaggtc     120
tttgattcac tgctggattc ctccattcgc attattccgg tacgccacga agccaacgcc     180
gcatttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata aagcgaagca ggtccaccag     360
agtatggata cggtggcgat gttcagcccg gtcaccaaat acgccatcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gcccggtcag cggcaaagtg     540
ctgccggcca gcgggccccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct gcgccgtttg ctggagacca gccatattcc agtcaccagc     720
acctatcagg ccgccggagc ggtgaatcag gataacttct ctcgcttcgc cggccgggtt     780
gggctgttta acaaccaggc cggggaccgt ctgctgcagc tcgccgacct ggtgatctgc     840
```

```
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctcaa ccagtttgcc ctgcatcccc tgcgcatcgt tcgcgccatg   1140
caggatatcg tcaacagcga cgtcacgttg accgtggaca tgggcagctt ccatatctgg   1200
attgcccgct acctgtacac gttccgcgcc cgtcaggtga tgatctccaa cggccagcag   1260
accatgggcg tcgccctgcc ctgggctatc ggcgcctggc tggtcaatcc tgagcgcaaa   1320
gtggtctccg tctccggcga cggcggcttc ctgcagtcga gcatggagct ggagaccgcc   1380
gtccgcctga agccaacgt gctgcatctt atctgggtcg ataacggcta caacatggtc   1440
gctatccagg aagagaaaaa atatcagcgc ctgtccggcg tcgagtttgg gccgatggat   1500
tttaaagcct atgccgaatc cttcggcgcg aaagggtttg ccgtggaaag cgccgaggcg   1560
ctggagccga ccctgcgcgc ggcgatggac gtcgacggcc cggcggtagt ggccatcccg   1620
gtggattatc gcgataaccc gctgctgatg ggccagctgc atctgagtca gattctgtaa   1680
```

<210> SEQ ID NO 2
<211> LENGTH: 559
<212> TYPE: PRT
<213> ORGANISM: K. pneumoniae

<400> SEQUENCE: 2

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Ile Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
```

```
                225                 230                 235                 240
     Thr Tyr Gln Ala Ala Gly Ala Val Asn Gln Asp Asn Phe Ser Arg Phe
                     245                 250                 255
     Ala Gly Arg Val Gly Leu Phe Asn Asn Gln Ala Gly Asp Arg Leu Leu
                     260                 265                 270
     Gln Leu Ala Asp Leu Val Ile Cys Ile Gly Tyr Ser Pro Val Glu Tyr
                     275                 280                 285
     Glu Pro Ala Met Trp Asn Ser Gly Asn Ala Thr Leu Val His Ile Asp
                     290                 295                 300
     Val Leu Pro Ala Tyr Glu Arg Asn Tyr Thr Pro Asp Val Glu Leu
     305                 310                 315                 320
     Val Gly Asp Ile Ala Gly Thr Leu Asn Lys Leu Ala Gln Asn Ile Asp
                     325                 330                 335
     His Arg Leu Val Leu Ser Pro Gln Ala Ala Glu Ile Leu Arg Asp Arg
                     340                 345                 350
     Gln His Gln Arg Glu Leu Leu Asp Arg Arg Gly Ala Gln Leu Asn Gln
                     355                 360                 365
     Phe Ala Leu His Pro Leu Arg Ile Val Arg Ala Met Gln Asp Ile Val
                     370                 375                 380
     Asn Ser Asp Val Thr Leu Thr Val Asp Met Gly Ser Phe His Ile Trp
     385                 390                 395                 400
     Ile Ala Arg Tyr Leu Tyr Thr Phe Arg Ala Arg Gln Val Met Ile Ser
                     405                 410                 415
     Asn Gly Gln Gln Thr Met Gly Val Ala Leu Pro Trp Ala Ile Gly Ala
                     420                 425                 430
     Trp Leu Val Asn Pro Glu Arg Lys Val Val Ser Val Ser Gly Asp Gly
                     435                 440                 445
     Gly Phe Leu Gln Ser Ser Met Glu Leu Glu Thr Ala Val Arg Leu Lys
                     450                 455                 460
     Ala Asn Val Leu His Leu Ile Trp Val Asp Asn Gly Tyr Asn Met Val
     465                 470                 475                 480
     Ala Ile Gln Glu Glu Lys Lys Tyr Gln Arg Leu Ser Gly Val Glu Phe
                     485                 490                 495
     Gly Pro Met Asp Phe Lys Ala Tyr Ala Glu Ser Phe Gly Ala Lys Gly
                     500                 505                 510
     Phe Ala Val Glu Ser Ala Glu Ala Leu Glu Pro Thr Leu Arg Ala Ala
                     515                 520                 525
     Met Asp Val Asp Gly Pro Ala Val Val Ala Ile Pro Val Asp Tyr Arg
                     530                 535                 540
     Asp Asn Pro Leu Leu Met Gly Gln Leu His Leu Ser Gln Ile Leu
     545                 550                 555

<210> SEQ ID NO 3
<211> LENGTH: 1716
<212> TYPE: DNA
<213> ORGANISM: Bacillus subtilis

<400> SEQUENCE: 3
atgttgacaa aagcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt taactggaaa accgggagtc     240
gtgttagtca catcaggacc gggtgcctct aacttggcaa caggcctgct gacagcgaac     300
```

```
actgaaggag accctgtcgt tgcgcttgct ggaaacgtga tccgtgcaga tcgtttaaaa      360
cggacacatc aatctttgga taatgcggcg ctattccagc cgattacaaa atacagtgta      420
gaagttcaag atgtaaaaaa tataccggaa gctgttacaa atgcatttag gatagcgtca      480
gcagggcagg ctggggccgc ttttgtgagc tttccgcaag atgttgtgaa tgaagtcaca      540
aatacgaaaa acgtgcgtgc tgttgcagcg ccaaaactcg gtcctgcagc agatgatgca      600
atcagtgcgg ccatagcaaa atccaaaca gcaaaacttc ctgtcgtttt ggtcggcatg      660
aaaggcggaa gaccggaagc aattaaagcg gttcgcaagc ttttgaaaaa ggttcagctt      720
ccatttgttg aaacatatca agctgccggt acccttccta gagatttaga ggatcaatat      780
tttggccgta tcggtttgtt ccgcaaccag cctggcgatt tactgctaga gcaggcagat      840
gttgttctga cgatcggcta tgacccgatt gaatatgatc cgaaattctg gaatatcaat      900
ggagaccgga caattatcca tttagacgag attatcgctg acattgatca tgcttaccag      960
cctgatcttg aattgatcgg tgacattccg tccacgatca atcatatcga acacgatgct      1020
gtgaaagtgg aatttgcaga gcgtgagcag aaaatccttt ctgatttaaa acaatatatg      1080
catgaaggtg agcaggtgcc tgcagattgg aaatcagaca gagcgcaccc tcttgaaatc      1140
gttaaagagt tgcgtaatgc agtcgatgat catgttacag taacttgcga tatcggttcg      1200
cacgccattt ggatgtcacg ttatttccgc agctacgagc cgttaacatt aatgatcagt      1260
aacggtatgc aaacactcgg cgttgcgctt ccttgggcaa tcggcgcttc attggtgaaa      1320 ccggagaaa aagtggtttc tgtctctggt gacggcggtt tcttattctc agcaatggaa       1380
ttagagacag cagttcgact aaaagcacca attgtacaca ttgtatggaa cgacagcaca      1440
tatgacatgg ttgcattcca gcaattgaaa aaatataacc gtacatctgc ggtcgatttc      1500
ggaaatatcg atatcgtgaa atatgcggaa agcttcggag caactggctt gcgcgtagaa      1560
tcaccagacc agctggcaga tgttctgcgt caaggcatga acgctgaagg tcctgtcatc      1620
atcgatgtcc cggttgacta cagtgataac attaatttag caagtgacaa gcttccgaaa      1680
gaattcgggg aactcatgaa aacgaaagct ctctag                                1716
```

<210> SEQ ID NO 4
<211> LENGTH: 571
<212> TYPE: PRT
<213> ORGANISM: Bacillus subtilis

<400> SEQUENCE: 4

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn

```
            115                 120                 125
Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
            165                 170                 175

Asn Glu Val Thr Asn Thr Lys Asn Val Arg Ala Val Ala Ala Pro Lys
        180                 185                 190

Leu Gly Pro Ala Ala Asp Asp Ala Ile Ser Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
            245                 250                 255

Glu Asp Gln Tyr Phe Gly Arg Ile Gly Leu Phe Arg Asn Gln Pro Gly
        260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
290                 295                 300

Ile Ile His Leu Asp Glu Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
        340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415

Leu Met Ile Ser Asn Gly Met Gln Thr Leu Gly Val Ala Leu Pro Trp
        420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
            485                 490                 495

Ala Val Asp Phe Gly Asn Ile Asp Ile Val Lys Tyr Ala Glu Ser Phe
        500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
530                 535                 540
```

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570

<210> SEQ ID NO 5
<211> LENGTH: 1665
<212> TYPE: DNA
<213> ORGANISM: Lactococcus lactis

<400> SEQUENCE: 5

| | |
|---|---:|
| atgtctgaga aacaatttgg ggcgaacttg gttgtcgata gtttgattaa ccataaagtg | 60 |
| aagtatgtat ttgggattcc aggagcaaaa attgaccggg ttttgatttt attagaaaat | 120 |
| gaagaaggcc ctcaaatggt cgtgactcgt catgagcaag agctgctttt catggctcaa | 180 |
| gctgtcggtc gtttaactgg cgaacctggt gtagtagttg ttacgagtgg gcctggtgta | 240 |
| tcaaaccttg cgactccgct tttgaccgcg acatcagaag gtgatgctat tttggctatc | 300 |
| ggtggacaag ttaaacgaag tgaccgtctt aaacgtgcgc accaatcaat ggataatgct | 360 |
| ggaatgatgc aatcagcaac aaaatattca gcagaagttc ttgaccctaa tacactttct | 420 |
| gaatcaattg ccaacgctta tcgtattgca aaatcaggac atccaggtgc aactttctta | 480 |
| tcaatccccc aagatgtaac ggatgccgaa gtatcaatca aagccattca accactttca | 540 |
| gaccctaaaa tggggaatgc ctctattgat gacattaatt atttagcaca agcaattaaa | 600 |
| aatgctgtat tgccagtaat tttggttgga gctggtgctt cagatgctaa agtcgcttca | 660 |
| tccttgcgta atctattgac tcatgttaat attcctgtcg ttgaaacatt ccaaggtgca | 720 |
| ggggttattt cacatgattt agaacatact ttttatggac gtatcggtct tttccgcaat | 780 |
| caaccaggcg atatgcttct gaaacgttct gaccttgtta ttgctgttgg ttatgaccca | 840 |
| attgaatatg aagctcgtaa ctggaatgca gaaattgata gtcgaattat cgttattgat | 900 |
| aatgccattg ctgaaattga tacttactac caaccagagc gtgaattaat tggtgatatc | 960 |
| gcagcaacat tggataatct tttaccagct gttcgtggct acaaaattcc aaaaggaaca | 1020 |
| aaagattatc tcgatggcct tcatgaagtt gctgagcaac acgaatttga tactgaaaat | 1080 |
| actgaagaag gtagaatgca ccctcttgat ttggtcagca ctttccaaga aatcgtcaag | 1140 |
| gatgatgaaa cagtaaccgt tgacgtaggt tcactctaca tttggatggc acgtcatttc | 1200 |
| aaatcatacg aaccacgtca tctcctcttc tcaaacggaa tgcaaacact cggagttgca | 1260 |
| cttccttggg caattacagc cgcattgttg cgcccaggta aaaagtttta ttcacactct | 1320 |
| ggtgatggag cttcctttt cacagggcaa gaattggaaa cagctgtacg tttgaatctt | 1380 |
| ccaatcgttc aaattatctg gaatgacggc cattatgata tggttaaatt ccaagaagaa | 1440 |
| atgaaatatg gtcgttcagc agccgttgat tttggctatg ttgattacgt aaaatatgct | 1500 |
| gaagcaatga gagcaaaagg ttaccgtgca cacagcaaag aagaacttgc tgaaattctc | 1560 |
| aaatcaatcc cagatactac tggaccggtg gtaattgacg ttcctttgga ctattctgat | 1620 |
| aacattaaat tagcagaaaa attattgcct gaagagtttt attga | 1665 |

<210> SEQ ID NO 6
<211> LENGTH: 554
<212> TYPE: PRT
<213> ORGANISM: Lactococcus lactis

<400> SEQUENCE: 6

```
Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
            20                  25                  30

Arg Val Phe Asp Leu Leu Glu Asn Glu Glu Gly Pro Gln Met Val Val
                35                  40                  45

Thr Arg His Glu Gln Gly Ala Ala Phe Met Ala Gln Ala Val Gly Arg
50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
                100                 105                 110

Ala His Gln Ser Met Asp Asn Ala Gly Met Met Gln Ser Ala Thr Lys
            115                 120                 125

Tyr Ser Ala Glu Val Leu Asp Pro Asn Thr Leu Ser Glu Ser Ile Ala
        130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
                180                 185                 190

Asn Tyr Leu Ala Gln Ala Ile Lys Asn Ala Val Leu Pro Val Ile Leu
            195                 200                 205

Val Gly Ala Gly Ala Ser Asp Ala Lys Val Ala Ser Ser Leu Arg Asn
        210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255

Leu Phe Arg Asn Gln Pro Gly Asp Met Leu Leu Lys Arg Ser Asp Leu
                260                 265                 270

Val Ile Ala Val Gly Tyr Asp Pro Ile Glu Tyr Glu Ala Arg Asn Trp
            275                 280                 285

Asn Ala Glu Ile Asp Ser Arg Ile Ile Val Ile Asp Asn Ala Ile Ala
290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Asp Tyr Leu Asp Gly Leu His Glu Val Ala Glu
            340                 345                 350

Gln His Glu Phe Asp Thr Glu Asn Thr Glu Glu Gly Arg Met His Pro
        355                 360                 365

Leu Asp Leu Val Ser Thr Phe Gln Glu Ile Val Lys Asp Asp Glu Thr
370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
```

```
                420           425           430
Gly Lys Lys Val Tyr Ser His Ser Gly Asp Gly Phe Leu Phe Thr
            435               440               445

Gly Gln Glu Leu Glu Thr Ala Arg Leu Asn Leu Pro Ile Val Gln
            450               455               460

Ile Ile Trp Asn Asp Gly His Tyr Asp Met Val Lys Phe Gln Glu
465               470               475               480

Met Lys Tyr Gly Arg Ser Ala Ala Val Asp Phe Gly Tyr Val Asp Tyr
                485               490               495

Val Lys Tyr Ala Glu Ala Met Arg Ala Lys Gly Tyr Arg Ala His Ser
            500               505               510

Lys Glu Glu Leu Ala Glu Ile Leu Lys Ser Ile Pro Asp Thr Thr Gly
            515               520               525

Pro Val Val Ile Asp Val Pro Leu Asp Tyr Ser Asp Asn Ile Lys Leu
            530               535               540

Ala Glu Lys Leu Leu Pro Glu Glu Phe Tyr
545               550
```

<210> SEQ ID NO 7
<211> LENGTH: 1665
<212> TYPE: DNA
<213> ORGANISM: Staphylococcus aureus
<220> FEATURE:
<221> NAME/KEY: CDS
<222> LOCATION: (1)..(1665)

<400> SEQUENCE: 7

```
atg act gat aaa aag tac act gca gcc gat atg gtt att gat act ttg    48
Met Thr Asp Lys Lys Tyr Thr Ala Ala Asp Met Val Ile Asp Thr Leu
1               5                  10                  15 aaa aat aat ggg gta gaa tat gtt ttt ggt att ccg ggt gca aag ata    96
Lys Asn Asn Gly Val Glu Tyr Val Phe Gly Ile Pro Gly Ala Lys Ile
            20                  25                  30 gac tat cta ttt aat gct tta att gat gat ggt cct gaa ctt att gtc   144
Asp Tyr Leu Phe Asn Ala Leu Ile Asp Asp Gly Pro Glu Leu Ile Val
        35                  40                  45 act cgt cat gaa caa aat gct gca atg atg gca caa ggt att gga aga   192
Thr Arg His Glu Gln Asn Ala Ala Met Met Ala Gln Gly Ile Gly Arg
    50                  55                  60 tta aca ggt aaa ccg ggt gta gta ctt gtt aca agt ggc cct ggt gta   240
Leu Thr Gly Lys Pro Gly Val Val Leu Val Thr Ser Gly Pro Gly Val
65                  70                  75                  80 agt aat tta acg act gga cta tta aca gct aca tct gaa ggg gat cct   288
Ser Asn Leu Thr Thr Gly Leu Leu Thr Ala Thr Ser Glu Gly Asp Pro
                85                  90                  95 gta tta gcg tta ggt ggc caa gtg aaa cgt aat gat tta tta cga tta   336
Val Leu Ala Leu Gly Gly Gln Val Lys Arg Asn Asp Leu Leu Arg Leu
            100                 105                 110 acg cat caa agt att gat aat gct gcg cta tta aaa tat tca tca aaa   384
Thr His Gln Ser Ile Asp Asn Ala Ala Leu Leu Lys Tyr Ser Ser Lys
        115                 120                 125 tac agt gaa gaa gta caa gat cct gaa tca tta tca gaa gtt atg aca   432
Tyr Ser Glu Glu Val Gln Asp Pro Glu Ser Leu Ser Glu Val Met Thr
    130                 135                 140 aat gca att cga att gct act tca gga aaa aat ggc gca agt ttt att   480
Asn Ala Ile Arg Ile Ala Thr Ser Gly Lys Asn Gly Ala Ser Phe Ile
145                 150                 155                 160 agt att ccg caa gac gtt att tct tca cca gtt gaa tct aaa gct ata   528
Ser Ile Pro Gln Asp Val Ile Ser Ser Pro Val Glu Ser Lys Ala Ile
```

-continued

| | | | | | | | | |
|---|---|---|---|---|---|---|---|---|
| | | 165 | | | 170 | | | 175 |

```
tca ctt tgc caa aaa cca aat tta gga gta ccg agt gaa caa gat att    576
Ser Leu Cys Gln Lys Pro Asn Leu Gly Val Pro Ser Glu Gln Asp Ile
            180                 185                 190 aat gat gtc att gaa gcg att aaa aat gca tca ttt cct gtt tta tta    624
Asn Asp Val Ile Glu Ala Ile Lys Asn Ala Ser Phe Pro Val Leu Leu
            195                 200                 205 gct ggt atg aga agt tca agt gca gaa gaa aca aat gcc att cgc aaa    672
Ala Gly Met Arg Ser Ser Ser Ala Glu Glu Thr Asn Ala Ile Arg Lys
            210                 215                 220 tta gtt gag cgc acg aat tta cca gtt gta gaa aca ttc caa ggt gca    720
Leu Val Glu Arg Thr Asn Leu Pro Val Val Glu Thr Phe Gln Gly Ala
225                 230                 235                 240 ggt gta att agt cgt gaa tta gaa aat cat ttc ttc ggt cgt gtg ggc    768
Gly Val Ile Ser Arg Glu Leu Glu Asn His Phe Phe Gly Arg Val Gly
                245                 250                 255 tta ttc cgc aat caa gtt ggt gat gaa tta tta cgt aaa agt gat tta    816
Leu Phe Arg Asn Gln Val Gly Asp Glu Leu Leu Arg Lys Ser Asp Leu
                260                 265                 270 gtt gtt aca atc ggt tat gat cca att gaa tac gaa gct agt aac tgg    864
Val Val Thr Ile Gly Tyr Asp Pro Ile Glu Tyr Glu Ala Ser Asn Trp
                275                 280                 285 aat aaa gaa tta gaa aca caa att atc aat att gac gaa gtt caa gct    912
Asn Lys Glu Leu Glu Thr Gln Ile Ile Asn Ile Asp Glu Val Gln Ala
290                 295                 300 gaa att act aat tat atg caa ccg aaa aaa gag ttg att ggt aat att    960
Glu Ile Thr Asn Tyr Met Gln Pro Lys Lys Glu Leu Ile Gly Asn Ile
305                 310                 315                 320 gct aaa acg att gaa atg att tct gaa aaa gtg gat gag cca ttt ata   1008
Ala Lys Thr Ile Glu Met Ile Ser Glu Lys Val Asp Glu Pro Phe Ile
                325                 330                 335 aat caa caa cat tta gac gaa tta gaa caa tta aga aca cat att gat   1056
Asn Gln Gln His Leu Asp Glu Leu Glu Gln Leu Arg Thr His Ile Asp
                340                 345                 350 gaa gaa act ggt att aaa gcg acg cat gaa gaa gga att cta cat cca   1104
Glu Glu Thr Gly Ile Lys Ala Thr His Glu Glu Gly Ile Leu His Pro
                355                 360                 365 gtg gaa att att gaa tct atg caa aag gta tta act gat gat act act   1152
Val Glu Ile Ile Glu Ser Met Gln Lys Val Leu Thr Asp Asp Thr Thr
                370                 375                 380 gta aca gtt gat gtt gga agt cac tat att tgg atg gca cgt aat ttc   1200
Val Thr Val Asp Val Gly Ser His Tyr Ile Trp Met Ala Arg Asn Phe
385                 390                 395                 400 aga agt tac aat cca aga cat tta tta ttt agc aat ggt atg caa acg   1248
Arg Ser Tyr Asn Pro Arg His Leu Leu Phe Ser Asn Gly Met Gln Thr
                405                 410                 415 ctt ggt gta gca tta ccg tgg gca att tca gct gca ctt gtg cgc cct   1296
Leu Gly Val Ala Leu Pro Trp Ala Ile Ser Ala Ala Leu Val Arg Pro
                420                 425                 430 aat acg caa gtt gtg tcc gtt gct ggc gat ggt ggc ttt tta ttt tca   1344
Asn Thr Gln Val Val Ser Val Ala Gly Asp Gly Gly Phe Leu Phe Ser
                435                 440                 445 tca caa gat tta gaa acg gcc gta cgt aaa aat tta aat atc atc cag   1392
Ser Gln Asp Leu Glu Thr Ala Val Arg Lys Asn Leu Asn Ile Ile Gln
450                 455                 460 ctt att tgg aat gat gga aaa tat aac atg gtt gaa ttc caa gaa gaa   1440
Leu Ile Trp Asn Asp Gly Lys Tyr Asn Met Val Glu Phe Gln Glu Glu
465                 470                 475                 480 atg aaa tat aaa cgt tcg tca ggt gta gac ttc ggt cct gta gat ttt   1488
```

```
                Met Lys Tyr Lys Arg Ser Ser Gly Val Asp Phe Gly Pro Val Asp Phe
                                485                 490                 495 gta aaa tat gca gaa tca ttt ggc gcg aaa ggt tta cga gtt act aat           1536
Val Lys Tyr Ala Glu Ser Phe Gly Ala Lys Gly Leu Arg Val Thr Asn
                500                 505                 510 caa gaa gaa tta gaa gcg gca att aaa gag ggc tat gaa aca gat ggt           1584
Gln Glu Glu Leu Glu Ala Ala Ile Lys Glu Gly Tyr Glu Thr Asp Gly
                515                 520                 525 cca gta tta att gat ata cct gta aat tac aaa gat aat atc aaa ctt           1632
Pro Val Leu Ile Asp Ile Pro Val Asn Tyr Lys Asp Asn Ile Lys Leu
            530                 535                 540 tca aca aat atg tta cct gac gta ttt aac taa                               1665
Ser Thr Asn Met Leu Pro Asp Val Phe Asn
545                 550

<210> SEQ ID NO 8
<211> LENGTH: 554
<212> TYPE: PRT
<213> ORGANISM: Staphylococcus aureus

<400> SEQUENCE: 8

Met Thr Asp Lys Lys Tyr Thr Ala Ala Asp Met Val Ile Asp Thr Leu
1               5                   10                  15

Lys Asn Asn Gly Val Glu Tyr Val Phe Gly Ile Pro Gly Ala Lys Ile
                20                  25                  30

Asp Tyr Leu Phe Asn Ala Leu Ile Asp Asp Gly Pro Glu Leu Ile Val
            35                  40                  45

Thr Arg His Glu Gln Asn Ala Ala Met Met Ala Gln Gly Ile Gly Arg
        50                  55                  60

Leu Thr Gly Lys Pro Gly Val Val Leu Val Thr Ser Gly Pro Gly Val
65                  70                  75                  80

Ser Asn Leu Thr Thr Gly Leu Leu Thr Ala Thr Ser Glu Gly Asp Pro
                85                  90                  95

Val Leu Ala Leu Gly Gly Gln Val Lys Arg Asn Asp Leu Leu Arg Leu
            100                 105                 110

Thr His Gln Ser Ile Asp Asn Ala Ala Leu Leu Lys Tyr Ser Ser Lys
        115                 120                 125

Tyr Ser Glu Glu Val Gln Asp Pro Glu Ser Leu Ser Glu Val Met Thr
    130                 135                 140

Asn Ala Ile Arg Ile Ala Thr Ser Gly Lys Asn Gly Ala Ser Phe Ile
145                 150                 155                 160

Ser Ile Pro Gln Asp Val Ile Ser Ser Pro Val Glu Ser Lys Ala Ile
                165                 170                 175

Ser Leu Cys Gln Lys Pro Asn Leu Gly Val Pro Ser Glu Gln Asp Ile
            180                 185                 190

Asn Asp Val Ile Glu Ala Ile Lys Asn Ala Ser Phe Pro Val Leu Leu
        195                 200                 205

Ala Gly Met Arg Ser Ser Ala Glu Glu Thr Asn Ala Ile Arg Lys
    210                 215                 220

Leu Val Glu Arg Thr Asn Leu Pro Val Val Glu Thr Phe Gln Gly Ala
225                 230                 235                 240

Gly Val Ile Ser Arg Glu Leu Glu Asn His Phe Phe Gly Arg Val Gly
                245                 250                 255

Leu Phe Arg Asn Gln Val Gly Asp Glu Leu Leu Arg Lys Ser Asp Leu
            260                 265                 270

Val Val Thr Ile Gly Tyr Asp Pro Ile Glu Tyr Glu Ala Ser Asn Trp
```

```
                    275                 280                 285
Asn Lys Glu Leu Glu Thr Gln Ile Ile Asn Ile Asp Glu Val Gln Ala
                290                 295                 300
Glu Ile Thr Asn Tyr Met Gln Pro Lys Lys Glu Leu Ile Gly Asn Ile
305                 310                 315                 320
Ala Lys Thr Ile Glu Met Ile Ser Glu Lys Val Asp Glu Pro Phe Ile
                325                 330                 335
Asn Gln Gln His Leu Asp Glu Leu Glu Gln Leu Arg Thr His Ile Asp
            340                 345                 350
Glu Glu Thr Gly Ile Lys Ala Thr His Glu Glu Gly Ile Leu His Pro
            355                 360                 365
Val Glu Ile Ile Glu Ser Met Gln Lys Val Leu Thr Asp Asp Thr Thr
        370                 375                 380
Val Thr Val Asp Val Gly Ser His Tyr Ile Trp Met Ala Arg Asn Phe
385                 390                 395                 400
Arg Ser Tyr Asn Pro Arg His Leu Leu Phe Ser Asn Gly Met Gln Thr
                405                 410                 415
Leu Gly Val Ala Leu Pro Trp Ala Ile Ser Ala Ala Leu Val Arg Pro
            420                 425                 430
Asn Thr Gln Val Val Ser Val Ala Gly Asp Gly Gly Phe Leu Phe Ser
            435                 440                 445
Ser Gln Asp Leu Glu Thr Ala Val Arg Lys Asn Leu Asn Ile Ile Gln
        450                 455                 460
Leu Ile Trp Asn Asp Gly Lys Tyr Asn Met Val Glu Phe Gln Glu Glu
465                 470                 475                 480
Met Lys Tyr Lys Arg Ser Ser Gly Val Asp Phe Gly Pro Val Asp Phe
                485                 490                 495
Val Lys Tyr Ala Glu Ser Phe Gly Ala Lys Gly Leu Arg Val Thr Asn
                500                 505                 510
Gln Glu Glu Leu Glu Ala Ala Ile Lys Glu Gly Tyr Glu Thr Asp Gly
            515                 520                 525
Pro Val Leu Ile Asp Ile Pro Val Asn Tyr Lys Asp Asn Ile Lys Leu
        530                 535                 540
Ser Thr Asn Met Leu Pro Asp Val Phe Asn
545                 550

<210> SEQ ID NO 9
<211> LENGTH: 1698
<212> TYPE: DNA
<213> ORGANISM: Listeria monocytogenes
<220> FEATURE:
<221> NAME/KEY: CDS
<222> LOCATION: (1)..(1698)

<400> SEQUENCE: 9 atg gcg aaa cta gaa aaa gac caa gaa aaa gta ata aca caa ggg aaa      48
Met Ala Lys Leu Glu Lys Asp Gln Glu Lys Val Ile Thr Gln Gly Lys
1               5                   10                  15 tca gga gcg gat tta gtt gta gac agc tta att aat caa ggt gtt acg      96
Ser Gly Ala Asp Leu Val Val Asp Ser Leu Ile Asn Gln Gly Val Thr
            20                  25                  30 cat gta ttc ggg att ccg gga gcg aaa att gat aaa gtt ttt gat gtg     144
His Val Phe Gly Ile Pro Gly Ala Lys Ile Asp Lys Val Phe Asp Val
        35                  40                  45 atg gaa gaa cgt gga cca gaa tta att gtc agt cgt cat gaa caa aat     192
Met Glu Glu Arg Gly Pro Glu Leu Ile Val Ser Arg His Glu Gln Asn
    50                  55                  60
```

-continued

| | | |
|---|---|---|
| gcg gcg ttt atg gct gct gct atc ggt cgt cta acc ggg aaa cct ggt<br>Ala Ala Phe Met Ala Ala Ala Ile Gly Arg Leu Thr Gly Lys Pro Gly<br>65                          70                       75                       80 | 240 |

```
gcg gcg ttt atg gct gct gct atc ggt cgt cta acc ggg aaa cct ggt    240
Ala Ala Phe Met Ala Ala Ala Ile Gly Arg Leu Thr Gly Lys Pro Gly
 65                  70                  75                  80 gtt gta ctt gta act agt gga cct ggc gca tcg aat ctt gca aca ggg    288
Val Val Leu Val Thr Ser Gly Pro Gly Ala Ser Asn Leu Ala Thr Gly
                 85                  90                  95 ctt gta acc gca act gca gaa gga gat cca gtc gtt gcg att gct ggt    336
Leu Val Thr Ala Thr Ala Glu Gly Asp Pro Val Val Ala Ile Ala Gly
            100                 105                 110 aac gta aca agg caa gac cgc tta aaa aga acc cac caa tca atg gat    384
Asn Val Thr Arg Gln Asp Arg Leu Lys Arg Thr His Gln Ser Met Asp
        115                 120                 125 aat gca gca ctt ttc cgt ccg att aca aaa tac agc gaa gaa gta gtt    432
Asn Ala Ala Leu Phe Arg Pro Ile Thr Lys Tyr Ser Glu Glu Val Val
130                 135                 140 cac gcc gaa agt att cca gaa gca atc act aac gct ttt cgc tcg gca    480
His Ala Glu Ser Ile Pro Glu Ala Ile Thr Asn Ala Phe Arg Ser Ala
145                 150                 155                 160 aca gaa cca aac caa ggc gct gct ttt gtc agt ttg cca caa gat atc    528
Thr Glu Pro Asn Gln Gly Ala Ala Phe Val Ser Leu Pro Gln Asp Ile
                165                 170                 175 gtg aac gaa cca aac gta cca gta aaa gcg att cgc cca ctt gct aaa    576
Val Asn Glu Pro Asn Val Pro Val Lys Ala Ile Arg Pro Leu Ala Lys
            180                 185                 190 cca gaa aat ggt cct gct tcc aaa gaa caa gtt gca aaa ctt gtt aca    624
Pro Glu Asn Gly Pro Ala Ser Lys Glu Gln Val Ala Lys Leu Val Thr
        195                 200                 205 cgt ttg aaa aaa gcg aaa tta ccg gta ttg cta ttg ggt atg cga gca    672
Arg Leu Lys Lys Ala Lys Leu Pro Val Leu Leu Leu Gly Met Arg Ala
210                 215                 220 tct agt cca gaa gta act ggt gca att cgt cgc tta ctc caa aaa aca    720
Ser Ser Pro Glu Val Thr Gly Ala Ile Arg Arg Leu Leu Gln Lys Thr
225                 230                 235                 240 agt atc cca gta gta gaa act ttc caa gca gct ggc gtc att tca cgc    768
Ser Ile Pro Val Val Glu Thr Phe Gln Ala Ala Gly Val Ile Ser Arg
                245                 250                 255 gac tta gaa gat aac ttc ttt gga cgt gtt ggt ctg ttc cgc aac caa    816
Asp Leu Glu Asp Asn Phe Phe Gly Arg Val Gly Leu Phe Arg Asn Gln
            260                 265                 270 cca ggg gat att ttg tta aat aaa gct gat tta gtt att aca gtg ggt    864
Pro Gly Asp Ile Leu Leu Asn Lys Ala Asp Leu Val Ile Thr Val Gly
        275                 280                 285 tat gat cca att gaa tac gat cca aaa gct tgg aat gcc tct ggt gat    912
Tyr Asp Pro Ile Glu Tyr Asp Pro Lys Ala Trp Asn Ala Ser Gly Asp
290                 295                 300 aga acg att gtc cat tta gac gac att cgc gct gat att gat cat tat    960
Arg Thr Ile Val His Leu Asp Asp Ile Arg Ala Asp Ile Asp His Tyr
305                 310                 315                 320 tac caa cca gtg aca gag cta gtc gga aac atc gcg ctt act tta gac   1008
Tyr Gln Pro Val Thr Glu Leu Val Gly Asn Ile Ala Leu Thr Leu Asp
                325                 330                 335 cga gtg aat gcg aaa ttc agc ggt tta gaa tta gcg gaa aaa gaa ctt   1056
Arg Val Asn Ala Lys Phe Ser Gly Leu Glu Leu Ala Glu Lys Glu Leu
            340                 345                 350 gaa aca tta aaa gaa ctt cat gct caa tta gaa gag cga gat gtt ccg   1104
Glu Thr Leu Lys Glu Leu His Ala Gln Leu Glu Glu Arg Asp Val Pro
        355                 360                 365 cca gaa agt gat gaa act aac cga gta cat cca ttg tcg gtc att caa   1152
Pro Glu Ser Asp Glu Thr Asn Arg Val His Pro Leu Ser Val Ile Gln
```

-continued

```
                    370                 375                 380
aca cta cgt tcg gca att gat gac aac gta act gtg aca gtc gac gtt      1200
Thr Leu Arg Ser Ala Ile Asp Asp Asn Val Thr Val Thr Val Asp Val
385                 390                 395                 400 ggt tca cat tat att tgg atg gca cgt cat ttc cgc tcc tat gaa cca      1248
Gly Ser His Tyr Ile Trp Met Ala Arg His Phe Arg Ser Tyr Glu Pro
                405                 410                 415 cgc cgt ctg ctt ttc agt aac ggt atg caa acg ctt ggt gtt gcg ctt      1296
Arg Arg Leu Leu Phe Ser Asn Gly Met Gln Thr Leu Gly Val Ala Leu
            420                 425                 430 cct tgg gga att gct gca aca ctt gta cat ccg ggt gaa aaa gtg gtt      1344
Pro Trp Gly Ile Ala Ala Thr Leu Val His Pro Gly Glu Lys Val Val
        435                 440                 445 tcg att tct ggt gac ggt ggt ttc tta ttt tcc gcg atg gaa tta gaa      1392
Ser Ile Ser Gly Asp Gly Gly Phe Leu Phe Ser Ala Met Glu Leu Glu
    450                 455                 460 aca gct gtc cgc ttg cgt gcg cca ctt gta cac cta gta tgg aat gac      1440
Thr Ala Val Arg Leu Arg Ala Pro Leu Val His Leu Val Trp Asn Asp
465                 470                 475                 480 gga agc tat gac atg gtt gct ttc caa caa aaa atg aaa tac ggc aaa      1488
Gly Ser Tyr Asp Met Val Ala Phe Gln Gln Lys Met Lys Tyr Gly Lys
                485                 490                 495 gaa gca gct gtt cgt ttt ggc gat gtt gat atc gta aaa ttt gca gaa      1536
Glu Ala Ala Val Arg Phe Gly Asp Val Asp Ile Val Lys Phe Ala Glu
            500                 505                 510 agt ttc gga gca aaa ggt ctt cgc gta aca aat cca gca gaa ctt tct      1584
Ser Phe Gly Ala Lys Gly Leu Arg Val Thr Asn Pro Ala Glu Leu Ser
        515                 520                 525 gat gtg tta aaa gaa gcg ctt gaa aca gaa gga ccc gtc gtt gta gat      1632
Asp Val Leu Lys Glu Ala Leu Glu Thr Glu Gly Pro Val Val Val Asp
    530                 535                 540 att cca att gat tac cgt gat aac atc aaa ctt ggc gaa act tta cta      1680
Ile Pro Ile Asp Tyr Arg Asp Asn Ile Lys Leu Gly Glu Thr Leu Leu
545                 550                 555                 560 cct gac caa ttt tat taa                                              1698
Pro Asp Gln Phe Tyr
                565
```

<210> SEQ ID NO 10
<211> LENGTH: 565
<212> TYPE: PRT
<213> ORGANISM: Listeria monocytogenes

<400> SEQUENCE: 10

```
Met Ala Lys Leu Glu Lys Asp Gln Glu Lys Val Ile Thr Gln Gly Lys
1               5                   10                  15

Ser Gly Ala Asp Leu Val Val Asp Ser Leu Ile Asn Gln Gly Val Thr
            20                  25                  30

His Val Phe Gly Ile Pro Gly Ala Lys Ile Asp Lys Val Phe Asp Val
        35                  40                  45

Met Glu Glu Arg Gly Pro Glu Leu Ile Val Ser Arg His Glu Gln Asn
    50                  55                  60

Ala Ala Phe Met Ala Ala Ala Ile Gly Arg Leu Thr Gly Lys Pro Gly
65                  70                  75                  80

Val Val Leu Val Thr Ser Gly Pro Gly Ala Ser Asn Leu Ala Thr Gly
            85                  90                  95

Leu Val Thr Ala Thr Ala Glu Gly Asp Pro Val Val Ala Ile Ala Gly
            100                 105                 110
```

```
Asn Val Thr Arg Gln Asp Arg Leu Lys Arg Thr His Gln Ser Met Asp
            115                 120                 125
Asn Ala Ala Leu Phe Arg Pro Ile Thr Lys Tyr Ser Glu Glu Val Val
130                 135                 140
His Ala Glu Ser Ile Pro Glu Ala Ile Thr Asn Ala Phe Arg Ser Ala
145                 150                 155                 160
Thr Glu Pro Asn Gln Gly Ala Ala Phe Val Ser Leu Pro Gln Asp Ile
                165                 170                 175
Val Asn Glu Pro Asn Val Pro Val Lys Ala Ile Arg Pro Leu Ala Lys
            180                 185                 190
Pro Glu Asn Gly Pro Ala Ser Lys Glu Gln Val Ala Lys Leu Val Thr
            195                 200                 205
Arg Leu Lys Lys Ala Lys Leu Pro Val Leu Leu Gly Met Arg Ala
210                 215                 220
Ser Ser Pro Glu Val Thr Gly Ala Ile Arg Arg Leu Leu Gln Lys Thr
225                 230                 235                 240
Ser Ile Pro Val Val Glu Thr Phe Gln Ala Ala Gly Val Ile Ser Arg
                245                 250                 255
Asp Leu Glu Asp Asn Phe Phe Gly Arg Val Gly Leu Phe Arg Asn Gln
                260                 265                 270
Pro Gly Asp Ile Leu Leu Asn Lys Ala Asp Leu Val Ile Thr Val Gly
            275                 280                 285
Tyr Asp Pro Ile Glu Tyr Asp Pro Lys Ala Trp Asn Ala Ser Gly Asp
            290                 295                 300
Arg Thr Ile Val His Leu Asp Asp Ile Arg Ala Asp Ile Asp His Tyr
305                 310                 315                 320
Tyr Gln Pro Val Thr Glu Leu Val Gly Asn Ile Ala Leu Thr Leu Asp
                325                 330                 335
Arg Val Asn Ala Lys Phe Ser Gly Leu Glu Leu Ala Glu Lys Glu Leu
            340                 345                 350
Glu Thr Leu Lys Glu Leu His Ala Gln Leu Glu Arg Asp Val Pro
            355                 360                 365
Pro Glu Ser Asp Glu Thr Asn Arg Val His Pro Leu Ser Val Ile Gln
370                 375                 380
Thr Leu Arg Ser Ala Ile Asp Asp Asn Val Thr Val Thr Val Asp Val
385                 390                 395                 400
Gly Ser His Tyr Ile Trp Met Ala Arg His Phe Arg Ser Tyr Glu Pro
                405                 410                 415
Arg Arg Leu Leu Phe Ser Asn Gly Met Gln Thr Leu Gly Val Ala Leu
            420                 425                 430
Pro Trp Gly Ile Ala Ala Thr Leu Val His Pro Gly Glu Lys Val Val
            435                 440                 445
Ser Ile Ser Gly Asp Gly Gly Phe Leu Phe Ser Ala Met Glu Leu Glu
450                 455                 460
Thr Ala Val Arg Leu Arg Ala Pro Leu Val His Leu Val Trp Asn Asp
465                 470                 475                 480
Gly Ser Tyr Asp Met Val Ala Phe Gln Gln Lys Met Lys Tyr Gly Lys
                485                 490                 495
Glu Ala Ala Val Arg Phe Gly Asp Val Asp Ile Val Lys Phe Ala Glu
            500                 505                 510
Ser Phe Gly Ala Lys Gly Leu Arg Val Thr Asn Pro Ala Glu Leu Ser
            515                 520                 525
Asp Val Leu Lys Glu Ala Leu Glu Thr Glu Gly Pro Val Val Val Asp
```

```
                530                 535                 540
Ile Pro Ile Asp Tyr Arg Asp Asn Ile Lys Leu Gly Glu Thr Leu Leu
545                 550                 555                 560

Pro Asp Gln Phe Tyr
                565

<210> SEQ ID NO 11
<211> LENGTH: 1680
<212> TYPE: DNA
<213> ORGANISM: Streptococcus mutans
<220> FEATURE:
<221> NAME/KEY: CDS
<222> LOCATION: (1)..(1680)

<400> SEQUENCE: 11 atg acc gaa ata aat aag gaa ggc tat ggg gct gac ctg att gta gac      48
Met Thr Glu Ile Asn Lys Glu Gly Tyr Gly Ala Asp Leu Ile Val Asp
1               5                   10                  15 agc ctc att aat cat gat gtc aac tat gtt ttt gga atc cct ggt gca      96
Ser Leu Ile Asn His Asp Val Asn Tyr Val Phe Gly Ile Pro Gly Ala
                20                  25                  30 aaa att gat cgt gtc ttt gat acc tta gaa gat aag ggg cca gaa ctt     144
Lys Ile Asp Arg Val Phe Asp Thr Leu Glu Asp Lys Gly Pro Glu Leu
            35                  40                  45 att gta gca cgc cat gag caa aat gct gct ttt atg gct caa gga att     192
Ile Val Ala Arg His Glu Gln Asn Ala Ala Phe Met Ala Gln Gly Ile
        50                  55                  60 ggc cgt att act ggt gag cct ggt gtt gtg att aca acc agc ggt ccc     240
Gly Arg Ile Thr Gly Glu Pro Gly Val Val Ile Thr Thr Ser Gly Pro
65                  70                  75                  80 ggt gtt tcc aat ctg gtg act ggt ctt gtt act gcg aca gct gag gga     288
Gly Val Ser Asn Leu Val Thr Gly Leu Val Thr Ala Thr Ala Glu Gly
                85                  90                  95 gat cct gtc ctt gct att ggt ggt cag gtt aaa cgt gct gat ttg ctc     336
Asp Pro Val Leu Ala Ile Gly Gly Gln Val Lys Arg Ala Asp Leu Leu
            100                 105                 110 aaa cgg gct cac cag tca atg aat aat gtt gct atg ctc gat ccc att     384
Lys Arg Ala His Gln Ser Met Asn Asn Val Ala Met Leu Asp Pro Ile
        115                 120                 125 acc aaa tat tca gca gaa att cag gat ccc gca aca ctt tca gaa aat     432
Thr Lys Tyr Ser Ala Glu Ile Gln Asp Pro Ala Thr Leu Ser Glu Asn
    130                 135                 140 att gct aat gcc tat cgt ttg gct aaa gca gga aag ccg gga gct agt     480
Ile Ala Asn Ala Tyr Arg Leu Ala Lys Ala Gly Lys Pro Gly Ala Ser
145                 150                 155                 160 ttc tta tct att cct caa gat ata act gat agt cct gtt act gtc aag     528
Phe Leu Ser Ile Pro Gln Asp Ile Thr Asp Ser Pro Val Thr Val Lys
                165                 170                 175 gcg att aag ccc ttg aca gat cct aaa cta ggt tca gcg tca gtt gct     576
Ala Ile Lys Pro Leu Thr Asp Pro Lys Leu Gly Ser Ala Ser Val Ala
            180                 185                 190 gat att aat tat ttg gca cag gcc ata aaa aat gcg gtc ctt cct gtc     624
Asp Ile Asn Tyr Leu Ala Gln Ala Ile Lys Asn Ala Val Leu Pro Val
        195                 200                 205 tta ctt tta gga aat ggt gcg tca acg gct gca gtt aca gct tct att     672
Leu Leu Leu Gly Asn Gly Ala Ser Thr Ala Ala Val Thr Ala Ser Ile
    210                 215                 220 cgc cgt ttg tta gga gct gtc aag ctg cca gtc gtt gaa act ttc caa     720
Arg Arg Leu Leu Gly Ala Val Lys Leu Pro Val Val Glu Thr Phe Gln
225                 230                 235                 240
```

```
gga gct ggt att gtt tca aga gat tta gaa gag gac act ttt ttt ggt       768
Gly Ala Gly Ile Val Ser Arg Asp Leu Glu Glu Asp Thr Phe Phe Gly
                245                 250                 255 cgt gtg ggg ctt ttt cgt aat cag ccc gga gat atg ttg ctg aag cgt       816
Arg Val Gly Leu Phe Arg Asn Gln Pro Gly Asp Met Leu Leu Lys Arg
                260                 265                 270 tct gac tta gtt atc gct att ggc tat gat cct att gaa tat gaa gcg       864
Ser Asp Leu Val Ile Ala Ile Gly Tyr Asp Pro Ile Glu Tyr Glu Ala
                275                 280                 285 cgc aat tgg aat gct gaa att tcg gct cgc att atc gtt att gat gtt       912
Arg Asn Trp Asn Ala Glu Ile Ser Ala Arg Ile Ile Val Ile Asp Val
                290                 295                 300 gct cca gct gaa att gat act tat ttc caa cct gaa cgt gaa tta att       960
Ala Pro Ala Glu Ile Asp Thr Tyr Phe Gln Pro Glu Arg Glu Leu Ile
305                 310                 315                 320 ggt gat ata gct gaa aca ctt gat tta ctc cta cct gct att agt ggc      1008
Gly Asp Ile Ala Glu Thr Leu Asp Leu Leu Leu Pro Ala Ile Ser Gly
                325                 330                 335 tac tca ctt cca aaa ggt tct ctt gac tat ctc aaa ggc ctt cgt gat      1056
Tyr Ser Leu Pro Lys Gly Ser Leu Asp Tyr Leu Lys Gly Leu Arg Asp
                340                 345                 350 aat gta gta gaa gat gtc aaa ttt gat aag aca gtc aaa tcc ggt ctg      1104
Asn Val Val Glu Asp Val Lys Phe Asp Lys Thr Val Lys Ser Gly Leu
                355                 360                 365 gtt cat ccg ctt gat gtg att gat gtc ctt caa aag caa acg act gat      1152
Val His Pro Leu Asp Val Ile Asp Val Leu Gln Lys Gln Thr Thr Asp
                370                 375                 380 gat atg aca gta acg gtt gat gtt ggc agc cat tat att tgg atg gct      1200
Asp Met Thr Val Thr Val Asp Val Gly Ser His Tyr Ile Trp Met Ala
385                 390                 395                 400 cgt tat ttt aaa agc tat gaa gca cgg cac tta ctt ttc tca aat ggt      1248
Arg Tyr Phe Lys Ser Tyr Glu Ala Arg His Leu Leu Phe Ser Asn Gly
                405                 410                 415 atg caa acc tta ggt gtt gct ttg cct tgg gca att tcg gca gct ctt      1296
Met Gln Thr Leu Gly Val Ala Leu Pro Trp Ala Ile Ser Ala Ala Leu
                420                 425                 430 gta cgg cca aat gag aag att att tct att tca ggt gat ggt ggt ttc      1344
Val Arg Pro Asn Glu Lys Ile Ile Ser Ile Ser Gly Asp Gly Gly Phe
                435                 440                 445 ctc ttt tct ggc caa gaa ttg gaa aca gct gtt cgt tta cat tta cca      1392
Leu Phe Ser Gly Gln Glu Leu Glu Thr Ala Val Arg Leu His Leu Pro
450                 455                 460 att gtt cat atc att tgg aat gat ggt aaa tat aat atg gtt gaa ttc      1440
Ile Val His Ile Ile Trp Asn Asp Gly Lys Tyr Asn Met Val Glu Phe
465                 470                 475                 480 caa gaa gaa atg aaa tac ggc cgt tca gca ggt gtt gat ttt ggt cct      1488
Gln Glu Glu Met Lys Tyr Gly Arg Ser Ala Gly Val Asp Phe Gly Pro
                485                 490                 495 gtt gat ttt gtc aag tat gct gat agt ttc ggt gct aaa ggt tac cgt      1536
Val Asp Phe Val Lys Tyr Ala Asp Ser Phe Gly Ala Lys Gly Tyr Arg
                500                 505                 510 gct gat agt aaa gaa aag ttt gat caa gtt ctt caa aca gca ctc aag      1584
Ala Asp Ser Lys Glu Lys Phe Asp Gln Val Leu Gln Thr Ala Leu Lys
                515                 520                 525 gaa gct gca aat ggc cca gtt ctc att gat gtt cca atg gac tat aaa      1632
Glu Ala Ala Asn Gly Pro Val Leu Ile Asp Val Pro Met Asp Tyr Lys
530                 535                 540 gat aat gta aaa ttg ggt gaa act att ttg cct gat gaa ttc tac taa      1680
Asp Asn Val Lys Leu Gly Glu Thr Ile Leu Pro Asp Glu Phe Tyr
545                 550                 555
```

<210> SEQ ID NO 12
<211> LENGTH: 559
<212> TYPE: PRT
<213> ORGANISM: Streptococcus mutans

<400> SEQUENCE: 12

| | | | | | | | | | | | | | | |
|---|---|---|---|---|---|---|---|---|---|---|---|---|---|---|
| Met | Thr | Glu | Ile | Asn | Lys | Glu | Gly | Tyr | Gly | Ala | Asp | Leu | Ile | Val | Asp |
| 1 | | | | 5 | | | | | 10 | | | | | 15 | |
| Ser | Leu | Ile | Asn | His | Asp | Val | Asn | Tyr | Val | Phe | Gly | Ile | Pro | Gly | Ala |
| | | | 20 | | | | | 25 | | | | | 30 | | |
| Lys | Ile | Asp | Arg | Val | Phe | Asp | Thr | Leu | Glu | Asp | Lys | Gly | Pro | Glu | Leu |
| | | 35 | | | | | 40 | | | | | 45 | | | |
| Ile | Val | Ala | Arg | His | Glu | Gln | Asn | Ala | Ala | Phe | Met | Ala | Gln | Gly | Ile |
| | 50 | | | | | 55 | | | | | 60 | | | | |
| Gly | Arg | Ile | Thr | Gly | Glu | Pro | Gly | Val | Val | Ile | Thr | Thr | Ser | Gly | Pro |
| 65 | | | | | 70 | | | | | 75 | | | | | 80 |
| Gly | Val | Ser | Asn | Leu | Val | Thr | Gly | Leu | Val | Thr | Ala | Thr | Ala | Glu | Gly |
| | | | | 85 | | | | | 90 | | | | | 95 | |
| Asp | Pro | Val | Leu | Ala | Ile | Gly | Gly | Gln | Val | Lys | Arg | Ala | Asp | Leu | Leu |
| | | | 100 | | | | | 105 | | | | | 110 | | |
| Lys | Arg | Ala | His | Gln | Ser | Met | Asn | Asn | Val | Ala | Met | Leu | Asp | Pro | Ile |
| | | 115 | | | | | 120 | | | | | 125 | | | |
| Thr | Lys | Tyr | Ser | Ala | Glu | Ile | Gln | Asp | Pro | Ala | Thr | Leu | Ser | Glu | Asn |
| | 130 | | | | | 135 | | | | | 140 | | | | |
| Ile | Ala | Asn | Ala | Tyr | Arg | Leu | Ala | Lys | Ala | Gly | Lys | Pro | Gly | Ala | Ser |
| 145 | | | | | 150 | | | | | 155 | | | | | 160 |
| Phe | Leu | Ser | Ile | Pro | Gln | Asp | Ile | Thr | Asp | Ser | Pro | Val | Thr | Val | Lys |
| | | | | 165 | | | | | 170 | | | | | 175 | |
| Ala | Ile | Lys | Pro | Leu | Thr | Asp | Pro | Lys | Leu | Gly | Ser | Ala | Ser | Val | Ala |
| | | | 180 | | | | | 185 | | | | | 190 | | |
| Asp | Ile | Asn | Tyr | Leu | Ala | Gln | Ala | Ile | Lys | Asn | Ala | Val | Leu | Pro | Val |
| | | 195 | | | | | 200 | | | | | 205 | | | |
| Leu | Leu | Leu | Gly | Asn | Gly | Ala | Ser | Thr | Ala | Ala | Val | Thr | Ala | Ser | Ile |
| | 210 | | | | | 215 | | | | | 220 | | | | |
| Arg | Arg | Leu | Leu | Gly | Ala | Val | Lys | Leu | Pro | Val | Val | Glu | Thr | Phe | Gln |
| 225 | | | | | 230 | | | | | 235 | | | | | 240 |
| Gly | Ala | Gly | Ile | Val | Ser | Arg | Asp | Leu | Glu | Glu | Asp | Thr | Phe | Phe | Gly |
| | | | | 245 | | | | | 250 | | | | | 255 | |
| Arg | Val | Gly | Leu | Phe | Arg | Asn | Gln | Pro | Gly | Asp | Met | Leu | Leu | Lys | Arg |
| | | | 260 | | | | | 265 | | | | | 270 | | |
| Ser | Asp | Leu | Val | Ile | Ala | Ile | Gly | Tyr | Asp | Pro | Ile | Glu | Tyr | Glu | Ala |
| | | 275 | | | | | 280 | | | | | 285 | | | |
| Arg | Asn | Trp | Asn | Ala | Glu | Ile | Ser | Ala | Arg | Ile | Ile | Val | Ile | Asp | Val |
| | 290 | | | | | 295 | | | | | 300 | | | | |
| Ala | Pro | Ala | Glu | Ile | Asp | Thr | Tyr | Phe | Gln | Pro | Glu | Arg | Glu | Leu | Ile |
| 305 | | | | | 310 | | | | | 315 | | | | | 320 |
| Gly | Asp | Ile | Ala | Glu | Thr | Leu | Asp | Leu | Leu | Pro | Ala | Ile | Ser | Gly | |
| | | | | 325 | | | | | 330 | | | | | 335 | |
| Tyr | Ser | Leu | Pro | Lys | Gly | Ser | Leu | Asp | Tyr | Leu | Lys | Gly | Leu | Arg | Asp |
| | | | 340 | | | | | 345 | | | | | 350 | | |
| Asn | Val | Val | Glu | Asp | Val | Lys | Phe | Asp | Lys | Thr | Val | Lys | Ser | Gly | Leu |
| | | 355 | | | | | 360 | | | | | 365 | | | |
| Val | His | Pro | Leu | Asp | Val | Ile | Asp | Val | Leu | Gln | Lys | Gln | Thr | Thr | Asp |

```
                370             375             380
Asp Met Thr Val Thr Val Asp Val Gly Ser His Tyr Ile Trp Met Ala
385                 390                 395                 400

Arg Tyr Phe Lys Ser Tyr Glu Ala Arg His Leu Leu Phe Ser Asn Gly
                405                 410                 415

Met Gln Thr Leu Gly Val Ala Leu Pro Trp Ala Ile Ser Ala Ala Leu
            420                 425                 430

Val Arg Pro Asn Glu Lys Ile Ile Ser Ile Ser Gly Asp Gly Gly Phe
                435                 440                 445

Leu Phe Ser Gly Gln Glu Leu Glu Thr Ala Val Arg Leu His Leu Pro
        450                 455                 460

Ile Val His Ile Ile Trp Asn Asp Gly Lys Tyr Asn Met Val Glu Phe
465                 470                 475                 480

Gln Glu Glu Met Lys Tyr Gly Arg Ser Ala Gly Val Asp Phe Gly Pro
                485                 490                 495

Val Asp Phe Val Lys Tyr Ala Asp Ser Phe Gly Ala Lys Gly Tyr Arg
            500                 505                 510

Ala Asp Ser Lys Glu Lys Phe Asp Gln Val Leu Gln Thr Ala Leu Lys
        515                 520                 525

Glu Ala Ala Asn Gly Pro Val Leu Ile Asp Val Pro Met Asp Tyr Lys
    530                 535                 540

Asp Asn Val Lys Leu Gly Glu Thr Ile Leu Pro Asp Glu Phe Tyr
545                 550                 555

<210> SEQ ID NO 13
<211> LENGTH: 1683
<212> TYPE: DNA
<213> ORGANISM: Streptococcus thermophilus
<220> FEATURE:
<221> NAME/KEY: CDS
<222> LOCATION: (1)..(1683)

<400> SEQUENCE: 13 gtg ttc atg tca gaa gaa aag caa ttg tat ggt gca gat tta gtg gtt        48
Val Phe Met Ser Glu Glu Lys Gln Leu Tyr Gly Ala Asp Leu Val Val
1               5                   10                  15 gat agt ttg atc aac cat gat gtt gag tat gtc ttt ggg att cca ggc        96
Asp Ser Leu Ile Asn His Asp Val Glu Tyr Val Phe Gly Ile Pro Gly
            20                  25                  30 gca aaa atc gat agg gtt ttt gat acc ttg gaa gat aag gga cct gaa       144
Ala Lys Ile Asp Arg Val Phe Asp Thr Leu Glu Asp Lys Gly Pro Glu
        35                  40                  45 ttg att gtt gcc cgt cat gag caa aat gct gct ttt atg gct caa ggt       192
Leu Ile Val Ala Arg His Glu Gln Asn Ala Ala Phe Met Ala Gln Gly
    50                  55                  60 gtt gga cgt att act ggg aaa cca ggt gta gta ttg gta aca tct ggt       240
Val Gly Arg Ile Thr Gly Lys Pro Gly Val Val Leu Val Thr Ser Gly
65                  70                  75                  80 cca ggt gtc tcc aat ttg gct act ggt ttg gta aca gcg acg gat gaa       288
Pro Gly Val Ser Asn Leu Ala Thr Gly Leu Val Thr Ala Thr Asp Glu
                85                  90                  95 gga gac cct gtt ctt gct att ggt ggt cag gtt aag cgt gca gat ctc       336
Gly Asp Pro Val Leu Ala Ile Gly Gly Gln Val Lys Arg Ala Asp Leu
            100                 105                 110 ttg aaa cgt gcc cac caa tca atg aat aac gtt gct atg ctt gag cca       384
Leu Lys Arg Ala His Gln Ser Met Asn Asn Val Ala Met Leu Glu Pro
        115                 120                 125 att acc aaa tat gct gct gaa gta cat gat gct aac acc ctt tct gaa       432
Ile Thr Lys Tyr Ala Ala Glu Val His Asp Ala Asn Thr Leu Ser Glu
```

```
Ile Thr Lys Tyr Ala Ala Glu Val His Asp Ala Asn Thr Leu Ser Glu
    130                 135                 140 acg gtt gct aat gcc tat cgt cac gct aag tca ggg aaa cca ggt gca      480
Thr Val Ala Asn Ala Tyr Arg His Ala Lys Ser Gly Lys Pro Gly Ala
145                 150                 155                 160 agc ttc att tca att cct caa gac gtg acg gat gct ccg gtc agt gtt      528
Ser Phe Ile Ser Ile Pro Gln Asp Val Thr Asp Ala Pro Val Ser Val
                165                 170                 175 aag gct att aag cct atg aca gat cca aaa ctt ggt tca gca tct gtt      576
Lys Ala Ile Lys Pro Met Thr Asp Pro Lys Leu Gly Ser Ala Ser Val
            180                 185                 190 tct gat att aac tat cta gca caa gcc att aaa aat gca gtg ttg cca      624
Ser Asp Ile Asn Tyr Leu Ala Gln Ala Ile Lys Asn Ala Val Leu Pro
        195                 200                 205 gtc ttt ctt ttg ggg aat ggt gcc tca tca gaa gcc gta act tac tct      672
Val Phe Leu Leu Gly Asn Gly Ala Ser Ser Glu Ala Val Thr Tyr Ser
    210                 215                 220 att cgc caa att ttg aag cat gtt aaa ttg cca gtt gtt gaa act ttc      720
Ile Arg Gln Ile Leu Lys His Val Lys Leu Pro Val Val Glu Thr Phe
225                 230                 235                 240 caa ggt gcc ggt atc gtg tca cgt gac ctt gaa gaa gat act ttc ttt      768
Gln Gly Ala Gly Ile Val Ser Arg Asp Leu Glu Glu Asp Thr Phe Phe
                245                 250                 255 ggt cgt gta ggt ctt ttc cgt aac caa ccc gga gac atg ttg ctt aaa      816
Gly Arg Val Gly Leu Phe Arg Asn Gln Pro Gly Asp Met Leu Leu Lys
            260                 265                 270 aaa tcc gac tta gtt att gcc att ggt tat gat cca atc gaa tat gaa      864
Lys Ser Asp Leu Val Ile Ala Ile Gly Tyr Asp Pro Ile Glu Tyr Glu
        275                 280                 285 gca cgt aac tgg aat gct gaa att tca gca cgt atc atc gtt att gat      912
Ala Arg Asn Trp Asn Ala Glu Ile Ser Ala Arg Ile Ile Val Ile Asp
    290                 295                 300 gtc gag ccg gcc gag gtg gac act tac ttc caa ccg gaa cgt gaa ttg      960
Val Glu Pro Ala Glu Val Asp Thr Tyr Phe Gln Pro Glu Arg Glu Leu
305                 310                 315                 320 att ggt aat gta gaa gcg agc tta gac ttg ctt ttg ccc gct att caa     1008
Ile Gly Asn Val Glu Ala Ser Leu Asp Leu Leu Leu Pro Ala Ile Gln
                325                 330                 335 ggt tat aaa ttg cct gaa ggt gcg gtt gaa tat ctt aaa ggt ttg aaa     1056
Gly Tyr Lys Leu Pro Glu Gly Ala Val Glu Tyr Leu Lys Gly Leu Lys
            340                 345                 350 aac aat gtt gtt gag gat gtt aag ttt gac cgt cag cct gat gaa ggt     1104
Asn Asn Val Val Glu Asp Val Lys Phe Asp Arg Gln Pro Asp Glu Gly
        355                 360                 365 acg gtg cat ccg cta gat ttc atc gaa aat ttg caa gaa cac aca gat     1152
Thr Val His Pro Leu Asp Phe Ile Glu Asn Leu Gln Glu His Thr Asp
    370                 375                 380 gat gat atg act gtt acg ttt gat gtt ggt agt cac tat att tgg atg     1200
Asp Asp Met Thr Val Thr Phe Asp Val Gly Ser His Tyr Ile Trp Met
385                 390                 395                 400 gca cgt tat ctc aaa tcg tat gaa cca cgt cat ttg ctt ttc tca aat     1248
Ala Arg Tyr Leu Lys Ser Tyr Glu Pro Arg His Leu Leu Phe Ser Asn
                405                 410                 415 ggg atg caa acg ata ggt att gct att aca tgg gct atc tct gca gca     1296
Gly Met Gln Thr Ile Gly Ile Ala Ile Thr Trp Ala Ile Ser Ala Ala
            420                 425                 430 ttg gtt cgt cct aag aca aaa gtg att tct gta tct ggt gat ggt ggt     1344
Leu Val Arg Pro Lys Thr Lys Val Ile Ser Val Ser Gly Asp Gly Gly
        435                 440                 445
```

| | | | | | | | | | | | | | | | |
|---|---|---|---|---|---|---|---|---|---|---|---|---|---|---|---|
| ttc | ctc | ttc | tca | gca | caa | gaa | ttg | gaa | aca | gca | gtt | cgt | ttg | aaa | ttg |
| Phe | Leu | Phe | Ser | Ala | Gln | Glu | Leu | Glu | Thr | Ala | Val | Arg | Leu | Lys | Leu |
| | 450 | | | | 455 | | | | 460 | | | | | | |

1392

| | | | | | | | | | | | | | | | |
|---|---|---|---|---|---|---|---|---|---|---|---|---|---|---|---|
| cca | att | gtc | cat | att | atc | tgg | aac | gat | ggt | cat | tac | aat | atg | gtg | gaa |
| Pro | Ile | Val | His | Ile | Ile | Trp | Asn | Asp | Gly | His | Tyr | Asn | Met | Val | Glu |
| 465 | | | | 470 | | | | | 475 | | | | | 480 | |

1440

| | | | | | | | | | | | | | | | |
|---|---|---|---|---|---|---|---|---|---|---|---|---|---|---|---|
| ttc | cag | gaa | gaa | atg | aag | tac | ggt | cgt | tca | tct | ggg | gtt | gac | ttt | ggt |
| Phe | Gln | Glu | Glu | Met | Lys | Tyr | Gly | Arg | Ser | Ser | Gly | Val | Asp | Phe | Gly |
| | | | | 485 | | | | | 490 | | | | | 495 | |

1488

| | | | | | | | | | | | | | | | |
|---|---|---|---|---|---|---|---|---|---|---|---|---|---|---|---|
| cct | gta | gat | ttt | gta | aaa | tat | gct | gag | agc | ttt | gga | gcc | aaa | ggt | tat |
| Pro | Val | Asp | Phe | Val | Lys | Tyr | Ala | Glu | Ser | Phe | Gly | Ala | Lys | Gly | Tyr |
| | | | 500 | | | | | 505 | | | | | 510 | | |

1536

| | | | | | | | | | | | | | | | |
|---|---|---|---|---|---|---|---|---|---|---|---|---|---|---|---|
| cgt | gca | aca | agt | aaa | gca | gcg | ttt | gct | agc | ttg | ctt | caa | gag | gct | ttg |
| Arg | Ala | Thr | Ser | Lys | Ala | Ala | Phe | Ala | Ser | Leu | Leu | Gln | Glu | Ala | Leu |
| | | | 515 | | | | | 520 | | | | | 525 | | |

1584

| | | | | | | | | | | | | | | | |
|---|---|---|---|---|---|---|---|---|---|---|---|---|---|---|---|
| act | cag | gct | gta | gat | gga | cca | gtc | ctt | att | gat | gtt | cca | att | gac | tat |
| Thr | Gln | Ala | Val | Asp | Gly | Pro | Val | Leu | Ile | Asp | Val | Pro | Ile | Asp | Tyr |
| | 530 | | | | | 535 | | | | | 540 | | | | |

1632

| | | | | | | | | | | | | | | | |
|---|---|---|---|---|---|---|---|---|---|---|---|---|---|---|---|
| aaa | gat | aac | att | aaa | ctc | ggc | gaa | act | att | ttg | cca | gat | gaa | ttt | tac |
| Lys | Asp | Asn | Ile | Lys | Leu | Gly | Glu | Thr | Ile | Leu | Pro | Asp | Glu | Phe | Tyr |
| 545 | | | | 550 | | | | | 555 | | | | | 560 | |

1680 taa        1683

<210> SEQ ID NO 14
<211> LENGTH: 560
<212> TYPE: PRT
<213> ORGANISM: Streptococcus thermophilus

<400> SEQUENCE: 14

Val Phe Met Ser Glu Glu Lys Gln Leu Tyr Gly Ala Asp Leu Val Val
1               5                   10                  15

Asp Ser Leu Ile Asn His Asp Val Glu Tyr Val Phe Gly Ile Pro Gly
                20                  25                  30

Ala Lys Ile Asp Arg Val Phe Asp Thr Leu Glu Asp Lys Gly Pro Glu
            35                  40                  45

Leu Ile Val Ala Arg His Glu Gln Asn Ala Ala Phe Met Ala Gln Gly
        50                  55                  60

Val Gly Arg Ile Thr Gly Lys Pro Gly Val Val Leu Val Thr Ser Gly
65                  70                  75                  80

Pro Gly Val Ser Asn Leu Ala Thr Gly Leu Val Thr Ala Thr Asp Glu
                85                  90                  95

Gly Asp Pro Val Leu Ala Ile Gly Gly Gln Val Lys Arg Ala Asp Leu
            100                 105                 110

Leu Lys Arg Ala His Gln Ser Met Asn Asn Val Ala Met Leu Glu Pro
        115                 120                 125

Ile Thr Lys Tyr Ala Ala Glu Val His Asp Ala Asn Thr Leu Ser Glu
    130                 135                 140

Thr Val Ala Asn Ala Tyr Arg His Ala Lys Ser Gly Lys Pro Gly Ala
145                 150                 155                 160

Ser Phe Ile Ser Ile Pro Gln Asp Val Thr Asp Ala Pro Val Ser Val
                165                 170                 175

Lys Ala Ile Lys Pro Met Thr Asp Pro Lys Leu Gly Ser Ala Ser Val
            180                 185                 190

Ser Asp Ile Asn Tyr Leu Ala Gln Ala Ile Lys Asn Ala Val Leu Pro
        195                 200                 205

Val Phe Leu Leu Gly Asn Gly Ala Ser Ser Glu Ala Val Thr Tyr Ser
    210                 215                 220

```
Ile Arg Gln Ile Leu Lys His Val Lys Leu Pro Val Glu Thr Phe
225                 230                 235                 240

Gln Gly Ala Gly Ile Val Ser Arg Asp Leu Glu Asp Thr Phe Phe
            245                 250                 255

Gly Arg Val Gly Leu Phe Arg Asn Gln Pro Gly Asp Met Leu Lys
        260                 265                 270

Lys Ser Asp Leu Val Ile Ala Ile Gly Tyr Asp Pro Ile Glu Tyr Glu
        275                 280                 285

Ala Arg Asn Trp Asn Ala Glu Ile Ser Ala Arg Ile Ile Val Ile Asp
        290                 295                 300

Val Glu Pro Ala Glu Val Asp Thr Tyr Phe Gln Pro Glu Arg Glu Leu
305                 310                 315                 320

Ile Gly Asn Val Glu Ala Ser Leu Asp Leu Leu Pro Ala Ile Gln
            325                 330                 335

Gly Tyr Lys Leu Pro Glu Gly Ala Val Glu Tyr Leu Lys Gly Leu Lys
            340                 345                 350

Asn Asn Val Val Glu Asp Val Lys Phe Asp Arg Gln Pro Asp Glu Gly
            355                 360                 365

Thr Val His Pro Leu Asp Phe Ile Glu Asn Leu Gln Glu His Thr Asp
        370                 375                 380

Asp Asp Met Thr Val Thr Phe Asp Val Gly Ser His Tyr Ile Trp Met
385                 390                 395                 400

Ala Arg Tyr Leu Lys Ser Tyr Glu Pro Arg His Leu Leu Phe Ser Asn
            405                 410                 415

Gly Met Gln Thr Ile Gly Ile Ala Ile Thr Trp Ala Ile Ser Ala Ala
            420                 425                 430

Leu Val Arg Pro Lys Thr Lys Val Ile Ser Val Ser Gly Asp Gly Gly
            435                 440                 445

Phe Leu Phe Ser Ala Gln Glu Leu Glu Thr Ala Val Arg Leu Lys Leu
            450                 455                 460

Pro Ile Val His Ile Ile Trp Asn Asp Gly His Tyr Asn Met Val Glu
465                 470                 475                 480

Phe Gln Glu Glu Met Lys Tyr Gly Arg Ser Ser Gly Val Asp Phe Gly
                485                 490                 495

Pro Val Asp Phe Val Lys Tyr Ala Glu Ser Phe Gly Ala Lys Gly Tyr
            500                 505                 510

Arg Ala Thr Ser Lys Ala Ala Phe Ala Ser Leu Leu Gln Glu Ala Leu
            515                 520                 525

Thr Gln Ala Val Asp Gly Pro Val Leu Ile Asp Val Pro Ile Asp Tyr
        530                 535                 540

Lys Asp Asn Ile Lys Leu Gly Glu Thr Ile Leu Pro Asp Glu Phe Tyr
545                 550                 555                 560

<210> SEQ ID NO 15
<211> LENGTH: 1665
<212> TYPE: DNA
<213> ORGANISM: Vibrio angustum
<220> FEATURE:
<221> NAME/KEY: CDS
<222> LOCATION: (1)..(1665)

<400> SEQUENCE: 15 atg tcg gat aaa acc gtc tct ggt gct gaa ctg gtt gtt gaa act tta        48
Met Ser Asp Lys Thr Val Ser Gly Ala Glu Leu Val Val Glu Thr Leu
1               5                   10                  15
```

| | | | | | | | | | | | | | | | | |
|---|---|---|---|---|---|---|---|---|---|---|---|---|---|---|---|---|
| aat | gca | cat | aac | gtt | cca | cac | att | ttt | ggt | att | cct | gga | gca | aag | gtg | 96 |
| Asn | Ala | His | Asn | Val | Pro | His | Ile | Phe | Gly | Ile | Pro | Gly | Ala | Lys | Val | |
| | | | 20 | | | | 25 | | | | 30 | | | | | |
| gat | gct | gtt | ttc | gat | gct | gtt | tgt | gat | aac | gga | cca | gaa | atc | att | att | 144 |
| Asp | Ala | Val | Phe | Asp | Ala | Val | Cys | Asp | Asn | Gly | Pro | Glu | Ile | Ile | Ile | |
| | | 35 | | | | 40 | | | | 45 | | | | | | |
| tgt | cat | cat | gaa | caa | aat | gca | gcg | ttt | atg | gca | gca | gca | act | ggg | cgt | 192 |
| Cys | His | His | Glu | Gln | Asn | Ala | Ala | Phe | Met | Ala | Ala | Ala | Thr | Gly | Arg | |
| | 50 | | | | | 55 | | | | | 60 | | | | | |
| tta | acg | ggt | aaa | gca | ggc | att | tgt | tta | gca | acc | tct | gga | cca | ggc | gca | 240 |
| Leu | Thr | Gly | Lys | Ala | Gly | Ile | Cys | Leu | Ala | Thr | Ser | Gly | Pro | Gly | Ala | |
| 65 | | | | | 70 | | | | | 75 | | | | | 80 | |
| tca | aac | ctt | gtc | aca | ggc | gtt | gca | aca | gcg | aat | agt | gaa | ggt | gat | cct | 288 |
| Ser | Asn | Leu | Val | Thr | Gly | Val | Ala | Thr | Ala | Asn | Ser | Glu | Gly | Asp | Pro | |
| | | | | 85 | | | | | 90 | | | | | 95 | | |
| gtg | gtt | gca | ctt | gca | ggt | gct | gta | cct | ctt | tct | atg | tat | tct | cac | aat | 336 |
| Val | Val | Ala | Leu | Ala | Gly | Ala | Val | Pro | Leu | Ser | Met | Tyr | Ser | His | Asn | |
| | | | 100 | | | | | 105 | | | | | 110 | | | |
| act | cat | caa | tcc | atg | gat | acc | cgt | tca | ctg | ttt | act | cct | atc | acc | aag | 384 |
| Thr | His | Gln | Ser | Met | Asp | Thr | Arg | Ser | Leu | Phe | Thr | Pro | Ile | Thr | Lys | |
| | | | 115 | | | | | 120 | | | | | 125 | | | |
| ttt | tca | gca | gaa | gtg | atg | gat | agc | agc | tcg | gta | tct | gat | gtt | gta | cat | 432 |
| Phe | Ser | Ala | Glu | Val | Met | Asp | Ser | Ser | Ser | Val | Ser | Asp | Val | Val | His | |
| 130 | | | | | 135 | | | | | 140 | | | | | | |
| aaa | gct | ttt | cgt | att | gca | gag | caa | cct | acc | caa | ggt | gct | agc | ttt | gtt | 480 |
| Lys | Ala | Phe | Arg | Ile | Ala | Glu | Gln | Pro | Thr | Gln | Gly | Ala | Ser | Phe | Val | |
| 145 | | | | | 150 | | | | | 155 | | | | | 160 | |
| agt | cta | ccg | caa | gat | att | cta | act | aac | cgt | att | cct | tac | cag | cca | gta | 528 |
| Ser | Leu | Pro | Gln | Asp | Ile | Leu | Thr | Asn | Arg | Ile | Pro | Tyr | Gln | Pro | Val | |
| | | | | 165 | | | | | 170 | | | | | 175 | | |
| caa | cag | cct | aat | cca | att | ttg | ttc | ggt | ggt | gca | cac | cca | caa | gct | att | 576 |
| Gln | Gln | Pro | Asn | Pro | Ile | Leu | Phe | Gly | Gly | Ala | His | Pro | Gln | Ala | Ile | |
| | | | 180 | | | | | 185 | | | | | 190 | | | |
| cgt | cag | gct | gct | gat | cgc | att | aat | gct | gca | aaa | aat | ccg | gta | tta | tta | 624 |
| Arg | Gln | Ala | Ala | Asp | Arg | Ile | Asn | Ala | Ala | Lys | Asn | Pro | Val | Leu | Leu | |
| | | | 195 | | | | | 200 | | | | | 205 | | | |
| ctg | ggc | atg | gat | gca | agc | cag | cct | ttt | gtt | gct | gat | gct | att | cgc | caa | 672 |
| Leu | Gly | Met | Asp | Ala | Ser | Gln | Pro | Phe | Val | Ala | Asp | Ala | Ile | Arg | Gln | |
| | 210 | | | | | 215 | | | | | 220 | | | | | |
| cta | ctc | aaa | caa | aca | cca | att | gcc | gtt | gtg | aat | acg | ttt | gcc | gca | gct | 720 |
| Leu | Leu | Lys | Gln | Thr | Pro | Ile | Ala | Val | Val | Asn | Thr | Phe | Ala | Ala | Ala | |
| 225 | | | | | 230 | | | | | 235 | | | | | 240 | |
| ggg | gtt | att | tct | cat | gat | tta | tac | aac | tgc | ttt | tta | ggt | cgt | gtt | ggc | 768 |
| Gly | Val | Ile | Ser | His | Asp | Leu | Tyr | Asn | Cys | Phe | Leu | Gly | Arg | Val | Gly | |
| | | | | 245 | | | | | 250 | | | | | 255 | | |
| tta | ttt | aaa | aat | caa | ccc | ggt | gat | att | gca | tta | aac | agt | gca | gat | tta | 816 |
| Leu | Phe | Lys | Asn | Gln | Pro | Gly | Asp | Ile | Ala | Leu | Asn | Ser | Ala | Asp | Leu | |
| | | | 260 | | | | | 265 | | | | | 270 | | | |
| atc | att | acc | att | ggc | tac | agc | cca | att | gaa | tac | gat | ccg | att | ctt | tgg | 864 |
| Ile | Ile | Thr | Ile | Gly | Tyr | Ser | Pro | Ile | Glu | Tyr | Asp | Pro | Ile | Leu | Trp | |
| | | 275 | | | | | 280 | | | | | 285 | | | | |
| aat | aaa | gat | gca | aac | aca | cca | att | att | cat | att | ggt | tat | caa | caa | gca | 912 |
| Asn | Lys | Asp | Ala | Asn | Thr | Pro | Ile | Ile | His | Ile | Gly | Tyr | Gln | Gln | Ala | |
| | 290 | | | | | 295 | | | | | 300 | | | | | |
| gat | tta | gaa | att | agc | tat | aac | cct | gtt | tgt | gaa | gtt | gtg | ggt | gac | tta | 960 |
| Asp | Leu | Glu | Ile | Ser | Tyr | Asn | Pro | Val | Cys | Glu | Val | Val | Gly | Asp | Leu | |
| 305 | | | | | 310 | | | | | 315 | | | | | 320 | |
| gcg | gtg | tct | gtc | acg | tct | att | gct | tct | gaa | tta | gat | aag | cga | gaa | tca | 1008 |
| Ala | Val | Ser | Val | Thr | Ser | Ile | Ala | Ser | Glu | Leu | Asp | Lys | Arg | Glu | Ser | |
| | | | | 325 | | | | | 330 | | | | | 335 | | |

```
tta gaa aat aac caa caa atc caa tta tta cgc cac gat tta caa cat    1056
Leu Glu Asn Asn Gln Gln Ile Gln Leu Leu Arg His Asp Leu Gln His
            340                 345                 350 att atg cag atg ggg gta aat aaa acc tca aca aac ggc gtt cac ccg    1104
Ile Met Gln Met Gly Val Asn Lys Thr Ser Thr Asn Gly Val His Pro
        355                 360                 365 ctt cgt ttt gtt cat gag tta cgt cgc ttt gtt agt gac gac acc act    1152
Leu Arg Phe Val His Glu Leu Arg Arg Phe Val Ser Asp Asp Thr Thr
    370                 375                 380 gta tgt tgt gat gta ggc tct att tat att tgg atg gca cgt tac ttc    1200
Val Cys Cys Asp Val Gly Ser Ile Tyr Ile Trp Met Ala Arg Tyr Phe
385                 390                 395                 400 cac agc ttt gaa cct cgt cgt tta ttg ttc agc aat ggc caa caa aca    1248
His Ser Phe Glu Pro Arg Arg Leu Leu Phe Ser Asn Gly Gln Gln Thr
                405                 410                 415 ttg ggc gta gct tta cct tgg gca att gca gct tcc ctt ctt cac cct    1296
Leu Gly Val Ala Leu Pro Trp Ala Ile Ala Ala Ser Leu Leu His Pro
            420                 425                 430 aat gaa aaa gta att tcc atg tct ggt gat ggt ggc ttc cta ttc tca    1344
Asn Glu Lys Val Ile Ser Met Ser Gly Asp Gly Gly Phe Leu Phe Ser
        435                 440                 445 tca atg gaa tta gcc acg gcc gtt cgc cat aaa tgt aat atc gtt cac    1392
Ser Met Glu Leu Ala Thr Ala Val Arg His Lys Cys Asn Ile Val His
    450                 455                 460 ttt gtt tgg aca gat cac agt tat gac atg gtt aag atc caa cag ctt    1440
Phe Val Trp Thr Asp His Ser Tyr Asp Met Val Lys Ile Gln Gln Leu
465                 470                 475                 480 aaa aag tat ggt cga gag agt gcc gtc agc ttt ata ggt cct gat att    1488
Lys Lys Tyr Gly Arg Glu Ser Ala Val Ser Phe Ile Gly Pro Asp Ile
                485                 490                 495 gtt aag tac gca gaa agc ttc ggc gca cat ggt tta gcg atc aat act    1536
Val Lys Tyr Ala Glu Ser Phe Gly Ala His Gly Leu Ala Ile Asn Thr
            500                 505                 510 gcc gat gat att gag cct gtt atg cga aaa gct atg agc tta agt ggc    1584
Ala Asp Asp Ile Glu Pro Val Met Arg Lys Ala Met Ser Leu Ser Gly
        515                 520                 525 cca gta ttg gtc aac gtc aat gtt gat tat agc gat aac agt cgc cta    1632
Pro Val Leu Val Asn Val Asn Val Asp Tyr Ser Asp Asn Ser Arg Leu
    530                 535                 540 ctt gat caa ctt cat cca tgc caa caa gat taa                        1665
Leu Asp Gln Leu His Pro Cys Gln Gln Asp
545                 550
```

<210> SEQ ID NO 16
<211> LENGTH: 554
<212> TYPE: PRT
<213> ORGANISM: Vibrio angustum

<400> SEQUENCE: 16

```
Met Ser Asp Lys Thr Val Ser Gly Ala Glu Leu Val Val Glu Thr Leu
1               5                   10                  15

Asn Ala His Asn Val Pro His Ile Phe Gly Ile Pro Gly Ala Lys Val
            20                  25                  30

Asp Ala Val Phe Asp Ala Val Cys Asp Asn Gly Pro Glu Ile Ile Ile
        35                  40                  45

Cys His His Glu Gln Asn Ala Ala Phe Met Ala Ala Thr Gly Arg
    50                  55                  60

Leu Thr Gly Lys Ala Gly Ile Cys Leu Ala Thr Ser Gly Pro Gly Ala
65                  70                  75                  80
```

```
Ser Asn Leu Val Thr Gly Val Ala Thr Ala Asn Ser Glu Gly Asp Pro
            85                  90                  95

Val Val Ala Leu Ala Gly Ala Val Pro Leu Ser Met Tyr Ser His Asn
        100                 105                 110

Thr His Gln Ser Met Asp Thr Arg Ser Leu Phe Thr Pro Ile Thr Lys
        115                 120                 125

Phe Ser Ala Glu Val Met Asp Ser Ser Val Ser Asp Val Val His
130                 135                 140

Lys Ala Phe Arg Ile Ala Glu Gln Pro Thr Gln Gly Ala Ser Phe Val
145                 150                 155                 160

Ser Leu Pro Gln Asp Ile Leu Thr Asn Arg Ile Pro Tyr Gln Pro Val
                165                 170                 175

Gln Gln Pro Asn Pro Ile Leu Phe Gly Gly Ala His Pro Gln Ala Ile
            180                 185                 190

Arg Gln Ala Ala Asp Arg Ile Asn Ala Ala Lys Asn Pro Val Leu Leu
        195                 200                 205

Leu Gly Met Asp Ala Ser Gln Pro Phe Val Ala Asp Ala Ile Arg Gln
210                 215                 220

Leu Leu Lys Gln Thr Pro Ile Ala Val Val Asn Thr Phe Ala Ala Ala
225                 230                 235                 240

Gly Val Ile Ser His Asp Leu Tyr Asn Cys Phe Leu Gly Arg Val Gly
                245                 250                 255

Leu Phe Lys Asn Gln Pro Gly Asp Ile Ala Leu Asn Ser Ala Asp Leu
            260                 265                 270

Ile Ile Thr Ile Gly Tyr Ser Pro Ile Glu Tyr Asp Pro Ile Leu Trp
        275                 280                 285

Asn Lys Asp Ala Asn Thr Pro Ile Ile His Ile Gly Tyr Gln Gln Ala
        290                 295                 300

Asp Leu Glu Ile Ser Tyr Asn Pro Val Cys Glu Val Val Gly Asp Leu
305                 310                 315                 320

Ala Val Ser Val Thr Ser Ile Ala Ser Glu Leu Asp Lys Arg Glu Ser
                325                 330                 335

Leu Glu Asn Asn Gln Gln Ile Gln Leu Leu Arg His Asp Leu Gln His
            340                 345                 350

Ile Met Gln Met Gly Val Asn Lys Thr Ser Thr Asn Gly Val His Pro
        355                 360                 365

Leu Arg Phe Val His Glu Leu Arg Arg Phe Val Ser Asp Asp Thr Thr
370                 375                 380

Val Cys Cys Asp Val Gly Ser Ile Tyr Ile Trp Met Ala Arg Tyr Phe
385                 390                 395                 400

His Ser Phe Glu Pro Arg Arg Leu Leu Phe Ser Asn Gly Gln Gln Thr
                405                 410                 415

Leu Gly Val Ala Leu Pro Trp Ala Ile Ala Ala Ser Leu Leu His Pro
            420                 425                 430

Asn Glu Lys Val Ile Ser Met Ser Gly Asp Gly Gly Phe Leu Phe Ser
        435                 440                 445

Ser Met Glu Leu Ala Thr Ala Val Arg His Lys Cys Asn Ile Val His
450                 455                 460

Phe Val Trp Thr Asp His Ser Tyr Asp Met Val Lys Ile Gln Gln Leu
465                 470                 475                 480

Lys Lys Tyr Gly Arg Glu Ser Ala Val Ser Phe Ile Gly Pro Asp Ile
                485                 490                 495
```

Val Lys Tyr Ala Glu Ser Phe Gly Ala His Gly Leu Ala Ile Asn Thr
        500                 505                 510

Ala Asp Asp Ile Glu Pro Val Met Arg Lys Ala Met Ser Leu Ser Gly
        515                 520                 525

Pro Val Leu Val Asn Val Asn Val Asp Tyr Ser Asp Asn Ser Arg Leu
        530                 535                 540

Leu Asp Gln Leu His Pro Cys Gln Gln Asp
545                 550

<210> SEQ ID NO 17
<211> LENGTH: 1689
<212> TYPE: DNA
<213> ORGANISM: Bacillus cereus

<400> SEQUENCE: 17

```
ttgagtacag gtgtaaaagc aaacgacgtg aagacaaaaa caaaaggagc agatcttgtt      60 gttg

```
<210> SEQ ID NO 18
<211> LENGTH: 562
<212> TYPE: PRT
<213> ORGANISM: Bacillus cereus

<400> SEQUENCE: 18

Met

```
Ser Leu Ile Ser Asp Asp Thr Thr Val Thr Cys Asp Ile Gly Ser His
385                 390                 395                 400

Ser Ile Trp Met Ala Arg Cys Phe Arg Ser Tyr Glu Pro Arg Arg Leu
            405                 410                 415

Leu Phe Ser Asn Gly Met Gln Thr Leu Gly Val Ala Leu Pro Trp Ala
        420                 425                 430

Ile Ala Ala Thr Leu Val Glu Pro Gly Lys Lys Val Ser Val Ser
    435                 440                 445

Gly Asp Gly Gly Phe Leu Phe Ser Ala Met Glu Leu Glu Thr Ala Val
450                 455                 460

Arg Leu Asn Ser Pro Ile Val His Leu Val Trp Arg Asp Gly Thr Tyr
465                 470                 475                 480

Asp Met Val Ala Phe Gln Gln Met Met Lys Tyr Gly Arg Thr Ser Ala
            485                 490                 495

Thr Glu Phe Gly Asp Val Asp Leu Val Lys Tyr Ala Glu Ser Phe Gly
        500                 505                 510

Ala Leu Gly Leu Arg Val Asn Thr Pro Asp Glu Leu Glu Gly Val Leu
    515                 520                 525

Lys Glu Ala Leu Ala Ala Asp Gly Pro Val Ile Ile Asp Ile Pro Ile
530                 535                 540

Asp Tyr Arg Asp Asn Ile Lys Leu Ser Glu Lys Leu Leu Pro Asn Gln
545                 550                 555                 560

Leu Asn
```

<210> SEQ ID NO 19
<211> LENGTH: 780
<212> TYPE: DNA
<213> ORGANISM: Klebsiella pneumoniae

<400> SEQUENCE: 19

```
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc      180
ggcacctta atgagctgga cggggagctg atcgccttca gcagtcaggt ctatcagctg      240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccggggcg     480
atgaccgacg tcctcgacga tcagccggtt ttccgcttta accagcgcga aggggtgctg      540
gtcggcttcc ggaccccgca gcatatgcag gggatcaacg tcgccgggta tcacgagcac     600
tttattaccg atgaccgcaa aggcggcggt cacctgctgg attaccagct cgaccatggg      660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780
```

<210> SEQ ID NO 20
<211> LENGTH: 259
<212> TYPE: PRT
<213> ORGANISM: Klebsiella pneumoniae

<400> SEQUENCE: 20

```
Met Asn His Ser Ala Glu Cys Thr Cys Glu Glu Ser Leu Cys Glu Thr
1               5                   10                  15
```

Leu Arg Ala Phe Ser Ala Gln His Pro Glu Ser Val Leu Tyr Gln Thr
                20                  25                  30

Ser Leu Met Ser Ala Leu Leu Ser Gly Val Tyr Glu Gly Ser Thr Thr
            35                  40                  45

Ile Ala Asp Leu Leu Lys His Gly Asp Phe Gly Leu Gly Thr Phe Asn
 50                  55                  60

Glu Leu Asp Gly Glu Leu Ile Ala Phe Ser Ser Gln Val Tyr Gln Leu
 65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 21
<211> LENGTH: 768
<212> TYPE: DNA
<213> ORGANISM: Bacillus subtilis

<400> SEQUENCE: 21
atgaaacgag aaagcaacat tcaagtgctc agccgtggtc aaaaagatca gcctgtgagc      60
cagatttatc aagtatcaac aatgacttct ctattagacg gagtatatga cggagatttt     120
gaactgtcag agattccgaa atatggagac ttcggtatcg gaacctttaa caagcttgac     180
ggagagctga ttgggtttga cggcgaattt taccgtcttc gctcagacgg aaccgcgaca     240
ccggtccaaa atgagaccg ttcaccgttc tgttcattta cgttctttac accggacatg     300
acgcacaaaa ttgatgcgaa atgacacgc gaagactttg aaaagagat caacagcatg     360 ctgccaagca gaaacttatt ttatgcaatt cgcattgacg gattgtttaa aaaggtgcag     420
acaagaacag tagaacttca agaaaaacct tacgtgccaa tggttgaagc ggtcaaaaca     480
cagccgattt tcaacttcga caacgtgaga ggaacgattg taggtttctt gacaccagct     540
tatgcaaacg gaatcgccgt ttctggctat cacctgcact tcattgacga aggacgcaat     600
tcaggcggac acgtttttga ctatgtgctt gaggattgca cggttacgat ttctcaaaaa     660
atgaacatga atctcagact tccgaacaca gcggatttct ttaatgcgaa tctggataac     720
cctgattttg cgaaagatat cgaaacaact gaaggaagcc ctgaataa            768

<210> SEQ ID NO 22
<211> LENGTH: 255
<212> TYPE: PRT
<213> ORGANISM: Bacillus subtilis

<400> SEQUENCE: 22

Met Lys Arg Glu Ser Asn Ile Gln Val Leu Ser Arg Gly Gln Lys Asp
1               5                   10                  15

Gln Pro Val Ser Gln Ile Tyr Gln Val Ser Thr Met Thr Ser Leu Leu
            20                  25                  30

Asp Gly Val Tyr Asp Gly Asp Phe Glu Leu Ser Glu Ile Pro Lys Tyr
        35                  40                  45

Gly Asp Phe Gly Ile Gly Thr Phe Asn Lys Leu Asp Gly Glu Leu Ile
    50                  55                  60

Gly Phe Asp Gly Glu Phe Tyr Arg Leu Arg Ser Asp Gly Thr Ala Thr
65                  70                  75                  80

Pro Val Gln Asn Gly Asp Arg Ser Pro Phe Cys Ser Phe Thr Phe Phe
                85                  90                  95

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160

Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
    210                 215                 220

Leu Arg Leu Pro Asn Thr Ala Asp Phe Asn Ala Asn Leu Asp Asn
225                 230                 235                 240

Pro Asp Phe Ala Lys Asp Ile Glu Thr Thr Glu Gly Ser Pro Glu
                245                 250                 255

<210> SEQ ID NO 23
<211> LENGTH: 780
<212> TYPE: DNA
<213> ORGANISM: Klebsiella terrigena

<400> SEQUENCE: 23
gtgaatcatt atcctgaatg cacctgccag gagagcctgt gcgaaaccgt acgcggcttc      60
tccgcccacc accctgatag cgttatctat cagacctctc tgatgagcgc gctgctgagc     120
ggggtctatg agggtagcac caccatcgcc gacctgctga cccacggcga cttcggtctc     180 ggcacctta acgaactcga tggcgaactg attgccttta gcagcgaggt ctaccagctg     240
cgcgctgacg gcagcgcgcg taaagcccgg gcggatcaaa aaacgccctt cgcggtgatg     300
acctggttca gaccgcagta ccgtaaaacc tttgaccacc cggtcagccg ccagcagctg     360

```
cacgacgtta tcgaccagca atcccctcc gataacctgt tctgcgccct gcatattgat    420
ggtcactttc gccacgccca cacccgcacc gtgccgcggc agacgccgcc ctatcgggcg    480
atgaccgacg tgctcgatga ccagccggtt ttccgcttca accagcgcaa ggggacgctg    540
gtcggctttc gcaccccgca gcatatgcag ggccttaacg ttgccggcta ccacgagcac    600
tttattaccg acgatcgcca gggcggcggc catctgctgg actaccagct cgatagcggc    660
gtgctgacct tcggcgagat ccacaagctg atgattgacc tcccggccga cagcgctttc    720
ctgcaggccg acctgcatcc tgacaatctc gatgccgcta ttcgtgcggt agaaaactaa    780
```

<210> SEQ ID NO 24
<211> LENGTH: 259
<212> TYPE: PRT
<213> ORGANISM: Klebsiella terrigena

<400> SEQUENCE: 24

Met Asn His Tyr Pro Glu Cys Thr Cys Gln Glu Ser Leu Cys Glu Thr
1               5                   10                  15

Val Arg Gly Phe Ser Ala His His Pro Asp Ser Val Ile Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Thr His Gly Asp Phe Gly Leu Gly Thr Phe Asn
    50                  55                  60

Glu Leu Asp Gly Glu Leu Ile Ala Phe Ser Ser Glu Val Tyr Gln Leu
65                  70                  75                  80

Arg Ala Asp Gly Ser Ala Arg Lys Ala Arg Ala Asp Gln Lys Thr Pro
                85                  90                  95

Phe Ala Val Met Thr Trp Phe Arg Pro Gln Tyr Arg Lys Thr Phe Asp
            100                 105                 110

His Pro Val Ser Arg Gln Gln Leu His Asp Val Ile Asp Gln Gln Ile
        115                 120                 125

Pro Ser Asp Asn Leu Phe Cys Ala Leu His Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Lys Gly Thr Leu Val Gly Phe Arg Thr Pro Gln His Met Gln Gly Leu
            180                 185                 190

Asn Val Ala Gly Tyr His Glu His Phe Ile Thr Asp Asp Arg Gln Gly
        195                 200                 205

Gly Gly His Leu Leu Asp Tyr Gln Leu Asp Ser Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asp Leu His Pro Asp Asn Leu Asp Ala Ala Ile Arg Ala
                245                 250                 255

Val Glu Asn

<210> SEQ ID NO 25
<211> LENGTH: 771
<212> TYPE: DNA
<213> ORGANISM: Klebsiella pneumoniae

<400> SEQUENCE: 25

```
atgaaaaaag tcgcacttgt taccggcgcc ggccagggga ttggtaaagc tatcgccctt    60
cgtctggtga aggatggatt tgccgtggcc attgccgatt ataacgacgc caccgccaaa   120
gcggtcgcct cggaaatcaa ccaggccggc ggacacgccg tggcggtgaa agtggatgtc   180
tccgaccgcg atcaggtatt tgccgccgtt gaacaggcgc gcaaaacgct gggcggcttc   240
gacgtcatcg tcaataacgc cggtgtggca ccgtctacgc cgatcgagtc cattaccccg   300
gagattgtcg acaaagtcta caacatcaac gtcaaagggg tgatctgggg tattcaggcg   360
gcggtcgagg cctttaagaa agaggggcac ggcgggaaaa tcatcaacgc ctgttcccag   420
gccggccacg tcggcaaccc ggagctggcg gtgtatagct ccagtaaatt cgcggtacgc   480
ggcttaaccc agaccgccgc tcgcgacctc gcgccgctgg gcatcacggt caacggctac   540
tgcccgggga ttgtcaaaac gccaatgtgg gccgaaattg accgccaggt gtccgaagcc   600
gccggtaaac cgctgggcta cggtaccgcc gagttcgcca aacgcatcac tctcggtcgt   660
ctgtccgagc cggaagatgt cgccgcctgc gtctcctatc ttgccagccc ggattctgat   720
tacatgaccg gtcagtcgtt gctgatcgac ggcgggatgg tatttaacta a            771
```

<210> SEQ ID NO 26
<211> LENGTH: 256
<212> TYPE: PRT
<213> ORGANISM: Klebsiella pneumoniae

<400> SEQUENCE: 26

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
                20                  25                  30

Asp Tyr Asn Asp Ala Thr Ala Lys Ala Val Ala Ser Glu Ile Asn Gln
            35                  40                  45

Ala Gly Gly His Ala Val Ala Val Lys Val Asp Val Ser Asp Arg Asp
        50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

```
Tyr Met Thr Gly Gln Ser Leu Leu Ile Asp Gly Gly Met Val Phe Asn
                245                 250                 255

<210> SEQ ID NO 27
<211> LENGTH: 1053
<212> TYPE: DNA
<213> ORGANISM: Bacillus cereus

<400> SEQUENCE: 27
atgaaagcac tactttggca taatcaacgt gatgtacgag tagaagaagt accagaacca      60
acagtaaaac caggaacagt gaaaatcaaa gttaaatggt gtggtatttg tgggacagac     120
ttgcatgaat atttagcagg gcctattttt attccaacag aagaacatcc attaacacat     180
gtgaaagcac ctgttatttt aggtcatgag tttagtggtg aggtaataga gattggtgaa     240
ggagttacat ctcataaagt gggagaccgc gttgttgtag agccaattta ttcttgtggt     300
aaatgtgaag cttgtaaaca tggacattac aatgtttgtg aacaacttgt tttccacggt     360
cttggcggag aaggcggcgg tttctctgaa tatacagtag taccagaaga tatggttcat     420
cacattccag atgaaatgac gtatgaacaa ggtgcgcttg tagaaccagc agcagtagca     480
gttcatgcag tacgtcaaag taaattaaaa gaaggggaag ctgtagcggt atttggttgc     540
ggtccaattg gacttcttgt tatccaagca gctaaagcag caggagcaac tcctgttatt     600
gcagttgaac tttctaaaga acgtcaagag ttagcgaaat tagcaggtgc ggattatgta     660
ttaaatccag caactcaaga tgtgttagct gaaattcgta acttaacaaa tggtttaggt     720
gtaaatgtta gctttgaagt aacaggtgtt gaagttgtac tacgccaagc gattgaaagt     780
acaagcttcg aaggacaaac tgtaattgtt agtgtatggg aaaaagacgc aacaattact     840
ccaaataact tagtattaaa agaaaaagaa gttattggta ttttaggata ccgtcacatc     900
ttcccagctg ttattaaatt gattagctcc ggtcaaattc aagcagagaa attaattacg     960
aaaaaaatta cagtggatca agttgttgaa gaaggatttg aagcacttgt aaaagataaa    1020
acacaagtga aaattcttgt ttcacctaaa taa                                 1053

<210> SEQ ID NO 28
<211> LENGTH: 350
<212> TYPE: PRT
<213> ORGANISM: Bacillus cereus

<400> SEQUENCE: 28

Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His Val Lys Ala Pro
    50                  55                  60

Val Ile Leu Gly His Glu Phe Ser Gly Glu Val Ile Glu Ile Gly Glu
65                  70                  75                  80

Gly Val Thr Ser His Lys Val Gly Asp Arg Val Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Glu Gly Gly Gly Phe
        115                 120                 125
```

```
Ser Glu Tyr Thr Val Val Pro Glu Asp Met Val His His Ile Pro Asp
    130                 135                 140

Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
            165                 170                 175

Val Phe Gly Cys Gly Pro Ile Gly Leu Leu Val Ile Gln Ala Ala Lys
        180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Thr Gln Asp Val Leu Ala Glu Ile Arg Asn Leu Thr Asn Gly Leu Gly
225                 230                 235                 240

Val Asn Val Ser Phe Glu Val Thr Gly Val Glu Val Val Leu Arg Gln
            245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
    275                 280                 285

Lys Glu Val Ile Gly Ile Leu Gly Tyr Arg His Ile Phe Pro Ala Val
    290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Gly Phe Glu Ala Leu
                325                 330                 335

Val Lys Asp Lys Thr Gln Val Lys Ile Leu Val Ser Pro Lys
            340                 345                 350

<210> SEQ ID NO 29
<211> LENGTH: 1113
<212> TYPE: DNA
<213> ORGANISM: Lactococcus lactis

<400> SEQUENCE: 29
ttgcctgaaa cgacaaccat cctatataga ggaggcgttt ttatgcgcgc agcacgtttt      60
tacgaccgcg gggatatccg cattgatgaa attaatgaac caatagtaaa agctggccaa     120
gttggcattg atgtggcttg tgtggaatt tgtggaacag atctccatga attttttagat     180 ggcccaattt tttgtccgtc agcagaacat cctaatccaa ttactggaga agtaccacca     240
gtcactcttg acatgaaat gtctggggtt gtaaatttta taggtgaagg agtaagcgga     300
cttaaagtag gtgaccatgt cgttgtcgaa ccttatatcg ttcccgaagg gactgataca     360
agtgaaactg acattataa cctctcagaa ggctcaaact ttattggttt gggcggaaat     420
ggtggaggtt tggctgaaaa aatttctgtt gatgaacgtt gggttcacaa aattcctgat     480
aacttaccat tggatgaagc tgctctaatt gagccactat cagtcggcta tcacgctgtt     540
gaacgagcaa atttaagtga aaagagtacg gtattagttg ttggtgctgg accaattgga     600
ctattaactg ctgccgttgc aaaagcgcaa ggacatactt tatcatcag tgaacctagt     660 ggacttcgtc gtaaaaaagc acaagaagca caagttgctg attatttctt caatccaatt     720
gaagatgaca ttcaagctaa agttcatgaa attaatgaaa aaggagtgga cgcagccttt     780
gaatgtacct ctgtccaacc gggatttgac gcttgtctag atgcgattcg tatgggtgga     840
```

```
acagttgtca ttgtcgcaat ttggggcaag cctgctagtg ttgatatggc aaaattagta    900
atcaaagaag ctaacctttt aggaacgatt gcttataata acactcatcc aaaaacaatt    960
gatttagtat caacaggtaa aataaaattg gaccaattca tcacagctaa aatcggtttg   1020
gatgatttga ttgataaagg attcgatacg ctgattcatc ataatgaaac agctgttaaa   1080
attttagttt caccaactgg taaaggtcta taa                                1113
```

<210> SEQ ID NO 30
<211> LENGTH: 370
<212> TYPE: PRT
<213> ORGANISM: Lactococcus lactis
<400> SEQUENCE: 30

```
Met Pro Glu Thr Thr Thr Ile Leu Tyr Arg Gly Gly Val Phe Met Arg
1               5                   10                  15

Ala Ala Arg Phe Tyr Asp Arg Gly Asp Ile Arg Ile Asp Glu Ile Asn
            20                  25                  30

Glu Pro Ile Val Lys Ala Gly Gln Val Gly Ile Asp Val Ala Trp Cys
        35                  40                  45

Gly Ile Cys Gly Thr Asp Leu His Glu Phe Leu Asp Gly Pro Ile Phe
    50                  55                  60

Cys Pro Ser Ala Glu His Pro Asn Pro Ile Thr Gly Glu Val Pro Pro
65                  70                  75                  80

Val Thr Leu Gly His Glu Met Ser Gly Val Val Asn Phe Ile Gly Glu
                85                  90                  95

Gly Val Ser Gly Leu Lys Val Gly Asp His Val Val Glu Pro Tyr
            100                 105                 110

Ile Val Pro Glu Gly Thr Asp Thr Ser Glu Thr Gly His Tyr Asn Leu
        115                 120                 125

Ser Glu Gly Ser Asn Phe Ile Gly Leu Gly Gly Asn Gly Gly Gly Leu
    130                 135                 140

Ala Glu Lys Ile Ser Val Asp Glu Arg Trp Val His Lys Ile Pro Asp
145                 150                 155                 160

Asn Leu Pro Leu Asp Glu Ala Ala Leu Ile Glu Pro Leu Ser Val Gly
                165                 170                 175

Tyr His Ala Val Glu Arg Ala Asn Leu Ser Glu Lys Ser Thr Val Leu
            180                 185                 190

Val Val Gly Ala Gly Pro Ile Gly Leu Leu Thr Ala Ala Val Ala Lys
        195                 200                 205

Ala Gln Gly His Thr Val Ile Ile Ser Glu Pro Ser Gly Leu Arg Arg
    210                 215                 220

Lys Lys Ala Gln Glu Ala Gln Val Ala Asp Tyr Phe Phe Asn Pro Ile
225                 230                 235                 240

Glu Asp Asp Ile Gln Ala Lys Val His Glu Ile Asn Glu Lys Gly Val
                245                 250                 255

Asp Ala Ala Phe Glu Cys Thr Ser Val Gln Pro Gly Phe Asp Ala Cys
            260                 265                 270

Leu Asp Ala Ile Arg Met Gly Gly Thr Val Val Ile Ala Ile Trp
        275                 280                 285

Gly Lys Pro Ala Ser Val Asp Met Ala Lys Leu Val Ile Lys Glu Ala
    290                 295                 300

Asn Leu Leu Gly Thr Ile Ala Tyr Asn Asn Thr His Pro Lys Thr Ile
305                 310                 315                 320

Asp Leu Val Ser Thr Gly Lys Ile Lys Leu Asp Gln Phe Ile Thr Ala
```

```
                    325                 330                 335
Lys Ile Gly Leu Asp Asp Leu Ile Asp Lys Gly Phe Asp Thr Leu Ile
            340                 345                 350

His His Asn Glu Thr Ala Val Lys Ile Leu Val Ser Pro Thr Gly Lys
            355                 360                 365

Gly Leu
    370

<210> SEQ ID NO 31
<211> LENGTH: 2532
<212> TYPE: DNA
<213> ORGANISM: Roseburia inulinivorans

<400> SEQUENCE: 31
atgggcaatt acgattcaac accgatagct aaaagtgata ggattaaaag attggttgat      60
catttgtatg ctaaaatgcc tgaaattgag gccgctagag cagagctaat tactgaatcc    120
tttaaggcca ccgaaggtca acctgttgtt atgagaaagg ctagagcttt tgaacatata    180
ctaaagaatt tgccaattat cataagacca gaagaactga ttgttggctc aactacaatt    240 gccctagag  gttgccaaac gtatccagaa ttctcatacg agtggttaga ggctgaattt    300
gaaactgtcg aaacgcgttc agctgaccca ttttatattt cagaagaaac gaagaaacgt    360
ttgctggctg ccgatgctta ttggaaaggt aaaacaaccct cagagttggc aacttcatat    420
atggccccag aaactctaag agccatgaag cataacttct tcacccctgg aaactacttc    480
tacaatggtg tcggtcatgt cacagttcaa tatgaaacag tattagcaat cggcttgaat    540
ggagtaaaag agaaggttag aaagagatg gagaattgtc attttggtga tgccgattat    600
agtacaaaga tgtgtttctt ggagagcatt ttaatatcgt gtgatgccgt aatcacttat    660
gctaatagat atgccaagat ggccgaggaa atggctgaaa agaaacaga tgctgcaagg    720 aggcaagaac tattaacaat cgccagggtt tgcaaaaacg ttcctgaatt cccagccgaa    780
agcttccagg aggcctgcca atccttttgg ttcatacaac aagtgcttca aattgaatcc    840
agtggtcatt caatttcccc aggtagattt gatcaatata tgtatcctta ttacgaaaag    900
gatttaaagg aaggtagctt aactagggaa tatgctcagg aactgatcga ttgtatctgg    960
gttaagttaa atgatctgaa taagtgcagg gatgctgcct ctgctgaggg ctttgcagga   1020
tattccttat ttcaaaactt aatcgttggg gccaaacgg ttcaaggaag ggacgccacc    1080
aatgatttga gttttatgtg tatcacggca tctgaacacg tcttttttacc gatgccgtcg   1140 ttgtctataa gagtttggca tggtagttcc aaagcactgc ttatgagagc agctgaattg   1200
actagaaccg gtataggctt acctgcttat tacaatgatg aagtcatcat accagctttg   1260
gtgcataggg gtgctactat ggatgaagca agaaattaca acataatagg atgtgtcgaa   1320
ccgcaggttc ctggtaaaac tgatggctgg cacgatgcag cattctttaa catgtgcaga   1380
cctttggaaa tggtgtttag taatggttat gataacggtg aaattgcatc tatacaaact   1440
ggtaacgtag aatcttttca gagttttgat gagtttatgg aagcttacag aaaacaaatg   1500
ctatataaca tagaacttat ggtaaatgcc gacaacgcga tagattatgc ccacgcaaag   1560
ttggccccat tgccatttga gtcatgtttg gttgatgact gtataaagag aggaatgtcc   1620
gctcaggaag gcggcgcaat ctataatttc actggtccac agggctttgg tattgcaaac   1680
gttgctgata gcttgtatac gattaagaaa ttggtgttcg aggagaagag aattacgatg   1740
ggtgaattaa agaaagcgtt ggaaatgaat tatggtaagg gtttggatgc cacaaccgct   1800
```

-continued

```
ggtgacatcg caatgcaggt cgcgaaggga ctaaagatcg ccggacagga agtgggtccc    1860
gacgtgatcg ctaatacaat ccgtcaagtt cttgaaatgg aattaccaga agatgtaaga    1920
aagagatatg aagagatcca tgaaatgata cttgagttac caaagtatgg taatgatata    1980
gatgaagttg atgaattagc tagagaagca gcttactttt acacaagacc attagaaact    2040
tttaagaatc aagggtgtgg catgtatcaa gccggccttt atcccgtgtc cgctaatgtg    2100
ccactaggcg ctcaaacggg ggccacaccc gatggacgtt tggcgcatac acccgtggcg    2160
gatggcgttg gtccgacatc aggcttcgat atatccggac caacagcttc ttgcaattct    2220
gtcgccaagt tggatcatgc tatagcctct aatggtacct tatttaatat gaagatgcac    2280
ccaaccgcaa tggcaggtga aaagggctta gaatccttca tatcgttgat ccgtggttat    2340
ttcgatcaac aaggtatgca catgcaattt aacgtagtag acagggctac actgcttgat    2400
gcgcaggccc accctgaaaa gtattcaggc ttaattgtca gagtggcagg ttattctgcc    2460 cttttttacca cattgtccaa gtcattacaa gatgatataa tcaaacgtac cgaacaagca    2520
gacaatagat ag                                                        2532
```

<210> SEQ ID NO 32
<211> LENGTH: 843
<212> TYPE: PRT
<213> ORGANISM: Roseburia inulinivorans

<400> SEQUENCE: 32

```
Met Gly Asn Tyr Asp Ser Thr Pro Ile Ala Lys Ser Asp Arg Ile Lys
1               5                   10                  15

Arg Leu Val Asp His Leu Tyr Ala Lys Met Pro Glu Ile Glu Ala Ala
            20                  25                  30

Arg Ala Glu Leu Ile Thr Glu Ser Phe Lys Ala Thr Glu Gly Gln Pro
        35                  40                  45

Val Val Met Arg Lys Ala Arg Ala Phe Glu His Ile Leu Lys Asn Leu
    50                  55                  60

Pro Ile Ile Ile Arg Pro Glu Glu Leu Ile Val Gly Ser Thr Thr Ile
65                  70                  75                  80

Ala Pro Arg Gly Cys Gln Thr Tyr Pro Glu Phe Ser Tyr Glu Trp Leu
                85                  90                  95

Glu Ala Glu Phe Glu Thr Val Glu Thr Arg Ser Ala Asp Pro Phe Tyr
            100                 105                 110

Ile Ser Glu Glu Thr Lys Lys Arg Leu Leu Ala Ala Asp Ala Tyr Trp
        115                 120                 125

Lys Gly Lys Thr Thr Ser Glu Leu Ala Thr Ser Tyr Met Ala Pro Glu
    130                 135                 140

Thr Leu Arg Ala Met Lys His Asn Phe Phe Thr Pro Gly Asn Tyr Phe
145                 150                 155                 160

Tyr Asn Gly Val Gly His Val Thr Val Gln Tyr Glu Thr Val Leu Ala
                165                 170                 175

Ile Gly Leu Asn Gly Val Lys Glu Lys Val Arg Lys Glu Met Glu Asn
            180                 185                 190

Cys His Phe Gly Asp Ala Asp Tyr Ser Thr Lys Met Cys Phe Leu Glu
        195                 200                 205

Ser Ile Leu Ile Ser Cys Asp Ala Val Ile Thr Tyr Ala Asn Arg Tyr
    210                 215                 220

Ala Lys Met Ala Glu Glu Met Ala Glu Lys Glu Thr Asp Ala Ala Arg
225                 230                 235                 240
```

```
Arg Gln Glu Leu Leu Thr Ile Ala Arg Val Cys Lys Asn Val Pro Glu
            245                 250                 255

Phe Pro Ala Glu Ser Phe Gln Glu Ala Cys Gln Ser Phe Trp Phe Ile
        260                 265                 270

Gln Gln Val Leu Gln Ile Glu Ser Ser Gly His Ser Ile Ser Pro Gly
        275                 280                 285

Arg Phe Asp Gln Tyr Met Tyr Pro Tyr Tyr Glu Lys Asp Leu Lys Glu
        290                 295                 300

Gly Ser Leu Thr Arg Glu Tyr Ala Gln Glu Leu Ile Asp Cys Ile Trp
305                 310                 315                 320

Val Lys Leu Asn Asp Leu Asn Lys Cys Arg Asp Ala Ala Ser Ala Glu
                325                 330                 335

Gly Phe Ala Gly Tyr Ser Leu Phe Gln Asn Leu Ile Val Gly Gly Gln
            340                 345                 350

Thr Val Gln Gly Arg Asp Ala Thr Asn Asp Leu Ser Phe Met Cys Ile
        355                 360                 365

Thr Ala Ser Glu His Val Phe Leu Pro Met Pro Ser Leu Ser Ile Arg
    370                 375                 380

Val Trp His Gly Ser Ser Lys Ala Leu Leu Met Arg Ala Ala Glu Leu
385                 390                 395                 400

Thr Arg Thr Gly Ile Gly Leu Pro Ala Tyr Tyr Asn Asp Glu Val Ile
                405                 410                 415

Ile Pro Ala Leu Val His Arg Gly Ala Thr Met Asp Glu Ala Arg Asn
            420                 425                 430

Tyr Asn Ile Ile Gly Cys Val Glu Pro Gln Val Pro Gly Lys Thr Asp
        435                 440                 445

Gly Trp His Asp Ala Ala Phe Phe Asn Met Cys Arg Pro Leu Glu Met
    450                 455                 460

Val Phe Ser Asn Gly Tyr Asp Asn Gly Glu Ile Ala Ser Ile Gln Thr
465                 470                 475                 480

Gly Asn Val Glu Ser Phe Gln Ser Phe Asp Glu Phe Met Glu Ala Tyr
                485                 490                 495

Arg Lys Gln Met Leu Tyr Asn Ile Glu Leu Met Val Asn Ala Asp Asn
            500                 505                 510

Ala Ile Asp Tyr Ala His Ala Lys Leu Ala Pro Leu Pro Phe Glu Ser
        515                 520                 525

Cys Leu Val Asp Asp Cys Ile Lys Arg Gly Met Ser Ala Gln Glu Gly
    530                 535                 540

Gly Ala Ile Tyr Asn Phe Thr Gly Pro Gln Gly Phe Gly Ile Ala Asn
545                 550                 555                 560

Val Ala Asp Ser Leu Tyr Thr Ile Lys Lys Leu Val Phe Glu Glu Lys
                565                 570                 575

Arg Ile Thr Met Gly Glu Leu Lys Lys Ala Leu Glu Met Asn Tyr Gly
            580                 585                 590

Lys Gly Leu Asp Ala Thr Thr Ala Gly Asp Ile Ala Met Gln Val Ala
        595                 600                 605

Lys Gly Leu Lys Asp Ala Gly Gln Glu Val Gly Pro Asp Val Ile Ala
    610                 615                 620

Asn Thr Ile Arg Gln Val Leu Glu Met Glu Leu Pro Glu Asp Val Arg
625                 630                 635                 640

Lys Arg Tyr Glu Glu Ile His Glu Met Ile Leu Glu Leu Pro Lys Tyr
                645                 650                 655

Gly Asn Asp Ile Asp Glu Val Asp Glu Leu Ala Arg Glu Ala Ala Tyr
```

```
                    660                 665                 670
Phe Tyr Thr Arg Pro Leu Glu Thr Phe Lys Asn Pro Arg Gly Gly Met
                675                 680                 685

Tyr Gln Ala Gly Leu Tyr Pro Val Ser Ala Asn Val Pro Leu Gly Ala
            690                 695                 700

Gln Thr Gly Ala Thr Pro Asp Gly Arg Leu Ala His Thr Pro Val Ala
705                 710                 715                 720

Asp Gly Val Gly Pro Thr Ser Gly Phe Asp Ile Ser Gly Pro Thr Ala
                725                 730                 735

Ser Cys Asn Ser Val Ala Lys Leu Asp His Ala Ile Ala Ser Asn Gly
            740                 745                 750

Thr Leu Phe Asn Met Lys Met His Pro Thr Ala Met Ala Gly Glu Lys
            755                 760                 765

Gly Leu Glu Ser Phe Ile Ser Leu Ile Arg Gly Tyr Phe Asp Gln Gln
        770                 775                 780

Gly Met His Met Gln Phe Asn Val Val Asp Arg Ala Thr Leu Leu Asp
785                 790                 795                 800

Ala Gln Ala His Pro Glu Lys Tyr Ser Gly Leu Ile Val Arg Val Ala
                805                 810                 815

Gly Tyr Ser Ala Leu Phe Thr Thr Leu Ser Lys Ser Leu Gln Asp Asp
            820                 825                 830

Ile Ile Lys Arg Thr Glu Gln Ala Asp Asn Arg
            835                 840

<210> SEQ ID NO 33
<211> LENGTH: 794
<212> TYPE: DNA
<213> ORGANISM: Roseburia inulinivorans

<400> SEQUENCE: 33
atgaaagaat atcttaatac ttcaggtaga atatttgata tccagaggta ttctattcac     60
gatggccctg gtgtgcgtac aattgtgttt ctaaaaggtt gtgcccttag atgcagatgg    120
tgctgtaatc ctgaaagcca aagcttcgaa gttgaaacaa tgacgattaa tggaaaacct    180
aaagtcatgg gtaaagatgt tacagtcgcc gaggttatga gacggtagaa agagacatg    240 ccttattacc ttcaatcagg tggtggtatc accttatcgg gtggcgaatg tactttgcaa    300 ccagaattt cccttggcct attgagagct gcaaaggatt gggcatatc cacggcaata    360 gagagcatgg cgtacgcaaa gtacgaagta atagaaactc ttcttccgta tttggatacg    420
tatttaatgg acatcaaaca tatgaatcct gagaaacata agaatacac tggtcatgat    480 aacttgagga tgttagaaaa cgccttaaga gtcgcgcatt ctggtcagac cgaactgatc    540
atcagagtac ctgtcatccc aggattcaac gcaactgagc aggaactact agatattgca    600
aaattcgcag atacactgcc tggagttaga caaatacaca tcttgccata tcataatttt    660
ggtcagggta aatacgaagg attgaacagg gactatccga tggggacac tgagaaaccc    720 tctaatgaac agatgaaagc ttttcaagaa atgattcaaa gaacacttc cctacattgc    780 caaatcggtg gtta                                                    794

<210> SEQ ID NO 34
<211> LENGTH: 264
<212> TYPE: PRT
<213> ORGANISM: roseburia inulinivorans

<400> SEQUENCE: 34
```

Met Lys Glu Tyr Leu Asn Thr Ser Gly Arg Ile Phe Asp Ile Gln Arg
1               5                   10                  15

Tyr Ser Ile His Asp Gly Pro Gly Val Arg Thr Ile Val Phe Leu Lys
            20                  25                  30

Gly Cys Ala Leu Arg Cys Arg Trp Cys Cys Asn Pro Glu Ser Gln Ser
        35                  40                  45

Phe Glu Val Glu Thr Met Thr Ile Asn Gly Lys Pro Lys Val Met Gly
    50                  55                  60

Lys Asp Val Thr Val Ala Glu Val Met Lys Thr Val Glu Arg Asp Met
65                  70                  75                  80

Pro Tyr Tyr Leu Gln Ser Gly Gly Ile Thr Leu Ser Gly Gly Glu
                85                  90                  95

Cys Thr Leu Gln Pro Glu Phe Ser Leu Gly Leu Leu Arg Ala Ala Lys
            100                 105                 110

Asp Leu Gly Ile Ser Thr Ala Ile Glu Ser Met Ala Tyr Ala Lys Tyr
            115                 120                 125

Glu Val Ile Glu Thr Leu Leu Pro Tyr Leu Asp Thr Tyr Leu Met Asp
            130                 135                 140

Ile Lys His Met Asn Pro Glu Lys His Lys Glu Tyr Thr Gly His Asp
145                 150                 155                 160

Asn Leu Arg Met Leu Glu Asn Ala Leu Arg Val Ala His Ser Gly Gln
                165                 170                 175

Thr Glu Leu Ile Ile Arg Val Pro Val Ile Pro Gly Phe Asn Ala Thr
            180                 185                 190

Glu Gln Glu Leu Leu Asp Ile Ala Lys Phe Ala Asp Thr Leu Pro Gly
            195                 200                 205

Val Arg Gln Ile His Ile Leu Pro Tyr His Asn Phe Gly Gln Gly Lys
            210                 215                 220

Tyr Glu Gly Leu Asn Arg Asp Tyr Pro Met Gly Asp Thr Glu Lys Pro
225                 230                 235                 240

Ser Asn Glu Gln Met Lys Ala Phe Gln Glu Met Ile Gln Lys Asn Thr
                245                 250                 255

Ser Leu His Cys Gln Ile Gly Gly
            260

<210> SEQ ID NO 35
<211> LENGTH: 1047
<212> TYPE: DNA
<213> ORGANISM: Achromobacter xylosoxidans

<400> SEQUENCE: 35
atgaaagctc tggtttatca cggtgaccac aagatctcgc ttgaagacaa gcccaagccc    60
acccttcaaa agcccacgga tgtagtagta cgggttttga agaccacgat ctgcggcacg   120
gatctcggca tctacaaagg caagaatcca gaggtcgccg acgggcgcat cctgggccat   180 gaagggggtag cgtcatcga ggaagtgggc gagagtgtca cgcagttcaa gaaaggcgac   240
aaggtcctga tttcctgcgt cacttcttgc ggctcgtgcg actactgcaa gaagcagctt   300
tactcccatt gccgcgacgg cgggtggatc ctgggttaca tgatcgatgg cgtgcaggcc   360
gaatacgtcc gcatcccgca tgccgacaac agcctctaca agatccccca gacaattgac   420
gacgaaatcg ccgtcctgct gagcgacatc ctgcccaccg ccacgaaat cggcgtccag   480 tatgggaatg tccagccggg cgatgcggtg gctattgtcg gcgcgggccc cgtcggcatg   540
tccgtactgt tgaccgccca gttctactcc cctcgaccat catcgtgat cgacatggac   600

```
gagaatcgcc tccagctcgc caaggagctc ggggcaacgc acaccatcaa ctccggcacg    660
gagaacgttg tcgaagccgt gcataggatt gcggcagagg gagtcgatgt tgcgatcgag    720
gcggtgggca taccggcgac ttgggacatc tgccaggaga tcgtcaagcc cggcgcgcac    780
atcgccaacg tcggcgtgca tggcgtcaag gttgacttcg agattcagaa gctctggatc    840
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc   1020
atcctctcga acgcaggcgc tgcctga                                       1047
```

<210> SEQ ID NO 36
<211> LENGTH: 348
<212> TYPE: PRT
<213> ORGANISM: Achromobacter xylosoxidans

<400> SEQUENCE: 36

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
```

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 37
<211> LENGTH: 1188
<212> TYPE: DNA
<213> ORGANISM: Saccharomyces cerevisiae

<400> SEQUENCE: 37
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc caggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatcttttgtt caaggaaggt cgtggtatta actcttctta cgccgtctgg     660
aacgatgtca ccggtaaggc tcacgaaaag gcccaagctt tggccgttgc cattggttcc     720
ggttacgttt accaaaccac tttcgaaaga gaagtcaact ctgacttgta cggtgaaaga     780
ggttgtttaa tgggtggtat ccacggtatg ttcttggctc aatacgacgt cttgagagaa     840
aacggtcact ccccatctga agctttcaac gaaaccgtcg aagaagctac ccaatctcta     900
tacccattga tcggtaagta cggtatggat acatgtacg atgcttgttc caccaccgcc     960
agaagaggtg ctttggactg gtacccaatc ttcaagaatg ctttgaagcc tgttttccaa    1020
gacttgtacg aatctaccaa gaacggtacc gaaaccaaga gatctttgga attcaactct    1080
caacctgact acagagaaaa gctagaaaag gaattagaca ccatcagaaa catggaaatc    1140
tggaaggttg gtaaggaagt cagaaagttg agaccagaaa accaataa                 1188

<210> SEQ ID NO 38
<211> LENGTH: 395
<212> TYPE: PRT
<213> ORGANISM: Saccharomyces cerevisiae

<400> SEQUENCE: 38

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

```
Asp Trp Pro Arg Glu Lys Leu Leu Asp Tyr Phe Lys Asn Asp Thr Phe
 65                  70                  75                  80

Ala Leu Ile Gly Tyr Gly Ser Gln Gly Tyr Gly Gln Gly Leu Asn Leu
                 85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395

<210> SEQ ID NO 39
<211> LENGTH: 1485
<212> TYPE: DNA
<213> ORGANISM: Vibrio cholerae

<400> SEQUENCE: 39
atggcgaatt atttcaatac gctgaatctg cgtgaacagt tggatcaact tggtcgttgc      60
cgttttatgg cgcgagaaga gtttgcaacc gaagctgatt acctaaaagg taagaaagtg     120
gtgatcgtag ttgtggggc tcaaggccta aaccaaggcc tcaatatgcg tgattccagt     180
ttggatgttt cttacgctct gcgtcaggct gcgattgatg aacagcgtca gtcatttaag     240
```

```
aatgccaaga ataatggctt caacgtgggt agttatgaac aactcatccc aaccgcagat    300
ttggtgatta acttgacgcc agacaagcag cacaccagtg tggtcaatgc ggtgatgcct    360
ctgatgaagc aaggtgctgc cttgggttac tcacacggtt ttaatatcgt tgaagagggc    420
atgcagatcc gtaaagacat cacggttgtg atggtggcac caaaatgtcc gggtacggaa    480
gttcgtgaag agtataagcg cggtttcggc gttcctactc ttatcgcggt acaccctgaa    540
aacgatccac aaggtgaagg ttgggaaatt gctaaagcgt gggctgcggc aacgggtggc    600
catcgtgcgg gctgtttagc ttcttctttt gtggcggaag tgaaatccga tttgatgggt    660
gagcaaacca ttctctgcgg tatgctgcaa gcgggctcta tcgtttgtta cgagaaaatg    720
gttgctgatg gcatcgaccc tggttatgcg ggcaagcttt tgcaatttgg ttgggaaacc    780
attaccgaag cactcaagtt tggcggtatt actcatatga tggatcgcct gtctaaccct    840
gcaaaaatca aagcgtttga gctgtctgaa gagttgaaag atctgatgcg cccactgtac    900
aacaagcata tggatgacat catttctggc cacttctcta gcaccatgat ggcggattgg    960
gcgaatgatg ataaagactt attcggctgg cgtgcagaaa ccgctgagac gacctttgaa   1020
aactatccaa caaccgacgt aaaaattgct gagcaagaat actttgataa cggtattttg   1080
atgattgcca tggtgcgtgc tggggttgag ttggcgtttg aagcgatgac ggcttcaggc   1140
atcatcgatg agtcggctta ctatgaatca ctgcacgaac tcccactgat tgccaatacg   1200
gtagcgcgta agcgtctgta tgaaatgaac gtggtaatct ctgacactgc tgagtacggt   1260
aactatctgt ttgccaatgt ggcggtacca ctattgcgtg aaaagtttat gccgaaagtg   1320
ggcactgatg tgattggtaa aggattaggc gtggtctcta atcaagttga taacgcaacg   1380
cttatcgaag taaacagcat catccgtaac catccggttg agtatatcgg tgaagagcta   1440
cgcggttaca tgaaagacat gaagcgcatc gccgtgggtg attaa              1485
```

<210> SEQ ID NO 40
<211> LENGTH: 494
<212> TYPE: PRT
<213> ORGANISM: Vibrio cholerae

<400> SEQUENCE: 40

```
Met Ala Asn Tyr Phe Asn Thr Leu Asn Leu Arg Glu Gln Leu Asp Gln
1               5                   10                  15

Leu Gly Arg Cys Arg Phe Met Ala Arg Glu Glu Phe Ala Thr Glu Ala
            20                  25                  30

Asp Tyr Leu Lys Gly Lys Lys Val Val Ile Val Gly Cys Gly Ala Gln
        35                  40                  45

Gly Leu Asn Gln Gly Leu Asn Met Arg Asp Ser Gly Leu Asp Val Ser
    50                  55                  60

Tyr Ala Leu Arg Gln Ala Ala Ile Asp Glu Arg Gln Ser Phe Lys
65                  70                  75                  80

Asn Ala Lys Asn Gly Phe Asn Val Gly Ser Tyr Glu Gln Leu Ile
                85                  90                  95

Pro Thr Ala Asp Leu Val Ile Asn Leu Thr Pro Asp Lys Gln His Thr
            100                 105                 110

Ser Val Val Asn Ala Val Met Pro Leu Met Lys Gln Gly Ala Ala Leu
        115                 120                 125

Gly Tyr Ser His Gly Phe Asn Ile Val Glu Glu Gly Met Gln Ile Arg
    130                 135                 140

Lys Asp Ile Thr Val Val Met Val Ala Pro Lys Cys Pro Gly Thr Glu
145                 150                 155                 160
```

Val Arg Glu Glu Tyr Lys Arg Gly Phe Gly Val Pro Thr Leu Ile Ala
            165                 170                 175

Val His Pro Glu Asn Asp Pro Gln Gly Glu Gly Trp Glu Ile Ala Lys
        180                 185                 190

Ala Trp Ala Ala Ala Thr Gly Gly His Arg Ala Gly Cys Leu Ala Ser
            195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Ile Val Cys Tyr Glu Lys Met
225                 230                 235                 240

Val Ala Asp Gly Ile Asp Pro Gly Tyr Ala Gly Lys Leu Leu Gln Phe
                245                 250                 255

Gly Trp Glu Thr Ile Thr Glu Ala Leu Lys Phe Gly Gly Ile Thr His
            260                 265                 270

Met Met Asp Arg Leu Ser Asn Pro Ala Lys Ile Lys Ala Phe Glu Leu
        275                 280                 285

Ser Glu Glu Leu Lys Asp Leu Met Arg Pro Leu Tyr Asn Lys His Met
    290                 295                 300

Asp Asp Ile Ile Ser Gly His Phe Ser Ser Thr Met Met Ala Asp Trp
305                 310                 315                 320

Ala Asn Asp Asp Lys Asp Leu Phe Gly Trp Arg Ala Glu Thr Ala Glu
                325                 330                 335

Thr Thr Phe Glu Asn Tyr Pro Thr Thr Asp Val Lys Ile Ala Glu Gln
            340                 345                 350

Glu Tyr Phe Asp Asn Gly Ile Leu Met Ile Ala Met Val Arg Ala Gly
        355                 360                 365

Val Glu Leu Ala Phe Glu Ala Met Thr Ala Ser Gly Ile Ile Asp Glu
    370                 375                 380

Ser Ala Tyr Tyr Glu Ser Leu His Glu Leu Pro Leu Ile Ala Asn Thr
385                 390                 395                 400

Val Ala Arg Lys Arg Leu Tyr Glu Met Asn Val Val Ile Ser Asp Thr
                405                 410                 415

Ala Glu Tyr Gly Asn Tyr Leu Phe Ala Asn Val Ala Val Pro Leu Leu
            420                 425                 430

Arg Glu Lys Phe Met Pro Lys Val Gly Thr Asp Val Ile Gly Lys Gly
        435                 440                 445

Leu Gly Val Val Ser Asn Gln Val Asp Asn Ala Thr Leu Ile Glu Val
    450                 455                 460

Asn Ser Ile Ile Arg Asn His Pro Val Glu Tyr Ile Gly Glu Glu Leu
465                 470                 475                 480

Arg Gly Tyr Met Lys Asp Met Lys Arg Ile Ala Val Gly Asp
                485                 490

<210> SEQ ID NO 41
<211> LENGTH: 1014
<212> TYPE: DNA
<213> ORGANISM: Pseudomonas

<400> SEQUENCE: 41
atgcgcgttt tctacgataa agactgtgac ctctcgatca tccagggcaa gaaagttgcc     60
atcatcggct acggctccca gggccacgcc catgcctgca acctgaagga ctccggcgtc    120
gacgtcaccg tgggcctgcg tagcggctcc gccaccgtgg ccaaggccga agcgcacggt    180
ctgaaggttg ccgacgtgaa gaccgccgtc gccgcagccg acgtggtcat gatcctcacc    240

```
ccggacgagt tccagggccg cctgtacaag gaagagatcg agccgaacct gaagaagggc    300
gccaccctgg ccttcgctca cggcttctcc atccactaca accaggtcgt cccgcgcgcc    360
gacctcgacg tgatcatgat cgcgccgaag caccgggtc acaccgtgcg ttccgagttc     420
gtcaagggcg gtggcatccc tgacctgatc gccatctacc aggacgcttc cggcaacgcc    480
aagaacgtcg ccctgtccta cgcctgcggc gtcggcggcg gtcgtaccgg tatcatcgaa    540
accaccttca aggacgagac cgaaaccgac ctgttcggtg agcaggccgt tctctgcggt    600
ggttgcgtcg agctggtcaa ggccggtttc gaaaccctgg tcgaagccgg ttacgcgccg    660
gaaatggcct acttcgagtg cctgcacgag ctgaagctga tcgtcgacct gatgtacgaa    720
ggcggcatcg ccaacatgaa ctactccatc tccaacaatg ccgaatacgg tgagtacgta    780
accggtccgg aggtgatcaa cgccgagtcc cgtgctgcca tgcgcaacgc cctgaagcgc    840
atccaggacg gcgagtacgc gaaaatgttc attaccgaag gtgcggccaa ctacccgtcg    900
atgactgcct accgccgcaa caacgccgct cacccgatcg agcagatcgg cgagaagctg    960
cgcgcgatga tgccgtggat cgcagccaac aagatcgtcg acaagagcaa gaac         1014
```

<210> SEQ ID NO 42
<211> LENGTH: 338
<212> TYPE: PRT
<213> ORGANISM: Pseudomonas

<400> SEQUENCE: 42

```
Met Arg Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala His Ala
            20                  25                  30

Cys Asn Leu Lys Asp Ser Gly Val Asp Val Thr Val Gly Leu Arg Ser
        35                  40                  45

Gly Ser Ala Thr Val Ala Lys Ala Glu Ala His Gly Leu Lys Val Ala
    50                  55                  60

Asp Val Lys Thr Ala Val Ala Ala Asp Val Val Met Ile Leu Thr
65                  70                  75                  80

Pro Asp Glu Phe Gln Gly Arg Leu Tyr Lys Glu Ile Glu Pro Asn
                85                  90                  95

Leu Lys Lys Gly Ala Thr Leu Ala Phe Ala His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Cys Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Cys Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240
```

Gly Gly Ile Ala Asn Met Asn Tyr Ser Ile Ser Asn Ala Glu Tyr
            245                 250                 255

Gly Glu Tyr Val Thr Gly Pro Glu Val Ile Asn Ala Glu Ser Arg Ala
        260                 265                 270

Ala Met Arg Asn Ala Leu Lys Arg Ile Gln Asp Gly Glu Tyr Ala Lys
    275                 280                 285

Met Phe Ile Thr Glu Gly Ala Ala Asn Tyr Pro Ser Met Thr Ala Tyr
290                 295                 300

Arg Arg Asn Asn Ala Ala His Pro Ile Glu Gln Ile Gly Glu Lys Leu
305                 310                 315                 320

Arg Ala Met Met Pro Trp Ile Ala Ala Asn Lys Ile Val Asp Lys Ser
                325                 330                 335

Lys Asn

<210> SEQ ID NO 43
<211> LENGTH: 1014
<212> TYPE: DNA
<213> ORGANISM: Pseudomonas fluorescens

<400> SEQUENCE: 43

```
atgaaagttt tctacgataa agactgcgac ctgtcgatca tccaaggtaa gaaagttgcc      60
atcatcggct acggttccca gggccacgct caagcatgca acctgaagga ttccggcgta     120
gacgtgactg ttggcctgcg taaaggctcg gctaccgttg ccaaggctga agcccacggc     180
ttgaaagtga ccgacgttgc tgcagccgtt gccggtgccg acttggtcat gatcctgacc     240
ccggacgagt tccagtccca gctgtacaag aacgaaatcg agccgaacat caagaagggc     300
gccactctgg ccttctccca cggcttcgcg atccactaca accaggttgt gcctcgtgcc     360
gacctcgacg tgatcatgat cgcgccgaag gctccaggcc acaccgtacg ttccgagttc     420
gtcaagggcg tgtggtattcc tgacctgatc gcgatctacc aggacgcttc cggcaacgcc     480
aagaacgttg ccctgtccta cgccgcaggc gtgggcggcg ccgtaccggg catcatcgaa     540
accaccttca aggacgagac tgaaaccgac ctgttcggtg agcaggctgt tctgtgtggc     600
ggtaccgtcg agctggtcaa agccggtttc gaaaccctgg ttgaagctgg ctacgctcca     660
gaaatggcct acttcgagtg cctgcacgaa ctgaagctga tcgttgacct catgtacgaa     720
ggcggtatcg ccaacatgaa ctactcgatc tccaacaacg ctgaatacgg cgagtacgtg     780
actggtccag aagtcatcaa cgccgaatcc cgtcaggcca tgcgcaatgc tctgaagcgc     840
atccaggacg gcgaatacgc gaagatgttc atcagcgaag gcgctaccgg ctacccatcg     900
atgaccgcca agcgtcgtaa caacgctgct cacggtatcg aaatcatcgg cgagcaactg     960
cgctcgatga tgccttggat cggtgccaac aaaatcgtcg acaaagccaa gaac          1014
```

<210> SEQ ID NO 44
<211> LENGTH: 338
<212> TYPE: PRT
<213> ORGANISM: Pseudomonas

<400> SEQUENCE: 44

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Arg Lys
        35                  40                  45

```
Gly Ser Ala Thr Val Ala Lys Ala Glu Ala His Gly Leu Lys Val Thr
     50                  55                  60
Asp Val Ala Ala Val Ala Gly Ala Asp Leu Val Met Ile Leu Thr
 65                  70                  75                  80
Pro Asp Glu Phe Gln Ser Gln Leu Tyr Lys Asn Glu Ile Glu Pro Asn
                 85                  90                  95
Ile Lys Lys Gly Ala Thr Leu Ala Phe Ser His Gly Phe Ala Ile His
            100                 105                 110
Tyr Asn Gln Val Val Pro Arg Ala Asp Leu Asp Val Ile Met Ile Ala
        115                 120                 125
Pro Lys Ala Pro Gly His Thr Val Arg Ser Glu Phe Val Lys Gly Gly
    130                 135                 140
Gly Ile Pro Asp Leu Ile Ala Ile Tyr Gln Asp Ala Ser Gly Asn Ala
145                 150                 155                 160
Lys Asn Val Ala Leu Ser Tyr Ala Ala Gly Val Gly Gly Gly Arg Thr
                165                 170                 175
Gly Ile Ile Glu Thr Thr Phe Lys Asp Glu Thr Glu Thr Asp Leu Phe
            180                 185                 190
Gly Glu Gln Ala Val Leu Cys Gly Gly Thr Val Glu Leu Val Lys Ala
        195                 200                 205
Gly Phe Glu Thr Leu Val Glu Ala Gly Tyr Ala Pro Glu Met Ala Tyr
    210                 215                 220
Phe Glu Cys Leu His Glu Leu Lys Leu Ile Val Asp Leu Met Tyr Glu
225                 230                 235                 240
Gly Gly Ile Ala Asn Met Asn Tyr Ser Ile Ser Asn Asn Ala Glu Tyr
                245                 250                 255
Gly Glu Tyr Val Thr Gly Pro Glu Val Ile Asn Ala Glu Ser Arg Gln
            260                 265                 270
Ala Met Arg Asn Ala Leu Lys Arg Ile Gln Asp Gly Glu Tyr Ala Lys
        275                 280                 285
Met Phe Ile Ser Glu Gly Ala Thr Gly Tyr Pro Ser Met Thr Ala Lys
    290                 295                 300
Arg Arg Asn Asn Ala Ala His Gly Ile Glu Ile Gly Glu Gln Leu
305                 310                 315                 320
Arg Ser Met Met Pro Trp Ile Gly Ala Asn Lys Ile Val Asp Lys Ala
                325                 330                 335
Lys Asn

<210> SEQ ID NO 45
<211> LENGTH: 1758
<212> TYPE: DNA
<213> ORGANISM: Saccharomyces cerevisiae

<400> SEQUENCE: 45
atgggcttgt taacgaaagt tgctacatct agacaattct ctacaacgag atgcgttgca        60
aagaagctca acaagtactc gtatatcatc actgaaccta agggccaagg tgcgtcccag       120
gccatgcttt atgccaccgg tttcaagaag gaagatttca agaagcctca agtcggggtt       180
ggttcctgtt ggtggtccgg taaccatgt aacatgcatc tattggactt gaataacaga       240
tgttctcaat ccattgaaaa agcgggtttg aaagctatgc agttcaacac catcggtgtt       300
tcagacggta tctctatggg tactaaaggt atgagatact cgttacaaag tagagaaatc       360
attgcagact cctttgaaac catcatgatg gcacaacact acgatgctaa catcgccatc       420
```

```
ccatcatgtg acaaaaacat gcccggtgtc atgatggcca tgggtagaca taacagacct    480
tccatcatgg tatatggtgg tactatcttg cccggtcatc caacatgtgg ttcttcgaag    540
atctctaaaa acatcgatat cgtctctgcg ttccaatcct acggtgaata tatttccaag    600
caattcactg aagaagaaag agaagatgtt gtggaacatg catgcccagg tcctggttct    660
tgtggtggta tgtatactgc aacacaatg gcttctgccg ctgaagtgct aggtttgacc    720
attccaaact cctcttcctt cccagccgtt tccaaggaga agttagctga gtgtgacaac    780
attggtgaat acatcaagaa gacaatggaa ttgggtattt acctcgtga tatcctcaca    840
aaagaggctt ttgaaaacgc cattacttat gtcgttgcaa ccggtgggtc cactaatgct    900
gttttgcatt tggtggctgt tgctcactct gcgggtgtca agttgtcacc agatgatttc    960
caaagaatca gtgatactac accattgatc ggtgacttca aaccttctgg taaatacgtc   1020
atggccgatt tgattaacgt tggtggtacc caatctgtga ttaagtatct atatgaaaac   1080
aacatgttgc acggtaacac aatgactgtt accggtgaca ctttggcaga acgtgcaaag   1140
aaagcaccaa gcctacctga aggacaagag attattaagc cactctccca cccaatcaag   1200
gccaacggtc acttgcaaat tctgtacggt tcattggcac aggtggagc tgtgggtaaa   1260
attaccggta aggaaggtac ttacttcaag ggtagacac gtgtgttcga agaggaaggt   1320
gcctttattg aagccttgga aagaggtgaa atcaagaagg gtgaaaaaac cgttgttgtt   1380
atcagatatg aaggtccaag aggtgcacca ggtatgcctg aaatgctaaa gccttcctct   1440
gctctgatgg gttacggttt gggtaaagat gttgcattgt tgactgatgg tagattctct   1500
ggtggttctc acgggttctt aatcggccac attgttcccg aagccgctga aggtggtcct   1560
atcgggttgg tcagagacgg cgatgagatt atcattgatg ctgataataa caagattgac   1620
ctattagtct ctgataagga aatggctcaa cgtaaacaaa gttgggttgc acctccacct   1680
cgttacacaa gaggtactct atccaagtat gctaagttgg tttccaacgc ttccaacggt   1740
tgtgttttag atgcttga                                                 1758
```

<210> SEQ ID NO 46
<211> LENGTH: 585
<212> TYPE: PRT
<213> ORGANISM: Saccharomyces cerevisiae

<400> SEQUENCE: 46

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
                20                  25                  30

Pro Lys Gly Gln Gly Ala Ser Gln Ala Met Leu Tyr Ala Thr Gly Phe
            35                  40                  45

Lys Lys Glu Asp Phe Lys Lys Pro Gln Val Gly Val Gly Ser Cys Trp
        50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
```

```
                130                 135                 140
Lys Asn Met Pro Gly Val Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
                180                 185                 190

Ser Tyr Gly Glu Tyr Ile Ser Lys Gln Phe Thr Glu Glu Arg Glu
                195                 200                 205

Asp Val Val Glu His Ala Cys Pro Gly Pro Ser Cys Gly Gly Met
210                 215                 220

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
                260                 265                 270

Ile Leu Pro Arg Asp Ile Leu Thr Lys Glu Ala Phe Glu Asn Ala Ile
                275                 280                 285

Thr Tyr Val Val Ala Thr Gly Gly Ser Thr Asn Ala Val Leu His Leu
290                 295                 300

Val Ala Val Ala His Ser Ala Gly Val Lys Leu Ser Pro Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
                340                 345                 350

Val Ile Lys Tyr Leu Tyr Glu Asn Asn Met Leu His Gly Asn Thr Met
                355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
                420                 425                 430

Ala Arg Val Phe Glu Glu Glu Gly Ala Phe Ile Glu Ala Leu Glu Arg
                435                 440                 445

Gly Glu Ile Lys Lys Gly Glu Lys Thr Val Val Ile Arg Tyr Glu
450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
                500                 505                 510

Pro Glu Ala Ala Glu Gly Gly Pro Ile Gly Leu Val Arg Asp Gly Asp
                515                 520                 525

Glu Ile Ile Ile Asp Ala Asp Asn Asn Lys Ile Asp Leu Leu Val Ser
530                 535                 540

Asp Lys Glu Met Ala Gln Arg Lys Gln Ser Trp Val Ala Pro Pro Pro
545                 550                 555                 560
```

Arg Tyr Thr Arg Gly Thr Leu Ser Lys Tyr Ala Lys Leu Val Ser Asn
            565                 570                 575

Ala Ser Asn Gly Cys Val Leu Asp Ala
            580                 585

<210> SEQ ID NO 47
<211> LENGTH: 1662
<212> TYPE: DNA
<213> ORGANISM: Lactococcus lactis

<400> SEQUENCE: 47

| | | | | | |
|---|---|---|---|---|---|
| tctagacata | tgtatactgt | ggggattac | ctgctggatc | gcctgcacga | actggggatt | 60 |
| gaagaaattt | tcggtgtgcc | aggcgattat | aacctgcagt | tcctggacca | gattatctcg | 120 |
| cacaaagata | tgaagtgggt | cggtaacgcc | aacgaactga | acgcgagcta | tatggcagat | 180 |
| ggttatgccc | gtaccaaaaa | agctgctgcg | tttctgacga | cctttggcgt | tggcgaactg | 240 |
| agcgccgtca | acggactggc | aggaagctac | gccgagaacc | tgccagttgt | cgaaattgtt | 300 |
| gggtcgccta | cttctaaggt | tcagaatgaa | ggcaaatttg | tgcaccatac | tctggctgat | 360 |
| ggggatttta | acatttat | gaaaatgcat | gaaccggtta | ctgcggcccg | cacgctgctg | 420 |
| acagcagaga | atgctacggt | tgagatcgac | cgcgtcctgt | ctgcgctgct | gaaagagcgc | 480 |
| aagccggtat | atatcaatct | gcctgtcgat | gttgccgcag | cgaaagccga | aaagccgtcg | 540 |
| ctgccactga | aaaagaaaa | cagcacctcc | aatacatcgg | accaggaaat | tctgaataaa | 600 |
| atccaggaat | cactgaagaa | tgcgaagaaa | ccgatcgtca | tcaccggaca | tgagatcatc | 660 |
| tcttttggcc | tggaaaaaac | ggtcacgcag | ttcatttcta | agaccaaact | gcctatcacc | 720 |
| accctgaact | tcggcaaatc | tagcgtcgat | gaagcgctgc | cgagttttct | gggtatctat | 780 |
| aatggtaccc | tgtccgaacc | gaacctgaaa | gaattcgtcg | aaagcgcgga | ctttatcctg | 840 |
| atgctgggcg | tgaaactgac | ggatagctcc | acaggcgcat | ttacccacca | tctgaacgag | 900 |
| aataaaatga | tttccctgaa | tatcgacgaa | ggcaaaatct | ttaacgagcg | catccagaac | 960 |
| ttcgattttg | aatctctgat | tagttcgctg | ctggatctgt | ccgaaattga | gtataaaggt | 1020 |
| aaatatattg | ataaaaaaca | ggaggatttt | gtgccgtcta | atgcgctgct | gagtcaggat | 1080 |
| cgtctgtggc | aagccgtaga | aaacctgaca | cagtctaatg | aaacgattgt | tgcggaacag | 1140 |
| ggaacttcat | ttttcggcgc | ctcatccatt | tttctgaaat | ccaaaagcca | tttcattggc | 1200 |
| caaccgctgt | ggggagtat | tggttatacc | tttccggcgg | cgctgggttc | acagattgca | 1260 |
| gataaggaat | cacgccatct | gctgtttatt | ggtgacggca | gcctgcagct | gactgtccag | 1320 |
| gaactggggc | tggcgatccg | tgaaaaaatc | aatccgattt | gctttatcat | caataacgac | 1380 |
| ggctacaccg | tcgaacgcga | aattcatgga | ccgaatcaaa | gttacaatga | catcccgatg | 1440 |
| tggaactata | gcaaactgcc | ggaatccttt | ggcgcgacag | aggatcgcgt | ggtgagtaaa | 1500 |
| attgtgcgta | cggaaaacga | atttgtgtcg | gttatgaaag | aagcgcaggc | tgacccgaat | 1560 |
| cgcatgtatt | ggattgaact | gatcctggca | aaagaaggcg | caccgaaagt | tctgaaaaag | 1620 |
| atggggaaac | tgtttgcgga | gcaaaataaa | agctaaggat | cc | | 1662 |

<210> SEQ ID NO 48
<211> LENGTH: 548
<212> TYPE: PRT
<213> ORGANISM: Lactococcus lactis

<400> SEQUENCE: 48

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
            35                  40                  45

Glu Leu Asn Ala Ser Tyr Met Ala Asp Gly Tyr Ala Arg Thr Lys Lys
50                  55                  60

Ala Ala Ala Phe Leu Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
            130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
```

```
                420             425             430
Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 49
<211> LENGTH: 1647
<212> TYPE: DNA
<213> ORGANISM: Lactococcus lactis

<400> SEQUENCE: 49
atgtatacag taggagatta cctattagac cgattacacg agttaggaat tgaagaaatt      60
tttggagtcc ctggagacta taacttacaa ttttttagatc aaattatttc ccacaaggat    120
atgaaatggg tcggaaatgc taatgaatta aatgcttcat atatggctga tggctatgct    180
cgtactaaaa aagctgccgc atttcttaca acctttggag taggtgaatt gagtgcagtt    240
aatggattag caggaagtta cgccgaaaat ttaccagtag tagaaatagt gggatcacct    300
acatcaaaag ttcaaaatga aggaaaattt gttcatcata cgctggctga cggtgatttt    360
aaacacttta tgaaaatgca cgaacctgtt acagcagctc gaactttact gacagcagaa    420
aatgcaaccg ttgaaattga ccgagtactt tctgcactat aaaagaaag aaaacctgtc    480 tatatcaact taccagttga tgttgctgct gcaaaagcag agaaaccctc actccctttg    540
aaaaaggaaa actcaacttc aaatacaagt gaccaagaaa ttttgaacaa aattcaagaa    600
agcttgaaaa atgccaaaaa accaatcgtg attacaggac atgaaataat tagttttggc    660
ttagaaaaaa cagtcactca atttatttca aagacaaaac tacctattac gacattaaac    720
tttggtaaaa gttcagttga tgaagccctc ccttcatttt taggaatcta taatggtaca    780
ctctcagagc ctaatcttaa agaattcgtg gaatcagccg acttcatctt gatgcttgga    840
gttaaactca cagactcttc aacaggagcc ttcactcatc atttaaatga aaataaaatg    900
atttcactga atatagatga aggaaaaata tttaacgaaa gaatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaaccctaac tcaaagcaat gaaacaatcg ttgctgaaca agggacatca   1140
ttctttggcg cttcatcaat tttcttaaaa tcaaagagtc atttattgg tcaaccctta   1200 tggggatcaa ttggatatac attcccagca gcattaggaa gccaaattgc agataaagaa   1260
agcagacacc ttttattta tggtgatggt tcacttcaac ttacagtgca agaattagga   1320
ttagcaatca gagaaaaaat taatccaatt tgctttatta tcaataatga tggttataca   1380
```

-continued

```
gtcgaaagag aaattcatgg accaaatcaa agctacaatg atattccaat gtggaattac    1440
tcaaaattac cagaatcgtt tggagcaaca gaagatcgag tagtctcaaa atcgttaga     1500 actgaaaatg aatttgtgtc tgtcatgaaa gaagctcaag cagatccaaa tagaatgtac    1560
tggattgagt taattttggc aaaagaaggt gcaccaaaag tactgaaaaa aatgggcaaa    1620
ctatttgctg aacaaaataa atcataa                                        1647
```

<210> SEQ ID NO 50
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 50

| | | | | | | | | | | | | | | | |
|---|---|---|---|---|---|---|---|---|---|---|---|---|---|---|---|
| atg | tct | gaa | att | act | ttg | ggt | aaa | tat | ttg | ttc | gaa | aga | tta | aag | caa | 48 |
| Met | Ser | Glu | Ile | Thr | Leu | Gly | Lys | Tyr | Leu | Phe | Glu | Arg | Leu | Lys | Gln | |
| 1 | | | | 5 | | | | | 10 | | | | | 15 | | |

| gtc | aac | gtt | aac | acc | gtt | ttc | ggt | ttg | cca | ggt | gac | ttc | aac | ttg | tcc | 96 |
|---|---|---|---|---|---|---|---|---|---|---|---|---|---|---|---|---|
| Val | Asn | Val | Asn | Thr | Val | Phe | Gly | Leu | Pro | Gly | Asp | Phe | Asn | Leu | Ser | |
| | | | 20 | | | | | 25 | | | | | 30 | | | |

| ttg | ttg | gac | aag | atc | tac | gaa | gtt | gaa | ggt | atg | aga | tgg | gct | ggt | aac | 144 |
|---|---|---|---|---|---|---|---|---|---|---|---|---|---|---|---|---|
| Leu | Leu | Asp | Lys | Ile | Tyr | Glu | Val | Glu | Gly | Met | Arg | Trp | Ala | Gly | Asn | |
| | | 35 | | | | | 40 | | | | | 45 | | | | |

| gcc | aac | gaa | ttg | aac | gct | gct | tac | gcc | gct | gat | ggt | tac | gct | cgt | atc | 192 |
|---|---|---|---|---|---|---|---|---|---|---|---|---|---|---|---|---|
| Ala | Asn | Glu | Leu | Asn | Ala | Ala | Tyr | Ala | Ala | Asp | Gly | Tyr | Ala | Arg | Ile | |
| | 50 | | | | | 55 | | | | | 60 | | | | | |

| aag | ggt | atg | tct | tgt | atc | atc | acc | acc | ttc | ggt | gtc | ggt | gaa | ttg | tct | 240 |
|---|---|---|---|---|---|---|---|---|---|---|---|---|---|---|---|---|
| Lys | Gly | Met | Ser | Cys | Ile | Ile | Thr | Thr | Phe | Gly | Val | Gly | Glu | Leu | Ser | |
| 65 | | | | | 70 | | | | | 75 | | | | | 80 | |

| gct | ttg | aac | ggt | att | gcc | ggt | tct | tac | gct | gaa | cac | gtc | ggt | gtt | ttg | 288 |
|---|---|---|---|---|---|---|---|---|---|---|---|---|---|---|---|---|
| Ala | Leu | Asn | Gly | Ile | Ala | Gly | Ser | Tyr | Ala | Glu | His | Val | Gly | Val | Leu | |
| | | | | 85 | | | | | 90 | | | | | 95 | | |

| cac | gtt | gtt | ggt | gtc | cca | tcc | atc | tct | gct | caa | gct | aag | caa | ttg | ttg | 336 |
|---|---|---|---|---|---|---|---|---|---|---|---|---|---|---|---|---|
| His | Val | Val | Gly | Val | Pro | Ser | Ile | Ser | Ala | Gln | Ala | Lys | Gln | Leu | Leu | |
| | | | 100 | | | | | 105 | | | | | 110 | | | |

| ttg | cac | cac | acc | ttg | ggt | aac | ggt | gac | ttc | act | gtt | ttc | cac | aga | atg | 384 |
|---|---|---|---|---|---|---|---|---|---|---|---|---|---|---|---|---|
| Leu | His | His | Thr | Leu | Gly | Asn | Gly | Asp | Phe | Thr | Val | Phe | His | Arg | Met | |
| | | 115 | | | | | 120 | | | | | 125 | | | | |

| tct | gcc | aac | att | tct | gaa | acc | act | gct | atg | atc | act | gac | att | gct | acc | 432 |
|---|---|---|---|---|---|---|---|---|---|---|---|---|---|---|---|---|
| Ser | Ala | Asn | Ile | Ser | Glu | Thr | Thr | Ala | Met | Ile | Thr | Asp | Ile | Ala | Thr | |
| | 130 | | | | | 135 | | | | | 140 | | | | | |

| gcc | cca | gct | gaa | att | gac | aga | tgt | atc | aga | acc | act | tac | gtc | acc | caa | 480 |
|---|---|---|---|---|---|---|---|---|---|---|---|---|---|---|---|---|
| Ala | Pro | Ala | Glu | Ile | Asp | Arg | Cys | Ile | Arg | Thr | Thr | Tyr | Val | Thr | Gln | |
| 145 | | | | | 150 | | | | | 155 | | | | | 160 | |

| aga | cca | gtc | tac | tta | ggt | ttg | cca | gct | aac | ttg | gtc | gac | ttg | aac | gtc | 528 |
|---|---|---|---|---|---|---|---|---|---|---|---|---|---|---|---|---|
| Arg | Pro | Val | Tyr | Leu | Gly | Leu | Pro | Ala | Asn | Leu | Val | Asp | Leu | Asn | Val | |
| | | | | 165 | | | | | 170 | | | | | 175 | | |

| cca | gct | aag | ttg | ttg | caa | act | cca | att | gac | atg | tct | ttg | aag | cca | aac | 576 |
|---|---|---|---|---|---|---|---|---|---|---|---|---|---|---|---|---|
| Pro | Ala | Lys | Leu | Leu | Gln | Thr | Pro | Ile | Asp | Met | Ser | Leu | Lys | Pro | Asn | |
| | | | 180 | | | | | 185 | | | | | 190 | | | |

| gat | gct | gaa | tcc | gaa | aag | gaa | gtc | att | gac | acc | atc | ttg | gct | ttg | gtc | 624 |
|---|---|---|---|---|---|---|---|---|---|---|---|---|---|---|---|---|
| Asp | Ala | Glu | Ser | Glu | Lys | Glu | Val | Ile | Asp | Thr | Ile | Leu | Ala | Leu | Val | |
| | | 195 | | | | | 200 | | | | | 205 | | | | |

| aag | gat | gct | aag | aac | cca | gtt | atc | ttg | gct | gat | gct | tgt | tgt | tcc | aga | 672 |
|---|---|---|---|---|---|---|---|---|---|---|---|---|---|---|---|---|
| Lys | Asp | Ala | Lys | Asn | Pro | Val | Ile | Leu | Ala | Asp | Ala | Cys | Cys | Ser | Arg | |
| | 210 | | | | | 215 | | | | | 220 | | | | | |

| cac | gac | gtc | aag | gct | gaa | act | aag | aag | ttg | att | gac | ttg | act | caa | ttc | 720 |
|---|---|---|---|---|---|---|---|---|---|---|---|---|---|---|---|---|
| His | Asp | Val | Lys | Ala | Glu | Thr | Lys | Lys | Leu | Ile | Asp | Leu | Thr | Gln | Phe | |

```
His Asp Val Lys Ala Glu Thr Lys Lys Leu Ile Asp Leu Thr Gln Phe
225                 230                 235                 240 cca gct ttc gtc acc cca atg ggt aag ggt tcc att gac gaa caa cac       768
Pro Ala Phe Val Thr Pro Met Gly Lys Gly Ser Ile Asp Glu Gln His
                    245                 250                 255 cca aga tac ggt ggt gtt tac gtc ggt acc ttg tcc aag cca gaa gtt       816
Pro Arg Tyr Gly Gly Val Tyr Val Gly Thr Leu Ser Lys Pro Glu Val
                260                 265                 270 aag gaa gcc gtt gaa tct gct gac ttg att ttg tct gtc ggt gct ttg       864
Lys Glu Ala Val Glu Ser Ala Asp Leu Ile Leu Ser Val Gly Ala Leu
            275                 280                 285 ttg tct gat ttc aac acc ggt tct ttc tct tac tct tac aag acc aag       912
Leu Ser Asp Phe Asn Thr Gly Ser Phe Ser Tyr Ser Tyr Lys Thr Lys
        290                 295                 300 aac att gtc gaa ttc cac tcc gac cac atg aag atc aga aac gcc act       960
Asn Ile Val Glu Phe His Ser Asp His Met Lys Ile Arg Asn Ala Thr
305                 310                 315                 320 ttc cca ggt gtc caa atg aaa ttc gtt ttg caa aag ttg ttg acc act      1008
Phe Pro Gly Val Gln Met Lys Phe Val Leu Gln Lys Leu Leu Thr Thr
                    325                 330                 335 att gct gac gcc gct aag ggt tac aag cca gtt gct gtc cca gct aga      1056
Ile Ala Asp Ala Ala Lys Gly Tyr Lys Pro Val Ala Val Pro Ala Arg
                340                 345                 350 act cca gct aac gct gct gtc cca gct tct acc cca ttg aag caa gaa      1104
Thr Pro Ala Asn Ala Ala Val Pro Ala Ser Thr Pro Leu Lys Gln Glu
            355                 360                 365 tgg atg tgg aac caa ttg ggt aac ttc ttg caa gaa ggt gat gtt gtc      1152
Trp Met Trp Asn Gln Leu Gly Asn Phe Leu Gln Glu Gly Asp Val Val
        370                 375                 380 att gct gaa acc ggt acc tcc gct ttc ggt atc aac caa acc act ttc      1200
Ile Ala Glu Thr Gly Thr Ser Ala Phe Gly Ile Asn Gln Thr Thr Phe
385                 390                 395                 400 cca aac aac acc tac ggt atc tct caa gtc tta tgg ggt tcc att ggt      1248
Pro Asn Asn Thr Tyr Gly Ile Ser Gln Val Leu Trp Gly Ser Ile Gly
                    405                 410                 415 ttc acc act ggt gct acc ttg ggt gct gct ttc gct gct gaa gaa att      1296
Phe Thr Thr Gly Ala Thr Leu Gly Ala Ala Phe Ala Ala Glu Glu Ile
                420                 425                 430 gat cca aag aag aga gtt atc tta ttc att ggt gac ggt tct ttg caa      1344
Asp Pro Lys Lys Arg Val Ile Leu Phe Ile Gly Asp Gly Ser Leu Gln
            435                 440                 445 ttg act gtt caa gaa atc tcc acc atg atc aga tgg ggc ttg aag cca      1392
Leu Thr Val Gln Glu Ile Ser Thr Met Ile Arg Trp Gly Leu Lys Pro
        450                 455                 460 tac ttg ttc gtc ttg aac aac gat ggt tac acc att gaa aag ttg att      1440
Tyr Leu Phe Val Leu Asn Asn Asp Gly Tyr Thr Ile Glu Lys Leu Ile
465                 470                 475                 480 cac ggt cca aag gct caa tac aac gaa att caa ggt tgg gac cac cta      1488
His Gly Pro Lys Ala Gln Tyr Asn Glu Ile Gln Gly Trp Asp His Leu
                    485                 490                 495 tcc ttg ttg cca act ttc ggt gct aag gac tat gaa acc cac aga gtc      1536
Ser Leu Leu Pro Thr Phe Gly Ala Lys Asp Tyr Glu Thr His Arg Val
                500                 505                 510 gct acc acc ggt gaa tgg gac aag ttg acc caa gac aag tct ttc aac      1584
Ala Thr Thr Gly Glu Trp Asp Lys Leu Thr Gln Asp Lys Ser Phe Asn
            515                 520                 525 gac aac tct aag atc aga atg att gaa atc atg ttg cca gtc ttc gat      1632
Asp Asn Ser Lys Ile Arg Met Ile Glu Ile Met Leu Pro Val Phe Asp
        530                 535                 540
```

```
gct cca caa aac ttg gtt gaa caa gct aag ttg act gct gct acc aac    1680
Ala Pro Gln Asn Leu Val Glu Gln Ala Lys Leu Thr Ala Ala Thr Asn
545                 550                 555                 560 gct aag caa taa                                                    1692
Ala Lys Gln
```

<210> SEQ ID NO 51
<211> LENGTH: 563
<212> TYPE: PRT
<213> ORGANISM: Saccharomyces cerevisiae

<400> SEQUENCE: 51

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
```

```
                340              345              350
Thr Pro Ala Asn Ala Val Pro Ala Ser Thr Pro Leu Lys Gln Glu
            355              360              365
Trp Met Trp Asn Gln Leu Gly Asn Phe Leu Gln Glu Gly Asp Val Val
    370              375              380
Ile Ala Glu Thr Gly Thr Ser Ala Phe Gly Ile Asn Gln Thr Thr Phe
385              390              395              400
Pro Asn Asn Thr Tyr Gly Ile Ser Gln Val Leu Trp Gly Ser Ile Gly
            405              410              415
Phe Thr Thr Gly Ala Thr Leu Gly Ala Ala Phe Ala Ala Glu Glu Ile
            420              425              430
Asp Pro Lys Lys Arg Val Ile Leu Phe Ile Gly Asp Gly Ser Leu Gln
            435              440              445
Leu Thr Val Gln Glu Ile Ser Thr Met Ile Arg Trp Gly Leu Lys Pro
        450              455              460
Tyr Leu Phe Val Leu Asn Asn Asp Gly Tyr Thr Ile Glu Lys Leu Ile
465              470              475              480
His Gly Pro Lys Ala Gln Tyr Asn Glu Ile Gln Gly Trp Asp His Leu
            485              490              495
Ser Leu Leu Pro Thr Phe Gly Ala Lys Asp Tyr Glu Thr His Arg Val
        500              505              510
Ala Thr Thr Gly Glu Trp Asp Lys Leu Thr Gln Asp Lys Ser Phe Asn
            515              520              525
Asp Asn Ser Lys Ile Arg Met Ile Glu Ile Met Leu Pro Val Phe Asp
        530              535              540
Ala Pro Gln Asn Leu Val Glu Gln Ala Lys Leu Thr Ala Ala Thr Asn
545              550              555              560
Ala Lys Gln

<210> SEQ ID NO 52
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 52 atg tct gaa ata acc tta ggt aaa tat tta ttt gaa aga ttg agc caa      48
Met Ser Glu Ile Thr Leu Gly Lys Tyr Leu Phe Glu Arg Leu Ser Gln
1               5                   10                  15 gtc aac tgt aac acc gtc ttc ggt ttg cca ggt gac ttt aac ttg tct      96
Val Asn Cys Asn Thr Val Phe Gly Leu Pro Gly Asp Phe Asn Leu Ser
                20                  25                  30 ctt ttg gat aag ctt tat gaa gtc aaa ggt atg aga tgg gct ggt aac     144
Leu Leu Asp Lys Leu Tyr Glu Val Lys Gly Met Arg Trp Ala Gly Asn
            35                  40                  45 gct aac gaa ttg aac gct gcc tat gct gct gat ggt tac gct cgt atc     192
Ala Asn Glu Leu Asn Ala Ala Tyr Ala Ala Asp Gly Tyr Ala Arg Ile
        50                  55                  60 aag ggt atg tcc tgt att att acc acc ttc ggt gtt ggt gaa ttg tct     240
Lys Gly Met Ser Cys Ile Ile Thr Thr Phe Gly Val Gly Glu Leu Ser
65                  70                  75                  80 gct ttg aat ggt att gcc ggt tct tac gct gaa cat gtc ggt gtt ttg     288
Ala Leu Asn Gly Ile Ala Gly Ser Tyr Ala Glu His Val Gly Val Leu
                85                  90                  95 cac gtt gtt ggt gtt cca tcc atc tct tct caa gct aag caa ttg ttg     336
```

```
                His Val Val Gly Val Pro Ser Ile Ser Ser Gln Ala Lys Gln Leu Leu
                                100                 105                 110 ttg cat cat acc ttg ggt aac ggt gac ttc act gtt ttc cac aga atg          384
Leu His His Thr Leu Gly Asn Gly Asp Phe Thr Val Phe His Arg Met
            115                 120                 125 tct gcc aac att tct gaa acc act gcc atg atc act gat att gct aac          432
Ser Ala Asn Ile Ser Glu Thr Thr Ala Met Ile Thr Asp Ile Ala Asn
130                 135                 140 gct cca gct gaa att gac aga tgt atc aga acc acc tac act acc caa          480
Ala Pro Ala Glu Ile Asp Arg Cys Ile Arg Thr Thr Tyr Thr Thr Gln
145                 150                 155                 160 aga cca gtc tac ttg ggt ttg cca gct aac ttg gtt gac ttg aac gtc          528
Arg Pro Val Tyr Leu Gly Leu Pro Ala Asn Leu Val Asp Leu Asn Val
                165                 170                 175 cca gcc aag tta ttg gaa act cca att gac ttg tct ttg aag cca aac          576
Pro Ala Lys Leu Leu Glu Thr Pro Ile Asp Leu Ser Leu Lys Pro Asn
            180                 185                 190 gac gct gaa gct gaa gct gaa gtt gtt aga act gtt gtt gaa ttg atc          624
Asp Ala Glu Ala Glu Ala Glu Val Val Arg Thr Val Val Glu Leu Ile
        195                 200                 205 aag gat gct aag aac cca gtt atc ttg gct gat gct tgt gct tct aga          672
Lys Asp Ala Lys Asn Pro Val Ile Leu Ala Asp Ala Cys Ala Ser Arg
210                 215                 220 cat gat gtc aag gct gaa act aag aag ttg atg gac ttg act caa ttc          720
His Asp Val Lys Ala Glu Thr Lys Lys Leu Met Asp Leu Thr Gln Phe
225                 230                 235                 240 cca gtt tac gtc acc cca atg ggt aag ggt gct att gac gaa caa cac          768
Pro Val Tyr Val Thr Pro Met Gly Lys Gly Ala Ile Asp Glu Gln His
                245                 250                 255 cca aga tac ggt ggt gtt tac gtt ggt acc ttg tct aga cca gaa gtt          816
Pro Arg Tyr Gly Gly Val Tyr Val Gly Thr Leu Ser Arg Pro Glu Val
            260                 265                 270 aag aag gct gta gaa tct gct gat ttg ata ttg tct atc ggt gct ttg          864
Lys Lys Ala Val Glu Ser Ala Asp Leu Ile Leu Ser Ile Gly Ala Leu
        275                 280                 285 ttg tct gat ttc aat acc ggt tct ttc tct tac tcc tac aag acc aaa          912
Leu Ser Asp Phe Asn Thr Gly Ser Phe Ser Tyr Ser Tyr Lys Thr Lys
290                 295                 300 aat atc gtt gaa ttc cac tct gac cac atc aag atc aga aac gcc acc          960
Asn Ile Val Glu Phe His Ser Asp His Ile Lys Ile Arg Asn Ala Thr
305                 310                 315                 320 ttc cca ggt gtt caa atg aaa ttt gcc ttg caa aaa ttg ttg gat gct         1008
Phe Pro Gly Val Gln Met Lys Phe Ala Leu Gln Lys Leu Leu Asp Ala
                325                 330                 335 att cca gaa gtc gtc aag gac tac aaa cct gtt gct gtc cca gct aga         1056
Ile Pro Glu Val Val Lys Asp Tyr Lys Pro Val Ala Val Pro Ala Arg
            340                 345                 350 gtt cca att acc aag tct act cca gct aac act cca atg aag caa gaa         1104
Val Pro Ile Thr Lys Ser Thr Pro Ala Asn Thr Pro Met Lys Gln Glu
        355                 360                 365 tgg atg tgg aac cat ttg ggt aac ttc ttg aga gaa ggt gat att gtt         1152
Trp Met Trp Asn His Leu Gly Asn Phe Leu Arg Glu Gly Asp Ile Val
370                 375                 380 att gct gaa acc ggt act tcc gcc ttc ggt att aac caa act act ttc         1200
Ile Ala Glu Thr Gly Thr Ser Ala Phe Gly Ile Asn Gln Thr Thr Phe
385                 390                 395                 400 cca aca gat gta tac gct atc gtc caa gtc ttg tgg ggt tcc att ggt         1248
Pro Thr Asp Val Tyr Ala Ile Val Gln Val Leu Trp Gly Ser Ile Gly
                405                 410                 415
```

-continued

| | | | | | | | | | | | | | | |
|---|---|---|---|---|---|---|---|---|---|---|---|---|---|---|
| ttc | aca | gtc | ggc | gct | cta | ttg | ggt | gct | act | atg | gcc | gct | gaa | gaa | ctt | 1296 |
| Phe | Thr | Val | Gly | Ala | Leu | Leu | Gly | Ala | Thr | Met | Ala | Ala | Glu | Glu | Leu |
| | | | 420 | | | | 425 | | | | 430 |

```
gat cca aag aag aga gtt att tta ttc att ggt gac ggt tct cta caa    1344
Asp Pro Lys Lys Arg Val Ile Leu Phe Ile Gly Asp Gly Ser Leu Gln
        435                 440                 445 ttg act gtt caa gaa atc tct acc atg att aga tgg ggt ttg aag cca    1392
Leu Thr Val Gln Glu Ile Ser Thr Met Ile Arg Trp Gly Leu Lys Pro
450                 455                 460 tac att ttt gtc ttg aat aac aac ggt tac acc att gaa aaa ttg att    1440
Tyr Ile Phe Val Leu Asn Asn Asn Gly Tyr Thr Ile Glu Lys Leu Ile
465                 470                 475                 480 cac ggt cct cat gcc gaa tat aat gaa att caa ggt tgg gac cac ttg    1488
His Gly Pro His Ala Glu Tyr Asn Glu Ile Gln Gly Trp Asp His Leu
            485                 490                 495 gcc tta ttg cca act ttt ggt gct aga aac tac gaa acc cac aga gtt    1536
Ala Leu Leu Pro Thr Phe Gly Ala Arg Asn Tyr Glu Thr His Arg Val
            500                 505                 510 gct acc act ggt gaa tgg gaa aag ttg act caa gac aag gac ttc caa    1584
Ala Thr Thr Gly Glu Trp Glu Lys Leu Thr Gln Asp Lys Asp Phe Gln
            515                 520                 525 gac aac tct aag att aga atg att gaa gtt atg ttg cca gtc ttt gat    1632
Asp Asn Ser Lys Ile Arg Met Ile Glu Val Met Leu Pro Val Phe Asp
530                 535                 540 gct cca caa aac ttg gtt aaa caa gct caa ttg act gcc gct act aac    1680
Ala Pro Gln Asn Leu Val Lys Gln Ala Gln Leu Thr Ala Ala Thr Asn
545                 550                 555                 560 gct aaa caa taa                                                    1692
Ala Lys Gln
```

<210> SEQ ID NO 53
<211> LENGTH: 563
<212> TYPE: PRT
<213> ORGANISM: Saccharomyces cerevisiae

<400> SEQUENCE: 53

```
Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175
```

```
Pro Ala Lys Leu Leu Glu Thr Pro Ile Asp Leu Ser Leu Lys Pro Asn
        180                 185                 190

Asp Ala Glu Ala Glu Ala Val Val Arg Thr Val Val Glu Leu Ile
        195                 200                 205

Lys Asp Ala Lys Asn Pro Val Ile Leu Ala Asp Ala Cys Ala Ser Arg
210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
                260                 265                 270

Lys Lys Ala Val Glu Ser Ala Asp Leu Ile Leu Ser Ile Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
                340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
            370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
                500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
530                 535                 540

Ala Pro Gln Asn Leu Val Lys Gln Ala Gln Leu Thr Ala Ala Thr Asn
545                 550                 555                 560

Ala Lys Gln
```

<210> SEQ ID NO 54
<211> LENGTH: 1599
<212> TYPE: DNA

<213> ORGANISM: Saccharomyces cerevisiae
<220> FEATURE:
<221> NAME/KEY: CDS
<222> LOCATION: (1)..(1599)

<400> SEQUENCE: 54

```
atg tct gaa att act ctt gga aaa tac tta ttt gaa aga ttg aag caa      48
Met Ser Glu Ile Thr Leu Gly Lys Tyr Leu Phe Glu Arg Leu Lys Gln
1               5                   10                  15 gtt aat gtt aac acc att ttt ggg cta cca ggc gac ttc aac ttg tcc      96
Val Asn Val Asn Thr Ile Phe Gly Leu Pro Gly Asp Phe Asn Leu Ser
            20                  25                  30 cta ttg gac aag att tac gag gta gat gga ttg aga tgg gct ggt aat     144
Leu Leu Asp Lys Ile Tyr Glu Val Asp Gly Leu Arg Trp Ala Gly Asn
        35                  40                  45 gca aat gag ctg aac gcc gcc tat gcc gcc gat ggt tac gca cgc atc     192
Ala Asn Glu Leu Asn Ala Ala Tyr Ala Ala Asp Gly Tyr Ala Arg Ile
    50                  55                  60 aag ggt tta tct gtg ctg gta act act ttt ggc gta ggt gaa tta tcc     240
Lys Gly Leu Ser Val Leu Val Thr Thr Phe Gly Val Gly Glu Leu Ser
65                  70                  75                  80 gcc ttg aat ggt att gca gga tcg tat gca gaa cac gtc ggt gta ctg     288
Ala Leu Asn Gly Ile Ala Gly Ser Tyr Ala Glu His Val Gly Val Leu
                85                  90                  95 cat gtt gtt ggt gtc ccc tct atc tcc gct cag gct aag caa ttg ttg     336
His Val Val Gly Val Pro Ser Ile Ser Ala Gln Ala Lys Gln Leu Leu
            100                 105                 110 ttg cat cat acc ttg ggt aac ggt gat ttt acc gtt ttt cac aga atg     384
Leu His His Thr Leu Gly Asn Gly Asp Phe Thr Val Phe His Arg Met
        115                 120                 125 tcc gcc aat atc tca gaa act aca tca atg att aca gac att gct aca     432
Ser Ala Asn Ile Ser Glu Thr Thr Ser Met Ile Thr Asp Ile Ala Thr
    130                 135                 140 gcc cct tca gaa atc gat agg ttg atc agg aca aca ttt ata aca caa     480
Ala Pro Ser Glu Ile Asp Arg Leu Ile Arg Thr Thr Phe Ile Thr Gln
145                 150                 155                 160 agg cct agc tac ttg ggg ttg cca gcg aat ttg gta gat cta aag gtt     528
Arg Pro Ser Tyr Leu Gly Leu Pro Ala Asn Leu Val Asp Leu Lys Val
                165                 170                 175 cct ggt tct ctt ttg gaa aaa ccg att gat cta tca tta aaa cct aac     576
Pro Gly Ser Leu Leu Glu Lys Pro Ile Asp Leu Ser Leu Lys Pro Asn
            180                 185                 190 gat ccc gaa gct gaa aag gaa gtt att gat acc gta cta gaa ttg atc     624
Asp Pro Glu Ala Glu Lys Glu Val Ile Asp Thr Val Leu Glu Leu Ile
        195                 200                 205 cag aat tcg aaa aac cct gtt ata cta tcg gat gcc tgt gct tct agg     672
Gln Asn Ser Lys Asn Pro Val Ile Leu Ser Asp Ala Cys Ala Ser Arg
    210                 215                 220 cac aac gtt aaa aaa gaa acc cag aag tta att gat ttg acg caa ttc     720
His Asn Val Lys Lys Glu Thr Gln Lys Leu Ile Asp Leu Thr Gln Phe
225                 230                 235                 240 cca gct ttt gtg aca cct cta ggt aaa ggg tca ata gat gaa cag cat     768
Pro Ala Phe Val Thr Pro Leu Gly Lys Gly Ser Ile Asp Glu Gln His
                245                 250                 255 ccc aga tat ggc ggt gtt tat gtg gga acg ctg tcc aaa caa gac gtg     816
Pro Arg Tyr Gly Gly Val Tyr Val Gly Thr Leu Ser Lys Gln Asp Val
            260                 265                 270 aaa cag gcc gtt gag tcg gct gat ttg atc ctt tcg gtc ggt gct ttg     864
Lys Gln Ala Val Glu Ser Ala Asp Leu Ile Leu Ser Val Gly Ala Leu
        275                 280                 285
```

```
ctc tct gat ttt aac aca ggt tcg ttt tcc tac tcc tac aag act aaa      912
Leu Ser Asp Phe Asn Thr Gly Ser Phe Ser Tyr Ser Tyr Lys Thr Lys
    290             295                 300 aat gta gtg gag ttt cat tcc gat tac gta aag gtg aag aac gct acg      960
Asn Val Val Glu Phe His Ser Asp Tyr Val Lys Val Lys Asn Ala Thr
305             310                 315                 320 ttc ctc ggt gta caa atg aaa ttt gca cta caa aac tta ctg aag gtt     1008
Phe Leu Gly Val Gln Met Lys Phe Ala Leu Gln Asn Leu Leu Lys Val
            325                 330                 335 att ccc gat gtt gtt aag ggc tac aag agc gtt ccc gta cca acc aaa     1056
Ile Pro Asp Val Val Lys Gly Tyr Lys Ser Val Pro Val Pro Thr Lys
        340                 345                 350 act ccc gca aac aaa ggt gta cct gct agc acg ccc ttg aaa caa gag     1104
Thr Pro Ala Asn Lys Gly Val Pro Ala Ser Thr Pro Leu Lys Gln Glu
    355                 360                 365 tgg ttg tgg aac gaa ttg tcc aaa ttc ttg caa gaa ggt gat gtt atc     1152
Trp Leu Trp Asn Glu Leu Ser Lys Phe Leu Gln Glu Gly Asp Val Ile
370             375                 380 att tcc gag acc ggc acg tct gcc ttc ggt atc aat caa act atc ttt     1200
Ile Ser Glu Thr Gly Thr Ser Ala Phe Gly Ile Asn Gln Thr Ile Phe
385             390                 395                 400 cct aag gac gcc tac ggt atc tcg cag gtg ttg tgg ggg tcc atc ggt     1248
Pro Lys Asp Ala Tyr Gly Ile Ser Gln Val Leu Trp Gly Ser Ile Gly
            405                 410                 415 ttt aca aca gga gca act tta ggt gct gcc ttt gcc gct gag gag att     1296
Phe Thr Thr Gly Ala Thr Leu Gly Ala Ala Phe Ala Ala Glu Glu Ile
        420                 425                 430 gac ccc aac aag aga gtc atc tta ttc ata ggt gac ggg tct ttg cag     1344
Asp Pro Asn Lys Arg Val Ile Leu Phe Ile Gly Asp Gly Ser Leu Gln
    435                 440                 445 tta acc gtc caa gaa atc tcc acc atg atc aga tgg ggg tta aag ccg     1392
Leu Thr Val Gln Glu Ile Ser Thr Met Ile Arg Trp Gly Leu Lys Pro
450             455                 460 tat ctt ttt gtc ctt aac aac gac ggc tac act atc gaa aag ctg att     1440
Tyr Leu Phe Val Leu Asn Asn Asp Gly Tyr Thr Ile Glu Lys Leu Ile
465             470                 475                 480 cat ggg cct cac gca gag tac aac gaa atc cag acc tgg gat cac ctc     1488
His Gly Pro His Ala Glu Tyr Asn Glu Ile Gln Thr Trp Asp His Leu
            485                 490                 495 gcc ctg ttg ccc gca ttt ggt gcg aaa aag tac gaa aat cac aag atc     1536
Ala Leu Leu Pro Ala Phe Gly Ala Lys Lys Tyr Glu Asn His Lys Ile
        500                 505                 510 gcc act acg ggt gag tgg gat gcc tta acc act gat tca gag ttc cag     1584
Ala Thr Thr Gly Glu Trp Asp Ala Leu Thr Thr Asp Ser Glu Phe Gln
    515                 520                 525 aaa aac tcg gtg atc                                                  1599
Lys Asn Ser Val Ile
    530
```

<210> SEQ ID NO 55
<211> LENGTH: 533
<212> TYPE: PRT
<213> ORGANISM: Saccharomyces cerevisiae

<400> SEQUENCE: 55

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
```

```
                35                  40                  45
Ala Asn Glu Leu Asn Ala Ala Tyr Ala Ala Asp Gly Tyr Ala Arg Ile
 50                  55                  60

Lys Gly Leu Ser Val Leu Val Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
                115                 120                 125

Ser Ala Asn Ile Ser Glu Thr Thr Ser Met Ile Thr Asp Ile Ala Thr
                130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
                180                 185                 190

Asp Pro Glu Ala Glu Lys Glu Val Ile Asp Thr Val Leu Glu Leu Ile
                195                 200                 205

Gln Asn Ser Lys Asn Pro Val Ile Leu Ser Asp Ala Cys Ala Ser Arg
210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
                260                 265                 270

Lys Gln Ala Val Glu Ser Ala Asp Leu Ile Leu Ser Val Gly Ala Leu
                275                 280                 285

Leu Ser Asp Phe Asn Thr Gly Ser Phe Ser Tyr Ser Tyr Lys Thr Lys
                290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
                340                 345                 350

Thr Pro Ala Asn Lys Gly Val Pro Ala Ser Thr Pro Leu Lys Gln Glu
                355                 360                 365

Trp Leu Trp Asn Glu Leu Ser Lys Phe Leu Gln Glu Gly Asp Val Ile
                370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Asn Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
                450                 455                 460
```

| Tyr | Leu | Phe | Val | Leu | Asn | Asn | Asp | Gly | Tyr | Thr | Ile | Glu | Lys | Leu | Ile |
| 465 | | | | 470 | | | | | 475 | | | | | 480 | |

| His | Gly | Pro | His | Ala | Glu | Tyr | Asn | Glu | Ile | Gln | Thr | Trp | Asp | His | Leu |
| | | | | 485 | | | | | 490 | | | | | 495 | |

| Ala | Leu | Leu | Pro | Ala | Phe | Gly | Ala | Lys | Lys | Tyr | Glu | Asn | His | Lys | Ile |
| | | | 500 | | | | | 505 | | | | | 510 | | |

| Ala | Thr | Thr | Gly | Glu | Trp | Asp | Ala | Leu | Thr | Thr | Asp | Ser | Glu | Phe | Gln |
| | | | 515 | | | | | 520 | | | | | 525 | | |

| Lys | Asn | Ser | Val | Ile |
| | | | | |
| | | | | 530 |

<210> SEQ ID NO 56
<211> LENGTH: 1695
<212> TYPE: DNA
<213> ORGANISM: Candida glabrata
<220> FEATURE:
<221> NAME/KEY: CDS
<222> LOCATION: (1)..(1695)

<400> SEQUENCE: 56

| atg | tct | gag | att | act | ttg | ggt | aga | tac | ttg | ttc | gag | aga | ttg | aac | caa | 48 |
| Met | Ser | Glu | Ile | Thr | Leu | Gly | Arg | Tyr | Leu | Phe | Glu | Arg | Leu | Asn | Gln | |
| 1 | | | | 5 | | | | | 10 | | | | | 15 | | |

| gtc | gac | gtt | aag | acc | atc | ttc | ggt | ttg | cca | ggt | gac | ttc | aac | ttg | tcc | 96 |
| Val | Asp | Val | Lys | Thr | Ile | Phe | Gly | Leu | Pro | Gly | Asp | Phe | Asn | Leu | Ser | |
| | | | 20 | | | | | 25 | | | | | 30 | | | |

| cta | ttg | gac | aag | atc | tac | gaa | gtt | gaa | ggt | atg | aga | tgg | gct | ggt | aac | 144 |
| Leu | Leu | Asp | Lys | Ile | Tyr | Glu | Val | Glu | Gly | Met | Arg | Trp | Ala | Gly | Asn | |
| | | | | 35 | | | | | 40 | | | | | 45 | | |

| gct | aac | gaa | ttg | aac | gct | gct | tac | gct | gct | gac | ggt | tac | gct | aga | atc | 192 |
| Ala | Asn | Glu | Leu | Asn | Ala | Ala | Tyr | Ala | Ala | Asp | Gly | Tyr | Ala | Arg | Ile | |
| | | | 50 | | | | | 55 | | | | | 60 | | | |

| aag | ggt | atg | tcc | tgt | atc | atc | acc | acc | ttc | ggt | gtc | ggt | gaa | ttg | tct | 240 |
| Lys | Gly | Met | Ser | Cys | Ile | Ile | Thr | Thr | Phe | Gly | Val | Gly | Glu | Leu | Ser | |
| 65 | | | | 70 | | | | | 75 | | | | | 80 | | |

| gcc | ttg | aac | ggt | att | gcc | ggt | tct | tac | gct | gaa | cac | gtc | ggt | gtc | ttg | 288 |
| Ala | Leu | Asn | Gly | Ile | Ala | Gly | Ser | Tyr | Ala | Glu | His | Val | Gly | Val | Leu | |
| | | | | 85 | | | | | 90 | | | | | 95 | | |

| cac | gtc | gtc | ggt | gtc | cca | tcc | atc | tcc | tct | caa | gct | aag | caa | ttg | ttg | 336 |
| His | Val | Val | Gly | Val | Pro | Ser | Ile | Ser | Ser | Gln | Ala | Lys | Gln | Leu | Leu | |
| | | | 100 | | | | | 105 | | | | | 110 | | | |

| ttg | cac | cac | acc | ttg | ggt | aac | ggt | gac | ttc | act | gtc | ttc | cac | aga | atg | 384 |
| Leu | His | His | Thr | Leu | Gly | Asn | Gly | Asp | Phe | Thr | Val | Phe | His | Arg | Met | |
| | | | 115 | | | | | 120 | | | | | 125 | | | |

| tcc | gct | aac | atc | tct | gag | acc | acc | gct | atg | gtc | act | gac | atc | gct | acc | 432 |
| Ser | Ala | Asn | Ile | Ser | Glu | Thr | Thr | Ala | Met | Val | Thr | Asp | Ile | Ala | Thr | |
| | | | 130 | | | | | 135 | | | | | 140 | | | |

| gct | cca | gct | gag | atc | gac | aga | tgt | atc | aga | acc | acc | tac | atc | acc | caa | 480 |
| Ala | Pro | Ala | Glu | Ile | Asp | Arg | Cys | Ile | Arg | Thr | Thr | Tyr | Ile | Thr | Gln | |
| 145 | | | | 150 | | | | | 155 | | | | | 160 | | |

| aga | cca | gtc | tac | ttg | ggt | cta | cca | gct | aac | ttg | gtc | gac | cta | aag | gtc | 528 |
| Arg | Pro | Val | Tyr | Leu | Gly | Leu | Pro | Ala | Asn | Leu | Val | Asp | Leu | Lys | Val | |
| | | | | 165 | | | | | 170 | | | | | 175 | | |

| cca | gcc | aag | ctt | ttg | gaa | acc | cca | att | gac | ttg | tcc | ttg | aag | cca | aac | 576 |
| Pro | Ala | Lys | Leu | Leu | Glu | Thr | Pro | Ile | Asp | Leu | Ser | Leu | Lys | Pro | Asn | |
| | | | 180 | | | | | 185 | | | | | 190 | | | |

| gac | cca | gaa | gcc | gaa | act | gaa | gtc | gtt | gac | acc | gtc | ttg | gaa | ttg | atc | 624 |
| Asp | Pro | Glu | Ala | Glu | Thr | Glu | Val | Val | Asp | Thr | Val | Leu | Glu | Leu | Ile | |
| | | | | 195 | | | | | 200 | | | | | 205 | | |

```
aag gct gct aag aac cca gtt atc ttg gct gat gct tgt gct tcc aga        672
Lys Ala Ala Lys Asn Pro Val Ile Leu Ala Asp Ala Cys Ala Ser Arg
        210                 215                 220 cac gac gtc aag gct gaa acc aag aag ttg att gac gcc act caa ttc        720
His Asp Val Lys Ala Glu Thr Lys Lys Leu Ile Asp Ala Thr Gln Phe
225                 230                 235                 240 cca tcc ttc gtt acc cca atg ggt aag ggt tcc atc gac gaa caa cac        768
Pro Ser Phe Val Thr Pro Met Gly Lys Gly Ser Ile Asp Glu Gln His
                245                 250                 255 cca aga ttc ggt ggt gtc tac gtc ggt acc ttg tcc aga cca gaa gtt        816
Pro Arg Phe Gly Gly Val Tyr Val Gly Thr Leu Ser Arg Pro Glu Val
            260                 265                 270 aag gaa gct gtt gaa tcc gct gac ttg atc ttg tct gtc ggt gct ttg        864
Lys Glu Ala Val Glu Ser Ala Asp Leu Ile Leu Ser Val Gly Ala Leu
        275                 280                 285 ttg tcc gat ttc aac act ggt tct ttc tct tac tct tac aag acc aag        912
Leu Ser Asp Phe Asn Thr Gly Ser Phe Ser Tyr Ser Tyr Lys Thr Lys
290                 295                 300 aac atc gtc gaa ttc cac tct gac tac atc aag atc aga aac gct acc        960
Asn Ile Val Glu Phe His Ser Asp Tyr Ile Lys Ile Arg Asn Ala Thr
305                 310                 315                 320 ttc cca ggt gtc caa atg aag ttc gct ttg caa aag ttg ttg aac gcc       1008
Phe Pro Gly Val Gln Met Lys Phe Ala Leu Gln Lys Leu Leu Asn Ala
                325                 330                 335 gtc cca gaa gct atc aag ggt tac aag cca gtc cct gtc cca gct aga       1056
Val Pro Glu Ala Ile Lys Gly Tyr Lys Pro Val Pro Val Pro Ala Arg
            340                 345                 350 gtc cca gaa aac aag tcc tgt gac cca gct acc cca ttg aag caa gaa       1104
Val Pro Glu Asn Lys Ser Cys Asp Pro Ala Thr Pro Leu Lys Gln Glu
        355                 360                 365 tgg atg tgg aac caa gtt tcc aag ttc ttg caa gaa ggt gat gtt gtt       1152
Trp Met Trp Asn Gln Val Ser Lys Phe Leu Gln Glu Gly Asp Val Val
370                 375                 380 atc act gaa acc ggt acc tcc gct ttt ggt atc aac caa acc cca ttc       1200
Ile Thr Glu Thr Gly Thr Ser Ala Phe Gly Ile Asn Gln Thr Pro Phe
385                 390                 395                 400 cca aac aac gct tac ggt atc tcc caa gtt cta tgg ggt tcc atc ggt       1248
Pro Asn Asn Ala Tyr Gly Ile Ser Gln Val Leu Trp Gly Ser Ile Gly
                405                 410                 415 ttc acc acc ggt gct tgt ttg ggt gcc gct ttc gct gct gaa gaa atc       1296
Phe Thr Thr Gly Ala Cys Leu Gly Ala Ala Phe Ala Ala Glu Glu Ile
            420                 425                 430 gac cca aag aag aga gtt atc ttg ttc att ggt gac ggt tct ttg caa       1344
Asp Pro Lys Lys Arg Val Ile Leu Phe Ile Gly Asp Gly Ser Leu Gln
        435                 440                 445 ttg act gtc caa gaa atc tcc acc atg atc aga tgg ggc ttg aag cca       1392
Leu Thr Val Gln Glu Ile Ser Thr Met Ile Arg Trp Gly Leu Lys Pro
450                 455                 460 tac ttg ttc gtc ttg aac aac gac ggt tac acc atc gaa aga ttg att       1440
Tyr Leu Phe Val Leu Asn Asn Asp Gly Tyr Thr Ile Glu Arg Leu Ile
465                 470                 475                 480 cac ggt gaa aag gct ggt tac aac gac atc caa aac tgg gac cac ttg       1488
His Gly Glu Lys Ala Gly Tyr Asn Asp Ile Gln Asn Trp Asp His Leu
                485                 490                 495 gct cta ttg cca acc ttc ggt gct aag gac tac gaa aac cac aga gtc       1536
Ala Leu Leu Pro Thr Phe Gly Ala Lys Asp Tyr Glu Asn His Arg Val
            500                 505                 510 gcc acc acc ggt gaa tgg gac aag ttg acc caa gac aag gaa ttc aac       1584
Ala Thr Thr Gly Glu Trp Asp Lys Leu Thr Gln Asp Lys Glu Phe Asn
        515                 520                 525
```

```
aag aac tcc aag atc aga atg atc gaa gtt atg ttg cca gtt atg gac    1632
Lys Asn Ser Lys Ile Arg Met Ile Glu Val Met Leu Pro Val Met Asp
        530             535                 540 gct cca act tcc ttg att gaa caa gct aag ttg acc gct tcc atc aac    1680
Ala Pro Thr Ser Leu Ile Glu Gln Ala Lys Leu Thr Ala Ser Ile Asn
545                 550                 555                 560 gct aag caa gaa taa                                                1695
Ala Lys Gln Glu <210> SEQ ID NO 57
<211> LENGTH: 564
<212> TYPE: PRT
<213> ORGANISM: Candida glabrata

<400> SEQUENCE: 57

Met Ser Glu Ile Thr Leu Gly Arg Tyr Leu Phe Glu Arg Leu Asn Gln
1               5                   10                  15

Val Asp Val Lys Thr Ile Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Val Thr Asp Ile Ala Thr
    130                 135                 140

Ala Pro Ala Glu Ile Asp Arg Cys Ile Arg Thr Thr Tyr Ile Thr Gln
145                 150                 155                 160

Arg Pro Val Tyr Leu Gly Leu Pro Ala Asn Leu Val Asp Leu Lys Val
                165                 170                 175

Pro Ala Lys Leu Leu Glu Thr Pro Ile Asp Leu Ser Leu Lys Pro Asn
            180                 185                 190

Asp Pro Glu Ala Glu Thr Glu Val Val Asp Thr Val Leu Glu Leu Ile
        195                 200                 205

Lys Ala Ala Lys Asn Pro Val Ile Leu Ala Asp Ala Cys Ala Ser Arg
    210                 215                 220

His Asp Val Lys Ala Glu Thr Lys Lys Leu Ile Asp Ala Thr Gln Phe
225                 230                 235                 240

Pro Ser Phe Val Thr Pro Met Gly Lys Gly Ser Ile Asp Glu Gln His
                245                 250                 255

Pro Arg Phe Gly Gly Val Tyr Val Gly Thr Leu Ser Arg Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp Tyr Ile Lys Ile Arg Asn Ala Thr
305                 310                 315                 320
```

```
Phe Pro Gly Val Gln Met Lys Phe Ala Leu Gln Lys Leu Leu Asn Ala
            325                 330                 335

Val Pro Glu Ala Ile Lys Gly Tyr Lys Pro Val Pro Ala Arg
        340                 345                 350

Val Pro Glu Asn Lys Ser Cys Asp Pro Ala Thr Pro Leu Lys Gln Glu
            355                 360                 365

Trp Met Trp Asn Gln Val Ser Lys Phe Leu Gln Glu Gly Asp Val Val
370                 375                 380

Ile Thr Glu Thr Gly Thr Ser Ala Phe Gly Ile Asn Gln Thr Pro Phe
385                 390                 395                 400

Pro Asn Asn Ala Tyr Gly Ile Ser Gln Val Leu Trp Gly Ser Ile Gly
            405                 410                 415

Phe Thr Thr Gly Ala Cys Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Lys Ala Gly Tyr Asn Asp Ile Gln Asn Trp Asp His Leu
            485                 490                 495

Ala Leu Leu Pro Thr Phe Gly Ala Lys Asp Tyr Glu Asn His Arg Val
            500                 505                 510

Ala Thr Thr Gly Glu Trp Asp Lys Leu Thr Gln Asp Lys Glu Phe Asn
            515                 520                 525

Lys Asn Ser Lys Ile Arg Met Ile Glu Val Met Leu Pro Val Met Asp
530                 535                 540

Ala Pro Thr Ser Leu Ile Glu Gln Ala Lys Leu Thr Ala Ser Ile Asn
545                 550                 555                 560

Ala Lys Gln Glu

<210> SEQ ID NO 58
<211> LENGTH: 1791
<212> TYPE: DNA
<213> ORGANISM: Pichia stipitis
<220> FEATURE:
<221> NAME/KEY: CDS
<222> LOCATION: (1)..(1791)

<400> SEQUENCE: 58 atg gct gaa gtc tca tta gga aga tat ctc ttc gag aga ttg tac caa    48
Met Ala Glu Val Ser Leu Gly Arg Tyr Leu Phe Glu Arg Leu Tyr Gln
1               5                   10                  15 ttg caa gtg cag acc atc ttc ggt gtc cct ggt gat ttc aac ttg tcg    96
Leu Gln Val Gln Thr Ile Phe Gly Val Pro Gly Asp Phe Asn Leu Ser
            20                  25                  30 ctt ttg gac aag atc tac gaa gtg gaa gat gcc cat ggc aag aat tcg   144
Leu Leu Asp Lys Ile Tyr Glu Val Glu Asp Ala His Gly Lys Asn Ser
        35                  40                  45 ttt aga tgg gct ggt aat gcc aac gaa ttg aat gca tcg tac gct gct   192
Phe Arg Trp Ala Gly Asn Ala Asn Glu Leu Asn Ala Ser Tyr Ala Ala
    50                  55                  60 gac ggt tac tcg aga gtc aag cgt tta ggg tgt ttg gtc act acc ttt   240
Asp Gly Tyr Ser Arg Val Lys Arg Leu Gly Cys Leu Val Thr Thr Phe
65                  70                  75                  80
```

-continued

| | | |
|---|---|---|
| ggt gtc ggt gaa ttg tct gct ttg aat ggt att gcc ggt tct tat gcc<br>Gly Val Gly Glu Leu Ser Ala Leu Asn Gly Ile Ala Gly Ser Tyr Ala<br>85 90 95 | | 288 |
| gaa cat gtt ggt ttg ctt cat gtc gta ggt gtt cca tcg att tcc tcg<br>Glu His Val Gly Leu Leu His Val Val Gly Val Pro Ser Ile Ser Ser<br>100 105 110 | | 336 |
| caa gct aag caa ttg tta ctt cac cac act ttg ggt aat ggt gat ttc<br>Gln Ala Lys Gln Leu Leu Leu His His Thr Leu Gly Asn Gly Asp Phe<br>115 120 125 | | 384 |
| act gtt ttc cat aga atg tcc aac aac att tct cag acc aca gcc ttt<br>Thr Val Phe His Arg Met Ser Asn Asn Ile Ser Gln Thr Thr Ala Phe<br>130 135 140 | | 432 |
| atc tcc gat atc aac tcg gct cca gct gaa att gat aga tgt atc aga<br>Ile Ser Asp Ile Asn Ser Ala Pro Ala Glu Ile Asp Arg Cys Ile Arg<br>145 150 155 160 | | 480 |
| gag gcc tac gtc aaa caa aga cca gtt tat atc ggg tta cca gct aac<br>Glu Ala Tyr Val Lys Gln Arg Pro Val Tyr Ile Gly Leu Pro Ala Asn<br>165 170 175 | | 528 |
| tta gtt gat ttg aat gtt ccg gcc tct ttg ctt gag tct cca atc aac<br>Leu Val Asp Leu Asn Val Pro Ala Ser Leu Leu Glu Ser Pro Ile Asn<br>180 185 190 | | 576 |
| ttg tcg ttg gaa aag aac gac cca gag gct caa gat gaa gtc att gac<br>Leu Ser Leu Glu Lys Asn Asp Pro Glu Ala Gln Asp Glu Val Ile Asp<br>195 200 205 | | 624 |
| tct gtc tta gac ttg atc aaa aag tcg ctg aac cca atc atc ttg gtc<br>Ser Val Leu Asp Leu Ile Lys Lys Ser Leu Asn Pro Ile Ile Leu Val<br>210 215 220 | | 672 |
| gat gcc tgt gcc tcg aga cat gac tgt aag gct gaa gtt act cag ttg<br>Asp Ala Cys Ala Ser Arg His Asp Cys Lys Ala Glu Val Thr Gln Leu<br>225 230 235 240 | | 720 |
| att gaa caa acc caa ttc cca gta ttt gtc act cca atg ggt aaa ggt<br>Ile Glu Gln Thr Gln Phe Pro Val Phe Val Thr Pro Met Gly Lys Gly<br>245 250 255 | | 768 |
| acc gtt gat gag ggt ggt gta gac gga gaa ttg tta gaa gat gat cct<br>Thr Val Asp Glu Gly Gly Val Asp Gly Glu Leu Leu Glu Asp Asp Pro<br>260 265 270 | | 816 |
| cat ttg att gcc aag gtc gct gct agg ttg tct gct ggc aag aac gct<br>His Leu Ile Ala Lys Val Ala Ala Arg Leu Ser Ala Gly Lys Asn Ala<br>275 280 285 | | 864 |
| gcc tct aga ttc gga ggt gtt tat gtc gga acc ttg tcg aag ccc gaa<br>Ala Ser Arg Phe Gly Gly Val Tyr Val Gly Thr Leu Ser Lys Pro Glu<br>290 295 300 | | 912 |
| gtc aag gac gct gta gag agt gca gat ttg att ttg tct gtc ggt gcc<br>Val Lys Asp Ala Val Glu Ser Ala Asp Leu Ile Leu Ser Val Gly Ala<br>305 310 315 320 | | 960 |
| ctt ttg tct gat ttc aac act ggt tca ttt tcc tac tcc tac aga acc<br>Leu Leu Ser Asp Phe Asn Thr Gly Ser Phe Ser Tyr Ser Tyr Arg Thr<br>325 330 335 | | 1008 |
| aag aac atc gtc gaa ttc cat tct gat tac act aag att aga caa gcc<br>Lys Asn Ile Val Glu Phe His Ser Asp Tyr Thr Lys Ile Arg Gln Ala<br>340 345 350 | | 1056 |
| act ttc cca ggt gtg cag atg aag gaa gcc ttg caa gaa ttg aac aag<br>Thr Phe Pro Gly Val Gln Met Lys Glu Ala Leu Gln Glu Leu Asn Lys<br>355 360 365 | | 1104 |
| aaa gtt tca tct gct gct agt cac tat gaa gtc aag cct gtg ccc aag<br>Lys Val Ser Ser Ala Ala Ser His Tyr Glu Val Lys Pro Val Pro Lys<br>370 375 380 | | 1152 |
| atc aag ttg gcc aat aca cca gcc acc aga gaa gtc aag tta act cag<br>Ile Lys Leu Ala Asn Thr Pro Ala Thr Arg Glu Val Lys Leu Thr Gln<br>385 390 395 400 | | 1200 |

```
gaa tgg ttg tgg acc aga gtg tct tcg tgg ttc aga gaa ggt gat att    1248
Glu Trp Leu Trp Thr Arg Val Ser Ser Trp Phe Arg Glu Gly Asp Ile
            405                 410                 415 att atc acc gaa acc ggt aca tcc tcc ttc ggt ata gtt caa tcc aga    1296
Ile Ile Thr Glu Thr Gly Thr Ser Ser Phe Gly Ile Val Gln Ser Arg
    420                 425                 430 ttc cca aac aac acc atc ggt atc tcc caa gta ttg tgg ggt tct att    1344
Phe Pro Asn Asn Thr Ile Gly Ile Ser Gln Val Leu Trp Gly Ser Ile
435                 440                 445 ggt ttc tct gtt ggt gcc act ttg ggt gct gcc atg gct gcc caa gaa    1392
Gly Phe Ser Val Gly Ala Thr Leu Gly Ala Ala Met Ala Ala Gln Glu
    450                 455                 460 ctc gac cct aac aag aga acc atc ttg ttt gtt gga gat ggt tct ttg    1440
Leu Asp Pro Asn Lys Arg Thr Ile Leu Phe Val Gly Asp Gly Ser Leu
465                 470                 475                 480 caa ttg acc gtt cag gaa atc tcc acc ata atc aga tgg ggt acc aca    1488
Gln Leu Thr Val Gln Glu Ile Ser Thr Ile Ile Arg Trp Gly Thr Thr
                485                 490                 495 cct tac ctt ttc gtg ttg aac aat gac ggt tac acc atc gag cgt ttg    1536
Pro Tyr Leu Phe Val Leu Asn Asn Asp Gly Tyr Thr Ile Glu Arg Leu
            500                 505                 510 atc cac ggt gta aat gcc tca tat aat gac atc caa cca tgg caa aac    1584
Ile His Gly Val Asn Ala Ser Tyr Asn Asp Ile Gln Pro Trp Gln Asn
        515                 520                 525 ttg gaa atc ttg cct act ttc tcg gcc aag aac tac gac gct gtg aga    1632
Leu Glu Ile Leu Pro Thr Phe Ser Ala Lys Asn Tyr Asp Ala Val Arg
530                 535                 540 atc tcc aac atc gga gaa gca gaa gat atc ttg aaa gac aag gaa ttc    1680
Ile Ser Asn Ile Gly Glu Ala Glu Asp Ile Leu Lys Asp Lys Glu Phe
545                 550                 555                 560 gga aag aac tcc aag att aga ttg ata gaa gtc atg tta cca aga ttg    1728
Gly Lys Asn Ser Lys Ile Arg Leu Ile Glu Val Met Leu Pro Arg Leu
                565                 570                 575 gat gca cca tct aac ctt gcc aaa caa gct gcc att aca gct gcc acc    1776
Asp Ala Pro Ser Asn Leu Ala Lys Gln Ala Ala Ile Thr Ala Ala Thr
            580                 585                 590 aac gcc gaa gct tag                                                1791
Asn Ala Glu Ala
        595

<210> SEQ ID NO 59
<211> LENGTH: 596
<212> TYPE: PRT
<213> ORGANISM: Pichia stipitis

<400> SEQUENCE: 59

Met Ala Glu Val Ser Leu Gly Arg Tyr Leu Phe Glu Arg Leu Tyr Gln
1               5                   10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
    50                  55                  60

Asp Gly Tyr Ser Arg Val Lys Arg Leu Gly Cys Leu Val Thr Thr Phe
65                  70                  75                  80

Gly Val Gly Glu Leu Ser Ala Leu Asn Gly Ile Ala Gly Ser Tyr Ala
                85                  90                  95
```

```
Glu His Val Gly Leu Leu His Val Val Gly Val Pro Ser Ile Ser Ser
                100                 105                 110

Gln Ala Lys Gln Leu Leu Leu His His Thr Leu Gly Asn Gly Asp Phe
            115                 120                 125

Thr Val Phe His Arg Met Ser Asn Asn Ile Ser Gln Thr Thr Ala Phe
        130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Leu Asn Pro Ile Ile Leu Val
210                 215                 220

Asp Ala Cys Ala Ser Arg His Asp Cys Lys Ala Glu Val Thr Gln Leu
225                 230                 235                 240

Ile Glu Gln Thr Gln Phe Pro Val Phe Val Thr Pro Met Gly Lys Gly
                245                 250                 255

Thr Val Asp Glu Gly Gly Val Asp Gly Glu Leu Leu Glu Asp Asp Pro
            260                 265                 270

His Leu Ile Ala Lys Val Ala Ala Arg Leu Ser Ala Gly Lys Asn Ala
        275                 280                 285

Ala Ser Arg Phe Gly Gly Val Tyr Val Gly Thr Leu Ser Lys Pro Glu
        290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
            340                 345                 350

Thr Phe Pro Gly Val Gln Met Lys Glu Ala Leu Gln Glu Leu Asn Lys
        355                 360                 365

Lys Val Ser Ser Ala Ala Ser His Tyr Glu Val Lys Pro Val Pro Lys
370                 375                 380

Ile Lys Leu Ala Asn Thr Pro Ala Thr Arg Glu Val Lys Leu Thr Gln
385                 390                 395                 400

Glu Trp Leu Trp Thr Arg Val Ser Ser Trp Phe Arg Glu Gly Asp Ile
                405                 410                 415

Ile Ile Thr Glu Thr Gly Thr Ser Ser Phe Gly Ile Val Gln Ser Arg
            420                 425                 430

Phe Pro Asn Asn Thr Ile Gly Ile Ser Gln Val Leu Trp Gly Ser Ile
        435                 440                 445

Gly Phe Ser Val Gly Ala Thr Leu Gly Ala Ala Met Ala Ala Gln Glu
        450                 455                 460

Leu Asp Pro Asn Lys Arg Thr Ile Leu Phe Val Gly Asp Gly Ser Leu
465                 470                 475                 480

Gln Leu Thr Val Gln Glu Ile Ser Thr Ile Arg Trp Gly Thr Thr
                485                 490                 495

Pro Tyr Leu Phe Val Leu Asn Asn Asp Gly Tyr Thr Ile Glu Arg Leu
            500                 505                 510

Ile His Gly Val Asn Ala Ser Tyr Asn Asp Ile Gln Pro Trp Gln Asn
```

```
            515                 520                 525
Leu Glu Ile Leu Pro Thr Phe Ser Ala Lys Asn Tyr Asp Ala Val Arg
    530                 535                 540

Ile Ser Asn Ile Gly Glu Ala Glu Asp Ile Leu Lys Asp Lys Glu Phe
545                 550                 555                 560

Gly Lys Asn Ser Lys Ile Arg Leu Ile Glu Val Met Leu Pro Arg Leu
                565                 570                 575

Asp Ala Pro Ser Asn Leu Ala Lys Gln Ala Ala Ile Thr Ala Ala Thr
            580                 585                 590

Asn Ala Glu Ala
        595

<210> SEQ ID NO 60
<211> LENGTH: 1710
<212> TYPE: DNA
<213> ORGANISM: Pichia stipitis
<220> FEATURE:
<221> NAME/KEY: CDS
<222> LOCATION: (1)..(1710)

<400> SEQUENCE: 60 atg gta tca acc tac cca gaa tca gag gtt act cta gga agg tac ctc      48
Met Val Ser Thr Tyr Pro Glu Ser Glu Val Thr Leu Gly Arg Tyr Leu
1               5                   10                  15 ttt gag cga ctc cac caa ttg aaa gtg gac acc att ttc ggc ttg ccg      96
Phe Glu Arg Leu His Gln Leu Lys Val Asp Thr Ile Phe Gly Leu Pro
            20                  25                  30 ggt gac ttc aac ctt tcc tta ttg gac aaa gtg tat gaa gtt ccg gat     144
Gly Asp Phe Asn Leu Ser Leu Leu Asp Lys Val Tyr Glu Val Pro Asp
        35                  40                  45 atg agg tgg gct gga aat gcc aac gaa ttg aat gct gcc tat gct gcc     192
Met Arg Trp Ala Gly Asn Ala Asn Glu Leu Asn Ala Ala Tyr Ala Ala
    50                  55                  60 gat ggt tac tcc aga ata aag gga ttg tct tgc ttg gtc aca act ttt     240
Asp Gly Tyr Ser Arg Ile Lys Gly Leu Ser Cys Leu Val Thr Thr Phe
65                  70                  75                  80 ggt gtt ggt gaa ttg tct gct tta aac gga gtt ggt ggt gcc tat gct     288
Gly Val Gly Glu Leu Ser Ala Leu Asn Gly Val Gly Gly Ala Tyr Ala
                85                  90                  95 gaa cac gta gga ctt cta cat gtc gtt gga gtt cca tcc ata tcg tca     336
Glu His Val Gly Leu Leu His Val Val Gly Val Pro Ser Ile Ser Ser
            100                 105                 110 cag gct aaa cag ttg ttg ctc cac cat acc ttg ggt aat ggt gac ttc     384
Gln Ala Lys Gln Leu Leu Leu His His Thr Leu Gly Asn Gly Asp Phe
        115                 120                 125 act gtt ttt cac aga atg tcc aat agc att tct caa act aca gca ttt     432
Thr Val Phe His Arg Met Ser Asn Ser Ile Ser Gln Thr Thr Ala Phe
    130                 135                 140 ctc tca gat atc tct att gca cca ggt caa ata gat aga tgc atc aga     480
Leu Ser Asp Ile Ser Ile Ala Pro Gly Gln Ile Asp Arg Cys Ile Arg
145                 150                 155                 160 gaa gca tat gtt cat cag aga cca gtt tat gtt ggt tta ccg gca aat     528
Glu Ala Tyr Val His Gln Arg Pro Val Tyr Val Gly Leu Pro Ala Asn
                165                 170                 175 atg gtt gat ctc aag gtt cct tct agt ctc tta gaa act cca att gat     576
Met Val Asp Leu Lys Val Pro Ser Ser Leu Leu Glu Thr Pro Ile Asp
            180                 185                 190 ttg aaa ttg aaa caa aat gat cct gaa gct caa gaa gtt gtt gaa aca     624
Leu Lys Leu Lys Gln Asn Asp Pro Glu Ala Gln Glu Val Val Glu Thr
        195                 200                 205
```

```
gtc ctg aag ttg gtg tcc caa gct aca aac ccc att atc ttg gta gac    672
Val Leu Lys Leu Val Ser Gln Ala Thr Asn Pro Ile Ile Leu Val Asp
    210             215                 220 gct tgt gcc ctc aga cac aat tgc aaa gag gaa gtc aaa caa ttg gtt    720
Ala Cys Ala Leu Arg His Asn Cys Lys Glu Glu Val Lys Gln Leu Val
225             230                 235                 240 gat gcc act aat ttt caa gtc ttt aca act cca atg ggt aaa tct ggt    768
Asp Ala Thr Asn Phe Gln Val Phe Thr Thr Pro Met Gly Lys Ser Gly
                245                 250                 255 atc tcc gaa tct cat cca aga ttg ggc ggt gtc tat gtc ggg aca atg    816
Ile Ser Glu Ser His Pro Arg Leu Gly Gly Val Tyr Val Gly Thr Met
            260                 265                 270 tcg agt cct caa gtc aaa aaa gcc gtt gaa aat gcc gat ctt ata cta    864
Ser Ser Pro Gln Val Lys Lys Ala Val Glu Asn Ala Asp Leu Ile Leu
        275                 280                 285 tct gtt ggt tcg ttg tta tcg gac ttc aat aca ggt tca ttt tca tac    912
Ser Val Gly Ser Leu Leu Ser Asp Phe Asn Thr Gly Ser Phe Ser Tyr
    290                 295                 300 tcc tac aag acg aag aat gtt gtt gaa ttc cac tct gac tat atg aaa    960
Ser Tyr Lys Thr Lys Asn Val Val Glu Phe His Ser Asp Tyr Met Lys
305             310                 315                 320 atc aga cag gcc acc ttc cca gga gtt caa atg aaa gaa gcc ttg caa    1008
Ile Arg Gln Ala Thr Phe Pro Gly Val Gln Met Lys Glu Ala Leu Gln
                325                 330                 335 cag ttg ata aaa agg gtc tct tct tac atc aat cca agc tac att cct    1056
Gln Leu Ile Lys Arg Val Ser Ser Tyr Ile Asn Pro Ser Tyr Ile Pro
                340                 345                 350 act cga gtt cct aaa agg aaa cag cca ttg aaa gct cca tca gaa gct    1104
Thr Arg Val Pro Lys Arg Lys Gln Pro Leu Lys Ala Pro Ser Glu Ala
        355                 360                 365 cct ttg acc caa gaa tat ttg tgg tct aaa gta tcc ggc tgg ttt aga    1152
Pro Leu Thr Gln Glu Tyr Leu Trp Ser Lys Val Ser Gly Trp Phe Arg
    370                 375                 380 gag ggt gat att atc gta acc gaa act ggt aca tct gct ttc gga att    1200
Glu Gly Asp Ile Ile Val Thr Glu Thr Gly Thr Ser Ala Phe Gly Ile
385             390                 395                 400 att caa tcc cat ttt ccc agc aac act atc ggt ata tcc caa gtc ttg    1248
Ile Gln Ser His Phe Pro Ser Asn Thr Ile Gly Ile Ser Gln Val Leu
                405                 410                 415 tgg ggc tca att ggt ttc aca gta ggt gca aca gtt ggt gct gcc atg    1296
Trp Gly Ser Ile Gly Phe Thr Val Gly Ala Thr Val Gly Ala Ala Met
                420                 425                 430 gca gcc cag gaa atc gac cct agc agg aga gta att ttg ttc gtc ggt    1344
Ala Ala Gln Glu Ile Asp Pro Ser Arg Arg Val Ile Leu Phe Val Gly
        435                 440                 445 gat ggt tca ttg cag ttg acg gtt cag gaa atc tct acg ttg tgt aaa    1392
Asp Gly Ser Leu Gln Leu Thr Val Gln Glu Ile Ser Thr Leu Cys Lys
    450                 455                 460 tgg gat tgt aac aat act tat ctt tac gtg ttg aac aat gat ggt tac    1440
Trp Asp Cys Asn Asn Thr Tyr Leu Tyr Val Leu Asn Asn Asp Gly Tyr
465             470                 475                 480 act ata gaa agg ttg atc cac ggc aaa agt gcc agc tac aac gat ata    1488
Thr Ile Glu Arg Leu Ile His Gly Lys Ser Ala Ser Tyr Asn Asp Ile
                485                 490                 495 cag cct tgg aac cat tta tcc ttg ctt cgc tta ttc aat gct aag aaa    1536
Gln Pro Trp Asn His Leu Ser Leu Leu Arg Leu Phe Asn Ala Lys Lys
                500                 505                 510 tac caa aat gtc aga gta tcg act gct gga gaa ttg gac tct ttg ttc    1584
Tyr Gln Asn Val Arg Val Ser Thr Ala Gly Glu Leu Asp Ser Leu Phe
```

-continued

```
               515                 520                 525
tct aag aaa ttt gct tct cca gat agg ata aga atg att gag gtg      1632
Ser Asp Lys Lys Phe Ala Ser Pro Asp Arg Ile Arg Met Ile Glu Val
530                 535                 540 atg tta tcg aga ttg gat gca cca gca aat ctt gtt gct caa gca aag  1680
Met Leu Ser Arg Leu Asp Ala Pro Ala Asn Leu Val Ala Gln Ala Lys
545                 550                 555                 560 ttg tct gaa cgg gta aac ctt gaa aat tga                          1710
Leu Ser Glu Arg Val Asn Leu Glu Asn
                565
```

<210> SEQ ID NO 61
<211> LENGTH: 569
<212> TYPE: PRT
<213> ORGANISM: Pichia stipitis

<400> SEQUENCE: 61

```
Met Val Ser Thr Tyr Pro Glu Ser Glu Val Thr Leu Gly Arg Tyr Leu
1               5                   10                  15

Phe Glu Arg Leu His Gln Leu Lys Val Asp Thr Ile Phe Gly Leu Pro
                20                  25                  30

Gly Asp Phe Asn Leu Ser Leu Leu Asp Lys Val Tyr Glu Val Pro Asp
            35                  40                  45

Met Arg Trp Ala Gly Asn Ala Asn Glu Leu Asn Ala Ala Tyr Ala Ala
        50                  55                  60

Asp Gly Tyr Ser Arg Ile Lys Gly Leu Ser Cys Leu Val Thr Thr Phe
65                  70                  75                  80

Gly Val Gly Glu Leu Ser Ala Leu Asn Gly Val Gly Ala Tyr Ala
                85                  90                  95

Glu His Val Gly Leu Leu His Val Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Ser Ile Ser Gln Thr Thr Ala Phe
    130                 135                 140

Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Leu Glu Thr Pro Ile Asp
            180                 185                 190

Leu Lys Leu Lys Gln Asn Asp Pro Glu Ala Gln Glu Val Val Glu Thr
        195                 200                 205

Val Leu Lys Leu Val Ser Gln Ala Thr Asn Pro Ile Ile Leu Val Asp
    210                 215                 220

Ala Cys Ala Leu Arg His Asn Cys Lys Glu Glu Val Lys Gln Leu Val
225                 230                 235                 240

Asp Ala Thr Asn Phe Gln Val Phe Thr Thr Pro Met Gly Lys Ser Gly
                245                 250                 255

Ile Ser Glu Ser His Pro Arg Leu Gly Gly Val Tyr Val Gly Thr Met
            260                 265                 270

Ser Ser Pro Gln Val Lys Lys Ala Val Glu Asn Ala Asp Leu Ile Leu
        275                 280                 285

Ser Val Gly Ser Leu Leu Ser Asp Phe Asn Thr Gly Ser Phe Ser Tyr
    290                 295                 300
```

| | | | | | | | | | | | | | | |
|---|---|---|---|---|---|---|---|---|---|---|---|---|---|---|
|Ser|Tyr|Lys|Thr|Lys|Asn|Val|Val|Glu|Phe|His|Ser|Asp|Tyr|Met|Lys|
|305| | | |310| | | |315| | | |320| | |

Ile Arg Gln Ala Thr Phe Pro Gly Val Gln Met Lys Glu Ala Leu Gln
                325                 330                 335

Gln Leu Ile Lys Arg Val Ser Ser Tyr Ile Asn Pro Ser Tyr Ile Pro
            340                 345                 350

Thr Arg Val Pro Lys Arg Lys Gln Pro Leu Lys Ala Pro Ser Glu Ala
        355                 360                 365

Pro Leu Thr Gln Glu Tyr Leu Trp Ser Lys Val Ser Gly Trp Phe Arg
    370                 375                 380

Glu Gly Asp Ile Ile Val Thr Glu Thr Gly Thr Ser Ala Phe Gly Ile
385                 390                 395                 400

Ile Gln Ser His Phe Pro Ser Asn Thr Ile Gly Ile Ser Gln Val Leu
                405                 410                 415

Trp Gly Ser Ile Gly Phe Thr Val Gly Ala Thr Val Gly Ala Ala Met
            420                 425                 430

Ala Ala Gln Glu Ile Asp Pro Ser Arg Arg Val Ile Leu Phe Val Gly
        435                 440                 445

Asp Gly Ser Leu Gln Leu Thr Val Gln Glu Ile Ser Thr Leu Cys Lys
450                 455                 460

Trp Asp Cys Asn Asn Thr Tyr Leu Tyr Val Leu Asn Asn Asp Gly Tyr
465                 470                 475                 480

Thr Ile Glu Arg Leu Ile His Gly Lys Ser Ala Ser Tyr Asn Asp Ile
                485                 490                 495

Gln Pro Trp Asn His Leu Ser Leu Leu Arg Leu Phe Asn Ala Lys Lys
            500                 505                 510

Tyr Gln Asn Val Arg Val Ser Thr Ala Gly Glu Leu Asp Ser Leu Phe
        515                 520                 525

Ser Asp Lys Lys Phe Ala Ser Pro Asp Arg Ile Arg Met Ile Glu Val
    530                 535                 540

Met Leu Ser Arg Leu Asp Ala Pro Ala Asn Leu Val Ala Gln Ala Lys
545                 550                 555                 560

Leu Ser Glu Arg Val Asn Leu Glu Asn
                565

<210> SEQ ID NO 62
<211> LENGTH: 1692
<212> TYPE: DNA
<213> ORGANISM: Kluyveromyces lactis
<220> FEATURE:
<221> NAME/KEY: CDS
<222> LOCATION: (1)..(1692)

<400> SEQUENCE: 62

| | | | | | | | | | | | | | | | |
|---|---|---|---|---|---|---|---|---|---|---|---|---|---|---|---|---|
|atg|tct|gaa|att|aca|tta|ggt|cgt|tac|ttg|ttc|gaa|aga|tta|aag|caa|48|
|Met|Ser|Glu|Ile|Thr|Leu|Gly|Arg|Tyr|Leu|Phe|Glu|Arg|Leu|Lys|Gln| |
|1| | | |5| | | |10| | | |15| | | | gtc gaa gtt caa acc atc ttt ggt cta cca ggt gat ttc aac ttg tcc    96
Val Glu Val Gln Thr Ile Phe Gly Leu Pro Gly Asp Phe Asn Leu Ser
            20                  25                  30 cta ttg gac aat atc tac gaa gtc cca ggt atg aga tgg gct ggt aat   144
Leu Leu Asp Asn Ile Tyr Glu Val Pro Gly Met Arg Trp Ala Gly Asn
        35                  40                  45 gcc aac gaa ttg aac gct gct tac gct gct gat ggt tac gcc aga tta   192
Ala Asn Glu Leu Asn Ala Ala Tyr Ala Ala Asp Gly Tyr Ala Arg Leu
    50                  55                  60 aag ggt atg tcc tgt atc atc acc acc ttc ggt gtc ggt gaa ttg tct   240

```
Lys Gly Met Ser Cys Ile Ile Thr Thr Phe Gly Val Gly Glu Leu Ser
 65                  70                  75                  80 gct ttg aac ggt att gcc ggt tct tac gct gaa cac gtt ggt gtc ttg        288
Ala Leu Asn Gly Ile Ala Gly Ser Tyr Ala Glu His Val Gly Val Leu
                     85                  90                  95 cac gtt gtc ggt gtt cca tcc gtc tct tct caa gct aag caa ttg ttg        336
His Val Val Gly Val Pro Ser Val Ser Ser Gln Ala Lys Gln Leu Leu
                100                 105                 110 ttg cac cac acc ttg ggt aac ggt gac ttc act gtt ttc cac aga atg        384
Leu His His Thr Leu Gly Asn Gly Asp Phe Thr Val Phe His Arg Met
            115                 120                 125 tcc tcc aac att tct gaa acc act gct atg atc acc gat atc aac act        432
Ser Ser Asn Ile Ser Glu Thr Thr Ala Met Ile Thr Asp Ile Asn Thr
        130                 135                 140 gcc cca gct gaa atc gac aga tgt atc aga acc act tac gtt tcc caa        480
Ala Pro Ala Glu Ile Asp Arg Cys Ile Arg Thr Thr Tyr Val Ser Gln
145                 150                 155                 160 aga cca gtc tac ttg ggt ttg cca gct aac ttg gtc gac ttg act gtc        528
Arg Pro Val Tyr Leu Gly Leu Pro Ala Asn Leu Val Asp Leu Thr Val
                    165                 170                 175 cca gct tct ttg ttg gac act cca att gat ttg agc ttg aag cca aat        576
Pro Ala Ser Leu Leu Asp Thr Pro Ile Asp Leu Ser Leu Lys Pro Asn
                180                 185                 190 gac cca gaa gcc gaa gaa gaa gtc atc gaa aac gtc ttg caa ctg atc        624
Asp Pro Glu Ala Glu Glu Glu Val Ile Glu Asn Val Leu Gln Leu Ile
            195                 200                 205 aag gaa gct aag aac cca gtt atc ttg gct gat gct tgt tgt tcc aga        672
Lys Glu Ala Lys Asn Pro Val Ile Leu Ala Asp Ala Cys Cys Ser Arg
        210                 215                 220 cac gat gcc aag gct gag acc aag aag ttg atc gac ttg act caa ttc        720
His Asp Ala Lys Ala Glu Thr Lys Lys Leu Ile Asp Leu Thr Gln Phe
225                 230                 235                 240 cca gcc ttc gtt acc cca atg ggt aag ggt tcc att gac gaa aag cac        768
Pro Ala Phe Val Thr Pro Met Gly Lys Gly Ser Ile Asp Glu Lys His
                    245                 250                 255 cca aga ttc ggt ggt gtc tac gtc ggt acc cta tct tct cca gct gtc        816
Pro Arg Phe Gly Gly Val Tyr Val Gly Thr Leu Ser Ser Pro Ala Val
                260                 265                 270 aag gaa gcc gtt gaa tct gct gac ttg gtt cta tcg gtc ggt gct cta        864
Lys Glu Ala Val Glu Ser Ala Asp Leu Val Leu Ser Val Gly Ala Leu
            275                 280                 285 ttg tcc gat ttc aac act ggt tct ttc tct tac tct tac aag acc aag        912
Leu Ser Asp Phe Asn Thr Gly Ser Phe Ser Tyr Ser Tyr Lys Thr Lys
        290                 295                 300 aac att gtc gaa ttc cac tct gac tac acc aag atc aga agc gct acc        960
Asn Ile Val Glu Phe His Ser Asp Tyr Thr Lys Ile Arg Ser Ala Thr
305                 310                 315                 320 ttc cca ggt gtc caa atg aag ttc gct tta caa aaa ttg ttg act aag       1008
Phe Pro Gly Val Gln Met Lys Phe Ala Leu Gln Lys Leu Leu Thr Lys
                    325                 330                 335 gtt gcc gat gct gct aag ggt tac aag cca gtt cca gtt cca tct gaa       1056
Val Ala Asp Ala Ala Lys Gly Tyr Lys Pro Val Pro Val Pro Ser Glu
                340                 345                 350 cca gaa cac aac gaa gct gtc gct gac tcc act cca ttg aag caa gaa       1104
Pro Glu His Asn Glu Ala Val Ala Asp Ser Thr Pro Leu Lys Gln Glu
            355                 360                 365 tgg gtc tgg act caa gtc ggt gaa ttc ttg aga gaa ggt gat gtt gtt       1152
Trp Val Trp Thr Gln Val Gly Glu Phe Leu Arg Glu Gly Asp Val Val
        370                 375                 380
```

```
atc act gaa acc ggt acc tct gcc ttc ggt atc aac caa act cat ttc      1200
Ile Thr Glu Thr Gly Thr Ser Ala Phe Gly Ile Asn Gln Thr His Phe
385                 390                 395                 400 cca aac aac aca tac ggt atc tct caa gtt tta tgg ggt tcc att ggt      1248
Pro Asn Asn Thr Tyr Gly Ile Ser Gln Val Leu Trp Gly Ser Ile Gly
                405                 410                 415 ttc acc act ggt gct acc ttg ggt gct gcc ttc gct gcc gaa gaa att      1296
Phe Thr Thr Gly Ala Thr Leu Gly Ala Ala Phe Ala Ala Glu Glu Ile
                420                 425                 430 gat cca aag aag aga gtt atc tta ttc att ggt gac ggt tct ttg caa      1344
Asp Pro Lys Lys Arg Val Ile Leu Phe Ile Gly Asp Gly Ser Leu Gln
                435                 440                 445 ttg act gtt caa gaa atc tcc acc atg atc aga tgg ggc ttg aag cca      1392
Leu Thr Val Gln Glu Ile Ser Thr Met Ile Arg Trp Gly Leu Lys Pro
                450                 455                 460 tac ttg ttc gta ttg aac aac gac ggt tac acc att gaa aga ttg att      1440
Tyr Leu Phe Val Leu Asn Asn Asp Gly Tyr Thr Ile Glu Arg Leu Ile
465                 470                 475                 480 cac ggt gaa acc gct caa tac aac tgt atc caa aac tgg caa cac ttg      1488
His Gly Glu Thr Ala Gln Tyr Asn Cys Ile Gln Asn Trp Gln His Leu
                485                 490                 495 gaa tta ttg cca act ttc ggt gcc aag gac tac gaa gct gtc aga gtt      1536
Glu Leu Leu Pro Thr Phe Gly Ala Lys Asp Tyr Glu Ala Val Arg Val
                500                 505                 510 tcc acc act ggt gaa tgg aac aag ttg acc act gac gaa aag ttc caa      1584
Ser Thr Thr Gly Glu Trp Asn Lys Leu Thr Thr Asp Glu Lys Phe Gln
                515                 520                 525 gac aac acc aga atc aga ttg atc gaa gtt atg ttg cca act atg gat      1632
Asp Asn Thr Arg Ile Arg Leu Ile Glu Val Met Leu Pro Thr Met Asp
                530                 535                 540 gct cca tct aac ttg gtt aag caa gct caa ttg act gct gct acc aac      1680
Ala Pro Ser Asn Leu Val Lys Gln Ala Gln Leu Thr Ala Ala Thr Asn
545                 550                 555                 560 gct aag aac taa                                                      1692
Ala Lys Asn <210> SEQ ID NO 63
<211> LENGTH: 563
<212> TYPE: PRT
<213> ORGANISM: Kluyveromyces lactis

<400> SEQUENCE: 63

Met Ser Glu Ile Thr Leu Gly Arg Tyr Leu Phe Glu Arg Leu Lys Gln
1               5                   10                  15

Val Glu Val Gln Thr Ile Phe Gly Leu Pro Gly Asp Phe Asn Leu Ser
                20                  25                  30

Leu Leu Asp Asn Ile Tyr Glu Val Pro Gly Met Arg Trp Ala Gly Asn
            35                  40                  45

Ala Asn Glu Leu Asn Ala Ala Tyr Ala Ala Asp Gly Tyr Ala Arg Leu
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Val Ser Ser Gln Ala Lys Gln Leu Leu
                100                 105                 110

Leu His His Thr Leu Gly Asn Gly Asp Phe Thr Val Phe His Arg Met
            115                 120                 125
```

```
Ser Ser Asn Ile Ser Glu Thr Thr Ala Met Ile Thr Asp Ile Asn Thr
130                 135                 140

Ala Pro Ala Glu Ile Asp Arg Cys Ile Arg Thr Thr Tyr Val Ser Gln
145                 150                 155                 160

Arg Pro Val Tyr Leu Gly Leu Pro Ala Asn Leu Val Asp Leu Thr Val
                165                 170                 175

Pro Ala Ser Leu Leu Asp Thr Pro Ile Asp Leu Ser Leu Lys Pro Asn
            180                 185                 190

Asp Pro Glu Ala Glu Glu Val Ile Glu Asn Val Leu Gln Leu Ile
        195                 200                 205

Lys Glu Ala Lys Asn Pro Val Ile Leu Ala Asp Ala Cys Cys Ser Arg
210                 215                 220

His Asp Ala Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Lys His
                245                 250                 255

Pro Arg Phe Gly Gly Val Tyr Val Gly Thr Leu Ser Ser Pro Ala Val
            260                 265                 270

Lys Glu Ala Val Glu Ser Ala Asp Leu Val Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp Tyr Thr Lys Ile Arg Ser Ala Thr
305                 310                 315                 320

Phe Pro Gly Val Gln Met Lys Phe Ala Leu Gln Lys Leu Leu Thr Lys
                325                 330                 335

Val Ala Asp Ala Ala Lys Gly Tyr Lys Pro Val Pro Val Pro Ser Glu
            340                 345                 350

Pro Glu His Asn Glu Ala Val Ala Asp Ser Thr Pro Leu Lys Gln Glu
        355                 360                 365

Trp Val Trp Thr Gln Val Gly Glu Phe Leu Arg Glu Gly Asp Val Val
370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
                485                 490                 495

Glu Leu Leu Pro Thr Phe Gly Ala Lys Asp Tyr Glu Ala Val Arg Val
            500                 505                 510

Ser Thr Thr Gly Glu Trp Asn Lys Leu Thr Thr Asp Glu Lys Phe Gln
        515                 520                 525

Asp Asn Thr Arg Ile Arg Leu Ile Glu Val Met Leu Pro Thr Met Asp
530                 535                 540

Ala Pro Ser Asn Leu Val Lys Gln Ala Gln Leu Thr Ala Ala Thr Asn
```

<210> SEQ ID NO 64
<211> LENGTH: 1716
<212> TYPE: DNA
<213> ORGANISM: Yarrowia lipolytica
<220> FEATURE:
<221> NAME/KEY: CDS
<222> LOCATION: (1)..(1716)

<400> SEQUENCE: 64

| | | |
|---|---|---|
| atg agc gac tcc gaa ccc caa atg gtc gac ctg ggc gac tat ctc ttt<br>Met Ser Asp Ser Glu Pro Gln Met Val Asp Leu Gly Asp Tyr Leu Phe<br>1                5                    10              15 | 48 | |
| gcc cga ttc aag cag cta ggc gtg gac tcc gtc ttt gga gtg ccc ggc<br>Ala Arg Phe Lys Gln Leu Gly Val Asp Ser Val Phe Gly Val Pro Gly<br>                    20                    25                    30 | 96 | |
| gac ttc aac ctc acc ctg ttg gac cac gtg tac aat gtc gac atg cgg<br>Asp Phe Asn Leu Thr Leu Leu Asp His Val Tyr Asn Val Asp Met Arg<br>                35                    40                    45 | 144 | |
| tgg gtt ggg aac aca aac gag ctg aat gcc ggc tac tcg gcc gac ggc<br>Trp Val Gly Asn Thr Asn Glu Leu Asn Ala Gly Tyr Ser Ala Asp Gly<br>50                    55                    60 | 192 | |
| tac tcc cgg gtc aag cgg ctg gca tgt ctt gtc acc acc ttt ggc gtg<br>Tyr Ser Arg Val Lys Arg Leu Ala Cys Leu Val Thr Thr Phe Gly Val<br>65                    70                    75                    80 | 240 | |
| gga gag ctg tct gcc gtg gct gct gtg gca ggc tcg tac gcc gag cat<br>Gly Glu Leu Ser Ala Val Ala Ala Val Ala Gly Ser Tyr Ala Glu His<br>                    85                    90                    95 | 288 | |
| gtg ggc gtg gtg cat gtt gtg ggc gtt ccc agc acc tct gct gag aac<br>Val Gly Val Val His Val Val Gly Val Pro Ser Thr Ser Ala Glu Asn<br>                100                 105                110 | 336 | |
| aag cat ctg ctg ctg cac cac aca ctc ggt aac ggc gac ttc cgg gtc<br>Lys His Leu Leu Leu His His Thr Leu Gly Asn Gly Asp Phe Arg Val<br>              115                 120                125 | 384 | |
| ttt gcc cag atg tcc aaa ctc atc tcc gag tac acc cac cat att gag<br>Phe Ala Gln Met Ser Lys Leu Ile Ser Glu Tyr Thr His His Ile Glu<br>130                    135                 140 | 432 | |
| gac ccc agc gag gct gcc gac gta atc gac acc gcc atc cga atc gcc<br>Asp Pro Ser Glu Ala Ala Asp Val Ile Asp Thr Ala Ile Arg Ile Ala<br>145                    150                 155                160 | 480 | |
| tac acc cac cag cgg ccc gtt tac att gct gtg ccc tcc aac ttc tcc<br>Tyr Thr His Gln Arg Pro Val Tyr Ile Ala Val Pro Ser Asn Phe Ser<br>                    165                 170                175 | 528 | |
| gag gtc gat att gcc gac cag gct aga ctg gat acc ccc ctg gac ctt<br>Glu Val Asp Ile Ala Asp Gln Ala Arg Leu Asp Thr Pro Leu Asp Leu<br>              180                 185                190 | 576 | |
| tcg ctg cag ccc aac gac ccc gag agc cag tac gag gtg att gag gag<br>Ser Leu Gln Pro Asn Asp Pro Glu Ser Gln Tyr Glu Val Ile Glu Glu<br>              195                 200                205 | 624 | |
| att tgc tcg cgt atc aag gcc gcc aag aag ccc gtg att ctc gtc gac<br>Ile Cys Ser Arg Ile Lys Ala Ala Lys Lys Pro Val Ile Leu Val Asp<br>210                    215                 220 | 672 | |
| gcc tgc gct tcg cga tac aga tgt gtg gac gag acc aag gag ctg gcc<br>Ala Cys Ala Ser Arg Tyr Arg Cys Val Asp Glu Thr Lys Glu Leu Ala<br>225                    230                 235                240 | 720 | |
| aag atc acc aac ttt gcc tac ttt gtc act ccc atg ggt aag ggt tct<br>Lys Ile Thr Asn Phe Ala Tyr Phe Val Thr Pro Met Gly Lys Gly Ser<br>                    245                 250                255 | 768 | |

```
                                                  -continued gtg gac gag gat act gac cgg tac gga gga aca tac gtc gga tcg ctg          816
Val Asp Glu Asp Thr Asp Arg Tyr Gly Gly Thr Tyr Val Gly Ser Leu
            260                 265                 270 act gct cct gct act gcc gag gtg gtt gag aca gct gat ctc atc atc          864
Thr Ala Pro Ala Thr Ala Glu Val Val Glu Thr Ala Asp Leu Ile Ile
        275                 280                 285 tcc gta gga gct ctt ctg tcg gac ttc aac acc ggt tcc ttc tcg tac          912
Ser Val Gly Ala Leu Leu Ser Asp Phe Asn Thr Gly Ser Phe Ser Tyr
    290                 295                 300 tcc tac tcc acc aaa aac gtg gtg gaa ttg cat tcg gac cac gtc aaa          960
Ser Tyr Ser Thr Lys Asn Val Val Glu Leu His Ser Asp His Val Lys
305                 310                 315                 320 atc aag tcc gcc acc tac aac aac gtc ggc atg aaa atg ctg ttc ccg         1008
Ile Lys Ser Ala Thr Tyr Asn Asn Val Gly Met Lys Met Leu Phe Pro
                325                 330                 335 ccc ctg ctc gaa gcc gtc aag aaa ctg gtt gcc gag acc cct gac ttt         1056
Pro Leu Leu Glu Ala Val Lys Lys Leu Val Ala Glu Thr Pro Asp Phe
            340                 345                 350 gca tcc aag gct ctg gct gtt ccc gac acc act ccc aag atc ccc gag         1104
Ala Ser Lys Ala Leu Ala Val Pro Asp Thr Thr Pro Lys Ile Pro Glu
        355                 360                 365 gta ccc gat gat cac att acg acc cag gca tgg ctg tgg cag cgt ctc         1152
Val Pro Asp Asp His Ile Thr Thr Gln Ala Trp Leu Trp Gln Arg Leu
    370                 375                 380 agt tac ttt ctg agg ccc acc gac atc gtg gtc acc gag acc gga acc         1200
Ser Tyr Phe Leu Arg Pro Thr Asp Ile Val Val Thr Glu Thr Gly Thr
385                 390                 395                 400 tcg tcc ttt gga atc atc cag acc aag ttc ccc cac aac gtc cga ggt         1248
Ser Ser Phe Gly Ile Ile Gln Thr Lys Phe Pro His Asn Val Arg Gly
                405                 410                 415 atc tcg cag gtg ctg tgg ggc tct att gga tac tcg gtg gga gca gcc         1296
Ile Ser Gln Val Leu Trp Gly Ser Ile Gly Tyr Ser Val Gly Ala Ala
            420                 425                 430 tgt gga gcc tcc att gct gca cag gag att gac ccc cag cag cga gtg         1344
Cys Gly Ala Ser Ile Ala Ala Gln Glu Ile Asp Pro Gln Gln Arg Val
        435                 440                 445 att ctg ttt gtg ggc gac ggc tct ctt cag ctg acg gtg acc gag atc         1392
Ile Leu Phe Val Gly Asp Gly Ser Leu Gln Leu Thr Val Thr Glu Ile
    450                 455                 460 tcg tgc atg atc cgc aac aac gtc aag ccg tac att ttt gtg ctc aac         1440
Ser Cys Met Ile Arg Asn Asn Val Lys Pro Tyr Ile Phe Val Leu Asn
465                 470                 475                 480 aac gac ggc tac acc atc gag agg ctc att cac ggc gaa aac gcc tcg         1488
Asn Asp Gly Tyr Thr Ile Glu Arg Leu Ile His Gly Glu Asn Ala Ser
                485                 490                 495 tac aac gat gtg cac atg tgg aag tac tcc aag att ctc gac acg ttc         1536
Tyr Asn Asp Val His Met Trp Lys Tyr Ser Lys Ile Leu Asp Thr Phe
            500                 505                 510 aac gcc aag gcc cac gag tcg att gtg gtc aac acc aag ggc gag atg         1584
Asn Ala Lys Ala His Glu Ser Ile Val Val Asn Thr Lys Gly Glu Met
        515                 520                 525 gac gct ctg ttc gac aac gaa gag ttt gcc aag ccc gac aag atc cgg         1632
Asp Ala Leu Phe Asp Asn Glu Glu Phe Ala Lys Pro Asp Lys Ile Arg
    530                 535                 540 ctc att gag gtc atg tgc gac aag atg gac gcg cct gcc tcg ttg atc         1680
Leu Ile Glu Val Met Cys Asp Lys Met Asp Ala Pro Ala Ser Leu Ile
545                 550                 555                 560 aag cag gct gag ctc tct gcc aag acc aac gtt tag                         1716
Lys Gln Ala Glu Leu Ser Ala Lys Thr Asn Val
                565                 570
```

<210> SEQ ID NO 65
<211> LENGTH: 571
<212> TYPE: PRT
<213> ORGANISM: Yarrowia lipolytica

<400> SEQUENCE: 65

| | | | | | | | | | | | | | | |
|---|---|---|---|---|---|---|---|---|---|---|---|---|---|---|
| Met | Ser | Asp | Ser | Glu | Pro | Gln | Met | Val | Asp | Leu | Gly | Asp | Tyr | Leu | Phe |
| 1 | | | | 5 | | | | | 10 | | | | | 15 | |
| Ala | Arg | Phe | Lys | Gln | Leu | Gly | Val | Asp | Ser | Val | Phe | Gly | Val | Pro | Gly |
| | | | 20 | | | | | 25 | | | | | 30 | | |
| Asp | Phe | Asn | Leu | Thr | Leu | Leu | Asp | His | Val | Tyr | Asn | Val | Asp | Met | Arg |
| | | | 35 | | | | | 40 | | | | | 45 | | |
| Trp | Val | Gly | Asn | Thr | Asn | Glu | Leu | Asn | Ala | Gly | Tyr | Ser | Ala | Asp | Gly |
| 50 | | | | | 55 | | | | | 60 | | | | | |
| Tyr | Ser | Arg | Val | Lys | Arg | Leu | Ala | Cys | Leu | Val | Thr | Thr | Phe | Gly | Val |
| 65 | | | | | 70 | | | | | 75 | | | | | 80 |
| Gly | Glu | Leu | Ser | Ala | Val | Ala | Val | Ala | Gly | Ser | Tyr | Ala | Glu | His | |
| | | | | 85 | | | | | 90 | | | | | 95 | |
| Val | Gly | Val | Val | His | Val | Gly | Val | Pro | Ser | Thr | Ser | Ala | Glu | Asn | |
| | | | 100 | | | | | 105 | | | | | 110 | | |
| Lys | His | Leu | Leu | His | His | Thr | Leu | Gly | Asn | Gly | Asp | Phe | Arg | Val | |
| | | | 115 | | | | | 120 | | | | | 125 | | |
| Phe | Ala | Gln | Met | Ser | Lys | Leu | Ile | Ser | Glu | Tyr | Thr | His | His | Ile | Glu |
| | | 130 | | | | | 135 | | | | | 140 | | | |
| Asp | Pro | Ser | Glu | Ala | Ala | Asp | Val | Ile | Asp | Thr | Ala | Ile | Arg | Ile | Ala |
| 145 | | | | | 150 | | | | | 155 | | | | | 160 |
| Tyr | Thr | His | Gln | Arg | Pro | Val | Tyr | Ile | Ala | Val | Pro | Ser | Asn | Phe | Ser |
| | | | | 165 | | | | | 170 | | | | | 175 | |
| Glu | Val | Asp | Ile | Ala | Asp | Gln | Ala | Arg | Leu | Asp | Thr | Pro | Leu | Asp | Leu |
| | | | 180 | | | | | 185 | | | | | 190 | | |
| Ser | Leu | Gln | Pro | Asn | Asp | Pro | Glu | Ser | Gln | Tyr | Glu | Val | Ile | Glu | Glu |
| | | | 195 | | | | | 200 | | | | | 205 | | |
| Ile | Cys | Ser | Arg | Ile | Lys | Ala | Ala | Lys | Pro | Val | Ile | Leu | Val | Asp | |
| | 210 | | | | | 215 | | | | | 220 | | | | |
| Ala | Cys | Ala | Ser | Arg | Tyr | Arg | Cys | Val | Asp | Glu | Thr | Lys | Glu | Leu | Ala |
| 225 | | | | | 230 | | | | | 235 | | | | | 240 |
| Lys | Ile | Thr | Asn | Phe | Ala | Tyr | Phe | Val | Thr | Pro | Met | Gly | Lys | Gly | Ser |
| | | | | 245 | | | | | 250 | | | | | 255 | |
| Val | Asp | Glu | Asp | Thr | Asp | Arg | Tyr | Gly | Gly | Thr | Tyr | Val | Gly | Ser | Leu |
| | | | 260 | | | | | 265 | | | | | 270 | | |
| Thr | Ala | Pro | Ala | Thr | Ala | Glu | Val | Val | Glu | Thr | Ala | Asp | Leu | Ile | Ile |
| | | 275 | | | | | 280 | | | | | 285 | | | |
| Ser | Val | Gly | Ala | Leu | Leu | Ser | Asp | Phe | Asn | Thr | Gly | Ser | Phe | Ser | Tyr |
| | 290 | | | | | 295 | | | | | 300 | | | | |
| Ser | Tyr | Ser | Thr | Lys | Asn | Val | Val | Glu | Leu | His | Ser | Asp | His | Val | Lys |
| 305 | | | | | 310 | | | | | 315 | | | | | 320 |
| Ile | Lys | Ser | Ala | Thr | Tyr | Asn | Asn | Val | Gly | Met | Lys | Met | Leu | Phe | Pro |
| | | | | 325 | | | | | 330 | | | | | 335 | |
| Pro | Leu | Leu | Glu | Ala | Val | Lys | Lys | Leu | Val | Ala | Glu | Thr | Pro | Asp | Phe |
| | | | 340 | | | | | 345 | | | | | 350 | | |
| Ala | Ser | Lys | Ala | Leu | Ala | Val | Pro | Asp | Thr | Thr | Pro | Lys | Ile | Pro | Glu |
| | | 355 | | | | | 360 | | | | | 365 | | | |
| Val | Pro | Asp | Asp | His | Ile | Thr | Thr | Gln | Ala | Trp | Leu | Trp | Gln | Arg | Leu |

```
              370                 375                 380
Ser Tyr Phe Leu Arg Pro Thr Asp Ile Val Val Thr Glu Thr Gly Thr
385                 390                 395                 400

Ser Ser Phe Gly Ile Ile Gln Thr Lys Phe Pro His Asn Val Arg Gly
                405                 410                 415

Ile Ser Gln Val Leu Trp Gly Ser Ile Gly Tyr Ser Val Gly Ala Ala
            420                 425                 430

Cys Gly Ala Ser Ile Ala Ala Gln Glu Ile Asp Pro Gln Gln Arg Val
        435                 440                 445

Ile Leu Phe Val Gly Asp Gly Ser Leu Gln Leu Thr Val Thr Glu Ile
    450                 455                 460

Ser Cys Met Ile Arg Asn Asn Val Lys Pro Tyr Ile Phe Val Leu Asn
465                 470                 475                 480

Asn Asp Gly Tyr Thr Ile Glu Arg Leu Ile His Gly Glu Asn Ala Ser
                485                 490                 495

Tyr Asn Asp Val His Met Trp Lys Tyr Ser Lys Ile Leu Asp Thr Phe
            500                 505                 510

Asn Ala Lys Ala His Glu Ser Ile Val Val Asn Thr Lys Gly Glu Met
        515                 520                 525

Asp Ala Leu Phe Asp Asn Glu Glu Phe Ala Lys Pro Asp Lys Ile Arg
    530                 535                 540

Leu Ile Glu Val Met Cys Asp Lys Met Asp Ala Pro Ala Ser Leu Ile
545                 550                 555                 560

Lys Gln Ala Glu Leu Ser Ala Lys Thr Asn Val
                565                 570
```

<210> SEQ ID NO 66
<211> LENGTH: 1716
<212> TYPE: DNA
<213> ORGANISM: Schizosaccharomyces pombe
<220> FEATURE:
<221> NAME/KEY: CDS
<222> LOCATION: (1)..(1716)

<400> SEQUENCE: 66

```
atg agt ggg gat att tta gtc ggt gaa tat cta ttc aaa agg ctt gaa      48
Met Ser Gly Asp Ile Leu Val Gly Glu Tyr Leu Phe Lys Arg Leu Glu
1               5                   10                  15 caa tta ggg gtc aag tcc att ctt ggt gtt cca gga gat ttc aat tta      96
Gln Leu Gly Val Lys Ser Ile Leu Gly Val Pro Gly Asp Phe Asn Leu
            20                  25                  30 gct cta ctt gac tta att gag aaa gtt gga gat gag aaa ttt cgt tgg     144
Ala Leu Leu Asp Leu Ile Glu Lys Val Gly Asp Glu Lys Phe Arg Trp
        35                  40                  45 gtt ggc aat acc aat gag ttg aat ggt gct tat gcc gct gat ggt tat     192
Val Gly Asn Thr Asn Glu Leu Asn Gly Ala Tyr Ala Ala Asp Gly Tyr
    50                  55                  60 gct cgt gtt aat ggt ctt tca gcc att gtt aca acg ttc ggc gtg gga     240
Ala Arg Val Asn Gly Leu Ser Ala Ile Val Thr Thr Phe Gly Val Gly
65                  70                  75                  80 gag ctt tcc gct att aat gga gtg gca ggt tct tat gcg gag cat gtc     288
Glu Leu Ser Ala Ile Asn Gly Val Ala Gly Ser Tyr Ala Glu His Val
                85                  90                  95 cca gta gtt cat att gtt gga atg cct tcc aca aag gtg caa gat act     336
Pro Val Val His Ile Val Gly Met Pro Ser Thr Lys Val Gln Asp Thr
            100                 105                 110 gga gct ttg ctt cat cat act tta gga gat gga gac ttt cgc act ttc     384
Gly Ala Leu Leu His His Thr Leu Gly Asp Gly Asp Phe Arg Thr Phe
```

```
            115                 120                 125
atg gat atg ttt aag aaa gtt tct gcc tac agt ata atg atc gat aac        432
Met Asp Met Phe Lys Lys Val Ser Ala Tyr Ser Ile Met Ile Asp Asn
    130                 135                 140 gga aac gat gca gct gaa aag atc gat gaa gcc ttg tcg att tgt tat        480
Gly Asn Asp Ala Ala Glu Lys Ile Asp Glu Ala Leu Ser Ile Cys Tyr
145                 150                 155                 160 aaa aag gct agg cct gtt tac att ggt att cct tct gat gct ggc tac        528
Lys Lys Ala Arg Pro Val Tyr Ile Gly Ile Pro Ser Asp Ala Gly Tyr
                165                 170                 175 ttc aaa gca tct tca tca aat ctt ggg aaa aga cta aag ctc gag gag        576
Phe Lys Ala Ser Ser Ser Asn Leu Gly Lys Arg Leu Lys Leu Glu Glu
            180                 185                 190 gat act aac gat cca gca gtt gag caa gaa gtc atc aat cat atc tcg        624
Asp Thr Asn Asp Pro Ala Val Glu Gln Glu Val Ile Asn His Ile Ser
        195                 200                 205 gaa atg gtt gtc aat gca aag aaa cca gtg att tta att gac gct tgt        672
Glu Met Val Val Asn Ala Lys Lys Pro Val Ile Leu Ile Asp Ala Cys
    210                 215                 220 gct gta aga cat cgt gtc gtt cca gaa gta cat gag ctg att aaa ttg        720
Ala Val Arg His Arg Val Val Pro Glu Val His Glu Leu Ile Lys Leu
225                 230                 235                 240 acc cat ttc cct aca tat gta act ccc atg ggt aaa tct gca att gac        768
Thr His Phe Pro Thr Tyr Val Thr Pro Met Gly Lys Ser Ala Ile Asp
                245                 250                 255 gaa act tcg caa ttt ttt gac ggc gtt tat gtt ggt tca att tca gat        816
Glu Thr Ser Gln Phe Phe Asp Gly Val Tyr Val Gly Ser Ile Ser Asp
            260                 265                 270 cct gaa gtt aaa gac aga att gaa tcc act gat ctg ttg cta tcc atc        864
Pro Glu Val Lys Asp Arg Ile Glu Ser Thr Asp Leu Leu Leu Ser Ile
        275                 280                 285 ggt gct ctc aaa tca gac ttt aac acg ggt tcc ttc tct tac cac ctc        912
Gly Ala Leu Lys Ser Asp Phe Asn Thr Gly Ser Phe Ser Tyr His Leu
    290                 295                 300 agc caa aag aat gcc gtt gag ttt cat tca gac cac atg cgc att cga        960
Ser Gln Lys Asn Ala Val Glu Phe His Ser Asp His Met Arg Ile Arg
305                 310                 315                 320 tat gct ctt tat cca aat gta gcc atg aag tat att ctt cgc aaa ctg       1008
Tyr Ala Leu Tyr Pro Asn Val Ala Met Lys Tyr Ile Leu Arg Lys Leu
                325                 330                 335 ttg aaa gta ctt gat gct tct atg tgt cat tcc aag gct gct cct acc       1056
Leu Lys Val Leu Asp Ala Ser Met Cys His Ser Lys Ala Ala Pro Thr
            340                 345                 350 att ggc tac aac atc aag cct aag cat gcg gaa gga tat tct tcc aac       1104
Ile Gly Tyr Asn Ile Lys Pro Lys His Ala Glu Gly Tyr Ser Ser Asn
        355                 360                 365 gag att act cat tgc tgg ttt tgg cct aaa ttt agt gaa ttt ttg aag       1152
Glu Ile Thr His Cys Trp Phe Trp Pro Lys Phe Ser Glu Phe Leu Lys
    370                 375                 380 ccc cga gat gtt ttg atc acc gag act gga act gca aac ttt ggt gtc       1200
Pro Arg Asp Val Leu Ile Thr Glu Thr Gly Thr Ala Asn Phe Gly Val
385                 390                 395                 400 ctt gat tgc agg ttt cca aag gat gta aca gcc att tcc cag gta tta       1248
Leu Asp Cys Arg Phe Pro Lys Asp Val Thr Ala Ile Ser Gln Val Leu
                405                 410                 415 tgg gga tct att gga tac tcc gtt ggt gca atg ttt ggt gct gtt ttg       1296
Trp Gly Ser Ile Gly Tyr Ser Val Gly Ala Met Phe Gly Ala Val Leu
            420                 425                 430 gcc gtc cac gat tct aaa gag ccc gat cgt cgt acc att ctt gta gta       1344
```

```
Ala Val His Asp Ser Lys Glu Pro Asp Arg Arg Thr Ile Leu Val Val
        435                 440                 445 ggt gat gga tcc tta caa ctg acg att aca gag att tca acc tgc att      1392
Gly Asp Gly Ser Leu Gln Leu Thr Ile Thr Glu Ile Ser Thr Cys Ile
450                 455                 460 cgc cat aac ctc aaa cca att att ttc ata att aac aac gac ggt tac      1440
Arg His Asn Leu Lys Pro Ile Ile Phe Ile Ile Asn Asn Asp Gly Tyr
465                 470                 475                 480 acc att gag cgt tta att cat ggt ttg cat gct agc tat aac gaa att      1488
Thr Ile Glu Arg Leu Ile His Gly Leu His Ala Ser Tyr Asn Glu Ile
            485                 490                 495 aac act aaa tgg ggc tac caa cag att ccc aag ttt ttc gga gct gct      1536
Asn Thr Lys Trp Gly Tyr Gln Gln Ile Pro Lys Phe Phe Gly Ala Ala
        500                 505                 510 gaa aac cac ttc cgc act tac tgt gtt aaa act cct act gac gtt gaa      1584
Glu Asn His Phe Arg Thr Tyr Cys Val Lys Thr Pro Thr Asp Val Glu
        515                 520                 525 aag ttg ttt agc gac aag gag ttt gca aat gca gat gtc att caa gta      1632
Lys Leu Phe Ser Asp Lys Glu Phe Ala Asn Ala Asp Val Ile Gln Val
530                 535                 540 gtt gag ctt gta atg cct atg ttg gat gca cct cgt gtc cta gtt gag      1680
Val Glu Leu Val Met Pro Met Leu Asp Ala Pro Arg Val Leu Val Glu
545                 550                 555                 560 caa gcc aag ttg acg tct aag atc aat aag caa tga                      1716
Gln Ala Lys Leu Thr Ser Lys Ile Asn Lys Gln
            565                 570

<210> SEQ ID NO 67
<211> LENGTH: 571
<212> TYPE: PRT
<213> ORGANISM: Schizosaccharomyces pombe

<400> SEQUENCE: 67

Met Ser Gly Asp Ile Leu Val Gly Glu Tyr Leu Phe Lys Arg Leu Glu
1               5                   10                  15

Gln Leu Gly Val Lys Ser Ile Leu Gly Val Pro Gly Asp Phe Asn Leu
            20                  25                  30

Ala Leu Leu Asp Leu Ile Glu Lys Val Gly Asp Glu Lys Phe Arg Trp
        35                  40                  45

Val Gly Asn Thr Asn Glu Leu Asn Gly Ala Tyr Ala Ala Asp Gly Tyr
50                  55                  60

Ala Arg Val Asn Gly Leu Ser Ala Ile Val Thr Thr Phe Gly Val Gly
65                  70                  75                  80

Glu Leu Ser Ala Ile Asn Gly Val Ala Gly Ser Tyr Ala Glu His Val
                85                  90                  95

Pro Val Val His Ile Val Gly Met Pro Ser Thr Lys Val Gln Asp Thr
            100                 105                 110

Gly Ala Leu Leu His His Thr Leu Gly Asp Gly Asp Phe Arg Thr Phe
        115                 120                 125

Met Asp Met Phe Lys Lys Val Ser Ala Tyr Ser Ile Met Ile Asp Asn
130                 135                 140

Gly Asn Asp Ala Ala Glu Lys Ile Asp Glu Ala Leu Ser Ile Cys Tyr
145                 150                 155                 160

Lys Lys Ala Arg Pro Val Tyr Ile Gly Ile Pro Ser Asp Ala Gly Tyr
                165                 170                 175

Phe Lys Ala Ser Ser Ser Asn Leu Gly Lys Arg Leu Lys Leu Glu Glu
            180                 185                 190
```

-continued

Asp Thr Asn Asp Pro Ala Val Glu Gln Val Ile Asn His Ile Ser
              195                 200                 205

Glu Met Val Val Asn Ala Lys Lys Pro Val Ile Leu Ile Asp Ala Cys
210                 215                 220

Ala Val Arg His Arg Val Val Pro Glu Val His Glu Leu Ile Lys Leu
225                 230                 235                 240

Thr His Phe Pro Thr Tyr Val Thr Pro Met Gly Lys Ser Ala Ile Asp
              245                 250                 255

Glu Thr Ser Gln Phe Phe Asp Gly Val Tyr Val Gly Ser Ile Ser Asp
              260                 265                 270

Pro Glu Val Lys Asp Arg Ile Glu Ser Thr Asp Leu Leu Leu Ser Ile
              275                 280                 285

Gly Ala Leu Lys Ser Asp Phe Asn Thr Gly Ser Phe Ser Tyr His Leu
290                 295                 300

Ser Gln Lys Asn Ala Val Glu Phe His Ser Asp His Met Arg Ile Arg
305                 310                 315                 320

Tyr Ala Leu Tyr Pro Asn Val Ala Met Lys Tyr Ile Leu Arg Lys Leu
              325                 330                 335

Leu Lys Val Leu Asp Ala Ser Met Cys His Ser Lys Ala Ala Pro Thr
              340                 345                 350

Ile Gly Tyr Asn Ile Lys Pro Lys His Ala Glu Gly Tyr Ser Ser Asn
              355                 360                 365

Glu Ile Thr His Cys Trp Phe Trp Pro Lys Phe Ser Glu Phe Leu Lys
              370                 375                 380

Pro Arg Asp Val Leu Ile Thr Glu Thr Gly Thr Ala Asn Phe Gly Val
385                 390                 395                 400

Leu Asp Cys Arg Phe Pro Lys Asp Val Thr Ala Ile Ser Gln Val Leu
              405                 410                 415

Trp Gly Ser Ile Gly Tyr Ser Val Gly Ala Met Phe Gly Ala Val Leu
              420                 425                 430

Ala Val His Asp Ser Lys Glu Pro Asp Arg Arg Thr Ile Leu Val Val
              435                 440                 445

Gly Asp Gly Ser Leu Gln Leu Thr Ile Thr Glu Ile Ser Thr Cys Ile
450                 455                 460

Arg His Asn Leu Lys Pro Ile Phe Ile Ile Asn Asn Asp Gly Tyr
465                 470                 475                 480

Thr Ile Glu Arg Leu Ile His Gly Leu His Ala Ser Tyr Asn Glu Ile
              485                 490                 495

Asn Thr Lys Trp Gly Tyr Gln Gln Ile Pro Lys Phe Phe Gly Ala Ala
              500                 505                 510

Glu Asn His Phe Arg Thr Tyr Cys Val Lys Thr Pro Thr Asp Val Glu
              515                 520                 525

Lys Leu Phe Ser Asp Lys Glu Phe Ala Asn Ala Asp Val Ile Gln Val
              530                 535                 540

Val Glu Leu Val Met Pro Met Leu Asp Ala Pro Arg Val Leu Val Glu
545                 550                 555                 560

Gln Ala Lys Leu Thr Ser Lys Ile Asn Lys Gln
              565                 570

<210> SEQ ID NO 68
<211> LENGTH: 1176
<212> TYPE: DNA
<213> ORGANISM: Saccharomyces cerevisiae
<220> FEATURE:
<221> NAME/KEY: CDS

<222> LOCATION: (1)..(1176)

<400> SEQUENCE: 68

| | | | | | | | | | | | | | | | | |
|---|---|---|---|---|---|---|---|---|---|---|---|---|---|---|---|---|
| atg | tct | gct | gct | gct | gat | aga | tta | aac | tta | act | tcc | ggc | cac | ttg | aat | 48 |
| Met | Ser | Ala | Ala | Ala | Asp | Arg | Leu | Asn | Leu | Thr | Ser | Gly | His | Leu | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gct | ggt | aga | aag | aga | agt | tcc | tct | tct | gtt | tct | ttg | aag | gct | gcc | gaa | 96 |
| Ala | Gly | Arg | Lys | Arg | Ser | Ser | Ser | Ser | Val | Ser | Leu | Lys | Ala | Ala | Glu | |
| | | 20 | | | | | 25 | | | | | 30 | | | | |

| | | | | | | | | | | | | | | | | |
|---|---|---|---|---|---|---|---|---|---|---|---|---|---|---|---|---|
| aag | cct | ttc | aag | gtt | act | gtg | att | gga | tct | ggt | aac | tgg | ggt | act | act | 144 |
| Lys | Pro | Phe | Lys | Val | Thr | Val | Ile | Gly | Ser | Gly | Asn | Trp | Gly | Thr | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| att | gcc | aag | gtg | gtt | gcc | gaa | aat | tgt | aag | gga | tac | cca | gaa | gtt | ttc | 192 |
| Ile | Ala | Lys | Val | Val | Ala | Glu | Asn | Cys | Lys | Gly | Tyr | Pro | Glu | Val | Phe | |
| 50 | | | | | 55 | | | | | 60 | | | | | | |

| | | | | | | | | | | | | | | | | |
|---|---|---|---|---|---|---|---|---|---|---|---|---|---|---|---|---|
| gct | cca | ata | gta | caa | atg | tgg | gtg | ttc | gaa | gaa | gag | atc | aat | ggt | gaa | 240 |
| Ala | Pro | Ile | Val | Gln | Met | Trp | Val | Phe | Glu | Glu | Glu | Ile | Asn | Gly | Glu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aaa | ttg | act | gaa | atc | ata | aat | act | aga | cat | caa | aac | gtg | aaa | tac | ttg | 288 |
| Lys | Leu | Thr | Glu | Ile | Ile | Asn | Thr | Arg | His | Gln | Asn | Val | Lys | Tyr | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| cct | ggc | atc | act | cta | ccc | gac | aat | ttg | gtt | gct | aat | cca | gac | ttg | att | 336 |
| Pro | Gly | Ile | Thr | Leu | Pro | Asp | Asn | Leu | Val | Ala | Asn | Pro | Asp | Leu | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| gat | tca | gtc | aag | gat | gtc | gac | atc | atc | gtt | ttc | aac | att | cca | cat | caa | 384 |
| Asp | Ser | Val | Lys | Asp | Val | Asp | Ile | Ile | Val | Phe | Asn | Ile | Pro | His | Gln | |
| | | | 115 | | | | | 120 | | | | | 125 | | | |

| | | | | | | | | | | | | | | | | |
|---|---|---|---|---|---|---|---|---|---|---|---|---|---|---|---|---|
| ttt | ttg | ccc | cgt | atc | tgt | agc | caa | ttg | aaa | ggt | cat | gtt | gat | tca | cac | 432 |
| Phe | Leu | Pro | Arg | Ile | Cys | Ser | Gln | Leu | Lys | Gly | His | Val | Asp | Ser | His | |
| 130 | | | | | 135 | | | | | 140 | | | | | | |

| | | | | | | | | | | | | | | | | |
|---|---|---|---|---|---|---|---|---|---|---|---|---|---|---|---|---|
| gtc | aga | gct | atc | tcc | tgt | cta | aag | ggt | ttt | gaa | gtt | ggt | gct | aaa | ggt | 480 |
| Val | Arg | Ala | Ile | Ser | Cys | Leu | Lys | Gly | Phe | Glu | Val | Gly | Ala | Lys | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtc | caa | ttg | cta | tcc | tct | tac | atc | act | gag | gaa | cta | ggt | att | caa | tgt | 528 |
| Val | Gln | Leu | Leu | Ser | Ser | Tyr | Ile | Thr | Glu | Glu | Leu | Gly | Ile | Gln | Cys | |
| | | | | 165 | | | | | 170 | | | | | 175 | | |

| | | | | | | | | | | | | | | | | |
|---|---|---|---|---|---|---|---|---|---|---|---|---|---|---|---|---|
| ggt | gct | cta | tct | ggt | gct | aac | att | gcc | acc | gaa | gtc | gct | caa | gaa | cac | 576 |
| Gly | Ala | Leu | Ser | Gly | Ala | Asn | Ile | Ala | Thr | Glu | Val | Ala | Gln | Glu | His | |
| | | | 180 | | | | | 185 | | | | | 190 | | | |

| | | | | | | | | | | | | | | | | |
|---|---|---|---|---|---|---|---|---|---|---|---|---|---|---|---|---|
| tgg | tct | gaa | aca | aca | gtt | gct | tac | cac | att | cca | aag | gat | ttc | aga | ggc | 624 |
| Trp | Ser | Glu | Thr | Thr | Val | Ala | Tyr | His | Ile | Pro | Lys | Asp | Phe | Arg | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| gag | ggc | aag | gac | gtc | gac | cat | aag | gtt | cta | aag | gcc | ttg | ttc | cac | aga | 672 |
| Glu | Gly | Lys | Asp | Val | Asp | His | Lys | Val | Leu | Lys | Ala | Leu | Phe | His | Arg | |
| 210 | | | | | 215 | | | | | 220 | | | | | | |

| | | | | | | | | | | | | | | | | |
|---|---|---|---|---|---|---|---|---|---|---|---|---|---|---|---|---|
| cct | tac | ttc | cac | gtt | agt | gtc | atc | gaa | gat | gtt | gct | ggt | atc | tcc | atc | 720 |
| Pro | Tyr | Phe | His | Val | Ser | Val | Ile | Glu | Asp | Val | Ala | Gly | Ile | Ser | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tgt | ggt | gct | ttg | aag | aac | gtt | gtt | gcc | tta | ggt | tgt | ggt | ttc | gtc | gaa | 768 |
| Cys | Gly | Ala | Leu | Lys | Asn | Val | Val | Ala | Leu | Gly | Cys | Gly | Phe | Val | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| ggt | cta | ggc | tgg | ggt | aac | aac | gct | tct | gct | gcc | atc | caa | aga | gtc | ggt | 816 |
| Gly | Leu | Gly | Trp | Gly | Asn | Asn | Ala | Ser | Ala | Ala | Ile | Gln | Arg | Val | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| ttg | ggt | gag | atc | atc | aga | ttc | ggt | caa | atg | ttt | ttc | cca | gaa | tct | aga | 864 |
| Leu | Gly | Glu | Ile | Ile | Arg | Phe | Gly | Gln | Met | Phe | Phe | Pro | Glu | Ser | Arg | |
| | | 275 | | | | | 280 | | | | | 285 | | | | |

| | | | | | | | | | | | | | | | | |
|---|---|---|---|---|---|---|---|---|---|---|---|---|---|---|---|---|
| gaa | gaa | aca | tac | tac | caa | gag | tct | gct | ggt | gtt | gct | gat | ttg | atc | acc | 912 |
| Glu | Glu | Thr | Tyr | Tyr | Gln | Glu | Ser | Ala | Gly | Val | Ala | Asp | Leu | Ile | Thr | |
| 290 | | | | | 295 | | | | | 300 | | | | | | |

```
acc tgc gct ggt ggt aga aac gtc aag gtt gct agg cta atg gct act      960
Thr Cys Ala Gly Gly Arg Asn Val Lys Val Ala Arg Leu Met Ala Thr
305                 310                 315                 320 tct ggt aag gac gcc tgg gaa tgt gaa aag gag ttg ttg aat ggc caa     1008
Ser Gly Lys Asp Ala Trp Glu Cys Glu Lys Glu Leu Leu Asn Gly Gln
                325                 330                 335 tcc gct caa ggt tta att acc tgc aaa gaa gtt cac gaa tgg ttg gaa     1056
Ser Ala Gln Gly Leu Ile Thr Cys Lys Glu Val His Glu Trp Leu Glu
            340                 345                 350 aca tgt ggc tct gtc gaa gac ttc cca tta ttt gaa gcc gta tac caa     1104
Thr Cys Gly Ser Val Glu Asp Phe Pro Leu Phe Glu Ala Val Tyr Gln
        355                 360                 365 atc gtt tac aac aac tac cca atg aag aac ctg ccg gac atg att gaa     1152
Ile Val Tyr Asn Asn Tyr Pro Met Lys Asn Leu Pro Asp Met Ile Glu
    370                 375                 380 gaa tta gat cta cat gaa gat tag                                     1176
Glu Leu Asp Leu His Glu Asp
385                 390

<210> SEQ ID NO 69
<211> LENGTH: 391
<212> TYPE: PRT
<213> ORGANISM: Saccharomyces cerevisiae

<400> SEQUENCE: 69

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
```

```
                    245                 250                 255
Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 70
<211> LENGTH: 1323
<212> TYPE: DNA
<213> ORGANISM: Saccharomyces cerevisiae
<220> FEATURE:
<221> NAME/KEY: CDS
<222> LOCATION: (1)..(1323)

<400> SEQUENCE: 70 atg ctt gct gtc aga aga tta aca aga tac aca ttc ctt aag cga acg      48
Met Leu Ala Val Arg Arg Leu Thr Arg Tyr Thr Phe Leu Lys Arg Thr
1               5                   10                  15 cat ccg gtg tta tat act cgt cgt gca tat aaa att ttg cct tca aga     96
His Pro Val Leu Tyr Thr Arg Arg Ala Tyr Lys Ile Leu Pro Ser Arg
            20                  25                  30 tct act ttc cta aga aga tca tta tta caa aca caa ctg cac tca aag    144
Ser Thr Phe Leu Arg Arg Ser Leu Leu Gln Thr Gln Leu His Ser Lys
        35                  40                  45 atg act gct cat act aat atc aaa cag cac aaa cac tgt cat gag gac    192
Met Thr Ala His Thr Asn Ile Lys Gln His Lys His Cys His Glu Asp
    50                  55                  60 cat cct atc aga aga tcg gac tct gcc gtg tca att gta cat ttg aaa    240
His Pro Ile Arg Arg Ser Asp Ser Ala Val Ser Ile Val His Leu Lys
65                  70                  75                  80 cgt gcg ccc ttc aag gtt aca gtg att ggt tct ggt aac tgg ggg acc    288
Arg Ala Pro Phe Lys Val Thr Val Ile Gly Ser Gly Asn Trp Gly Thr
                85                  90                  95 acc atc gcc aaa gtc att gcg gaa aac aca gaa ttg cat tcc cat atc    336
Thr Ile Ala Lys Val Ile Ala Glu Asn Thr Glu Leu His Ser His Ile
            100                 105                 110 ttc gag cca gag gtg aga atg tgg gtt ttt gat gaa aag atc ggc gac    384
Phe Glu Pro Glu Val Arg Met Trp Val Phe Asp Glu Lys Ile Gly Asp
        115                 120                 125 gaa aat ctg acg gat atc ata aat aca aga cac cag aac gtt aaa tat    432
Glu Asn Leu Thr Asp Ile Ile Asn Thr Arg His Gln Asn Val Lys Tyr
    130                 135                 140 cta ccc aat att gac ctg ccc cat aat cta gtg gcc gat cct gat ctt    480
Leu Pro Asn Ile Asp Leu Pro His Asn Leu Val Ala Asp Pro Asp Leu
145                 150                 155                 160
```

```
tta cac tcc atc aag ggt gct gac atc ctt gtt ttc aac atc cct cat    528
Leu His Ser Ile Lys Gly Ala Asp Ile Leu Val Phe Asn Ile Pro His
            165                 170                 175 caa ttt tta cca aac ata gtc aaa caa ttg caa ggc cac gtg gcc cct    576
Gln Phe Leu Pro Asn Ile Val Lys Gln Leu Gln Gly His Val Ala Pro
                180                 185                 190 cat gta agg gcc atc tcg tgt cta aaa ggg ttc gag ttg ggc tcc aag    624
His Val Arg Ala Ile Ser Cys Leu Lys Gly Phe Glu Leu Gly Ser Lys
                    195                 200                 205 ggt gtg caa ttg cta tcc tcc tat gtt act gat gag tta gga atc caa    672
Gly Val Gln Leu Leu Ser Ser Tyr Val Thr Asp Glu Leu Gly Ile Gln
        210                 215                 220 tgt ggc gca cta tct ggt gca aac ttg gca ccg gaa gtg gcc aag gag    720
Cys Gly Ala Leu Ser Gly Ala Asn Leu Ala Pro Glu Val Ala Lys Glu
225                 230                 235                 240 cat tgg tcc gaa acc acc gtg gct tac caa cta cca aag gat tat caa    768
His Trp Ser Glu Thr Thr Val Ala Tyr Gln Leu Pro Lys Asp Tyr Gln
                    245                 250                 255 ggt gat ggc aag gat gta gat cat aag att ttg aaa ttg ctg ttc cac    816
Gly Asp Gly Lys Asp Val Asp His Lys Ile Leu Lys Leu Leu Phe His
                260                 265                 270 aga cct tac ttc cac gtc aat gtc atc gat gat gtt gct ggt ata tcc    864
Arg Pro Tyr Phe His Val Asn Val Ile Asp Asp Val Ala Gly Ile Ser
            275                 280                 285 att gcc ggt gcc ttg aag aac gtc gtg gca ctt gca tgt ggt ttc gta    912
Ile Ala Gly Ala Leu Lys Asn Val Val Ala Leu Ala Cys Gly Phe Val
        290                 295                 300 gaa ggt atg gga tgg ggt aac aat gcc tcc gca gcc att caa agg ctg    960
Glu Gly Met Gly Trp Gly Asn Asn Ala Ser Ala Ala Ile Gln Arg Leu
305                 310                 315                 320 ggt tta ggt gaa att atc aag ttc ggt aga atg ttt ttc cca gaa tcc   1008
Gly Leu Gly Glu Ile Ile Lys Phe Gly Arg Met Phe Phe Pro Glu Ser
                    325                 330                 335 aaa gtc gag acc tac tat caa gaa tcc gct ggt gtt gca gat ctg atc   1056
Lys Val Glu Thr Tyr Tyr Gln Glu Ser Ala Gly Val Ala Asp Leu Ile
                340                 345                 350 acc acc tgc tca ggc ggt aga aac gtc aag gtt gcc aca tac atg gcc   1104
Thr Thr Cys Ser Gly Gly Arg Asn Val Lys Val Ala Thr Tyr Met Ala
            355                 360                 365 aag acc ggt aag tca gcc ttg gaa gca gaa aag gaa ttg ctt aac ggt   1152
Lys Thr Gly Lys Ser Ala Leu Glu Ala Glu Lys Glu Leu Leu Asn Gly
        370                 375                 380 caa tcc gcc caa ggg ata atc aca tgc aga gaa gtt cac gag tgg cta   1200
Gln Ser Ala Gln Gly Ile Ile Thr Cys Arg Glu Val His Glu Trp Leu
385                 390                 395                 400 caa aca tgt gag ttg acc caa gaa ttc cca tta ttc gag gca gtc tac   1248
Gln Thr Cys Glu Leu Thr Gln Glu Phe Pro Leu Phe Glu Ala Val Tyr
                    405                 410                 415 cag ata gtc tac aac aac gtc cgc atg gaa gac cta ccg gag atg att   1296
Gln Ile Val Tyr Asn Asn Val Arg Met Glu Asp Leu Pro Glu Met Ile
                420                 425                 430 gaa gag cta gac atc gat gac gaa tag                               1323
Glu Glu Leu Asp Ile Asp Asp Glu
            435                 440

<210> SEQ ID NO 71
<211> LENGTH: 440
<212> TYPE: PRT
<213> ORGANISM: Saccharomyces cerevisiae
```

```
<400> SEQUENCE: 71

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415
```

```
Gln Ile Val Tyr Asn Asn Val Arg Met Glu Asp Leu Pro Glu Met Ile
            420                 425                 430

Glu Glu Leu Asp Ile Asp Asp Glu
            435                 440

<210> SEQ ID NO 72
<211> LENGTH: 1113
<212> TYPE: DNA
<213> ORGANISM: Pichia stipitis
<220> FEATURE:
<221> NAME/KEY: CDS
<222> LOCATION: (1)..(1113)

<400> SEQUENCE: 72 atg acc gct act act att cct tac aac atc cct tcg cgt ttc aga att      48
Met Thr Ala Thr Thr Ile Pro Tyr Asn Ile Pro Ser Arg Phe Arg Ile
1               5                   10                  15 gca att atc ggc tcc ggg aac tgg ggt acg gcc gtc gcc aaa atc gta      96
Ala Ile Ile Gly Ser Gly Asn Trp Gly Thr Ala Val Ala Lys Ile Val
                20                  25                  30 tct gaa aac aca gct gaa aaa tcg gat atc ttc gag ccc atc gtt aag     144
Ser Glu Asn Thr Ala Glu Lys Ser Asp Ile Phe Glu Pro Ile Val Lys
            35                  40                  45 atg tgg gtt ttt gaa gaa gat gtc cag gga aga aaa ttg acg gaa atc     192
Met Trp Val Phe Glu Glu Asp Val Gln Gly Arg Lys Leu Thr Glu Ile
        50                  55                  60 ata aac aat gac cac gaa aat gtc cgt tat ttg cca gga gtg caa ttg     240
Ile Asn Asn Asp His Glu Asn Val Arg Tyr Leu Pro Gly Val Gln Leu
65                  70                  75                  80 cca gaa aac ttg gta gcc gtc cca gac atc gtc gac aca gtt aaa gat     288
Pro Glu Asn Leu Val Ala Val Pro Asp Ile Val Asp Thr Val Lys Asp
                85                  90                  95 gct gat ttg ctc att ttc aac gtt cca cac cag ttt ttg ggc aga atc     336
Ala Asp Leu Leu Ile Phe Asn Val Pro His Gln Phe Leu Gly Arg Ile
                100                 105                 110 tgc aag caa ttg atc ggc aaa gtt tct cca tct gtg aga gct atc tcg     384
Cys Lys Gln Leu Ile Gly Lys Val Ser Pro Ser Val Arg Ala Ile Ser
            115                 120                 125 tgt ttg aaa ggt ttg gaa gtc aat tcc gac ggc tgc aaa ttg ttg tct     432
Cys Leu Lys Gly Leu Glu Val Asn Ser Asp Gly Cys Lys Leu Leu Ser
        130                 135                 140 caa gta gtc aca gac act ttg gga atc tac tgt ggt gtc ttg tct gga     480
Gln Val Val Thr Asp Thr Leu Gly Ile Tyr Cys Gly Val Leu Ser Gly
145                 150                 155                 160 gcc aac atc gcc aat gaa gtt gct aga caa aga tgg tcc gaa acc tca     528
Ala Asn Ile Ala Asn Glu Val Ala Arg Gln Arg Trp Ser Glu Thr Ser
                165                 170                 175 atc gca tat aca gct cca aag gac ttc cgt ggt cct gga ctc gac att     576
Ile Ala Tyr Thr Ala Pro Lys Asp Phe Arg Gly Pro Gly Leu Asp Ile
                180                 185                 190 gac gat ttc gtc ttg aaa caa gct ttc cac aga cct tac ttc cac gtt     624
Asp Asp Phe Val Leu Lys Gln Ala Phe His Arg Pro Tyr Phe His Val
            195                 200                 205 aga gtt att gaa gat gtc att ggt gct tct ata gct ggt gct ctc aag     672
Arg Val Ile Glu Asp Val Ile Gly Ala Ser Ile Ala Gly Ala Leu Lys
        210                 215                 220 aat gtc gtg gcc att gca gtg ggt ctc gta gaa ggc gct gga tgg ggt     720
Asn Val Val Ala Ile Ala Val Gly Leu Val Glu Gly Ala Gly Trp Gly
225                 230                 235                 240 gac aat gcc aag gct gct atc atg aga att ggt atc aag gaa act atc     768
```

```
Asp Asn Ala Lys Ala Ala Ile Met Arg Ile Gly Ile Lys Glu Thr Ile
                245                 250                 255 cgg ttt gct tct tac tac aag aag ttt ggc atc aga ggc gca gct cca        816
Arg Phe Ala Ser Tyr Tyr Lys Lys Phe Gly Ile Arg Gly Ala Ala Pro
            260                 265                 270 gag ccc act aca ttt aca gaa gaa agt gcc ggt gtg gcc gat ctt atc        864
Glu Pro Thr Thr Phe Thr Glu Glu Ser Ala Gly Val Ala Asp Leu Ile
        275                 280                 285 act aca tgt tcc ggg ggt aga aac gtc aag gtc gcc aga tac atg gtc        912
Thr Thr Cys Ser Gly Gly Arg Asn Val Lys Val Ala Arg Tyr Met Val
    290                 295                 300 gaa aat ggt gtc gat gcc tgg gaa gct gaa aag ata ttg ttg aac ggg        960
Glu Asn Gly Val Asp Ala Trp Glu Ala Glu Lys Ile Leu Leu Asn Gly
305                 310                 315                 320 cag agt tca caa ggt atc ttg act gca aag gaa gtg cac gag ctc ttg       1008
Gln Ser Ser Gln Gly Ile Leu Thr Ala Lys Glu Val His Glu Leu Leu
                325                 330                 335 gag aac ttt gac ttg aag gag gaa ttc ccc ttg ttc gaa gca act tat       1056
Glu Asn Phe Asp Leu Lys Glu Glu Phe Pro Leu Phe Glu Ala Thr Tyr
            340                 345                 350 gcg gta att tac caa aac cat tct gtg gac gac ttc cca gca ttg ttg       1104
Ala Val Ile Tyr Gln Asn His Ser Val Asp Asp Phe Pro Ala Leu Leu
        355                 360                 365 gag tgt taa                                                            1113
Glu Cys
    370

<210> SEQ ID NO 73
<211> LENGTH: 370
<212> TYPE: PRT
<213> ORGANISM: Pichia stipitis

<400> SEQUENCE: 73

Met Thr Ala Thr Thr Ile Pro Tyr Asn Ile Pro Ser Arg Phe Arg Ile
1               5                   10                  15

Ala Ile Ile Gly Ser Gly Asn Trp Gly Thr Ala Val Ala Lys Ile Val
            20                  25                  30

Ser Glu Asn Thr Ala Glu Lys Ser Asp Ile Phe Glu Pro Ile Val Lys
        35                  40                  45

Met Trp Val Phe Glu Glu Asp Val Gln Gly Arg Lys Leu Thr Glu Ile
    50                  55                  60

Ile Asn Asn Asp His Glu Asn Val Arg Tyr Leu Pro Gly Val Gln Leu
65                  70                  75                  80

Pro Glu Asn Leu Val Ala Val Pro Asp Ile Val Asp Thr Val Lys Asp
                85                  90                  95

Ala Asp Leu Leu Ile Phe Asn Val Pro His Gln Phe Leu Gly Arg Ile
            100                 105                 110

Cys Lys Gln Leu Ile Gly Lys Val Ser Pro Ser Val Arg Ala Ile Ser
        115                 120                 125

Cys Leu Lys Gly Leu Glu Val Asn Ser Asp Gly Cys Lys Leu Leu Ser
    130                 135                 140

Gln Val Val Thr Asp Thr Leu Gly Ile Tyr Cys Gly Val Leu Ser Gly
145                 150                 155                 160

Ala Asn Ile Ala Asn Glu Val Ala Arg Gln Arg Trp Ser Glu Thr Ser
                165                 170                 175

Ile Ala Tyr Thr Ala Pro Lys Asp Phe Arg Gly Pro Gly Leu Asp Ile
            180                 185                 190
```

```
Asp Asp Phe Val Leu Lys Gln Ala Phe His Arg Pro Tyr Phe His Val
            195                 200                 205

Arg Val Ile Glu Asp Val Ile Gly Ala Ser Ile Ala Gly Ala Leu Lys
        210                 215                 220

Asn Val Ala Ile Ala Val Gly Leu Val Glu Gly Ala Gly Trp Gly
225                 230                 235                 240

Asp Asn Ala Lys Ala Ala Ile Met Arg Ile Gly Ile Lys Glu Thr Ile
                245                 250                 255

Arg Phe Ala Ser Tyr Tyr Lys Lys Phe Gly Ile Arg Gly Ala Ala Pro
            260                 265                 270

Glu Pro Thr Thr Phe Thr Glu Glu Ser Ala Gly Val Ala Asp Leu Ile
        275                 280                 285

Thr Thr Cys Ser Gly Gly Arg Asn Val Lys Val Ala Arg Tyr Met Val
        290                 295                 300

Glu Asn Gly Val Asp Ala Trp Glu Ala Glu Lys Ile Leu Leu Asn Gly
305                 310                 315                 320

Gln Ser Ser Gln Gly Ile Leu Thr Ala Lys Glu Val His Glu Leu Leu
                325                 330                 335

Glu Asn Phe Asp Leu Lys Glu Glu Phe Pro Leu Phe Glu Ala Thr Tyr
            340                 345                 350

Ala Val Ile Tyr Gln Asn His Ser Val Asp Asp Phe Pro Ala Leu Leu
        355                 360                 365

Glu Cys
    370

<210> SEQ ID NO 74
<211> LENGTH: 1176
<212> TYPE: DNA
<213> ORGANISM: Pichia stipitis
<220> FEATURE:
<221> NAME/KEY: CDS
<222> LOCATION: (1)..(1176)

<400> SEQUENCE: 74 atg tct acg cct gtt gcc cgt ttg gcc caa cta gcc aac att ttg gca      48
Met Ser Thr Pro Val Ala Arg Leu Ala Gln Leu Ala Asn Ile Leu Ala
1               5                   10                  15 cct aat ccc acc gca gca tac gct gca cat ctg cac cac cca gag gcc      96
Pro Asn Pro Thr Ala Ala Tyr Ala Ala His Leu His His Pro Glu Ala
            20                  25                  30 tcc ttg tct cca gaa cac cct ttc cgt gtt gct gtg atc ggc tcg ggt     144
Ser Leu Ser Pro Glu His Pro Phe Arg Val Ala Val Ile Gly Ser Gly
        35                  40                  45 aac tgg ggg acg acc ata gct aaa gtg atc gcc gaa aac gct gcg gca     192
Asn Trp Gly Thr Thr Ile Ala Lys Val Ile Ala Glu Asn Ala Ala Ala
    50                  55                  60 aga ccc cgt ttg ttc cgt cac caa gtc aat atg tgg gtg cac gat gaa     240
Arg Pro Arg Leu Phe Arg His Gln Val Asn Met Trp Val His Asp Glu
65                  70                  75                  80 atc atc gat ggt gaa aaa ttg act cac atc atc aac acc aga cac gaa     288
Ile Ile Asp Gly Glu Lys Leu Thr His Ile Ile Asn Thr Arg His Glu
                85                  90                  95 aac gtc aag tac ttg ccc ggt gtg atc ttg ccg aga aac atc aga gcc     336
Asn Val Lys Tyr Leu Pro Gly Val Ile Leu Pro Arg Asn Ile Arg Ala
            100                 105                 110 gaa gca gat atc ggc aat gta gtc cat gac gcc gac ttg att gtc ttt     384
Glu Ala Asp Ile Gly Asn Val Val His Asp Ala Asp Leu Ile Val Phe
        115                 120                 125
```

```
aac ttg cct cat cag ttc ttg ccc cgt gta gtc aaa tcg ttg aag ggt      432
Asn Leu Pro His Gln Phe Leu Pro Arg Val Val Lys Ser Leu Lys Gly
    130             135                 140 aag ata aag cac ggt gcc aga gcc atc tcg tgc ttg aag ggt ttg gaa      480
Lys Ile Lys His Gly Ala Arg Ala Ile Ser Cys Leu Lys Gly Leu Glu
145             150                 155                 160 gtg act cca gaa ggc tgc aaa ttg ttg tct acc tac atc acg gaa gag      528
Val Thr Pro Glu Gly Cys Lys Leu Leu Ser Thr Tyr Ile Thr Glu Glu
                165                 170                 175 tta ggc atc gtt tgc ggt gct ctc agt ggt gcc aac att gct cca gaa      576
Leu Gly Ile Val Cys Gly Ala Leu Ser Gly Ala Asn Ile Ala Pro Glu
            180                 185                 190 gtt gct aga tgc aaa tgg tca gag act acc gta gcc tac aag ctc cca      624
Val Ala Arg Cys Lys Trp Ser Glu Thr Thr Val Ala Tyr Lys Leu Pro
        195                 200                 205 gag gac ttc aga ggt gcg ggt aag gac atc gac aag ttc gtg ttg aga      672
Glu Asp Phe Arg Gly Ala Gly Lys Asp Ile Asp Lys Phe Val Leu Arg
210                 215                 220 gca tgt ttc cac aga ccc tac ttc cac gtc aat gtt atc gag gat gtt      720
Ala Cys Phe His Arg Pro Tyr Phe His Val Asn Val Ile Glu Asp Val
225                 230                 235                 240 gcc ggt gta tct gta gct gga gct ttg aag aat gtg gtt gct tta gct      768
Ala Gly Val Ser Val Ala Gly Ala Leu Lys Asn Val Val Ala Leu Ala
                245                 250                 255 gta gga ttt gta gag ggc ttg ggc tgg ggt gac aac gct aag gct gct      816
Val Gly Phe Val Glu Gly Leu Gly Trp Gly Asp Asn Ala Lys Ala Ala
            260                 265                 270 gtc atg aga gta gga ttg ttg gag acg atc aag ttc tca gaa aca ttc      864
Val Met Arg Val Gly Leu Leu Glu Thr Ile Lys Phe Ser Glu Thr Phe
        275                 280                 285 ttc cct gag tcc att gca tcc act ttc aca gcc gag tcg gct ggt gta      912
Phe Pro Glu Ser Ile Ala Ser Thr Phe Thr Ala Glu Ser Ala Gly Val
290                 295                 300 gct gat ttg atc aca tca tgc tct ggt ggt aga aat gtg aaa gtc ggt      960
Ala Asp Leu Ile Thr Ser Cys Ser Gly Gly Arg Asn Val Lys Val Gly
305                 310                 315                 320 aga tac atg gcc caa acc gga tct tcg gcc gaa aac gct gaa aag atg     1008
Arg Tyr Met Ala Gln Thr Gly Ser Ser Ala Glu Asn Ala Glu Lys Met
                325                 330                 335 tta ttg aac ggc cag agc tcc cag ggt atc gta act gtt cgt gaa gtt     1056
Leu Leu Asn Gly Gln Ser Ser Gln Gly Ile Val Thr Val Arg Glu Val
            340                 345                 350 cac gac ttg ttg acc aac gta ggc atg ctc gac aaa ttc ccc ttg ttt     1104
His Asp Leu Leu Thr Asn Val Gly Met Leu Asp Lys Phe Pro Leu Phe
        355                 360                 365 gaa gct acc tat caa atc atc tat ggc tca gag tcc atc gaa aac ttg     1152
Glu Ala Thr Tyr Gln Ile Ile Tyr Gly Ser Glu Ser Ile Glu Asn Leu
370                 375                 380 cct ctc ttg tta gta gga gaa taa                                     1176
Pro Leu Leu Leu Val Gly Glu
385                 390
```

<210> SEQ ID NO 75
<211> LENGTH: 391
<212> TYPE: PRT
<213> ORGANISM: Pichia stipitis

<400> SEQUENCE: 75

```
Met Ser Thr Pro Val Ala Arg Leu Ala Gln Leu Ala Asn Ile Leu Ala
1               5                   10                  15
```

-continued

Pro Asn Pro Thr Ala Ala Tyr Ala Ala His Leu His His Pro Glu Ala
            20                  25                  30

Ser Leu Ser Pro Glu His Pro Phe Arg Val Ala Val Ile Gly Ser Gly
        35                  40                  45

Asn Trp Gly Thr Thr Ile Ala Lys Val Ile Ala Glu Asn Ala Ala Ala
    50                  55                  60

Arg Pro Arg Leu Phe Arg His Gln Val Asn Met Trp Val His Asp Glu
65                  70                  75                  80

Ile Ile Asp Gly Glu Lys Leu Thr His Ile Ile Asn Thr Arg His Glu
                85                  90                  95

Asn Val Lys Tyr Leu Pro Gly Val Ile Leu Pro Arg Asn Ile Arg Ala
            100                 105                 110

Glu Ala Asp Ile Gly Asn Val Val His Asp Ala Asp Leu Ile Val Phe
        115                 120                 125

Asn Leu Pro His Gln Phe Leu Pro Arg Val Val Lys Ser Leu Lys Gly
    130                 135                 140

Lys Ile Lys His Gly Ala Arg Ala Ile Ser Cys Leu Lys Gly Leu Glu
145                 150                 155                 160

Val Thr Pro Glu Gly Cys Lys Leu Leu Ser Thr Tyr Ile Thr Glu Glu
                165                 170                 175

Leu Gly Ile Val Cys Gly Ala Leu Ser Gly Ala Asn Ile Ala Pro Glu
            180                 185                 190

Val Ala Arg Cys Lys Trp Ser Glu Thr Thr Val Ala Tyr Lys Leu Pro
        195                 200                 205

Glu Asp Phe Arg Gly Ala Gly Lys Asp Ile Asp Lys Phe Val Leu Arg
    210                 215                 220

Ala Cys Phe His Arg Pro Tyr Phe His Val Asn Val Ile Glu Asp Val
225                 230                 235                 240

Ala Gly Val Ser Val Ala Gly Ala Leu Lys Asn Val Val Ala Leu Ala
                245                 250                 255

Val Gly Phe Val Glu Gly Leu Gly Trp Gly Asp Asn Ala Lys Ala Ala
            260                 265                 270

Val Met Arg Val Gly Leu Leu Glu Thr Ile Lys Phe Ser Glu Thr Phe
        275                 280                 285

Phe Pro Glu Ser Ile Ala Ser Thr Phe Thr Ala Glu Ser Ala Gly Val
    290                 295                 300

Ala Asp Leu Ile Thr Ser Cys Ser Gly Gly Arg Asn Val Lys Val Gly
305                 310                 315                 320

Arg Tyr Met Ala Gln Thr Gly Ser Ser Ala Glu Asn Ala Glu Lys Met
                325                 330                 335

Leu Leu Asn Gly Gln Ser Ser Gln Gly Ile Val Thr Val Arg Glu Val
            340                 345                 350

His Asp Leu Leu Thr Asn Val Gly Met Leu Asp Lys Phe Pro Leu Phe
        355                 360                 365

Glu Ala Thr Tyr Gln Ile Ile Tyr Gly Ser Glu Ser Ile Glu Asn Leu
    370                 375                 380

Pro Leu Leu Leu Val Gly Glu
385                 390

<210> SEQ ID NO 76
<211> LENGTH: 1236
<212> TYPE: DNA
<213> ORGANISM: Kluyveromyces thermotolerans
<220> FEATURE:
<221> NAME/KEY: CDS

<222> LOCATION: (1)..(1236)

<400> SEQUENCE: 76

| | | | | | | | | | | | | | | | | |
|---|---|---|---|---|---|---|---|---|---|---|---|---|---|---|---|---|
| atg | ttt | tca | atc | tcc | aga | atc | act | aga | act | tct | agt | ttc | act | aca | cag | 48 |
| Met | Phe | Ser | Ile | Ser | Arg | Ile | Thr | Arg | Thr | Ser | Ser | Phe | Thr | Thr | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | aga | gcg | cta | tac | cgt | ttt | aaa | cac | tca | gca | agg | aaa | ctc | cag | agc | 96 |
| Phe | Arg | Ala | Leu | Tyr | Arg | Phe | Lys | His | Ser | Ala | Arg | Lys | Leu | Gln | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| atc | cct | ttc | agc | ata | tac | aag | aaa | atg | tcc | gct | gcc | gac | aga | ctg | aat | 144 |
| Ile | Pro | Phe | Ser | Ile | Tyr | Lys | Lys | Met | Ser | Ala | Ala | Asp | Arg | Leu | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| cag | acc | cac | gac | atc | cta | tcc | gaa | tcc | gtg | caa | gcc | gtg | gaa | aac | cct | 192 |
| Gln | Thr | His | Asp | Ile | Leu | Ser | Glu | Ser | Val | Gln | Ala | Val | Glu | Asn | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| ttc | aaa | gtc | acc | gtg | att | ggg | tcc | ggt | aac | tgg | ggt | acc | acc | atc | tcc | 240 |
| Phe | Lys | Val | Thr | Val | Ile | Gly | Ser | Gly | Asn | Trp | Gly | Thr | Thr | Ile | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aag | gtt | gtg | gcc | gag | aac | gct | gcg | cta | aga | cca | cac | ttg | ttc | gtc | aag | 288 |
| Lys | Val | Val | Ala | Glu | Asn | Ala | Ala | Leu | Arg | Pro | His | Leu | Phe | Val | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| cgt | gtc | gac | atg | tgg | gtg | ttt | gag | gag | acc | gtc | gac | ggc | cag | aag | ttg | 336 |
| Arg | Val | Asp | Met | Trp | Val | Phe | Glu | Glu | Thr | Val | Asp | Gly | Gln | Lys | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| acc | gag | atc | atc | aac | acc | aag | cac | cag | aac | gtc | aag | tac | ctg | cct | aac | 384 |
| Thr | Glu | Ile | Ile | Asn | Thr | Lys | His | Gln | Asn | Val | Lys | Tyr | Leu | Pro | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| atc | gac | ctg | cca | gag | aac | ctg | gtc | gcc | aac | cca | gac | ttg | gtc | tct | gcc | 432 |
| Ile | Asp | Leu | Pro | Glu | Asn | Leu | Val | Ala | Asn | Pro | Asp | Leu | Val | Ser | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| gtc | aag | gac | gcc | gac | atc | ctg | gtc | ttc | aac | atc | cct | cac | cag | ttc | ttg | 480 |
| Val | Lys | Asp | Ala | Asp | Ile | Leu | Val | Phe | Asn | Ile | Pro | His | Gln | Phe | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cca | cgc | att | gtc | tcc | cag | ttg | cag | ggc | aac | atc | aag | aag | gac | gcc | cgt | 528 |
| Pro | Arg | Ile | Val | Ser | Gln | Leu | Gln | Gly | Asn | Ile | Lys | Lys | Asp | Ala | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| gcc | atc | tcc | tgt | ttg | aag | ggt | ttc | gac | gtg | tcc | aag | gac | ggt | gtc | aag | 576 |
| Ala | Ile | Ser | Cys | Leu | Lys | Gly | Phe | Asp | Val | Ser | Lys | Asp | Gly | Val | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| ctg | cta | tcc | acc | tac | gtc | acc | gag | aag | ctc | gga | atc | acc | tgt | ggt | gcc | 624 |
| Leu | Leu | Ser | Thr | Tyr | Val | Thr | Glu | Lys | Leu | Gly | Ile | Thr | Cys | Gly | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| ctt | tcc | ggt | gct | aac | ttg | gcc | cca | gag | gtt | gcc | aag | gag | aac | tgg | tcc | 672 |
| Leu | Ser | Gly | Ala | Asn | Leu | Ala | Pro | Glu | Val | Ala | Lys | Glu | Asn | Trp | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| gag | acc | act | gtt | gcc | tac | gag | ttg | cca | aag | gac | ttc | aag | ggc | gag | ggc | 720 |
| Glu | Thr | Thr | Val | Ala | Tyr | Glu | Leu | Pro | Lys | Asp | Phe | Lys | Gly | Glu | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | gac | gtc | gac | cac | gcc | gtc | ttg | aag | gct | ttg | ttc | cac | aga | cca | tac | 768 |
| Lys | Asp | Val | Asp | His | Ala | Val | Leu | Lys | Ala | Leu | Phe | His | Arg | Pro | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| ttc | cac | gtc | aac | gtc | att | gac | gat | gtc | gct | ggt | atc | tct | gtt | gcc | ggt | 816 |
| Phe | His | Val | Asn | Val | Ile | Asp | Asp | Val | Ala | Gly | Ile | Ser | Val | Ala | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| gcc | ttg | aag | aac | gtt | gtc | gct | cta | ggt | tgc | ggt | ttc | gtc | gag | ggt | cta | 864 |
| Ala | Leu | Lys | Asn | Val | Val | Ala | Leu | Gly | Cys | Gly | Phe | Val | Glu | Gly | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| ggc | tgg | ggt | aac | aac | gcc | tcc | gct | gcc | atc | cag | aga | gtt | ggt | ttg | ggt | 912 |
| Gly | Trp | Gly | Asn | Asn | Ala | Ser | Ala | Ala | Ile | Gln | Arg | Val | Gly | Leu | Gly | |
| | 290 | | | | | 295 | | | | | 300 | | | | | |

```
gag atc atc aag ttc ggt cag atg ttc ttc cca gac tcc cgt gtc gag      960
Glu Ile Ile Lys Phe Gly Gln Met Phe Phe Pro Asp Ser Arg Val Glu
305                 310                 315                 320 acc tac tac cag gag tcc gcc ggt gtt gct gac ttg atc acc acc tgc     1008
Thr Tyr Tyr Gln Glu Ser Ala Gly Val Ala Asp Leu Ile Thr Thr Cys
                325                 330                 335 tct ggt ggt aga aac gtc aga gtc gcc acc cac atg gcc aag act ggt     1056
Ser Gly Gly Arg Asn Val Arg Val Ala Thr His Met Ala Lys Thr Gly
            340                 345                 350 aag tct gcc gag gag tgc gag aag gag ctg ttg aac ggc cag tcc gcc     1104
Lys Ser Ala Glu Glu Cys Glu Lys Glu Leu Leu Asn Gly Gln Ser Ala
        355                 360                 365 cag gta ttc aca cat gta agg agg tcc acg agt ggt tgg ccg agt gcg     1152
Gln Val Phe Thr His Val Arg Arg Ser Thr Ser Gly Trp Pro Ser Ala
370                 375                 380 gta aga ccg atg aat tcg ttc tgt tcg agg ccg ttt acc aga ttg tct     1200
Val Arg Pro Met Asn Ser Phe Cys Ser Arg Pro Phe Thr Arg Leu Ser
385                 390                 395                 400 acg aga acg ctc cta tgg aca ctt tgc cag aca tga                     1236
Thr Arg Thr Leu Leu Trp Thr Leu Cys Gln Thr
                405                 410
```

<210> SEQ ID NO 77
<211> LENGTH: 411
<212> TYPE: PRT
<213> ORGANISM: Kluyveromyces thermotolerans

<400> SEQUENCE: 77

```
Met Phe Ser Ile Ser Arg Ile Thr Arg Thr Ser Ser Phe Thr Thr Gln
1               5                   10                  15

Phe Arg Ala Leu Tyr Arg Phe Lys His Ser Ala Arg Lys Leu Gln Ser
            20                  25                  30

Ile Pro Phe Ser Ile Tyr Lys Lys Met Ser Ala Ala Asp Arg Leu Asn
        35                  40                  45

Gln Thr His Asp Ile Leu Ser Glu Ser Val Gln Ala Val Glu Asn Pro
    50                  55                  60

Phe Lys Val Thr Val Ile Gly Ser Gly Asn Trp Gly Thr Thr Ile Ser
65                  70                  75                  80

Lys Val Val Ala Glu Asn Ala Ala Leu Arg Pro His Leu Phe Val Lys
                85                  90                  95

Arg Val Asp Met Trp Val Phe Glu Glu Thr Val Asp Gly Gln Lys Leu
            100                 105                 110

Thr Glu Ile Ile Asn Thr Lys His Gln Asn Val Lys Tyr Leu Pro Asn
        115                 120                 125

Ile Asp Leu Pro Glu Asn Leu Val Ala Asn Pro Asp Leu Val Ser Ala
    130                 135                 140

Val Lys Asp Ala Asp Ile Leu Val Phe Asn Ile Pro His Gln Phe Leu
145                 150                 155                 160

Pro Arg Ile Val Ser Gln Leu Gln Gly Asn Ile Lys Lys Asp Ala Arg
                165                 170                 175

Ala Ile Ser Cys Leu Lys Gly Phe Asp Val Ser Lys Asp Gly Val Lys
            180                 185                 190

Leu Leu Ser Thr Tyr Val Thr Glu Lys Leu Gly Ile Thr Cys Gly Ala
        195                 200                 205

Leu Ser Gly Ala Asn Leu Ala Pro Glu Val Ala Lys Glu Asn Trp Ser
    210                 215                 220
```

```
Glu Thr Thr Val Ala Tyr Glu Leu Pro Lys Asp Phe Lys Gly Glu Gly
225                 230                 235                 240

Lys Asp Val Asp His Ala Val Leu Lys Ala Leu Phe His Arg Pro Tyr
            245                 250                 255

Phe His Val Asn Val Ile Asp Asp Val Ala Gly Ile Ser Val Ala Gly
            260                 265                 270

Ala Leu Lys Asn Val Val Ala Leu Gly Cys Gly Phe Val Glu Gly Leu
            275                 280                 285

Gly Trp Gly Asn Asn Ala Ser Ala Ala Ile Gln Arg Val Gly Leu Gly
            290                 295                 300

Glu Ile Ile Lys Phe Gly Gln Met Phe Phe Pro Asp Ser Arg Val Glu
305                 310                 315                 320

Thr Tyr Tyr Gln Glu Ser Ala Gly Val Ala Asp Leu Ile Thr Thr Cys
                325                 330                 335

Ser Gly Gly Arg Asn Val Arg Val Ala Thr His Met Ala Lys Thr Gly
            340                 345                 350

Lys Ser Ala Glu Glu Cys Glu Lys Glu Leu Leu Asn Gly Gln Ser Ala
            355                 360                 365

Gln Val Phe Thr His Val Arg Arg Ser Thr Ser Gly Trp Pro Ser Ala
370                 375                 380

Val Arg Pro Met Asn Ser Phe Cys Ser Arg Pro Phe Thr Arg Leu Ser
385                 390                 395                 400

Thr Arg Thr Leu Leu Trp Thr Leu Cys Gln Thr
                405                 410

<210> SEQ ID NO 78
<211> LENGTH: 1158
<212> TYPE: DNA
<213> ORGANISM: Schizosaccharomyces pombe
<220> FEATURE:
<221> NAME/KEY: CDS
<222> LOCATION: (1)..(1158)

<400> SEQUENCE: 78 atg tct gga tat ggt caa caa ggt gtt tct gct gcc aac atc gac agc      48
Met Ser Gly Tyr Gly Gln Gln Gly Val Ser Ala Ala Asn Ile Asp Ser
1               5                   10                  15 atc cgc ccc aag aaa cgt ttg tca att ggt gta gtt ggc tcc ggt aac      96
Ile Arg Pro Lys Lys Arg Leu Ser Ile Gly Val Val Gly Ser Gly Asn
            20                  25                  30 tgg ggt act gcc att gcc aag att tgc ggt gaa aat gcc cgt gcc cac     144
Trp Gly Thr Ala Ile Ala Lys Ile Cys Gly Glu Asn Ala Arg Ala His
        35                  40                  45 ggt cac cat ttc aga agt aag gtc cgc atg tgg gtc ttt gag gag gag     192
Gly His His Phe Arg Ser Lys Val Arg Met Trp Val Phe Glu Glu Glu
    50                  55                  60 att gag tac aag ggt gag aag aga aag ctc acc gaa gta ttc aac gaa     240
Ile Glu Tyr Lys Gly Glu Lys Arg Lys Leu Thr Glu Val Phe Asn Glu
65                  70                  75                  80 gct cac gag aat gtc aaa tac tta ccc ggc atc gaa tgc cct ccc aac     288
Ala His Glu Asn Val Lys Tyr Leu Pro Gly Ile Glu Cys Pro Pro Asn
                85                  90                  95 gtt att gcc gtc ccc gat gtt cgt gag gtc gct aga cgt gcc gac atc     336
Val Ile Ala Val Pro Asp Val Arg Glu Val Ala Arg Arg Ala Asp Ile
            100                 105                 110 ctt gtc ttt gtc gtt cct cat caa ttt att gaa cgc gtt tgc gac caa     384
Leu Val Phe Val Val Pro His Gln Phe Ile Glu Arg Val Cys Asp Gln
        115                 120                 125
```

| | | | | | | | | | | | | | | | | |
|---|---|---|---|---|---|---|---|---|---|---|---|---|---|---|---|---|
| atg | gtc | ggt | ctc | att | cgc | cct | ggt | gcc | gtt | ggt | att | tcc | tgt | atc | aag | 432 |
| Met | Val | Gly | Leu | Ile | Arg | Pro | Gly | Ala | Val | Gly | Ile | Ser | Cys | Ile | Lys | |
| 130 | | | | | 135 | | | | | 140 | | | | | | |
| ggt | gtt | gct | gtc | agc | aag | gaa | ggc | gtc | cgc | ctt | tac | tct | gag | gtt | atc | 480 |
| Gly | Val | Ala | Val | Ser | Lys | Glu | Gly | Val | Arg | Leu | Tyr | Ser | Glu | Val | Ile | |
| 145 | | | | | 150 | | | | | 155 | | | | | 160 | |
| agc | gag | aaa | ctc | ggt | att | tac | tgt | ggt | gtt | ctt | tct | ggt | gct | aac | gtt | 528 |
| Ser | Glu | Lys | Leu | Gly | Ile | Tyr | Cys | Gly | Val | Leu | Ser | Gly | Ala | Asn | Val | |
| | | | | 165 | | | | | 170 | | | | | 175 | | |
| gca | aac | gaa | gtt | gcc | cgt | gag | caa | ttc | tgt | gag | act | act | att | ggt | ttc | 576 |
| Ala | Asn | Glu | Val | Ala | Arg | Glu | Gln | Phe | Cys | Glu | Thr | Thr | Ile | Gly | Phe | |
| | | | 180 | | | | | 185 | | | | | 190 | | | |
| aac | cct | cct | aat | gaa | gtt | gat | atc | cct | cgc | gag | caa | atc | gcc | gcc | gtc | 624 |
| Asn | Pro | Pro | Asn | Glu | Val | Asp | Ile | Pro | Arg | Glu | Gln | Ile | Ala | Ala | Val | |
| | | 195 | | | | | 200 | | | | | 205 | | | | |
| ttt | gat | cgc | cct | tac | ttc | tca | gtt | gtc | tcc | gtt | gac | gac | gtt | gcc | ggt | 672 |
| Phe | Asp | Arg | Pro | Tyr | Phe | Ser | Val | Val | Ser | Val | Asp | Asp | Val | Ala | Gly | |
| | 210 | | | | | 215 | | | | | 220 | | | | | |
| gtc | gcc | ttg | ggt | ggt | gct | ttg | aag | aac | gta | gtt | gcc | atg | gcc | gtt | ggt | 720 |
| Val | Ala | Leu | Gly | Gly | Ala | Leu | Lys | Asn | Val | Val | Ala | Met | Ala | Val | Gly | |
| 225 | | | | | 230 | | | | | 235 | | | | | 240 | |
| ttc | gct | gat | ggt | ttg | gaa | tgg | ggc | ggt | aat | acc | aag | gcc | gct | att | atg | 768 |
| Phe | Ala | Asp | Gly | Leu | Glu | Trp | Gly | Gly | Asn | Thr | Lys | Ala | Ala | Ile | Met | |
| | | | | 245 | | | | | 250 | | | | | 255 | | |
| cgt | cgt | ggt | ttg | ttg | gag | atg | caa | aag | ttt | gct | act | acc | ttc | ttc | gac | 816 |
| Arg | Arg | Gly | Leu | Leu | Glu | Met | Gln | Lys | Phe | Ala | Thr | Thr | Phe | Phe | Asp | |
| | | | 260 | | | | | 265 | | | | | 270 | | | |
| tct | gat | cct | cgt | acc | atg | gtt | gag | caa | tct | tgc | ggt | atc | gct | gac | ttg | 864 |
| Ser | Asp | Pro | Arg | Thr | Met | Val | Glu | Gln | Ser | Cys | Gly | Ile | Ala | Asp | Leu | |
| | | 275 | | | | | 280 | | | | | 285 | | | | |
| gtc | act | tct | tgt | ttg | ggt | ggc | cgt | aac | aat | cgt | tgt | gct | gaa | gca | ttt | 912 |
| Val | Thr | Ser | Cys | Leu | Gly | Gly | Arg | Asn | Asn | Arg | Cys | Ala | Glu | Ala | Phe | |
| | 290 | | | | | 295 | | | | | 300 | | | | | |
| gtc | aag | act | ggt | aaa | tct | tta | gag | acg | ctt | gaa | aaa | gag | ctc | tta | ggt | 960 |
| Val | Lys | Thr | Gly | Lys | Ser | Leu | Glu | Thr | Leu | Glu | Lys | Glu | Leu | Leu | Gly | |
| 305 | | | | | 310 | | | | | 315 | | | | | 320 | |
| ggt | caa | ctt | ctt | caa | gga | gct | gcc | act | tcc | aag | gat | gtt | cat | gaa | ttc | 1008 |
| Gly | Gln | Leu | Leu | Gln | Gly | Ala | Ala | Thr | Ser | Lys | Asp | Val | His | Glu | Phe | |
| | | | | 325 | | | | | 330 | | | | | 335 | | |
| ctt | ctc | acc | aag | gat | atg | gtc | aag | gat | ttc | ccc | ttg | ttc | act | gcc | gtt | 1056 |
| Leu | Leu | Thr | Lys | Asp | Met | Val | Lys | Asp | Phe | Pro | Leu | Phe | Thr | Ala | Val | |
| | | | 340 | | | | | 345 | | | | | 350 | | | |
| tat | aac | att | tcc | tat | gaa | gac | atg | gat | ccc | aag | gat | ttg | atc | atc | gtc | 1104 |
| Tyr | Asn | Ile | Ser | Tyr | Glu | Asp | Met | Asp | Pro | Lys | Asp | Leu | Ile | Ile | Val | |
| | | 355 | | | | | 360 | | | | | 365 | | | | |
| ctt | caa | ccc | ctt | aag | gag | gac | tct | gag | aac | gag | ggc | ggt | act | gaa | acc | 1152 |
| Leu | Gln | Pro | Leu | Lys | Glu | Asp | Ser | Glu | Asn | Glu | Gly | Gly | Thr | Glu | Thr | |
| | 370 | | | | | 375 | | | | | 380 | | | | | |
| gag | taa | | | | | | | | | | | | | | | 1158 |
| Glu | | | | | | | | | | | | | | | | |
| 385 | | | | | | | | | | | | | | | | |

<210> SEQ ID NO 79
<211> LENGTH: 385
<212> TYPE: PRT
<213> ORGANISM: Schizosaccharomyces pombe

<400> SEQUENCE: 79

Met Ser Gly Tyr Gly Gln Gln Gly Val Ser Ala Ala Asn Ile Asp Ser
1               5                   10                  15

Ile Arg Pro Lys Lys Arg Leu Ser Ile Gly Val Gly Ser Gly Asn
              20                  25                  30

Trp Gly Thr Ala Ile Ala Lys Ile Cys Gly Glu Asn Ala Arg Ala His
         35                  40                  45

Gly His His Phe Arg Ser Lys Val Arg Met Trp Val Phe Glu Glu Glu
     50                  55                  60

Ile Glu Tyr Lys Gly Glu Lys Arg Lys Leu Thr Glu Val Phe Asn Glu
65                  70                  75                  80

Ala His Glu Asn Val Lys Tyr Leu Pro Gly Ile Glu Cys Pro Pro Asn
                 85                  90                  95

Val Ile Ala Val Pro Asp Val Arg Glu Val Ala Arg Arg Ala Asp Ile
            100                 105                 110

Leu Val Phe Val Val Pro His Gln Phe Ile Glu Arg Val Cys Asp Gln
        115                 120                 125

Met Val Gly Leu Ile Arg Pro Gly Ala Val Gly Ile Ser Cys Ile Lys
    130                 135                 140

Gly Val Ala Val Ser Lys Glu Gly Val Arg Leu Tyr Ser Glu Val Ile
145                 150                 155                 160

Ser Glu Lys Leu Gly Ile Tyr Cys Gly Val Leu Ser Gly Ala Asn Val
                165                 170                 175

Ala Asn Glu Val Ala Arg Glu Gln Phe Cys Glu Thr Thr Ile Gly Phe
            180                 185                 190

Asn Pro Pro Asn Glu Val Asp Ile Pro Arg Glu Gln Ile Ala Ala Val
        195                 200                 205

Phe Asp Arg Pro Tyr Phe Ser Val Val Ser Val Asp Asp Val Ala Gly
    210                 215                 220

Val Ala Leu Gly Gly Ala Leu Lys Asn Val Val Ala Met Ala Val Gly
225                 230                 235                 240

Phe Ala Asp Gly Leu Glu Trp Gly Gly Asn Thr Lys Ala Ala Ile Met
                245                 250                 255

Arg Arg Gly Leu Leu Glu Met Gln Lys Phe Ala Thr Thr Phe Phe Asp
            260                 265                 270

Ser Asp Pro Arg Thr Met Val Glu Gln Ser Cys Gly Ile Ala Asp Leu
        275                 280                 285

Val Thr Ser Cys Leu Gly Gly Arg Asn Asn Arg Cys Ala Glu Ala Phe
    290                 295                 300

Val Lys Thr Gly Lys Ser Leu Glu Thr Leu Glu Lys Glu Leu Leu Gly
305                 310                 315                 320

Gly Gln Leu Leu Gln Gly Ala Ala Thr Ser Lys Asp Val His Glu Phe
                325                 330                 335

Leu Leu Thr Lys Asp Met Val Lys Asp Phe Pro Leu Phe Thr Ala Val
            340                 345                 350

Tyr Asn Ile Ser Tyr Glu Asp Met Asp Pro Lys Asp Leu Ile Ile Val
        355                 360                 365

Leu Gln Pro Leu Lys Glu Asp Ser Glu Asn Glu Gly Gly Thr Glu Thr
    370                 375                 380

Glu
385

<210> SEQ ID NO 80
<211> LENGTH: 1122
<212> TYPE: DNA
<213> ORGANISM: Schizosaccharomyces pombe
<220> FEATURE:
<221> NAME/KEY: CDS

<222> LOCATION: (1)..(1122)

<400> SEQUENCE: 80

```
atg act gtg gct gct ttg aac aaa ctc agc gct ctc tcc gga agt att      48
Met Thr Val Ala Ala Leu Asn Lys Leu Ser Ala Leu Ser Gly Ser Ile
1               5                   10                  15 caa aaa tct ttt tca cct aaa ctt att tct gtt ggt atc atc gga tca      96
Gln Lys Ser Phe Ser Pro Lys Leu Ile Ser Val Gly Ile Ile Gly Ser
                20                  25                  30 gga aat tgg gga acc gct att gct aaa ata tgt ggt gaa aat gcc aag     144
Gly Asn Trp Gly Thr Ala Ile Ala Lys Ile Cys Gly Glu Asn Ala Lys
            35                  40                  45 gct cat cct gat att ttc cat cct caa gta cac atg tgg atg tat gaa     192
Ala His Pro Asp Ile Phe His Pro Gln Val His Met Trp Met Tyr Glu
        50                  55                  60 gag aag att caa cat gag gga aaa gag tgc aat ctc acg gaa gtt ttt     240
Glu Lys Ile Gln His Glu Gly Lys Glu Cys Asn Leu Thr Glu Val Phe
65                  70                  75                  80 aac act act cat gaa aac gtt aaa tat ctc aaa ggt atc aaa tgc cct     288
Asn Thr Thr His Glu Asn Val Lys Tyr Leu Lys Gly Ile Lys Cys Pro
                85                  90                  95 tct aac gtc ttc gca aac ccg gac att cgt gat gta ggt tca cgt agc     336
Ser Asn Val Phe Ala Asn Pro Asp Ile Arg Asp Val Gly Ser Arg Ser
                100                 105                 110 gac att ctg gta tgg gtt ctc cct cac cag ttc gtt gtg cgt att tgc     384
Asp Ile Leu Val Trp Val Leu Pro His Gln Phe Val Val Arg Ile Cys
            115                 120                 125 aat caa ttg aag gga tgc cta aag aag gat gct gtt gca att tca tgc     432
Asn Gln Leu Lys Gly Cys Leu Lys Lys Asp Ala Val Ala Ile Ser Cys
        130                 135                 140 atc aaa ggt gta tct gtc acc aag gac cgt gtt cgc ctc ttt tct gat     480
Ile Lys Gly Val Ser Val Thr Lys Asp Arg Val Arg Leu Phe Ser Asp
145                 150                 155                 160 att atc gaa gaa aac acg gga atg tat tgt ggc gtt ctc tct ggc gcc     528
Ile Ile Glu Glu Asn Thr Gly Met Tyr Cys Gly Val Leu Ser Gly Ala
                165                 170                 175 aac att gcc agc gaa gtt gct caa gag aag ttt tgc gaa act act atc     576
Asn Ile Ala Ser Glu Val Ala Gln Glu Lys Phe Cys Glu Thr Thr Ile
                180                 185                 190 gga tat ttg cct aat agt tct gtt aat ccc cgc tat act cct aag act     624
Gly Tyr Leu Pro Asn Ser Ser Val Asn Pro Arg Tyr Thr Pro Lys Thr
            195                 200                 205 atc caa gct ttg ttt aac cgt ccc tac ttc cgt gtc aac att gtt gag     672
Ile Gln Ala Leu Phe Asn Arg Pro Tyr Phe Arg Val Asn Ile Val Glu
        210                 215                 220 gat gtt cct ggt gtt gct ttg ggc ggt gca ctc aag aat atc gtc gct     720
Asp Val Pro Gly Val Ala Leu Gly Gly Ala Leu Lys Asn Ile Val Ala
225                 230                 235                 240 gtc gct gcc ggt att att gat gga ctt gaa ttg gga gat aat acc aaa     768
Val Ala Ala Gly Ile Ile Asp Gly Leu Glu Leu Gly Asp Asn Thr Lys
                245                 250                 255 tct gct gtt atg cgc att ggc ctt ctg gaa atg cag aaa ttc ggc agg     816
Ser Ala Val Met Arg Ile Gly Leu Leu Glu Met Gln Lys Phe Gly Arg
                260                 265                 270 atg ttt ttc gat tgt aag cct ctt act atg agc gag gaa tct tgt ggc     864
Met Phe Phe Asp Cys Lys Pro Leu Thr Met Ser Glu Glu Ser Cys Gly
            275                 280                 285 ata gcc gat tta att aca act tgc tta ggc ggc cgt aac cac aaa tgc     912
Ile Ala Asp Leu Ile Thr Thr Cys Leu Gly Gly Arg Asn His Lys Cys
        290                 295                 300
```

```
gct gtg gca ttt gtc aag aca gga aag ccc atg cat gtt gtt gaa caa      960
Ala Val Ala Phe Val Lys Thr Gly Lys Pro Met His Val Val Glu Gln
305                 310                 315                 320 gaa ctt ctt gat ggt cag aag ttg caa ggt gca gct acc gcg aag gag     1008
Glu Leu Leu Asp Gly Gln Lys Leu Gln Gly Ala Ala Thr Ala Lys Glu
                325                 330                 335 gtt tat gag ttc ctt gat aac cag aat aag gta agc gaa ttc cca ttg     1056
Val Tyr Glu Phe Leu Asp Asn Gln Asn Lys Val Ser Glu Phe Pro Leu
            340                 345                 350 ttt aca gct gtt tat cgc att gtt tat gag gga ctt cca cct aat aag     1104
Phe Thr Ala Val Tyr Arg Ile Val Tyr Glu Gly Leu Pro Pro Asn Lys
        355                 360                 365 ctt ctg gag gct att taa                                              1122
Leu Leu Glu Ala Ile
    370

<210> SEQ ID NO 81
<211> LENGTH: 373
<212> TYPE: PRT
<213> ORGANISM: Schizosaccharomyces pombe

<400> SEQUENCE: 81

Met Thr Val Ala Ala Leu Asn Lys Leu Ser Ala Leu Ser Gly Ser Ile
1               5                   10                  15

Gln Lys Ser Phe Ser Pro Lys Leu Ile Ser Val Gly Ile Ile Gly Ser
            20                  25                  30

Gly Asn Trp Gly Thr Ala Ile Ala Lys Ile Cys Gly Glu Asn Ala Lys
        35                  40                  45

Ala His Pro Asp Ile Phe His Pro Gln Val His Met Trp Met Tyr Glu
    50                  55                  60

Glu Lys Ile Gln His Glu Gly Lys Glu Cys Asn Leu Thr Glu Val Phe
65                  70                  75                  80

Asn Thr Thr His Glu Asn Val Lys Tyr Leu Lys Gly Ile Lys Cys Pro
                85                  90                  95

Ser Asn Val Phe Ala Asn Pro Asp Ile Arg Asp Val Gly Ser Arg Ser
            100                 105                 110

Asp Ile Leu Val Trp Val Leu Pro His Gln Phe Val Arg Ile Cys
        115                 120                 125

Asn Gln Leu Lys Gly Cys Leu Lys Lys Asp Ala Val Ala Ile Ser Cys
    130                 135                 140

Ile Lys Gly Val Ser Val Thr Lys Asp Arg Val Arg Leu Phe Ser Asp
145                 150                 155                 160

Ile Ile Glu Glu Asn Thr Gly Met Tyr Cys Gly Val Leu Ser Gly Ala
                165                 170                 175

Asn Ile Ala Ser Glu Val Ala Gln Glu Lys Phe Cys Glu Thr Thr Ile
            180                 185                 190

Gly Tyr Leu Pro Asn Ser Ser Val Asn Pro Arg Tyr Thr Pro Lys Thr
        195                 200                 205

Ile Gln Ala Leu Phe Asn Arg Pro Tyr Phe Arg Val Asn Ile Val Glu
    210                 215                 220

Asp Val Pro Gly Val Ala Leu Gly Gly Ala Leu Lys Asn Ile Val Ala
225                 230                 235                 240

Val Ala Ala Gly Ile Ile Asp Gly Leu Glu Leu Gly Asp Asn Thr Lys
                245                 250                 255

Ser Ala Val Met Arg Ile Gly Leu Leu Glu Met Gln Lys Phe Gly Arg
            260                 265                 270
```

```
Met Phe Phe Asp Cys Lys Pro Leu Thr Met Ser Glu Glu Ser Cys Gly
        275                 280                 285

Ile Ala Asp Leu Ile Thr Thr Cys Leu Gly Gly Arg Asn His Lys Cys
        290                 295                 300

Ala Val Ala Phe Val Lys Thr Gly Lys Pro Met His Val Val Glu Gln
305                 310                 315                 320

Glu Leu Leu Asp Gly Gln Lys Leu Gln Gly Ala Ala Thr Ala Lys Glu
                325                 330                 335

Val Tyr Glu Phe Leu Asp Asn Gln Asn Lys Val Ser Glu Phe Pro Leu
                340                 345                 350

Phe Thr Ala Val Tyr Arg Ile Val Tyr Glu Gly Leu Pro Pro Asn Lys
        355                 360                 365

Leu Leu Glu Ala Ile
        370

<210> SEQ ID NO 82
<211> LENGTH: 1263
<212> TYPE: DNA
<213> ORGANISM: Saccharomyces cerevisiae
<220> FEATURE:
<221> NAME/KEY: CDS
<222> LOCATION: (1)..(1263)

<400> SEQUENCE: 82
```

| | | | | | | | | | | | | | | | | |
|---|---|---|---|---|---|---|---|---|---|---|---|---|---|---|---|---|
| atg | ctt | gct | gct | tca | ttc | aaa | cgc | caa | cca | tca | caa | ttg | gtc | cgc | ggg | 48 |
| Met | Leu | Ala | Ala | Ser | Phe | Lys | Arg | Gln | Pro | Ser | Gln | Leu | Val | Arg | Gly | |
| 1 | | | | 5 | | | | | 10 | | | | | 15 | | |
| tta | gga | gct | gtt | ctt | cgc | act | ccc | acc | agg | ata | ggt | cat | gtt | cgt | acc | 96 |
| Leu | Gly | Ala | Val | Leu | Arg | Thr | Pro | Thr | Arg | Ile | Gly | His | Val | Arg | Thr | |
| | | | | 20 | | | | | 25 | | | | | 30 | | |
| atg | gca | act | tta | aaa | aca | act | gat | aag | aag | gcc | cct | gag | gac | atc | gag | 144 |
| Met | Ala | Thr | Leu | Lys | Thr | Thr | Asp | Lys | Lys | Ala | Pro | Glu | Asp | Ile | Glu | |
| | | | 35 | | | | | 40 | | | | | 45 | | | |
| ggc | tcg | gac | aca | gtg | caa | att | gag | ttg | cct | gaa | tct | tcc | ttc | gag | tcg | 192 |
| Gly | Ser | Asp | Thr | Val | Gln | Ile | Glu | Leu | Pro | Glu | Ser | Ser | Phe | Glu | Ser | |
| | 50 | | | | | 55 | | | | | 60 | | | | | |
| tat | atg | cta | gag | cct | cca | gac | ttg | tct | tat | gag | act | tcg | aaa | gcc | acc | 240 |
| Tyr | Met | Leu | Glu | Pro | Pro | Asp | Leu | Ser | Tyr | Glu | Thr | Ser | Lys | Ala | Thr | |
| 65 | | | | | 70 | | | | | 75 | | | | | 80 | |
| ttg | tta | cag | atg | tat | aaa | gat | atg | gtc | atc | atc | aga | aga | atg | gag | atg | 288 |
| Leu | Leu | Gln | Met | Tyr | Lys | Asp | Met | Val | Ile | Ile | Arg | Arg | Met | Glu | Met | |
| | | | | 85 | | | | | 90 | | | | | 95 | | |
| gct | tgt | gac | gcc | ttg | tac | aag | gcc | aag | aaa | atc | aga | ggt | ttt | tgc | cat | 336 |
| Ala | Cys | Asp | Ala | Leu | Tyr | Lys | Ala | Lys | Lys | Ile | Arg | Gly | Phe | Cys | His | |
| | | | | 100 | | | | | 105 | | | | | 110 | | |
| cta | tct | gtt | ggt | cag | gag | gcc | att | gct | gtc | ggt | atc | gag | aat | gcc | atc | 384 |
| Leu | Ser | Val | Gly | Gln | Glu | Ala | Ile | Ala | Val | Gly | Ile | Glu | Asn | Ala | Ile | |
| | | | 115 | | | | | 120 | | | | | 125 | | | |
| aca | aaa | ttg | gat | tcc | atc | atc | aca | tct | tac | aga | tgt | cac | ggt | ttc | act | 432 |
| Thr | Lys | Leu | Asp | Ser | Ile | Ile | Thr | Ser | Tyr | Arg | Cys | His | Gly | Phe | Thr | |
| | 130 | | | | | 135 | | | | | 140 | | | | | |
| ttt | atg | aga | ggt | gcc | tca | gtg | aaa | gcc | gtt | ctg | gct | gaa | ttg | atg | ggt | 480 |
| Phe | Met | Arg | Gly | Ala | Ser | Val | Lys | Ala | Val | Leu | Ala | Glu | Leu | Met | Gly | |
| 145 | | | | | 150 | | | | | 155 | | | | | 160 | |
| aga | aga | gcc | ggt | gtc | tct | tat | ggt | aag | ggt | ggt | tcc | atg | cac | ctt | tac | 528 |
| Arg | Arg | Ala | Gly | Val | Ser | Tyr | Gly | Lys | Gly | Gly | Ser | Met | His | Leu | Tyr | |
| | | | | 165 | | | | | 170 | | | | | 175 | | |
| gct | cca | ggc | ttc | tat | ggt | ggt | aat | ggt | atc | gtg | ggt | gcc | cag | gtt | cct | 576 |
| Ala | Pro | Gly | Phe | Tyr | Gly | Gly | Asn | Gly | Ile | Val | Gly | Ala | Gln | Val | Pro | |

```
                   180                 185                 190
tta ggt gca ggt tta gct ttt gct cac caa tac aag aac gag gac gcc    624
Leu Gly Ala Gly Leu Ala Phe Ala His Gln Tyr Lys Asn Glu Asp Ala
            195                 200                 205 tgc tct ttc act ttg tat ggt gat ggt gcc tct aat caa ggt caa gtt    672
Cys Ser Phe Thr Leu Tyr Gly Asp Gly Ala Ser Asn Gln Gly Gln Val
210                 215                 220 ttt gaa tct ttc aac atg gcc aaa tta tgg aat ttg ccc gtc gtg ttt    720
Phe Glu Ser Phe Asn Met Ala Lys Leu Trp Asn Leu Pro Val Val Phe
225                 230                 235                 240 tgc tgt gag aac aac aag tac ggt atg ggt acc gcc gct tca aga tcc    768
Cys Cys Glu Asn Asn Lys Tyr Gly Met Gly Thr Ala Ala Ser Arg Ser
            245                 250                 255 tcc gcg atg act gaa tat ttc aag cgt ggt caa tat att cca ggt tta    816
Ser Ala Met Thr Glu Tyr Phe Lys Arg Gly Gln Tyr Ile Pro Gly Leu
        260                 265                 270 aaa gtt aac ggt atg gat att cta gct gtc tac caa gca tcc aag ttt    864
Lys Val Asn Gly Met Asp Ile Leu Ala Val Tyr Gln Ala Ser Lys Phe
        275                 280                 285 gct aag gac tgg tgt cta tcc ggc aaa ggt cct ctc gtt cta gaa tat    912
Ala Lys Asp Trp Cys Leu Ser Gly Lys Gly Pro Leu Val Leu Glu Tyr
290                 295                 300 gaa acc tat agg tac ggt ggc cat tct atg tct gat ccc ggt act acc    960
Glu Thr Tyr Arg Tyr Gly Gly His Ser Met Ser Asp Pro Gly Thr Thr
305                 310                 315                 320 tac aga act aga gac gag att cag cat atg aga tcc aag aac gat cca    1008
Tyr Arg Thr Arg Asp Glu Ile Gln His Met Arg Ser Lys Asn Asp Pro
            325                 330                 335 att gct ggt ctt aag atg cat ttg att gat cta ggt att gcc act gaa    1056
Ile Ala Gly Leu Lys Met His Leu Ile Asp Leu Gly Ile Ala Thr Glu
        340                 345                 350 gct gaa gtc aaa gct tac gac aag tcc gct aga aaa tac gtt gac gaa    1104
Ala Glu Val Lys Ala Tyr Asp Lys Ser Ala Arg Lys Tyr Val Asp Glu
        355                 360                 365 caa gtt gaa tta gct gat gct gct cct cct cca gaa gcc aaa tta tcc    1152
Gln Val Glu Leu Ala Asp Ala Ala Pro Pro Pro Glu Ala Lys Leu Ser
370                 375                 380 atc ttg ttt gaa gac gtc tac gtg aaa ggt aca gaa act cca acc cta    1200
Ile Leu Phe Glu Asp Val Tyr Val Lys Gly Thr Glu Thr Pro Thr Leu
385                 390                 395                 400 aga ggt agg atc cct gaa gat act tgg gac ttc aaa aag caa ggt ttt    1248
Arg Gly Arg Ile Pro Glu Asp Thr Trp Asp Phe Lys Lys Gln Gly Phe
            405                 410                 415 gcc tct agg gat taa                                                1263
Ala Ser Arg Asp
            420

<210> SEQ ID NO 83
<211> LENGTH: 420
<212> TYPE: PRT
<213> ORGANISM: Saccharomyces cerevisiae

<400> SEQUENCE: 83

Met Leu Ala Ala Ser Phe Lys Arg Gln Pro Ser Gln Leu Val Arg Gly
1               5                   10                  15

Leu Gly Ala Val Leu Arg Thr Pro Thr Arg Ile Gly His Val Arg Thr
            20                  25                  30

Met Ala Thr Leu Lys Thr Asp Lys Lys Ala Pro Glu Asp Ile Glu
        35                  40                  45
```

Gly Ser Asp Thr Val Gln Ile Glu Leu Pro Glu Ser Ser Phe Glu Ser
    50                  55                  60

Tyr Met Leu Glu Pro Pro Asp Leu Ser Tyr Glu Thr Ser Lys Ala Thr
65                  70                  75                  80

Leu Leu Gln Met Tyr Lys Asp Met Val Ile Ile Arg Arg Met Glu Met
                85                  90                  95

Ala Cys Asp Ala Leu Tyr Lys Ala Lys Lys Ile Arg Gly Phe Cys His
            100                 105                 110

Leu Ser Val Gly Gln Glu Ala Ile Ala Val Gly Ile Glu Asn Ala Ile
        115                 120                 125

Thr Lys Leu Asp Ser Ile Ile Thr Ser Tyr Arg Cys His Gly Phe Thr
    130                 135                 140

Phe Met Arg Gly Ala Ser Val Lys Ala Val Leu Ala Glu Leu Met Gly
145                 150                 155                 160

Arg Arg Ala Gly Val Ser Tyr Gly Lys Gly Gly Ser Met His Leu Tyr
                165                 170                 175

Ala Pro Gly Phe Tyr Gly Asn Gly Ile Val Gly Ala Gln Val Pro
            180                 185                 190

Leu Gly Ala Gly Leu Ala Phe Ala His Gln Tyr Lys Asn Glu Asp Ala
        195                 200                 205

Cys Ser Phe Thr Leu Tyr Gly Asp Gly Ala Ser Asn Gln Gly Gln Val
    210                 215                 220

Phe Glu Ser Phe Asn Met Ala Lys Leu Trp Asn Leu Pro Val Val Phe
225                 230                 235                 240

Cys Cys Glu Asn Asn Lys Tyr Gly Met Gly Thr Ala Ala Ser Arg Ser
                245                 250                 255

Ser Ala Met Thr Glu Tyr Phe Lys Arg Gly Gln Tyr Ile Pro Gly Leu
            260                 265                 270

Lys Val Asn Gly Met Asp Ile Leu Ala Val Tyr Gln Ala Ser Lys Phe
        275                 280                 285

Ala Lys Asp Trp Cys Leu Ser Gly Lys Gly Pro Leu Val Leu Glu Tyr
    290                 295                 300

Glu Thr Tyr Arg Tyr Gly Gly His Ser Met Ser Asp Pro Gly Thr Thr
305                 310                 315                 320

Tyr Arg Thr Arg Asp Glu Ile Gln His Met Arg Ser Lys Asn Asp Pro
                325                 330                 335

Ile Ala Gly Leu Lys Met His Leu Ile Asp Leu Gly Ile Ala Thr Glu
            340                 345                 350

Ala Glu Val Lys Ala Tyr Asp Lys Ser Ala Arg Lys Tyr Val Asp Glu
        355                 360                 365

Gln Val Glu Leu Ala Asp Ala Ala Pro Pro Glu Ala Lys Leu Ser
    370                 375                 380

Ile Leu Phe Glu Asp Val Tyr Val Lys Gly Thr Glu Thr Pro Thr Leu
385                 390                 395                 400

Arg Gly Arg Ile Pro Glu Asp Thr Trp Asp Phe Lys Lys Gln Gly Phe
                405                 410                 415

Ala Ser Arg Asp
            420

<210> SEQ ID NO 84
<211> LENGTH: 1101
<212> TYPE: DNA
<213> ORGANISM: Sccharomyces cerevisiae
<220> FEATURE:
<221> NAME/KEY: CDS

<220> LOCATION: (1)..(1101)

<400> SEQUENCE: 84

| | | | | | | | | | | | | | | | | |
|---|---|---|---|---|---|---|---|---|---|---|---|---|---|---|---|---|
| atg | ttt | tcc | aga | ctg | cca | aca | tca | ttg | gcc | aga | aat | gtt | gca | cgt | cgt | 48 |
| Met | Phe | Ser | Arg | Leu | Pro | Thr | Ser | Leu | Ala | Arg | Asn | Val | Ala | Arg | Arg | |
| 1 | | | | 5 | | | | | 10 | | | | | 15 | | |
| gcc | cca | act | tct | ttt | gta | aga | ccc | tct | gca | gca | gca | gca | ttg | aga | | 96 |
| Ala | Pro | Thr | Ser | Phe | Val | Arg | Pro | Ser | Ala | Ala | Ala | Ala | Leu | Arg | | |
| | | 20 | | | | | 25 | | | | | 30 | | | | |
| ttc | tca | tca | aca | aag | acg | atg | acc | gtc | aga | gag | gcc | ttg | aat | agt | gcc | 144 |
| Phe | Ser | Ser | Thr | Lys | Thr | Met | Thr | Val | Arg | Glu | Ala | Leu | Asn | Ser | Ala | |
| | | 35 | | | | | 40 | | | | | 45 | | | | |
| atg | gcg | gaa | gaa | ttg | gac | cgt | gat | gat | gat | gtc | ttc | ctt | att | ggt | gaa | 192 |
| Met | Ala | Glu | Glu | Leu | Asp | Arg | Asp | Asp | Asp | Val | Phe | Leu | Ile | Gly | Glu | |
| | 50 | | | | | 55 | | | | | 60 | | | | | |
| gaa | gtt | gca | caa | tat | aac | ggg | gct | tat | aag | gtg | tca | aag | ggt | tta | ttg | 240 |
| Glu | Val | Ala | Gln | Tyr | Asn | Gly | Ala | Tyr | Lys | Val | Ser | Lys | Gly | Leu | Leu | |
| 65 | | | | | 70 | | | | | 75 | | | | | 80 | |
| gac | agg | ttc | ggt | gaa | cgt | cgt | gtg | gtt | gac | aca | cct | att | acc | gaa | tac | 288 |
| Asp | Arg | Phe | Gly | Glu | Arg | Arg | Val | Val | Asp | Thr | Pro | Ile | Thr | Glu | Tyr | |
| | | | | 85 | | | | | 90 | | | | | 95 | | |
| ggg | ttc | aca | ggt | ttg | gcc | gtt | ggt | gcc | gct | ttg | aag | ggt | ttg | aag | cca | 336 |
| Gly | Phe | Thr | Gly | Leu | Ala | Val | Gly | Ala | Ala | Leu | Lys | Gly | Leu | Lys | Pro | |
| | | | 100 | | | | | 105 | | | | | 110 | | | |
| att | gta | gag | ttt | atg | tcg | ttc | aat | ttc | tct | atg | caa | gct | atc | gat | cat | 384 |
| Ile | Val | Glu | Phe | Met | Ser | Phe | Asn | Phe | Ser | Met | Gln | Ala | Ile | Asp | His | |
| | | | 115 | | | | | 120 | | | | | 125 | | | |
| gtt | gtc | aat | tcc | gct | gca | aag | act | cac | tac | atg | tct | ggt | ggt | act | caa | 432 |
| Val | Val | Asn | Ser | Ala | Ala | Lys | Thr | His | Tyr | Met | Ser | Gly | Gly | Thr | Gln | |
| | 130 | | | | | 135 | | | | | 140 | | | | | |
| aaa | tgt | caa | atg | gtc | ttc | aga | ggt | cct | aat | ggt | gct | gca | gtg | ggt | gtt | 480 |
| Lys | Cys | Gln | Met | Val | Phe | Arg | Gly | Pro | Asn | Gly | Ala | Ala | Val | Gly | Val | |
| 145 | | | | | 150 | | | | | 155 | | | | | 160 | |
| ggt | gct | caa | cat | tca | cag | gac | ttt | tct | cct | tgg | tac | ggt | tcc | att | cca | 528 |
| Gly | Ala | Gln | His | Ser | Gln | Asp | Phe | Ser | Pro | Trp | Tyr | Gly | Ser | Ile | Pro | |
| | | | | 165 | | | | | 170 | | | | | 175 | | |
| ggg | tta | aag | gtc | ctt | gtc | cct | tat | tct | gct | gaa | gat | gct | agg | ggt | ttg | 576 |
| Gly | Leu | Lys | Val | Leu | Val | Pro | Tyr | Ser | Ala | Glu | Asp | Ala | Arg | Gly | Leu | |
| | | | 180 | | | | | 185 | | | | | 190 | | | |
| tta | aag | gcc | gcc | atc | aga | gat | cca | aac | cct | gtt | gta | ttt | tta | gag | aac | 624 |
| Leu | Lys | Ala | Ala | Ile | Arg | Asp | Pro | Asn | Pro | Val | Val | Phe | Leu | Glu | Asn | |
| | | | 195 | | | | | 200 | | | | | 205 | | | |
| gaa | ttg | ttg | tac | ggt | gaa | tct | ttt | gaa | atc | tca | gaa | gaa | gct | tta | tcc | 672 |
| Glu | Leu | Leu | Tyr | Gly | Glu | Ser | Phe | Glu | Ile | Ser | Glu | Glu | Ala | Leu | Ser | |
| | 210 | | | | | 215 | | | | | 220 | | | | | |
| cct | gag | ttc | acc | ttg | cca | tac | aag | gct | aag | atc | gaa | aga | gaa | ggt | acc | 720 |
| Pro | Glu | Phe | Thr | Leu | Pro | Tyr | Lys | Ala | Lys | Ile | Glu | Arg | Glu | Gly | Thr | |
| 225 | | | | | 230 | | | | | 235 | | | | | 240 | |
| gat | att | tcc | att | gtt | acg | tac | aca | aga | aac | gtt | cag | ttt | tct | ttg | gaa | 768 |
| Asp | Ile | Ser | Ile | Val | Thr | Tyr | Thr | Arg | Asn | Val | Gln | Phe | Ser | Leu | Glu | |
| | | | | 245 | | | | | 250 | | | | | 255 | | |
| gcc | gct | gaa | att | cta | caa | aag | aaa | tat | ggt | gtc | tct | gca | gaa | gtt | atc | 816 |
| Ala | Ala | Glu | Ile | Leu | Gln | Lys | Lys | Tyr | Gly | Val | Ser | Ala | Glu | Val | Ile | |
| | | | 260 | | | | | 265 | | | | | 270 | | | |
| aac | ttg | cgt | tct | att | aga | cct | tta | gat | act | gaa | gct | atc | atc | aaa | act | 864 |
| Asn | Leu | Arg | Ser | Ile | Arg | Pro | Leu | Asp | Thr | Glu | Ala | Ile | Ile | Lys | Thr | |
| | | 275 | | | | | 280 | | | | | 285 | | | | |
| gtc | aag | aag | aca | aac | cac | ttg | att | act | gtt | gaa | tcc | act | ttc | cca | tca | 912 |
| Val | Lys | Lys | Thr | Asn | His | Leu | Ile | Thr | Val | Glu | Ser | Thr | Phe | Pro | Ser | |
| | 290 | | | | | 295 | | | | | 300 | | | | | |

```
ttt  ggt  gtt  ggt  gct  gaa  att  gtc  gcc  caa  gtt  atg  gag  tct  gaa  gcc        960
Phe  Gly  Val  Gly  Ala  Glu  Ile  Val  Ala  Gln  Val  Met  Glu  Ser  Glu  Ala
305                      310                      315                      320 ttt  gat  tac  ttg  gat  gct  cca  atc  caa  aga  gtt  act  ggt  gcc  gat  gtt       1008
Phe  Asp  Tyr  Leu  Asp  Ala  Pro  Ile  Gln  Arg  Val  Thr  Gly  Ala  Asp  Val
                         325                      330                      335 cca  aca  cct  tac  gct  aaa  gaa  tta  gaa  gat  ttc  gct  ttc  cct  gat  act       1056
Pro  Thr  Pro  Tyr  Ala  Lys  Glu  Leu  Glu  Asp  Phe  Ala  Phe  Pro  Asp  Thr
                    340                      345                      350 cca  acc  atc  gtt  aaa  gct  gtc  aaa  gaa  gtc  ttg  tca  att  gaa  taa             1101
Pro  Thr  Ile  Val  Lys  Ala  Val  Lys  Glu  Val  Leu  Ser  Ile  Glu
               355                      360                      365
```

<210> SEQ ID NO 85
<211> LENGTH: 366
<212> TYPE: PRT
<213> ORGANISM: Sccharomyces cerevisiae

<400> SEQUENCE: 85

```
Met Phe Ser Arg Leu Pro Thr Ser Leu Ala Arg Asn Val Ala Arg Arg
1               5                   10                  15

Ala Pro Thr Ser Phe Val Arg Pro Ser Ala Ala Ala Ala Ala Leu Arg
            20                  25                  30

Phe Ser Ser Thr Lys Thr Met Thr Val Arg Glu Ala Leu Asn Ser Ala
        35                  40                  45

Met Ala Glu Glu Leu Asp Arg Asp Asp Val Phe Leu Ile Gly Glu
    50                  55                  60

Glu Val Ala Gln Tyr Asn Gly Ala Tyr Lys Val Ser Lys Gly Leu Leu
65                  70                  75                  80

Asp Arg Phe Gly Glu Arg Arg Val Val Asp Thr Pro Ile Thr Glu Tyr
                85                  90                  95

Gly Phe Thr Gly Leu Ala Val Gly Ala Ala Leu Lys Gly Leu Lys Pro
            100                 105                 110

Ile Val Glu Phe Met Ser Phe Asn Phe Ser Met Gln Ala Ile Asp His
        115                 120                 125

Val Val Asn Ser Ala Ala Lys Thr His Tyr Met Ser Gly Gly Thr Gln
    130                 135                 140

Lys Cys Gln Met Val Phe Arg Gly Pro Asn Gly Ala Ala Val Gly Val
145                 150                 155                 160

Gly Ala Gln His Ser Gln Asp Phe Ser Pro Trp Tyr Gly Ser Ile Pro
                165                 170                 175

Gly Leu Lys Val Leu Val Pro Tyr Ser Ala Glu Asp Ala Arg Gly Leu
            180                 185                 190

Leu Lys Ala Ala Ile Arg Asp Pro Asn Pro Val Val Phe Leu Glu Asn
        195                 200                 205

Glu Leu Leu Tyr Gly Glu Ser Phe Glu Ile Ser Glu Glu Ala Leu Ser
    210                 215                 220

Pro Glu Phe Thr Leu Pro Tyr Lys Ala Lys Ile Glu Arg Glu Gly Thr
225                 230                 235                 240

Asp Ile Ser Ile Val Thr Tyr Thr Arg Asn Val Gln Phe Ser Leu Glu
                245                 250                 255

Ala Ala Glu Ile Leu Gln Lys Lys Tyr Gly Val Ser Ala Glu Val Ile
            260                 265                 270

Asn Leu Arg Ser Ile Arg Pro Leu Asp Thr Glu Ala Ile Ile Lys Thr
        275                 280                 285
```

```
Val Lys Lys Thr Asn His Leu Ile Thr Val Glu Ser Thr Phe Pro Ser
    290                 295                 300

Phe Gly Val Gly Ala Glu Ile Val Ala Gln Val Met Glu Ser Glu Ala
305                 310                 315                 320

Phe Asp Tyr Leu Asp Ala Pro Ile Gln Arg Val Thr Gly Ala Asp Val
                325                 330                 335

Pro Thr Pro Tyr Ala Lys Glu Leu Glu Asp Phe Ala Phe Pro Asp Thr
            340                 345                 350

Pro Thr Ile Val Lys Ala Val Lys Glu Val Leu Ser Ile Glu
            355                 360                 365

<210> SEQ ID NO 86
<211> LENGTH: 1449
<212> TYPE: DNA
<213> ORGANISM: Saccharomyces cerevisiae
<220> FEATURE:
<221> NAME/KEY: CDS
<222> LOCATION: (1)..(1449)

<400> SEQUENCE: 86
```

| | | | | | | | | | | | | | | | | |
|---|---|---|---|---|---|---|---|---|---|---|---|---|---|---|---|---|
| atg | tct | gcc | ttt | gtc | agg | gtg | gtt | cca | aga | ata | tcc | aga | agt | tca | gta | 48 |
| Met | Ser | Ala | Phe | Val | Arg | Val | Val | Pro | Arg | Ile | Ser | Arg | Ser | Ser | Val | |
| 1 | | | | 5 | | | | | 10 | | | | | 15 | | |
| ctc | acc | aga | tca | ttg | aga | ctg | caa | ttg | aga | tgc | tac | gca | tcg | tac | cca | 96 |
| Leu | Thr | Arg | Ser | Leu | Arg | Leu | Gln | Leu | Arg | Cys | Tyr | Ala | Ser | Tyr | Pro | |
| | | | 20 | | | | | 25 | | | | | 30 | | | |
| gag | cac | acc | att | att | ggt | atg | ccg | gca | ctg | tct | cct | acg | atg | acg | caa | 144 |
| Glu | His | Thr | Ile | Ile | Gly | Met | Pro | Ala | Leu | Ser | Pro | Thr | Met | Thr | Gln | |
| | | 35 | | | | | 40 | | | | | 45 | | | | |
| ggt | aat | ctt | gct | gct | tgg | act | aag | aag | gaa | ggt | gac | caa | ttg | tct | ccc | 192 |
| Gly | Asn | Leu | Ala | Ala | Trp | Thr | Lys | Lys | Glu | Gly | Asp | Gln | Leu | Ser | Pro | |
| 50 | | | | | 55 | | | | | 60 | | | | | | |
| ggt | gaa | gtt | att | gcc | gaa | ata | gaa | aca | gac | aag | gct | caa | atg | gac | ttt | 240 |
| Gly | Glu | Val | Ile | Ala | Glu | Ile | Glu | Thr | Asp | Lys | Ala | Gln | Met | Asp | Phe | |
| 65 | | | | | 70 | | | | | 75 | | | | | 80 | |
| gag | ttc | caa | gaa | gat | ggt | tac | tta | gcc | aag | att | cta | gtt | cct | gaa | ggt | 288 |
| Glu | Phe | Gln | Glu | Asp | Gly | Tyr | Leu | Ala | Lys | Ile | Leu | Val | Pro | Glu | Gly | |
| | | | | 85 | | | | | 90 | | | | | 95 | | |
| aca | aag | gac | att | cct | gtc | aac | aag | cct | att | gcc | gtc | tat | gtg | gag | gac | 336 |
| Thr | Lys | Asp | Ile | Pro | Val | Asn | Lys | Pro | Ile | Ala | Val | Tyr | Val | Glu | Asp | |
| | | | 100 | | | | | 105 | | | | | 110 | | | |
| aaa | gct | gat | gtg | cca | gct | ttt | aag | gac | ttt | aag | ctg | gag | gat | tca | ggt | 384 |
| Lys | Ala | Asp | Val | Pro | Ala | Phe | Lys | Asp | Phe | Lys | Leu | Glu | Asp | Ser | Gly | |
| | | 115 | | | | | 120 | | | | | 125 | | | | |
| tct | gat | tca | aag | acc | agt | acg | aag | gct | cag | cct | gcc | gaa | cca | cag | gca | 432 |
| Ser | Asp | Ser | Lys | Thr | Ser | Thr | Lys | Ala | Gln | Pro | Ala | Glu | Pro | Gln | Ala | |
| | 130 | | | | | 135 | | | | | 140 | | | | | |
| gaa | aag | aaa | caa | gaa | gcg | cca | gct | gaa | gag | acc | aag | act | tct | gca | cct | 480 |
| Glu | Lys | Lys | Gln | Glu | Ala | Pro | Ala | Glu | Glu | Thr | Lys | Thr | Ser | Ala | Pro | |
| 145 | | | | | 150 | | | | | 155 | | | | | 160 | |
| gaa | gct | aag | aaa | tct | gac | gtt | gct | gct | cct | caa | ggt | agg | att | ttt | gcc | 528 |
| Glu | Ala | Lys | Lys | Ser | Asp | Val | Ala | Ala | Pro | Gln | Gly | Arg | Ile | Phe | Ala | |
| | | | | 165 | | | | | 170 | | | | | 175 | | |
| tct | cca | ctt | gcc | aag | act | atc | gcc | ttg | gaa | aag | ggt | att | tct | ttg | aag | 576 |
| Ser | Pro | Leu | Ala | Lys | Thr | Ile | Ala | Leu | Glu | Lys | Gly | Ile | Ser | Leu | Lys | |
| | | | 180 | | | | | 185 | | | | | 190 | | | |
| gat | gtt | cac | ggc | act | gga | ccc | cgc | ggt | aga | att | acc | aag | gct | gac | att | 624 |
| Asp | Val | His | Gly | Thr | Gly | Pro | Arg | Gly | Arg | Ile | Thr | Lys | Ala | Asp | Ile | |
| | | 195 | | | | | 200 | | | | | 205 | | | | |
| gag | tca | tat | cta | gaa | aag | tcg | tct | aag | cag | tct | tct | caa | acc | agt | ggt | 672 |

| | | | | | | | | | | | | | |
|---|---|---|---|---|---|---|---|---|---|---|---|---|---|
| Glu | Ser | Tyr | Leu | Glu | Lys | Ser | Ser | Lys | Gln | Ser | Ser | Gln | Thr | Ser | Gly |
| | 210 | | | | | 215 | | | | 220 | | | |

```
gct gcc gcc gcc act cct gcc gcc gct acc tca agc act act gct ggc     720
Ala Ala Ala Ala Thr Pro Ala Ala Ala Thr Ser Ser Thr Thr Ala Gly
225                 230                 235                 240 tct gct cca tcg cct tct tct aca gca tca tat gag gat gtt cca att     768
Ser Ala Pro Ser Pro Ser Ser Thr Ala Ser Tyr Glu Asp Val Pro Ile
            245                 250                 255 tca acc atg aga agc atc att gga gaa cgt tta ttg caa tct act caa     816
Ser Thr Met Arg Ser Ile Ile Gly Glu Arg Leu Leu Gln Ser Thr Gln
        260                 265                 270 ggc att cca tca tac atc gtt tcc tcc aag ata tcc atc tcc aaa ctt     864
Gly Ile Pro Ser Tyr Ile Val Ser Ser Lys Ile Ser Ile Ser Lys Leu
    275                 280                 285 ttg aaa ttg aga cag tcc ttg aac gct aca gca aac gac aag tac aaa     912
Leu Lys Leu Arg Gln Ser Leu Asn Ala Thr Ala Asn Asp Lys Tyr Lys
290                 295                 300 ctg tcc att aat gac cta tta gta aaa gcc atc act gtt gcg gct aag     960
Leu Ser Ile Asn Asp Leu Leu Val Lys Ala Ile Thr Val Ala Ala Lys
305                 310                 315                 320 agg gtg cca gat gcc aat gcc tac tgg tta cct aat gag aac gtt atc    1008
Arg Val Pro Asp Ala Asn Ala Tyr Trp Leu Pro Asn Glu Asn Val Ile
            325                 330                 335 cgt aaa ttc aag aat gtc gat gtc tca gtc gct gtt gcc aca cca aca    1056
Arg Lys Phe Lys Asn Val Asp Val Ser Val Ala Val Ala Thr Pro Thr
        340                 345                 350 gga tta ttg aca cca att gtc aag aat tgt gag gcc aag ggc ttg tcg    1104
Gly Leu Leu Thr Pro Ile Val Lys Asn Cys Glu Ala Lys Gly Leu Ser
    355                 360                 365 caa atc tct aac gaa atc aag gaa cta gtc aag cgt gcc aga ata aac    1152
Gln Ile Ser Asn Glu Ile Lys Glu Leu Val Lys Arg Ala Arg Ile Asn
370                 375                 380 aaa ttg gca cca gag gaa ttc caa ggt ggg acc att tgc ata tcc aat    1200
Lys Leu Ala Pro Glu Glu Phe Gln Gly Gly Thr Ile Cys Ile Ser Asn
385                 390                 395                 400 atg ggc atg aat aat gct gtt aac atg ttt act tcg att atc aac cca    1248
Met Gly Met Asn Asn Ala Val Asn Met Phe Thr Ser Ile Ile Asn Pro
            405                 410                 415 cca cag tct aca atc ttg gcc atc gct act gtt gaa agg gtc gct gtg    1296
Pro Gln Ser Thr Ile Leu Ala Ile Ala Thr Val Glu Arg Val Ala Val
        420                 425                 430 gaa gac gcc gct gct gag aac gga ttc tcc ttt gat aac cag gtt acc    1344
Glu Asp Ala Ala Ala Glu Asn Gly Phe Ser Phe Asp Asn Gln Val Thr
    435                 440                 445 ata aca ggg acc ttt gat cat aga acc att gat ggc gcc aaa ggt gca    1392
Ile Thr Gly Thr Phe Asp His Arg Thr Ile Asp Gly Ala Lys Gly Ala
450                 455                 460 gaa ttc atg aag gaa ttg aaa act gtt att gaa aat cct ttg gaa atg    1440
Glu Phe Met Lys Glu Leu Lys Thr Val Ile Glu Asn Pro Leu Glu Met
465                 470                 475                 480 cta ttg tga                                                         1449
Leu Leu
```

<210> SEQ ID NO 87
<211> LENGTH: 482
<212> TYPE: PRT
<213> ORGANISM: Saccharomyces cerevisiae

<400> SEQUENCE: 87

Met Ser Ala Phe Val Arg Val Val Pro Arg Ile Ser Arg Ser Ser Val

-continued

```
1               5                   10                  15
Leu Thr Arg Ser Leu Arg Leu Gln Leu Arg Cys Tyr Ala Ser Tyr Pro
            20                  25                  30
Glu His Thr Ile Ile Gly Met Pro Ala Leu Ser Pro Thr Met Thr Gln
            35                  40                  45
Gly Asn Leu Ala Ala Trp Thr Lys Lys Glu Gly Asp Gln Leu Ser Pro
 50                  55                  60
Gly Glu Val Ile Ala Glu Ile Glu Thr Asp Lys Ala Gln Met Asp Phe
 65                  70                  75                  80
Glu Phe Gln Glu Asp Gly Tyr Leu Ala Lys Ile Leu Val Pro Glu Gly
            85                  90                  95
Thr Lys Asp Ile Pro Val Asn Lys Pro Ile Ala Val Tyr Val Glu Asp
            100                 105                 110
Lys Ala Asp Val Pro Ala Phe Lys Asp Phe Lys Leu Glu Asp Ser Gly
            115                 120                 125
Ser Asp Ser Lys Thr Ser Thr Lys Ala Gln Pro Ala Glu Pro Gln Ala
            130                 135                 140
Glu Lys Lys Gln Glu Ala Pro Ala Glu Thr Lys Thr Ser Ala Pro
145                 150                 155                 160
Glu Ala Lys Lys Ser Asp Val Ala Ala Pro Gln Gly Arg Ile Phe Ala
                165                 170                 175
Ser Pro Leu Ala Lys Thr Ile Ala Leu Glu Lys Gly Ile Ser Leu Lys
                180                 185                 190
Asp Val His Gly Thr Gly Pro Arg Gly Arg Ile Thr Lys Ala Asp Ile
                195                 200                 205
Glu Ser Tyr Leu Glu Lys Ser Ser Lys Gln Ser Gln Thr Ser Gly
210                 215                 220
Ala Ala Ala Ala Thr Pro Ala Ala Ala Thr Ser Ser Thr Ala Gly
225                 230                 235                 240
Ser Ala Pro Ser Pro Ser Ser Thr Ala Ser Tyr Glu Asp Val Pro Ile
                245                 250                 255
Ser Thr Met Arg Ser Ile Ile Gly Glu Arg Leu Leu Gln Ser Thr Gln
                260                 265                 270
Gly Ile Pro Ser Tyr Ile Val Ser Ser Lys Ile Ser Ile Ser Lys Leu
                275                 280                 285
Leu Lys Leu Arg Gln Ser Leu Asn Ala Thr Ala Asn Asp Lys Tyr Lys
                290                 295                 300
Leu Ser Ile Asn Asp Leu Leu Val Lys Ala Ile Thr Val Ala Ala Lys
305                 310                 315                 320
Arg Val Pro Asp Ala Asn Ala Tyr Trp Leu Pro Asn Glu Asn Val Ile
                325                 330                 335
Arg Lys Phe Lys Asn Val Asp Val Ser Val Ala Val Ala Thr Pro Thr
                340                 345                 350
Gly Leu Leu Thr Pro Ile Val Lys Asn Cys Glu Ala Lys Gly Leu Ser
                355                 360                 365
Gln Ile Ser Asn Glu Ile Lys Glu Leu Val Lys Arg Ala Arg Ile Asn
                370                 375                 380
Lys Leu Ala Pro Glu Glu Phe Gln Gly Gly Thr Ile Cys Ile Ser Asn
385                 390                 395                 400
Met Gly Met Asn Asn Ala Val Asn Met Phe Thr Ser Ile Ile Asn Pro
                405                 410                 415
Pro Gln Ser Thr Ile Leu Ala Ile Ala Thr Val Glu Arg Val Ala Val
                420                 425                 430
```

Glu Asp Ala Ala Ala Glu Asn Gly Phe Ser Phe Asp Asn Gln Val Thr
    435                 440                 445

Ile Thr Gly Thr Phe Asp His Arg Thr Ile Asp Gly Ala Lys Gly Ala
    450                 455                 460

Glu Phe Met Lys Glu Leu Lys Thr Val Ile Glu Asn Pro Leu Glu Met
465                 470                 475                 480

Leu Leu

<210> SEQ ID NO 88
<211> LENGTH: 1500
<212> TYPE: DNA
<213> ORGANISM: Saccharomyces cerevisiae
<220> FEATURE:
<221> NAME/KEY: CDS
<222> LOCATION: (1)..(1500)

<400> SEQUENCE: 88

| | | | | | | | | | | | | | | | |
|---|---|---|---|---|---|---|---|---|---|---|---|---|---|---|---|
| atg | tta | aga | atc | aga | tca | ctc | cta | aat | aat | aag | cgt | gcc | ttt | tcg | tcc | 48 |
| Met | Leu | Arg | Ile | Arg | Ser | Leu | Leu | Asn | Asn | Lys | Arg | Ala | Phe | Ser | Ser | |
| 1 | | | | 5 | | | | | 10 | | | | | 15 | | |

| aca | gtc | agg | aca | ttg | acc | att | aac | aag | tca | cat | gat | gta | gtc | atc | atc | 96 |
|---|---|---|---|---|---|---|---|---|---|---|---|---|---|---|---|---|
| Thr | Val | Arg | Thr | Leu | Thr | Ile | Asn | Lys | Ser | His | Asp | Val | Val | Ile | Ile | |
| | | 20 | | | | | 25 | | | | | 30 | | | | |

| ggt | ggt | ggc | cct | gct | ggt | tac | gtg | gct | gct | atc | aaa | gct | gct | caa | ttg | 144 |
|---|---|---|---|---|---|---|---|---|---|---|---|---|---|---|---|---|
| Gly | Gly | Gly | Pro | Ala | Gly | Tyr | Val | Ala | Ala | Ile | Lys | Ala | Ala | Gln | Leu | |
| | | | | 35 | | | | | 40 | | | | | 45 | | |

| gga | ttt | aac | act | gca | tgt | gta | gaa | aaa | aga | ggc | aaa | tta | ggc | ggt | acc | 192 |
|---|---|---|---|---|---|---|---|---|---|---|---|---|---|---|---|---|
| Gly | Phe | Asn | Thr | Ala | Cys | Val | Glu | Lys | Arg | Gly | Lys | Leu | Gly | Gly | Thr | |
| | 50 | | | | | 55 | | | | | 60 | | | | | |

| tgt | ctt | aac | gtt | gga | tgt | atc | ccc | tcc | aaa | gca | ctt | cta | aat | aat | tct | 240 |
|---|---|---|---|---|---|---|---|---|---|---|---|---|---|---|---|---|
| Cys | Leu | Asn | Val | Gly | Cys | Ile | Pro | Ser | Lys | Ala | Leu | Leu | Asn | Asn | Ser | |
| 65 | | | | | 70 | | | | | 75 | | | | | 80 | |

| cat | tta | ttc | cac | caa | atg | cat | acg | gaa | gcg | caa | aag | aga | ggt | att | gac | 288 |
|---|---|---|---|---|---|---|---|---|---|---|---|---|---|---|---|---|
| His | Leu | Phe | His | Gln | Met | His | Thr | Glu | Ala | Gln | Lys | Arg | Gly | Ile | Asp | |
| | | | | 85 | | | | | 90 | | | | | 95 | | |

| gtc | aac | ggt | gat | atc | aaa | att | aac | gta | gca | aac | ttc | caa | aag | gct | aag | 336 |
|---|---|---|---|---|---|---|---|---|---|---|---|---|---|---|---|---|
| Val | Asn | Gly | Asp | Ile | Lys | Ile | Asn | Val | Ala | Asn | Phe | Gln | Lys | Ala | Lys | |
| | | | 100 | | | | | 105 | | | | | 110 | | | |

| gat | gac | gct | gtt | aag | caa | tta | act | gga | ggt | att | gag | ctt | ctg | ttc | aag | 384 |
|---|---|---|---|---|---|---|---|---|---|---|---|---|---|---|---|---|
| Asp | Asp | Ala | Val | Lys | Gln | Leu | Thr | Gly | Gly | Ile | Glu | Leu | Leu | Phe | Lys | |
| | | | | 115 | | | | | 120 | | | | | 125 | | |

| aaa | aat | aag | gtc | acc | tat | tat | aaa | ggt | aat | ggt | tca | ttc | gaa | gac | gaa | 432 |
|---|---|---|---|---|---|---|---|---|---|---|---|---|---|---|---|---|
| Lys | Asn | Lys | Val | Thr | Tyr | Tyr | Lys | Gly | Asn | Gly | Ser | Phe | Glu | Asp | Glu | |
| | 130 | | | | | 135 | | | | | 140 | | | | | |

| acg | aag | atc | aga | gta | act | ccc | gtt | gat | ggg | ttg | gaa | ggc | act | gtc | aag | 480 |
|---|---|---|---|---|---|---|---|---|---|---|---|---|---|---|---|---|
| Thr | Lys | Ile | Arg | Val | Thr | Pro | Val | Asp | Gly | Leu | Glu | Gly | Thr | Val | Lys | |
| 145 | | | | | 150 | | | | | 155 | | | | | 160 | |

| gaa | gac | cac | ata | cta | gat | gtt | aag | aac | atc | ata | gtc | gcc | acg | ggc | tct | 528 |
|---|---|---|---|---|---|---|---|---|---|---|---|---|---|---|---|---|
| Glu | Asp | His | Ile | Leu | Asp | Val | Lys | Asn | Ile | Ile | Val | Ala | Thr | Gly | Ser | |
| | | | | 165 | | | | | 170 | | | | | 175 | | |

| gaa | gtt | aca | ccc | ttc | ccc | ggt | att | gaa | ata | gat | gag | gaa | aaa | att | gtc | 576 |
|---|---|---|---|---|---|---|---|---|---|---|---|---|---|---|---|---|
| Glu | Val | Thr | Pro | Phe | Pro | Gly | Ile | Glu | Ile | Asp | Glu | Glu | Lys | Ile | Val | |
| | | | 180 | | | | | 185 | | | | | 190 | | | |

| tct | tca | aca | ggt | gct | ctt | tcg | tta | aag | gaa | att | ccc | aaa | aga | tta | acc | 624 |
|---|---|---|---|---|---|---|---|---|---|---|---|---|---|---|---|---|
| Ser | Ser | Thr | Gly | Ala | Leu | Ser | Leu | Lys | Glu | Ile | Pro | Lys | Arg | Leu | Thr | |
| | | | | 195 | | | | | 200 | | | | | 205 | | |

| atc | att | ggt | gga | gga | atc | atc | gga | ttg | gaa | atg | ggt | tca | gtt | tac | tct | 672 |
|---|---|---|---|---|---|---|---|---|---|---|---|---|---|---|---|---|
| Ile | Ile | Gly | Gly | Gly | Ile | Ile | Gly | Leu | Glu | Met | Gly | Ser | Val | Tyr | Ser | |
| | 210 | | | | | 215 | | | | | 220 | | | | | |

```
aga tta ggc tcc aag gtt act gta gta gaa ttt caa cct caa att ggt      720
Arg Leu Gly Ser Lys Val Thr Val Val Glu Phe Gln Pro Gln Ile Gly
225                 230                 235                 240 gca tct atg gac ggc gag gtt gcc aaa gcc acc caa aag ttc ttg aaa      768
Ala Ser Met Asp Gly Glu Val Ala Lys Ala Thr Gln Lys Phe Leu Lys
            245                 250                 255 aag caa ggt ttg gac ttc aaa tta agc acc aaa gtt att tct gca aag      816
Lys Gln Gly Leu Asp Phe Lys Leu Ser Thr Lys Val Ile Ser Ala Lys
        260                 265                 270 aga aac gac gac aag aac gtc gtc gaa att gtt gta gaa gat act aaa      864
Arg Asn Asp Asp Lys Asn Val Val Glu Ile Val Val Glu Asp Thr Lys
    275                 280                 285 acg aat aag caa gaa aat ttg gaa gct gaa gtt ttg ctg gtt gct gtt      912
Thr Asn Lys Gln Glu Asn Leu Glu Ala Glu Val Leu Leu Val Ala Val
290                 295                 300 ggt aga aga cct tac att gct ggc tta ggg gct gaa aag att gga tta      960
Gly Arg Arg Pro Tyr Ile Ala Gly Leu Gly Ala Glu Lys Ile Gly Leu
305                 310                 315                 320 gaa gta gac aaa agg gga cgc cta gtc att gat gac caa ttt aat tcc     1008
Glu Val Asp Lys Arg Gly Arg Leu Val Ile Asp Asp Gln Phe Asn Ser
            325                 330                 335 aag ttc cca cac att aaa gtg gta gga gat gtt aca ttt ggt cca atg     1056
Lys Phe Pro His Ile Lys Val Val Gly Asp Val Thr Phe Gly Pro Met
        340                 345                 350 ctg gct cac aaa gcc gaa gag gaa ggt att gca gct gtc gaa atg ttg     1104
Leu Ala His Lys Ala Glu Glu Glu Gly Ile Ala Ala Val Glu Met Leu
    355                 360                 365 aaa act ggt cac ggt cat gtc aac tat aac aac att cct tcg gtc atg     1152
Lys Thr Gly His Gly His Val Asn Tyr Asn Asn Ile Pro Ser Val Met
370                 375                 380 tat tct cac cca gaa gta gca tgg gtt ggt aaa acc gaa gag caa ttg     1200
Tyr Ser His Pro Glu Val Ala Trp Val Gly Lys Thr Glu Glu Gln Leu
385                 390                 395                 400 aaa gaa gcc ggc att gac tat aaa att ggt aag ttc ccc ttt gcg gcc     1248
Lys Glu Ala Gly Ile Asp Tyr Lys Ile Gly Lys Phe Pro Phe Ala Ala
            405                 410                 415 aat tca aga gcc aag acc aac caa gac act gaa ggt ttc gtg aag att     1296
Asn Ser Arg Ala Lys Thr Asn Gln Asp Thr Glu Gly Phe Val Lys Ile
        420                 425                 430 ttg atc gat tcc aag acc gag cgt att ttg ggg gct cac att atc ggt     1344
Leu Ile Asp Ser Lys Thr Glu Arg Ile Leu Gly Ala His Ile Ile Gly
    435                 440                 445 cca aat gcc ggt gaa atg att gct gaa gct ggc tta gcc tta gaa tat     1392
Pro Asn Ala Gly Glu Met Ile Ala Glu Ala Gly Leu Ala Leu Glu Tyr
450                 455                 460 ggc gct tcc gca gaa gat gtt gct agg gtc tgc cat gct cat cct act     1440
Gly Ala Ser Ala Glu Asp Val Ala Arg Val Cys His Ala His Pro Thr
465                 470                 475                 480 ttg tcc gaa gca ttt aag gaa gct aac atg gct gcc tat gat aaa gct     1488
Leu Ser Glu Ala Phe Lys Glu Ala Asn Met Ala Ala Tyr Asp Lys Ala
            485                 490                 495 att cat tgt tga                                                     1500
Ile His Cys <210> SEQ ID NO 89
<211> LENGTH: 499
<212> TYPE: PRT
<213> ORGANISM: Saccharomyces cerevisiae

<400> SEQUENCE: 89
```

```
Met Leu Arg Ile Arg Ser Leu Leu Asn Asn Lys Arg Ala Phe Ser Ser
1               5                   10                  15

Thr Val Arg Thr Leu Thr Ile Asn Lys Ser His Asp Val Val Ile Ile
            20                  25                  30

Gly Gly Gly Pro Ala Gly Tyr Val Ala Ala Ile Lys Ala Ala Gln Leu
            35                  40                  45

Gly Phe Asn Thr Ala Cys Val Glu Lys Arg Gly Lys Leu Gly Gly Thr
            50                  55                  60

Cys Leu Asn Val Gly Cys Ile Pro Ser Lys Ala Leu Leu Asn Asn Ser
65                      70                  75                  80

His Leu Phe His Gln Met His Thr Glu Ala Gln Lys Arg Gly Ile Asp
                85                  90                  95

Val Asn Gly Asp Ile Lys Ile Asn Val Ala Asn Phe Gln Lys Ala Lys
            100                 105                 110

Asp Asp Ala Val Lys Gln Leu Thr Gly Gly Ile Glu Leu Leu Phe Lys
            115                 120                 125

Lys Asn Lys Val Thr Tyr Tyr Lys Gly Asn Gly Ser Phe Glu Asp Glu
            130                 135                 140

Thr Lys Ile Arg Val Thr Pro Val Asp Gly Leu Glu Gly Thr Val Lys
145                 150                 155                 160

Glu Asp His Ile Leu Asp Val Lys Asn Ile Ile Val Ala Thr Gly Ser
            165                 170                 175

Glu Val Thr Pro Phe Pro Gly Ile Glu Ile Asp Glu Lys Ile Val
            180                 185                 190

Ser Ser Thr Gly Ala Leu Ser Leu Lys Glu Ile Pro Lys Arg Leu Thr
            195                 200                 205

Ile Ile Gly Gly Gly Ile Ile Gly Leu Glu Met Gly Ser Val Tyr Ser
            210                 215                 220

Arg Leu Gly Ser Lys Val Thr Val Val Glu Phe Gln Pro Gln Ile Gly
225                 230                 235                 240

Ala Ser Met Asp Gly Glu Val Ala Lys Ala Thr Gln Lys Phe Leu Lys
            245                 250                 255

Lys Gln Gly Leu Asp Phe Lys Leu Ser Thr Lys Val Ile Ser Ala Lys
            260                 265                 270

Arg Asn Asp Asp Lys Asn Val Val Glu Ile Val Val Glu Asp Thr Lys
            275                 280                 285

Thr Asn Lys Gln Glu Asn Leu Glu Ala Glu Val Leu Leu Val Ala Val
            290                 295                 300

Gly Arg Arg Pro Tyr Ile Ala Gly Leu Gly Ala Glu Lys Ile Gly Leu
305                 310                 315                 320

Glu Val Asp Lys Arg Gly Arg Leu Val Ile Asp Asp Gln Phe Asn Ser
            325                 330                 335

Lys Phe Pro His Ile Lys Val Val Gly Asp Val Thr Phe Gly Pro Met
            340                 345                 350

Leu Ala His Lys Ala Glu Glu Gly Ile Ala Ala Val Glu Met Leu
            355                 360                 365

Lys Thr Gly His Gly His Val Asn Tyr Asn Asn Ile Pro Ser Val Met
            370                 375                 380

Tyr Ser His Pro Glu Val Ala Trp Val Gly Lys Thr Glu Glu Gln Leu
385                 390                 395                 400

Lys Glu Ala Gly Ile Asp Tyr Lys Ile Gly Lys Phe Pro Phe Ala Ala
            405                 410                 415

Asn Ser Arg Ala Lys Thr Asn Gln Asp Thr Glu Gly Phe Val Lys Ile
```

```
                420             425             430
Leu Ile Asp Ser Lys Thr Glu Arg Ile Leu Gly Ala His Ile Ile Gly
                435             440             445

Pro Asn Ala Gly Glu Met Ile Ala Glu Ala Gly Leu Ala Leu Glu Tyr
        450             455             460

Gly Ala Ser Ala Glu Asp Val Ala Arg Val Cys His Ala His Pro Thr
465             470             475             480

Leu Ser Glu Ala Phe Lys Glu Ala Asn Met Ala Ala Tyr Asp Lys Ala
                485             490             495

Ile His Cys

<210> SEQ ID NO 90
<211> LENGTH: 1233
<212> TYPE: DNA
<213> ORGANISM: Saccharomyces cerevisiae
<220> FEATURE:
<221> NAME/KEY: CDS
<222> LOCATION: (1)..(1233)

<400> SEQUENCE: 90
```

| | | | | | | | | | | | | | | | | |
|---|---|---|---|---|---|---|---|---|---|---|---|---|---|---|---|---|
| atg | cta | agt | gca | att | tcc | aaa | gtc | tcc | act | tta | aaa | tca | tgt | aca | aga | 48 |
| Met | Leu | Ser | Ala | Ile | Ser | Lys | Val | Ser | Thr | Leu | Lys | Ser | Cys | Thr | Arg | |
| 1 | | | | 5 | | | | | 10 | | | | | 15 | | |
| tat | tta | acc | aaa | tgc | aac | tat | cat | gca | tca | gct | aaa | tta | ctt | gct | gta | 96 |
| Tyr | Leu | Thr | Lys | Cys | Asn | Tyr | His | Ala | Ser | Ala | Lys | Leu | Leu | Ala | Val | |
| | | | 20 | | | | | 25 | | | | | 30 | | | |
| aag | aca | ttt | tca | atg | cct | gca | atg | tct | cct | act | atg | gag | aaa | ggg | ggg | 144 |
| Lys | Thr | Phe | Ser | Met | Pro | Ala | Met | Ser | Pro | Thr | Met | Glu | Lys | Gly | Gly | |
| | | 35 | | | | | 40 | | | | | 45 | | | | |
| att | gtg | tct | tgg | aaa | tat | aaa | gtt | ggc | gaa | cca | ttc | agc | gcg | ggc | gat | 192 |
| Ile | Val | Ser | Trp | Lys | Tyr | Lys | Val | Gly | Glu | Pro | Phe | Ser | Ala | Gly | Asp | |
| | 50 | | | | | 55 | | | | | 60 | | | | | |
| gtg | ata | tta | gaa | gtg | gaa | aca | gat | aaa | tct | caa | att | gat | gtg | gaa | gca | 240 |
| Val | Ile | Leu | Glu | Val | Glu | Thr | Asp | Lys | Ser | Gln | Ile | Asp | Val | Glu | Ala | |
| 65 | | | | | 70 | | | | | 75 | | | | | 80 | |
| ctg | gac | gat | ggt | aaa | cta | gct | aag | atc | ctg | aaa | gat | gaa | ggc | tct | aaa | 288 |
| Leu | Asp | Asp | Gly | Lys | Leu | Ala | Lys | Ile | Leu | Lys | Asp | Glu | Gly | Ser | Lys | |
| | | | | 85 | | | | | 90 | | | | | 95 | | |
| gat | gtt | gat | gtt | ggt | gaa | cct | att | gct | tat | att | gct | gat | gtt | gat | gat | 336 |
| Asp | Val | Asp | Val | Gly | Glu | Pro | Ile | Ala | Tyr | Ile | Ala | Asp | Val | Asp | Asp | |
| | | | 100 | | | | | 105 | | | | | 110 | | | |
| gat | tta | gct | act | ata | aag | tta | ccc | caa | gag | gcc | aac | acc | gca | aat | gcg | 384 |
| Asp | Leu | Ala | Thr | Ile | Lys | Leu | Pro | Gln | Glu | Ala | Asn | Thr | Ala | Asn | Ala | |
| | | 115 | | | | | 120 | | | | | 125 | | | | |
| aaa | tct | att | gaa | att | aag | aag | cca | tcc | gca | gat | agt | act | gaa | gca | aca | 432 |
| Lys | Ser | Ile | Glu | Ile | Lys | Lys | Pro | Ser | Ala | Asp | Ser | Thr | Glu | Ala | Thr | |
| | 130 | | | | | 135 | | | | | 140 | | | | | |
| caa | caa | cat | tta | aaa | aaa | gcc | aca | gtt | aca | cca | ata | aaa | acc | gtt | gac | 480 |
| Gln | Gln | His | Leu | Lys | Lys | Ala | Thr | Val | Thr | Pro | Ile | Lys | Thr | Val | Asp | |
| 145 | | | | | 150 | | | | | 155 | | | | | 160 | |
| ggc | agc | caa | gcc | aat | ctt | gaa | cag | acg | cta | tta | cca | tcc | gtg | tca | tta | 528 |
| Gly | Ser | Gln | Ala | Asn | Leu | Glu | Gln | Thr | Leu | Leu | Pro | Ser | Val | Ser | Leu | |
| | | | | 165 | | | | | 170 | | | | | 175 | | |
| cta | ctg | gct | gag | aac | aat | ata | tcc | aaa | caa | aag | gct | ttg | aag | gaa | att | 576 |
| Leu | Leu | Ala | Glu | Asn | Asn | Ile | Ser | Lys | Gln | Lys | Ala | Leu | Lys | Glu | Ile | |
| | | | 180 | | | | | 185 | | | | | 190 | | | |
| gcg | cca | tct | ggt | tcc | aac | ggt | aga | cta | tta | aag | ggt | gat | gtg | cta | gca | 624 |
| Ala | Pro | Ser | Gly | Ser | Asn | Gly | Arg | Leu | Leu | Lys | Gly | Asp | Val | Leu | Ala | |
| | | 195 | | | | | 200 | | | | | 205 | | | | |

-continued

```
tac cta ggg aaa ata cca caa gat tcg gtt aac aag gta aca gaa ttt      672
Tyr Leu Gly Lys Ile Pro Gln Asp Ser Val Asn Lys Val Thr Glu Phe
210             215                 220 atc aag aag aac gaa cgt ctc gat tta tcg aac att aaa cct ata cag      720
Ile Lys Lys Asn Glu Arg Leu Asp Leu Ser Asn Ile Lys Pro Ile Gln
225             230                 235                 240 ctc aaa cca aaa ata gcc gag caa gct caa aca aaa gct gcc gac aag      768
Leu Lys Pro Lys Ile Ala Glu Gln Ala Gln Thr Lys Ala Ala Asp Lys
                245                 250                 255 cca aag att act cct gta gaa ttt gaa gag caa tta gtg ttc cat gct      816
Pro Lys Ile Thr Pro Val Glu Phe Glu Glu Gln Leu Val Phe His Ala
            260                 265                 270 ccc gcc tct att ccg ttt gac aaa ctg agt gaa tca ttg aac tct ttc      864
Pro Ala Ser Ile Pro Phe Asp Lys Leu Ser Glu Ser Leu Asn Ser Phe
        275                 280                 285 atg aaa gaa gct tac cag ttc tca cac gga aca cca cta atg gac aca      912
Met Lys Glu Ala Tyr Gln Phe Ser His Gly Thr Pro Leu Met Asp Thr
290                 295                 300 aat tcg aaa tac ttt gac cct att ttc gag gac ctt gtc acc ttg agc      960
Asn Ser Lys Tyr Phe Asp Pro Ile Phe Glu Asp Leu Val Thr Leu Ser
305             310                 315                 320 cca aga gag cca aga ttt aaa ttt tcc tat gac ttg atg caa att ccc     1008
Pro Arg Glu Pro Arg Phe Lys Phe Ser Tyr Asp Leu Met Gln Ile Pro
                325                 330                 335 aaa gct aat aac atg caa gac acg tac ggt caa gaa gac ata ttt gac     1056
Lys Ala Asn Asn Met Gln Asp Thr Tyr Gly Gln Glu Asp Ile Phe Asp
            340                 345                 350 ctc tta aca ggt tca gac gcg act gcc tca tca gta aga ccc gtt gaa     1104
Leu Leu Thr Gly Ser Asp Ala Thr Ala Ser Ser Val Arg Pro Val Glu
        355                 360                 365 aag aac tta cct gaa aaa aac gaa tat ata cta gcg ttg aat gtt agc     1152
Lys Asn Leu Pro Glu Lys Asn Glu Tyr Ile Leu Ala Leu Asn Val Ser
370                 375                 380 gtc aac aac aag aag ttt aat gac gcg gag gcc aag gca aaa aga ttc     1200
Val Asn Asn Lys Lys Phe Asn Asp Ala Glu Ala Lys Ala Lys Arg Phe
385             390                 395                 400 ctt gat tac gta agg gag tta gaa tca ttt tga                         1233
Leu Asp Tyr Val Arg Glu Leu Glu Ser Phe
                405                 410

<210> SEQ ID NO 91
<211> LENGTH: 410
<212> TYPE: PRT
<213> ORGANISM: Saccharomyces cerevisiae

<400> SEQUENCE: 91

Met Leu Ser Ala Ile Ser Lys Val Ser Thr Leu Lys Ser Cys Thr Arg
1               5                   10                  15

Tyr Leu Thr Lys Cys Asn Tyr His Ala Ser Ala Lys Leu Leu Ala Val
                20                  25                  30

Lys Thr Phe Ser Met Pro Ala Met Ser Pro Thr Met Glu Lys Gly Gly
            35                  40                  45

Ile Val Ser Trp Lys Tyr Lys Val Gly Glu Pro Phe Ser Ala Gly Asp
        50                  55                  60

Val Ile Leu Glu Val Glu Thr Asp Lys Ser Gln Ile Asp Val Glu Ala
65                  70                  75                  80

Leu Asp Asp Gly Lys Leu Ala Lys Ile Leu Lys Asp Glu Gly Ser Lys
                85                  90                  95

Asp Val Asp Val Gly Glu Pro Ile Ala Tyr Ile Ala Asp Val Asp Asp
```

```
                    100                 105                 110
Asp Leu Ala Thr Ile Lys Leu Pro Gln Glu Ala Asn Thr Ala Asn Ala
                115                 120                 125

Lys Ser Ile Glu Ile Lys Lys Pro Ser Ala Asp Ser Thr Glu Ala Thr
            130                 135                 140

Gln Gln His Leu Lys Lys Ala Thr Val Thr Pro Ile Lys Thr Val Asp
145                 150                 155                 160

Gly Ser Gln Ala Asn Leu Glu Gln Thr Leu Leu Pro Ser Val Ser Leu
                165                 170                 175

Leu Leu Ala Glu Asn Asn Ile Ser Lys Gln Lys Ala Leu Lys Glu Ile
            180                 185                 190

Ala Pro Ser Gly Ser Asn Gly Arg Leu Leu Lys Gly Asp Val Leu Ala
        195                 200                 205

Tyr Leu Gly Lys Ile Pro Gln Asp Ser Val Asn Lys Val Thr Glu Phe
    210                 215                 220

Ile Lys Lys Asn Glu Arg Leu Asp Leu Ser Asn Ile Lys Pro Ile Gln
225                 230                 235                 240

Leu Lys Pro Lys Ile Ala Glu Gln Ala Gln Thr Lys Ala Ala Asp Lys
                245                 250                 255

Pro Lys Ile Thr Pro Val Glu Phe Glu Gln Leu Val Phe His Ala
            260                 265                 270

Pro Ala Ser Ile Pro Phe Asp Lys Leu Ser Glu Ser Leu Asn Ser Phe
        275                 280                 285

Met Lys Glu Ala Tyr Gln Phe Ser His Gly Thr Pro Leu Met Asp Thr
    290                 295                 300

Asn Ser Lys Tyr Phe Asp Pro Ile Phe Glu Asp Leu Val Thr Leu Ser
305                 310                 315                 320

Pro Arg Glu Pro Arg Phe Lys Phe Ser Tyr Asp Leu Met Gln Ile Pro
                325                 330                 335

Lys Ala Asn Asn Met Gln Asp Thr Tyr Gly Gln Glu Asp Ile Phe Asp
            340                 345                 350

Leu Leu Thr Gly Ser Asp Ala Thr Ala Ser Ser Val Arg Pro Val Glu
        355                 360                 365

Lys Asn Leu Pro Glu Lys Asn Glu Tyr Ile Leu Ala Leu Asn Val Ser
    370                 375                 380

Val Asn Asn Lys Lys Phe Asn Asp Ala Glu Ala Lys Ala Lys Arg Phe
385                 390                 395                 400

Leu Asp Tyr Val Arg Glu Leu Glu Ser Phe
                405                 410

<210> SEQ ID NO 92
<211> LENGTH: 1191
<212> TYPE: DNA
<213> ORGANISM: Pichia stipitis
<220> FEATURE:
<221> NAME/KEY: CDS
<222> LOCATION: (1)..(1191)

<400> SEQUENCE: 92 atg tta cgt act gct gct gtt cgt cct ctt aag ggc ggt gtt gtc atc      48
Met Leu Arg Thr Ala Ala Val Arg Pro Leu Lys Gly Gly Val Val Ile
1               5                   10                  15 gcc aga aga gcc atg gcc tcg tcc agc gac ttg gtc agc atc gaa ttg      96
Ala Arg Arg Ala Met Ala Ser Ser Ser Asp Leu Val Ser Ile Glu Leu
            20                  25                  30 cct gaa tcg tcg ttt gaa ggc tac aac ttg gag atc ccc gag ttg act     144
```

```
                Pro Glu Ser Ser Phe Glu Gly Tyr Asn Leu Glu Ile Pro Glu Leu Thr
                         35                  40                  45 ttc gaa acc gaa aag gaa acc ttg ttg aag atg tac aag gat atg atc            192
Phe Glu Thr Glu Lys Glu Thr Leu Leu Lys Met Tyr Lys Asp Met Ile
 50                  55                  60 atc atc aga aga atg gaa atg gct tca gac gcc ttg tac aag gcc aag            240
Ile Ile Arg Arg Met Glu Met Ala Ser Asp Ala Leu Tyr Lys Ala Lys
 65                  70                  75                  80 aag atc aga ggg ttc tgc cac ttg tct gtt ggt caa gaa gcc att gcc            288
Lys Ile Arg Gly Phe Cys His Leu Ser Val Gly Gln Glu Ala Ile Ala
                 85                  90                  95 gtt gga att gag aac gcc att act cct gaa gat act gtc atc acc tct            336
Val Gly Ile Glu Asn Ala Ile Thr Pro Glu Asp Thr Val Ile Thr Ser
            100                 105                 110 tac aga tgt cac ggt ttt gct ttc atg aga ggt gct tct gtc aag gaa            384
Tyr Arg Cys His Gly Phe Ala Phe Met Arg Gly Ala Ser Val Lys Glu
        115                 120                 125 gtt ctc gga gaa ttg atg ggt aag aga tct ggt gtt tct tat ggt aaa            432
Val Leu Gly Glu Leu Met Gly Lys Arg Ser Gly Val Ser Tyr Gly Lys
130                 135                 140 ggt ggt tct atg cac atg ttt gcc cca ggc ttt tac gga gga aac ggt            480
Gly Gly Ser Met His Met Phe Ala Pro Gly Phe Tyr Gly Gly Asn Gly
145                 150                 155                 160 atc gtt gga gct caa gtt cca ttg ggt gct ggt tta gct ttc tcc cac            528
Ile Val Gly Ala Gln Val Pro Leu Gly Ala Gly Leu Ala Phe Ser His
                165                 170                 175 aag tac agg gga cag aag gct gct gcc ttc act ttg tac ggt gac ggt            576
Lys Tyr Arg Gly Gln Lys Ala Ala Ala Phe Thr Leu Tyr Gly Asp Gly
            180                 185                 190 gcc tcc aac cag gga caa gtt ttc gaa gcc tac aac atg gcc aag ttg            624
Ala Ser Asn Gln Gly Gln Val Phe Glu Ala Tyr Asn Met Ala Lys Leu
        195                 200                 205 tgg aac ttg cct tgt atc ttt gcc tgt gaa aac aac aag tac ggt atg            672
Trp Asn Leu Pro Cys Ile Phe Ala Cys Glu Asn Asn Lys Tyr Gly Met
210                 215                 220 ggt act gct gct gcc aga tcc tct gct att act gag tac tac aag aga            720
Gly Thr Ala Ala Ala Arg Ser Ser Ala Ile Thr Glu Tyr Tyr Lys Arg
225                 230                 235                 240 ggt caa tac att cct ggt ttg aag atc aac ggt atg gac gtt ttg gct            768
Gly Gln Tyr Ile Pro Gly Leu Lys Ile Asn Gly Met Asp Val Leu Ala
                245                 250                 255 acc tac cag gct tcc aag ttt gcc aag gac tgg gct gct caa ggc aac            816
Thr Tyr Gln Ala Ser Lys Phe Ala Lys Asp Trp Ala Ala Gln Gly Asn
            260                 265                 270 gga cca ttg gtt ttg gaa tac gaa acc tac aga tac ggt ggt cac tcc            864
Gly Pro Leu Val Leu Glu Tyr Glu Thr Tyr Arg Tyr Gly Gly His Ser
        275                 280                 285 atg tct gac cca ggt acc acc tac aga aca aga gaa gaa gtg caa cac            912
Met Ser Asp Pro Gly Thr Thr Tyr Arg Thr Arg Glu Glu Val Gln His
290                 295                 300 atg aga tcc aga aac gat cct att gcc ggc tta aag gct act ttg ttg            960
Met Arg Ser Arg Asn Asp Pro Ile Ala Gly Leu Lys Ala Thr Leu Leu
305                 310                 315                 320 gac aag ggc att gct acc gaa gaa gaa atc aag tcc tat gac aag gct           1008
Asp Lys Gly Ile Ala Thr Glu Glu Glu Ile Lys Ser Tyr Asp Lys Ala
                325                 330                 335 gcc aga aag tac gtc gac gaa caa gtc gct gct gct gaa gct gac gct           1056
Ala Arg Lys Tyr Val Asp Glu Gln Val Ala Ala Ala Glu Ala Asp Ala
            340                 345                 350
```

```
cct cct gaa gcc aag atg gac atc tta ttc gaa gat gta tat gtc cca      1104
Pro Pro Glu Ala Lys Met Asp Ile Leu Phe Glu Asp Val Tyr Val Pro
    355                 360                 365 gga tct gaa atc cca gtg ttg aga ggc aga atc tcg gac gac tcg tgg      1152
Gly Ser Glu Ile Pro Val Leu Arg Gly Arg Ile Ser Asp Asp Ser Trp
370                 375                 380 gac ttc aag aac aaa act ttc ttg aac aag gtc tac tag                  1191
Asp Phe Lys Asn Lys Thr Phe Leu Asn Lys Val Tyr
385                 390                 395
```

<210> SEQ ID NO 93
<211> LENGTH: 396
<212> TYPE: PRT
<213> ORGANISM: Pichia stipitis

<400> SEQUENCE: 93

```
Met Leu Arg Thr Ala Ala Val Arg Pro Leu Lys Gly Gly Val Val Ile
1               5                   10                  15

Ala Arg Arg Ala Met Ala Ser Ser Ser Asp Leu Val Ser Ile Glu Leu
            20                  25                  30

Pro Glu Ser Ser Phe Glu Gly Tyr Asn Leu Glu Ile Pro Glu Leu Thr
        35                  40                  45

Phe Glu Thr Glu Lys Glu Thr Leu Leu Lys Met Tyr Lys Asp Met Ile
    50                  55                  60

Ile Ile Arg Arg Met Glu Met Ala Ser Asp Ala Leu Tyr Lys Ala Lys
65                  70                  75                  80

Lys Ile Arg Gly Phe Cys His Leu Ser Val Gly Gln Glu Ala Ile Ala
                85                  90                  95

Val Gly Ile Glu Asn Ala Ile Thr Pro Glu Asp Thr Val Ile Thr Ser
            100                 105                 110

Tyr Arg Cys His Gly Phe Ala Phe Met Arg Gly Ala Ser Val Lys Glu
        115                 120                 125

Val Leu Gly Glu Leu Met Gly Lys Arg Ser Gly Val Ser Tyr Gly Lys
    130                 135                 140

Gly Gly Ser Met His Met Phe Ala Pro Gly Phe Tyr Gly Gly Asn Gly
145                 150                 155                 160

Ile Val Gly Ala Gln Val Pro Leu Gly Ala Gly Leu Ala Phe Ser His
                165                 170                 175

Lys Tyr Arg Gly Gln Lys Ala Ala Ala Phe Thr Leu Tyr Gly Asp Gly
            180                 185                 190

Ala Ser Asn Gln Gly Gln Val Phe Glu Ala Tyr Asn Met Ala Lys Leu
        195                 200                 205

Trp Asn Leu Pro Cys Ile Phe Ala Cys Glu Asn Asn Lys Tyr Gly Met
    210                 215                 220

Gly Thr Ala Ala Ala Arg Ser Ser Ala Ile Thr Glu Tyr Tyr Lys Arg
225                 230                 235                 240

Gly Gln Tyr Ile Pro Gly Leu Lys Ile Asn Gly Met Asp Val Leu Ala
                245                 250                 255

Thr Tyr Gln Ala Ser Lys Phe Ala Lys Asp Trp Ala Ala Gln Gly Asn
            260                 265                 270

Gly Pro Leu Val Leu Glu Tyr Glu Thr Tyr Arg Tyr Gly Gly His Ser
        275                 280                 285

Met Ser Asp Pro Gly Thr Thr Tyr Arg Thr Arg Glu Glu Val Gln His
    290                 295                 300

Met Arg Ser Arg Asn Asp Pro Ile Ala Gly Leu Lys Ala Thr Leu Leu
305                 310                 315                 320
```

```
Asp Lys Gly Ile Ala Thr Glu Glu Ile Lys Ser Tyr Asp Lys Ala
            325                 330                 335

Ala Arg Lys Tyr Val Asp Glu Gln Val Ala Ala Glu Ala Asp Ala
            340                 345                 350

Pro Pro Glu Ala Lys Met Asp Ile Leu Phe Glu Asp Val Tyr Val Pro
            355                 360                 365

Gly Ser Glu Ile Pro Val Leu Arg Gly Arg Ile Ser Asp Ser Trp
        370                 375                 380

Asp Phe Lys Asn Lys Thr Phe Leu Asn Lys Val Tyr
385                 390                 395

<210> SEQ ID NO 94
<211> LENGTH: 1170
<212> TYPE: DNA
<213> ORGANISM: Pichia stipitis
<220> FEATURE:
<221> NAME/KEY: CDS
<222> LOCATION: (1)..(1170)

<400> SEQUENCE: 94
```

| | | | | | | | | | | | | | | | | |
|---|---|---|---|---|---|---|---|---|---|---|---|---|---|---|---|---|
| atg | gct | ccc | aag | tta | tcc | cag | atc | gcc | cag | acg | gcc | cgc | ttg | gcc | gct | 48 |
| Met | Ala | Pro | Lys | Leu | Ser | Gln | Ile | Ala | Gln | Thr | Ala | Arg | Leu | Ala | Ala | |
| 1 | | | | 5 | | | | | 10 | | | | | 15 | | |
| tcg | gcc | act | aga | gcc | cac | aac | atc | gcc | aat | gtg | act | gga | aac | act | acc | 96 |
| Ser | Ala | Thr | Arg | Ala | His | Asn | Ile | Ala | Asn | Val | Thr | Gly | Asn | Thr | Thr | |
| | | 20 | | | | 25 | | | | | 30 | | | | | |
| aga | tcc | gta | gcc | caa | gct | ggc | cag | tac | cag | gca | ttg | aga | atg | atg | gat | 144 |
| Arg | Ser | Val | Ala | Gln | Ala | Gly | Gln | Tyr | Gln | Ala | Leu | Arg | Met | Met | Asp | |
| | 35 | | | | | 40 | | | | | 45 | | | | | |
| tcg | cgt | gcc | gct | tcg | tcg | tcg | gct | gta | ggc | tca | aag | acc | atc | acc | gtc | 192 |
| Ser | Arg | Ala | Ala | Ser | Ser | Ser | Ala | Val | Gly | Ser | Lys | Thr | Ile | Thr | Val | |
| 50 | | | | | 55 | | | | | 60 | | | | | | |
| aga | gac | gcc | ctt | aat | gcc | ggg | ctt | gcc | gag | gag | ttg | gac | aag | gac | gac | 240 |
| Arg | Asp | Ala | Leu | Asn | Ala | Gly | Leu | Ala | Glu | Glu | Leu | Asp | Lys | Asp | Asp | |
| 65 | | | | 70 | | | | | 75 | | | | | 80 | | |
| gat | gtc | ttc | ctc | atg | ggt | gaa | gaa | gtg | gcc | caa | tac | aac | ggt | gcc | tac | 288 |
| Asp | Val | Phe | Leu | Met | Gly | Glu | Glu | Val | Ala | Gln | Tyr | Asn | Gly | Ala | Tyr | |
| | | | | 85 | | | | | 90 | | | | | 95 | | |
| aag | gtg | tca | cgt | ggt | ttg | ttg | gat | cgt | ttt | ggt | gaa | aga | cgt | gtg | att | 336 |
| Lys | Val | Ser | Arg | Gly | Leu | Leu | Asp | Arg | Phe | Gly | Glu | Arg | Arg | Val | Ile | |
| | | | 100 | | | | | 105 | | | | | 110 | | | |
| gat | acc | cct | atc | act | gaa | atg | ggt | ttc | act | ggt | ttg | gct | gtt | gga | gct | 384 |
| Asp | Thr | Pro | Ile | Thr | Glu | Met | Gly | Phe | Thr | Gly | Leu | Ala | Val | Gly | Ala | |
| | | | | 115 | | | | | 120 | | | | | 125 | | |
| gcc | ctt | cat | ggt | ttg | aag | cct | gtg | ttg | gag | ttc | atg | acc | ttc | aac | ttc | 432 |
| Ala | Leu | His | Gly | Leu | Lys | Pro | Val | Leu | Glu | Phe | Met | Thr | Phe | Asn | Phe | |
| | 130 | | | | | 135 | | | | | 140 | | | | | |
| gct | atg | caa | gct | atc | gat | caa | atc | gtt | aac | tct | gcc | gct | aag | acc | tat | 480 |
| Ala | Met | Gln | Ala | Ile | Asp | Gln | Ile | Val | Asn | Ser | Ala | Ala | Lys | Thr | Tyr | |
| 145 | | | | | 150 | | | | | 155 | | | | | 160 | |
| tac | atg | tcc | gga | ggt | aaa | caa | ccg | tgt | aac | atc | acc | ttc | cgt | ggt | ccc | 528 |
| Tyr | Met | Ser | Gly | Gly | Lys | Gln | Pro | Cys | Asn | Ile | Thr | Phe | Arg | Gly | Pro | |
| | | | | 165 | | | | | 170 | | | | | 175 | | |
| aat | ggt | gct | gct | gcc | ggt | gtc | ggt | gct | caa | cat | tcg | caa | tgt | tac | gct | 576 |
| Asn | Gly | Ala | Ala | Ala | Gly | Val | Gly | Ala | Gln | His | Ser | Gln | Cys | Tyr | Ala | |
| | | | 180 | | | | | 185 | | | | | 190 | | | |
| gca | tgg | tat | gga | tct | att | cct | ggt | ttg | aag | gtt | gtt | tcg | ccc | tac | tct | 624 |
| Ala | Trp | Tyr | Gly | Ser | Ile | Pro | Gly | Leu | Lys | Val | Val | Ser | Pro | Tyr | Ser | |
| | | | | 195 | | | | | 200 | | | | | 205 | | |

| | | | | | | | | | | | | | | | |
|---|---|---|---|---|---|---|---|---|---|---|---|---|---|---|---|
| gcc | gag | gac | tac | aag | ggt | ttg | atc | aag | gct | gcc | atc | aga | gac | cct | aac | 672
| Ala | Glu | Asp | Tyr | Lys | Gly | Leu | Ile | Lys | Ala | Ala | Ile | Arg | Asp | Pro | Asn |
| | 210 | | | | 215 | | | | 220 | | | | | | |

```
gcc gag gac tac aag ggt ttg atc aag gct gcc atc aga gac cct aac    672
Ala Glu Asp Tyr Lys Gly Leu Ile Lys Ala Ala Ile Arg Asp Pro Asn
    210                 215                 220 cca gtt gtg ttt ttg gaa aac gaa atc gcc tac ggt gaa acc ttc gat    720
Pro Val Val Phe Leu Glu Asn Glu Ile Ala Tyr Gly Glu Thr Phe Asp
225                 230                 235                 240 atc tcc gag gaa gct ctc tcc aca gac ttt gtt ttg cct atc ggc aag    768
Ile Ser Glu Glu Ala Leu Ser Thr Asp Phe Val Leu Pro Ile Gly Lys
                245                 250                 255 gcc aat gtc gaa aga gaa gga act gac ttg aca ttt gta tcg cat tcc    816
Ala Asn Val Glu Arg Glu Gly Thr Asp Leu Thr Phe Val Ser His Ser
            260                 265                 270 aga tct gtc aag ttc tgt atg gaa gcc gct gaa acc ttg gag aag gaa    864
Arg Ser Val Lys Phe Cys Met Glu Ala Ala Glu Thr Leu Glu Lys Glu
        275                 280                 285 tac ggc gtc aag gcc gaa gtc atc aac ttg aga tcc atc aag cct ttg    912
Tyr Gly Val Lys Ala Glu Val Ile Asn Leu Arg Ser Ile Lys Pro Leu
    290                 295                 300 gat gtt cct acc att gtt gag tca gtc aag aag act aac cac ttg gtc    960
Asp Val Pro Thr Ile Val Glu Ser Val Lys Lys Thr Asn His Leu Val
305                 310                 315                 320 act gtt gaa gcc gga ttc cca gcc ttt ggt gtt ggt tct gaa atc tgt   1008
Thr Val Glu Ala Gly Phe Pro Ala Phe Gly Val Gly Ser Glu Ile Cys
                325                 330                 335 gcc cag atc atg gaa tcc gag gct ttt gat tac ttg gat gct cca gtc   1056
Ala Gln Ile Met Glu Ser Glu Ala Phe Asp Tyr Leu Asp Ala Pro Val
            340                 345                 350 gaa aga gtc act ggt tgc gaa gtt cca act cca tat gct aag gaa ttg   1104
Glu Arg Val Thr Gly Cys Glu Val Pro Thr Pro Tyr Ala Lys Glu Leu
        355                 360                 365 gaa gac ttt gct ttc cca gac gaa cct acc gta atc aga gcc gcc aaa   1152
Glu Asp Phe Ala Phe Pro Asp Glu Pro Thr Val Ile Arg Ala Ala Lys
    370                 375                 380 aag gtg tta tct ttg taa                                           1170
Lys Val Leu Ser Leu
385
```

<210> SEQ ID NO 95
<211> LENGTH: 389
<212> TYPE: PRT
<213> ORGANISM: Pichia stipitis

<400> SEQUENCE: 95

```
Met Ala Pro Lys Leu Ser Gln Ile Ala Gln Thr Ala Arg Leu Ala Ala
1               5                   10                  15

Ser Ala Thr Arg Ala His Asn Ile Ala Asn Val Thr Gly Asn Thr Thr
            20                  25                  30

Arg Ser Val Ala Gln Ala Gly Gln Tyr Gln Ala Leu Arg Met Met Asp
        35                  40                  45

Ser Arg Ala Ala Ser Ser Ala Val Gly Ser Lys Thr Ile Thr Val
    50                  55                  60

Arg Asp Ala Leu Asn Ala Gly Leu Ala Glu Glu Leu Asp Lys Asp Asp
65                  70                  75                  80

Asp Val Phe Leu Met Gly Glu Glu Val Ala Gln Tyr Asn Gly Ala Tyr
                85                  90                  95

Lys Val Ser Arg Gly Leu Leu Asp Arg Phe Gly Glu Arg Arg Val Ile
            100                 105                 110

Asp Thr Pro Ile Thr Glu Met Gly Phe Thr Gly Leu Ala Val Gly Ala
        115                 120                 125
```

Ala Leu His Gly Leu Lys Pro Val Leu Glu Phe Met Thr Phe Asn Phe
130                 135                 140

Ala Met Gln Ala Ile Asp Gln Ile Val Asn Ser Ala Ala Lys Thr Tyr
145                 150                 155                 160

Tyr Met Ser Gly Gly Lys Gln Pro Cys Asn Ile Thr Phe Arg Gly Pro
                165                 170                 175

Asn Gly Ala Ala Ala Gly Val Gly Ala Gln His Ser Gln Cys Tyr Ala
            180                 185                 190

Ala Trp Tyr Gly Ser Ile Pro Gly Leu Lys Val Val Ser Pro Tyr Ser
        195                 200                 205

Ala Glu Asp Tyr Lys Gly Leu Ile Lys Ala Ala Ile Arg Asp Pro Asn
210                 215                 220

Pro Val Val Phe Leu Glu Asn Glu Ile Ala Tyr Gly Glu Thr Phe Asp
225                 230                 235                 240

Ile Ser Glu Glu Ala Leu Ser Thr Asp Phe Val Leu Pro Ile Gly Lys
                245                 250                 255

Ala Asn Val Glu Arg Glu Gly Thr Asp Leu Thr Phe Val Ser His Ser
            260                 265                 270

Arg Ser Val Lys Phe Cys Met Glu Ala Ala Glu Thr Leu Glu Lys Glu
        275                 280                 285

Tyr Gly Val Lys Ala Glu Val Ile Asn Leu Arg Ser Ile Lys Pro Leu
290                 295                 300

Asp Val Pro Thr Ile Val Glu Ser Val Lys Lys Thr Asn His Leu Val
305                 310                 315                 320

Thr Val Glu Ala Gly Phe Pro Ala Phe Gly Val Gly Ser Glu Ile Cys
                325                 330                 335

Ala Gln Ile Met Glu Ser Glu Ala Phe Asp Tyr Leu Asp Ala Pro Val
            340                 345                 350

Glu Arg Val Thr Gly Cys Glu Val Pro Thr Pro Tyr Ala Lys Glu Leu
        355                 360                 365

Glu Asp Phe Ala Phe Pro Asp Glu Pro Thr Val Ile Arg Ala Ala Lys
370                 375                 380

Lys Val Leu Ser Leu
385

<210> SEQ ID NO 96
<211> LENGTH: 1239
<212> TYPE: DNA
<213> ORGANISM: Kluyveromyces lactis
<220> FEATURE:
<221> NAME/KEY: CDS
<222> LOCATION: (1)..(1239)

<400> SEQUENCE: 96

```
atg cta tct ttg aaa gct caa tcc tct gtg gtt ggg aag tcc agc tct     48
Met Leu Ser Leu Lys Ala Gln Ser Ser Val Val Gly Lys Ser Ser Ser
1               5                   10                  15 ttg aga ttg gtt aga aac ttt tct aaa aac gtc cgt gct ttg tcc cag     96
Leu Arg Leu Val Arg Asn Phe Ser Lys Asn Val Arg Ala Leu Ser Gln
                20                  25                  30 gtt gct gat gaa act aag cca ggt gat gat gac cta gtt caa att gat    144
Val Ala Asp Glu Thr Lys Pro Gly Asp Asp Asp Leu Val Gln Ile Asp
            35                  40                  45 ttg cca gaa acc tct ttt gaa ggt tat ctt ttg gat gtt cct gaa tta    192
Leu Pro Glu Thr Ser Phe Glu Gly Tyr Leu Leu Asp Val Pro Glu Leu
        50                  55                  60
```

```
agt tat caa acc acc aag tcc aat ttg cta caa atg tac aag gat atg      240
Ser Tyr Gln Thr Thr Lys Ser Asn Leu Leu Gln Met Tyr Lys Asp Met
65                  70                  75                  80 att atc gtt aga aga atg gaa atg gcc tgt gac gct ttg tac aag gct      288
Ile Ile Val Arg Arg Met Glu Met Ala Cys Asp Ala Leu Tyr Lys Ala
                85                  90                  95 aag aaa att aga ggt ttc tgt cac tcc tct gtc ggt caa gaa gcc att      336
Lys Lys Ile Arg Gly Phe Cys His Ser Ser Val Gly Gln Glu Ala Ile
            100                 105                 110 gcc gtt ggt att gaa aac gct atc act aag cgt gat acc gtc atc acc      384
Ala Val Gly Ile Glu Asn Ala Ile Thr Lys Arg Asp Thr Val Ile Thr
        115                 120                 125 tct tac aga tgt cat ggt ttc acc tac atg aga ggt gct gct gtt caa      432
Ser Tyr Arg Cys His Gly Phe Thr Tyr Met Arg Gly Ala Ala Val Gln
    130                 135                 140 gct gtg ttg gct gaa ttg atg ggt aga aga act ggt gtg tcc ttc ggt      480
Ala Val Leu Ala Glu Leu Met Gly Arg Arg Thr Gly Val Ser Phe Gly
145                 150                 155                 160 aag ggt ggt tcc atg cac ttg tac gcc cct ggt ttc tac ggt ggt aat      528
Lys Gly Gly Ser Met His Leu Tyr Ala Pro Gly Phe Tyr Gly Gly Asn
                165                 170                 175 ggt atc gtt ggt gcc caa gtc cca ttg ggt gct ggt ttg gcc ttc gct      576
Gly Ile Val Gly Ala Gln Val Pro Leu Gly Ala Gly Leu Ala Phe Ala
            180                 185                 190 cat caa tac aaa cac gaa gat gct tgt tct ttt gcc ttg tac ggt gat      624
His Gln Tyr Lys His Glu Asp Ala Cys Ser Phe Ala Leu Tyr Gly Asp
        195                 200                 205 ggt gcc tct aac caa ggt caa gtt ttc gaa tcc ttc aac atg gcc aag      672
Gly Ala Ser Asn Gln Gly Gln Val Phe Glu Ser Phe Asn Met Ala Lys
    210                 215                 220 tta tgg aac tta cca gcc gtc ttc tgt tgt gaa aac aac aag tac ggt      720
Leu Trp Asn Leu Pro Ala Val Phe Cys Cys Glu Asn Asn Lys Tyr Gly
225                 230                 235                 240 atg ggt acc gct gcc gca aga tct tca gcc atg act gaa tac ttc aag      768
Met Gly Thr Ala Ala Ala Arg Ser Ser Ala Met Thr Glu Tyr Phe Lys
                245                 250                 255 cgt ggt caa tac att cct ggt ttg aag gtt aac ggt atg gat atc ttg      816
Arg Gly Gln Tyr Ile Pro Gly Leu Lys Val Asn Gly Met Asp Ile Leu
            260                 265                 270 gct gtt tac caa gct tcc aag ttc gct aag gac tgg act gtc tcc ggt      864
Ala Val Tyr Gln Ala Ser Lys Phe Ala Lys Asp Trp Thr Val Ser Gly
        275                 280                 285 aac ggt cca atc gtt ctt gaa tac gaa act tac aga tat ggt ggt cac      912
Asn Gly Pro Ile Val Leu Glu Tyr Glu Thr Tyr Arg Tyr Gly Gly His
    290                 295                 300 tct atg tct gat cca ggt act act tac aga acc aga gat gaa atc caa      960
Ser Met Ser Asp Pro Gly Thr Thr Tyr Arg Thr Arg Asp Glu Ile Gln
305                 310                 315                 320 cac atg aga tct aag aac gat cca att gca ggt tta aag atg cac tta     1008
His Met Arg Ser Lys Asn Asp Pro Ile Ala Gly Leu Lys Met His Leu
                325                 330                 335 ttg gaa ttg ggt atc gcc acg gaa gat gaa att aag gct tac gac aag     1056
Leu Glu Leu Gly Ile Ala Thr Glu Asp Glu Ile Lys Ala Tyr Asp Lys
            340                 345                 350 gct gct aga aag tac gtc gat gag caa gtc gaa tta gct gat gct gcc     1104
Ala Ala Arg Lys Tyr Val Asp Glu Gln Val Glu Leu Ala Asp Ala Ala
        355                 360                 365 cca gct cca gaa gct aag atg tcc atc ttg ttc gag gat gtc tac gtt     1152
Pro Ala Pro Glu Ala Lys Met Ser Ile Leu Phe Glu Asp Val Tyr Val
    370                 375                 380
```

```
cca ggt tct gaa act cca acc cta aga ggt aga ttg caa gaa gat act    1200
Pro Gly Ser Glu Thr Pro Thr Leu Arg Gly Arg Leu Gln Glu Asp Thr
385                 390                 395                 400 tgg gat ttt gct aag aag agc ttt gct ttc aga gat tag                1239
Trp Asp Phe Ala Lys Lys Ser Phe Ala Phe Arg Asp
                405                 410

<210> SEQ ID NO 97
<211> LENGTH: 412
<212> TYPE: PRT
<213> ORGANISM: Kluyveromyces lactis

<400> SEQUENCE: 97

Met Leu Ser Leu Lys Ala Gln Ser Ser Val Val Gly Lys Ser Ser
1               5                   10                  15

Leu Arg Leu Val Arg Asn Phe Ser Lys Asn Val Arg Ala Leu Ser Gln
                20                  25                  30

Val Ala Asp Glu Thr Lys Pro Gly Asp Asp Leu Val Gln Ile Asp
            35                  40                  45

Leu Pro Glu Thr Ser Phe Glu Gly Tyr Leu Leu Asp Val Pro Glu Leu
    50                  55                  60

Ser Tyr Gln Thr Thr Lys Ser Asn Leu Leu Gln Met Tyr Lys Asp Met
65                  70                  75                  80

Ile Ile Val Arg Arg Met Glu Met Ala Cys Asp Ala Leu Tyr Lys Ala
                85                  90                  95

Lys Lys Ile Arg Gly Phe Cys His Ser Ser Val Gly Gln Glu Ala Ile
                100                 105                 110

Ala Val Gly Ile Glu Asn Ala Ile Thr Lys Arg Asp Thr Val Ile Thr
            115                 120                 125

Ser Tyr Arg Cys His Gly Phe Thr Tyr Met Arg Gly Ala Ala Val Gln
            130                 135                 140

Ala Val Leu Ala Glu Leu Met Gly Arg Arg Thr Gly Val Ser Phe Gly
145                 150                 155                 160

Lys Gly Gly Ser Met His Leu Tyr Ala Pro Gly Phe Tyr Gly Gly Asn
                165                 170                 175

Gly Ile Val Gly Ala Gln Val Pro Leu Gly Ala Gly Leu Ala Phe Ala
            180                 185                 190

His Gln Tyr Lys His Glu Asp Ala Cys Ser Phe Ala Leu Tyr Gly Asp
            195                 200                 205

Gly Ala Ser Asn Gln Gly Gln Val Phe Glu Ser Phe Asn Met Ala Lys
    210                 215                 220

Leu Trp Asn Leu Pro Ala Val Phe Cys Cys Glu Asn Asn Lys Tyr Gly
225                 230                 235                 240

Met Gly Thr Ala Ala Ala Arg Ser Ser Ala Met Thr Glu Tyr Phe Lys
                245                 250                 255

Arg Gly Gln Tyr Ile Pro Gly Leu Lys Val Asn Gly Met Asp Ile Leu
            260                 265                 270

Ala Val Tyr Gln Ala Ser Lys Phe Ala Lys Asp Trp Thr Val Ser Gly
            275                 280                 285

Asn Gly Pro Ile Val Leu Glu Tyr Glu Thr Tyr Arg Tyr Gly Gly His
    290                 295                 300

Ser Met Ser Asp Pro Gly Thr Thr Tyr Arg Thr Arg Asp Glu Ile Gln
305                 310                 315                 320

His Met Arg Ser Lys Asn Asp Pro Ile Ala Gly Leu Lys Met His Leu
                325                 330                 335
```

```
Leu Glu Leu Gly Ile Ala Thr Glu Asp Glu Ile Lys Ala Tyr Asp Lys
            340                 345                 350

Ala Ala Arg Lys Tyr Val Asp Glu Gln Val Glu Leu Ala Asp Ala Ala
            355                 360                 365

Pro Ala Pro Glu Ala Lys Met Ser Ile Leu Phe Glu Asp Val Tyr Val
370                 375                 380

Pro Gly Ser Glu Thr Pro Thr Leu Arg Gly Arg Leu Gln Glu Asp Thr
385                 390                 395                 400

Trp Asp Phe Ala Lys Lys Ser Phe Ala Phe Arg Asp
                405                 410

<210> SEQ ID NO 98
<211> LENGTH: 1230
<212> TYPE: DNA
<213> ORGANISM: Schizosaccharomyces pombe
<220> FEATURE:
<221> NAME/KEY: CDS
<222> LOCATION: (1)..(1230)

<400> SEQUENCE: 98
```

| | | | | | | | | | | | | | | | | |
|---|---|---|---|---|---|---|---|---|---|---|---|---|---|---|---|---|
| atg | ttt | cga | act | tgt | acg | aag | att | gga | aca | gtt | ccc | aag | gtt | ctt | gtg | 48 |
| Met | Phe | Arg | Thr | Cys | Thr | Lys | Ile | Gly | Thr | Val | Pro | Lys | Val | Leu | Val | |
| 1 | | | | 5 | | | | | 10 | | | | | 15 | | |
| aac | caa | aag | ggc | ttg | atc | gat | ggc | ctt | cgt | cgg | gtc | acc | aca | gac | gca | 96 |
| Asn | Gln | Lys | Gly | Leu | Ile | Asp | Gly | Leu | Arg | Arg | Val | Thr | Thr | Asp | Ala | |
| | | 20 | | | | | 25 | | | | | 30 | | | | |
| acc | act | tct | cgt | gcc | aat | ccg | gct | cat | gtg | cct | gag | gaa | cat | gac | aag | 144 |
| Thr | Thr | Ser | Arg | Ala | Asn | Pro | Ala | His | Val | Pro | Glu | Glu | His | Asp | Lys | |
| | 35 | | | | | 40 | | | | | 45 | | | | | |
| cca | ttt | cct | gtt | aaa | tta | gat | gat | agt | gta | ttc | gaa | gga | tac | aag | atc | 192 |
| Pro | Phe | Pro | Val | Lys | Leu | Asp | Asp | Ser | Val | Phe | Glu | Gly | Tyr | Lys | Ile | |
| 50 | | | | | 55 | | | | | 60 | | | | | | |
| gat | gtc | cct | tct | act | gaa | atc | gaa | gtt | aca | aag | gga | gag | tta | ttg | ggt | 240 |
| Asp | Val | Pro | Ser | Thr | Glu | Ile | Glu | Val | Thr | Lys | Gly | Glu | Leu | Leu | Gly | |
| 65 | | | | 70 | | | | | 75 | | | | | 80 | | |
| ttg | tac | gag | aag | atg | gtg | act | att | cgt | cgt | cta | gaa | ctt | gca | tgc | gat | 288 |
| Leu | Tyr | Glu | Lys | Met | Val | Thr | Ile | Arg | Arg | Leu | Glu | Leu | Ala | Cys | Asp | |
| | | | | 85 | | | | | 90 | | | | | 95 | | |
| gcc | ttg | tat | aag | gct | aag | aag | att | cgt | gga | ttc | tgt | cat | ctt | agc | att | 336 |
| Ala | Leu | Tyr | Lys | Ala | Lys | Lys | Ile | Arg | Gly | Phe | Cys | His | Leu | Ser | Ile | |
| | | | 100 | | | | | 105 | | | | | 110 | | | |
| ggc | caa | gaa | gct | gta | gct | gca | gga | att | gaa | ggt | gct | att | aca | ctt | gac | 384 |
| Gly | Gln | Glu | Ala | Val | Ala | Ala | Gly | Ile | Glu | Gly | Ala | Ile | Thr | Leu | Asp | |
| | | 115 | | | | | 120 | | | | | 125 | | | | |
| gac | agt | att | atc | aca | tct | tat | aga | tgc | cac | ggt | ttt | gct | tat | acc | cgt | 432 |
| Asp | Ser | Ile | Ile | Thr | Ser | Tyr | Arg | Cys | His | Gly | Phe | Ala | Tyr | Thr | Arg | |
| | 130 | | | | | 135 | | | | | 140 | | | | | |
| ggt | ttg | tca | att | cga | agc | att | att | ggt | gag | ctc | atg | gga | cgt | caa | tgt | 480 |
| Gly | Leu | Ser | Ile | Arg | Ser | Ile | Ile | Gly | Glu | Leu | Met | Gly | Arg | Gln | Cys | |
| 145 | | | | | 150 | | | | | 155 | | | | | 160 | |
| ggt | gct | tcc | aag | ggc | aag | ggt | ggt | tct | atg | cac | att | ttc | gcc | aaa | aac | 528 |
| Gly | Ala | Ser | Lys | Gly | Lys | Gly | Gly | Ser | Met | His | Ile | Phe | Ala | Lys | Asn | |
| | | | | 165 | | | | | 170 | | | | | 175 | | |
| ttc | tat | ggt | ggt | aat | ggt | att | gtt | ggt | gct | caa | att | cct | ttg | ggt | gct | 576 |
| Phe | Tyr | Gly | Gly | Asn | Gly | Ile | Val | Gly | Ala | Gln | Ile | Pro | Leu | Gly | Ala | |
| | | | 180 | | | | | 185 | | | | | 190 | | | |
| ggt | att | ggt | ttc | gca | cag | aag | tat | ctt | gaa | aaa | ccc | act | act | act | ttt | 624 |
| Gly | Ile | Gly | Phe | Ala | Gln | Lys | Tyr | Leu | Glu | Lys | Pro | Thr | Thr | Thr | Phe | |
| | | 195 | | | | | 200 | | | | | 205 | | | | |

```
gct cta tat ggt gat ggt gca tct aac caa ggt caa gct ttc gag gcc      672
Ala Leu Tyr Gly Asp Gly Ala Ser Asn Gln Gly Gln Ala Phe Glu Ala
    210             215                 220 ttc aac atg gcc aaa tta tgg ggt ctt ccc gtt att ttt gct tgt gaa      720
Phe Asn Met Ala Lys Leu Trp Gly Leu Pro Val Ile Phe Ala Cys Glu
225             230                 235                 240 aac aac aaa tac ggt atg ggt act agt gct gaa cgc tct tct gcc atg      768
Asn Asn Lys Tyr Gly Met Gly Thr Ser Ala Glu Arg Ser Ser Ala Met
                245                 250                 255 act gag ttc tac aaa cgt gga cag tac att ccc ggt ctt ttg gtt aac      816
Thr Glu Phe Tyr Lys Arg Gly Gln Tyr Ile Pro Gly Leu Leu Val Asn
        260                 265                 270 ggt atg gat gtt ttg gct gtt ttg cag gct tca aag ttt gct aag aag      864
Gly Met Asp Val Leu Ala Val Leu Gln Ala Ser Lys Phe Ala Lys Lys
            275                 280                 285 tac act gtt gaa aac tct caa cct ctg ctt atg gaa ttt gtg act tat      912
Tyr Thr Val Glu Asn Ser Gln Pro Leu Leu Met Glu Phe Val Thr Tyr
    290                 295                 300 cgt tat ggt ggt cac tcc atg tcc gat ccc ggt act act tat cgt agc      960
Arg Tyr Gly Gly His Ser Met Ser Asp Pro Gly Thr Thr Tyr Arg Ser
305                 310                 315                 320 cgt gaa gaa gtg caa aaa gta cgt gct gct aga gat cct att gag ggt     1008
Arg Glu Glu Val Gln Lys Val Arg Ala Ala Arg Asp Pro Ile Glu Gly
                325                 330                 335 ttg aag aag cac atc atg gag tgg ggc gtc gct aat gcc aat gag ctt     1056
Leu Lys Lys His Ile Met Glu Trp Gly Val Ala Asn Ala Asn Glu Leu
            340                 345                 350 aaa aac att gag aag aga atc cgt ggt atg gtt gat gag gag gtt cgt     1104
Lys Asn Ile Glu Lys Arg Ile Arg Gly Met Val Asp Glu Glu Val Arg
        355                 360                 365 atc gct gaa gaa agc cct ttc ccc gat cct att gag gag agt ttg ttt     1152
Ile Ala Glu Glu Ser Pro Phe Pro Asp Pro Ile Glu Glu Ser Leu Phe
    370                 375                 380 tca gat gtt tac gtt gca gga act gaa ccc gct tac gcc cgt ggt aga     1200
Ser Asp Val Tyr Val Ala Gly Thr Glu Pro Ala Tyr Ala Arg Gly Arg
385                 390                 395                 400 aat tcc ctg gaa tat cat caa tat aag taa                             1230
Asn Ser Leu Glu Tyr His Gln Tyr Lys
                405
```

<210> SEQ ID NO 99
<211> LENGTH: 409
<212> TYPE: PRT
<213> ORGANISM: Schizosaccharomyces pombe

<400> SEQUENCE: 99

```
Met Phe Arg Thr Cys Thr Lys Ile Gly Thr Val Pro Lys Val Leu Val
1               5                   10                  15

Asn Gln Lys Gly Leu Ile Asp Gly Leu Arg Arg Val Thr Thr Asp Ala
            20                  25                  30

Thr Thr Ser Arg Ala Asn Pro Ala His Val Pro Glu Glu His Asp Lys
        35                  40                  45

Pro Phe Pro Val Lys Leu Asp Asp Ser Val Phe Glu Gly Tyr Lys Ile
    50                  55                  60

Asp Val Pro Ser Thr Glu Ile Glu Val Thr Lys Gly Glu Leu Leu Gly
65                  70                  75                  80

Leu Tyr Glu Lys Met Val Thr Ile Arg Arg Leu Glu Leu Ala Cys Asp
                85                  90                  95

Ala Leu Tyr Lys Ala Lys Lys Ile Arg Gly Phe Cys His Leu Ser Ile
```

```
                    100                 105                 110
Gly Gln Glu Ala Val Ala Gly Ile Glu Gly Ala Ile Thr Leu Asp
            115                 120                 125
Asp Ser Ile Ile Thr Ser Tyr Arg Cys His Gly Phe Ala Tyr Thr Arg
130                 135                 140
Gly Leu Ser Ile Arg Ser Ile Ile Gly Glu Leu Met Gly Arg Gln Cys
145                 150                 155                 160
Gly Ala Ser Lys Gly Lys Gly Gly Ser Met His Ile Phe Ala Lys Asn
            165                 170                 175
Phe Tyr Gly Gly Asn Gly Ile Val Gly Ala Gln Ile Pro Leu Gly Ala
            180                 185                 190
Gly Ile Gly Phe Ala Gln Lys Tyr Leu Glu Lys Pro Thr Thr Thr Phe
            195                 200                 205
Ala Leu Tyr Gly Asp Gly Ala Ser Asn Gln Gly Gln Ala Phe Glu Ala
            210                 215                 220
Phe Asn Met Ala Lys Leu Trp Gly Leu Pro Val Ile Phe Ala Cys Glu
225                 230                 235                 240
Asn Asn Lys Tyr Gly Met Gly Thr Ser Ala Glu Arg Ser Ser Ala Met
            245                 250                 255
Thr Glu Phe Tyr Lys Arg Gly Gln Tyr Ile Pro Gly Leu Leu Val Asn
            260                 265                 270
Gly Met Asp Val Leu Ala Val Leu Gln Ala Ser Lys Phe Ala Lys Lys
            275                 280                 285
Tyr Thr Val Glu Asn Ser Gln Pro Leu Leu Met Glu Phe Val Thr Tyr
            290                 295                 300
Arg Tyr Gly Gly His Ser Met Ser Asp Pro Gly Thr Thr Tyr Arg Ser
305                 310                 315                 320
Arg Glu Glu Val Gln Lys Val Arg Ala Ala Arg Asp Pro Ile Glu Gly
            325                 330                 335
Leu Lys Lys His Ile Met Glu Trp Gly Val Ala Asn Ala Asn Glu Leu
            340                 345                 350
Lys Asn Ile Glu Lys Arg Ile Arg Gly Met Val Asp Glu Glu Val Arg
            355                 360                 365
Ile Ala Glu Glu Ser Pro Phe Pro Asp Pro Ile Glu Glu Ser Leu Phe
            370                 375                 380
Ser Asp Val Tyr Val Ala Gly Thr Glu Pro Ala Tyr Ala Arg Gly Arg
385                 390                 395                 400
Asn Ser Leu Glu Tyr His Gln Tyr Lys
            405

<210> SEQ ID NO 100
<211> LENGTH: 1101
<212> TYPE: DNA
<213> ORGANISM: Schizosaccharomyces pombe
<220> FEATURE:
<221> NAME/KEY: CDS
<222> LOCATION: (1)..(1101)

<400> SEQUENCE: 100 atg att cgt ctt caa aag ttt ggt gaa att gtt ggg acc agt cgt tct    48
Met Ile Arg Leu Gln Lys Phe Gly Glu Ile Val Gly Thr Ser Arg Ser
1               5                   10                  15 tgg aaa ctt ctt agt tca acc atc gca aag cgc tat tct tct tct tcc    96
Trp Lys Leu Leu Ser Ser Thr Ile Ala Lys Arg Tyr Ser Ser Ser Ser
            20                  25                  30 aat gga gtg aag gaa atg acc gtt cgt gat gct ttg aac agt gca atg   144
```

```
                    Asn Gly Val Lys Glu Met Thr Val Arg Asp Ala Leu Asn Ser Ala Met
                                 35                  40                  45 gaa gaa gaa atg aaa cgt gac gat cgt gtc ttc ttg att ggc gaa gag         192
Glu Glu Glu Met Lys Arg Asp Asp Arg Val Phe Leu Ile Gly Glu Glu
         50                  55                  60 gtt gcg caa tac aat ggt gct tat aag ata tct aga ggt tta tta gac         240
Val Ala Gln Tyr Asn Gly Ala Tyr Lys Ile Ser Arg Gly Leu Leu Asp
 65                  70                  75                  80 aag ttt ggt cct aaa cgt gtt atc gac act ccc att act gaa atg ggt         288
Lys Phe Gly Pro Lys Arg Val Ile Asp Thr Pro Ile Thr Glu Met Gly
                 85                  90                  95 ttt act ggt ttg gca aca ggt gct gct ttt gct ggt tta cgt cct att         336
Phe Thr Gly Leu Ala Thr Gly Ala Ala Phe Ala Gly Leu Arg Pro Ile
            100                 105                 110 tgt gag ttt atg act ttc aat ttt tcc atg cag gct atc gat cat atc         384
Cys Glu Phe Met Thr Phe Asn Phe Ser Met Gln Ala Ile Asp His Ile
            115                 120                 125 gtt aac tcg gcc gcc aga acc ctg tac atg tct ggt ggt att cag gct         432
Val Asn Ser Ala Ala Arg Thr Leu Tyr Met Ser Gly Gly Ile Gln Ala
        130                 135                 140 tgt cct att gtc ttc cgt gga cct aat ggg cct gcc gct gca gtt gct         480
Cys Pro Ile Val Phe Arg Gly Pro Asn Gly Pro Ala Ala Ala Val Ala
145                 150                 155                 160 gct cag cat tct caa cac ttt gct cca tgg tat ggt agt atc cct ggt         528
Ala Gln His Ser Gln His Phe Ala Pro Trp Tyr Gly Ser Ile Pro Gly
                165                 170                 175 ctt aaa gta gtt tct cct tac tca gca gaa gat gct cgt ggt ttg ttg         576
Leu Lys Val Val Ser Pro Tyr Ser Ala Glu Asp Ala Arg Gly Leu Leu
            180                 185                 190 aag gct gct att cgt gat cct aat ccc gtt gtt gta ctt gaa aac gaa         624
Lys Ala Ala Ile Arg Asp Pro Asn Pro Val Val Val Leu Glu Asn Glu
            195                 200                 205 att ctt tat ggt aaa acc ttt cca att tcg aaa gaa gcg ttg agc gag         672
Ile Leu Tyr Gly Lys Thr Phe Pro Ile Ser Lys Glu Ala Leu Ser Glu
        210                 215                 220 gac ttt gtg ctt ccc ttt ggc ctt gct aag gtg gag cgc ccc ggt aaa         720
Asp Phe Val Leu Pro Phe Gly Leu Ala Lys Val Glu Arg Pro Gly Lys
225                 230                 235                 240 gat atc acc atc gtt ggt gag tct att tct gtt gtt act gct tta gaa         768
Asp Ile Thr Ile Val Gly Glu Ser Ile Ser Val Val Thr Ala Leu Glu
                245                 250                 255 gca gct gac aag ctc aag gct gac tat ggt gtt gaa gct gaa gtt ata         816
Ala Ala Asp Lys Leu Lys Ala Asp Tyr Gly Val Glu Ala Glu Val Ile
            260                 265                 270 aac ttg cgt agt att cgt cct tta gac atc aat act atc gcg gcc agt         864
Asn Leu Arg Ser Ile Arg Pro Leu Asp Ile Asn Thr Ile Ala Ala Ser
        275                 280                 285 gtt aag aag aca aat cgt att gtg act gtt gac cag gca tat agt caa         912
Val Lys Lys Thr Asn Arg Ile Val Thr Val Asp Gln Ala Tyr Ser Gln
290                 295                 300 cat ggt att ggt agt gaa att gct gct caa att atg gag tct gac gca         960
His Gly Ile Gly Ser Glu Ile Ala Ala Gln Ile Met Glu Ser Asp Ala
305                 310                 315                 320 ttt gat tat ctt gat gct cct gtt gaa cgt gta agt atg gca gat gtt        1008
Phe Asp Tyr Leu Asp Ala Pro Val Glu Arg Val Ser Met Ala Asp Val
                325                 330                 335 ccc atg cct tat agt cat cct gtt gag gct gct tct gtc cca aat gcc        1056
Pro Met Pro Tyr Ser His Pro Val Glu Ala Ala Ser Val Pro Asn Ala
            340                 345                 350
```

```
gat gtt gtt gtt gct gct gct aaa aaa tgc ttg tat att aaa taa          1101
Asp Val Val Val Ala Ala Ala Lys Lys Cys Leu Tyr Ile Lys
        355             360             365
```

<210> SEQ ID NO 101
<211> LENGTH: 366
<212> TYPE: PRT
<213> ORGANISM: Schizosaccharomyces pombe

<400> SEQUENCE: 101

```
Met Ile Arg Leu Gln Lys Phe Gly Glu Ile Val Gly Thr Ser Arg Ser
1               5                   10                  15

Trp Lys Leu Leu Ser Ser Thr Ile Ala Lys Arg Tyr Ser Ser Ser
            20                  25                  30

Asn Gly Val Lys Glu Met Thr Val Arg Asp Ala Leu Asn Ser Ala Met
        35                  40                  45

Glu Glu Glu Met Lys Arg Asp Asp Arg Val Phe Leu Ile Gly Glu Glu
    50                  55                  60

Val Ala Gln Tyr Asn Gly Ala Tyr Lys Ile Ser Arg Gly Leu Leu Asp
65                  70                  75                  80

Lys Phe Gly Pro Lys Arg Val Ile Asp Thr Pro Ile Thr Glu Met Gly
                85                  90                  95

Phe Thr Gly Leu Ala Thr Gly Ala Ala Phe Ala Gly Leu Arg Pro Ile
            100                 105                 110

Cys Glu Phe Met Thr Phe Asn Phe Ser Met Gln Ala Ile Asp His Ile
        115                 120                 125

Val Asn Ser Ala Ala Arg Thr Leu Tyr Met Ser Gly Gly Ile Gln Ala
    130                 135                 140

Cys Pro Ile Val Phe Arg Gly Pro Asn Gly Pro Ala Ala Ala Val Ala
145                 150                 155                 160

Ala Gln His Ser Gln His Phe Ala Pro Trp Tyr Gly Ser Ile Pro Gly
                165                 170                 175

Leu Lys Val Val Ser Pro Tyr Ser Ala Glu Asp Ala Arg Gly Leu Leu
            180                 185                 190

Lys Ala Ala Ile Arg Asp Pro Asn Pro Val Val Val Leu Glu Asn Glu
        195                 200                 205

Ile Leu Tyr Gly Lys Thr Phe Pro Ile Ser Lys Glu Ala Leu Ser Glu
    210                 215                 220

Asp Phe Val Leu Pro Phe Gly Leu Ala Lys Val Glu Arg Pro Gly Lys
225                 230                 235                 240

Asp Ile Thr Ile Val Gly Glu Ser Ile Ser Val Val Thr Ala Leu Glu
                245                 250                 255

Ala Ala Asp Lys Leu Lys Ala Asp Tyr Gly Val Glu Ala Glu Val Ile
            260                 265                 270

Asn Leu Arg Ser Ile Arg Pro Leu Asp Ile Asn Thr Ile Ala Ala Ser
        275                 280                 285

Val Lys Lys Thr Asn Arg Ile Val Thr Val Asp Gln Ala Tyr Ser Gln
    290                 295                 300

His Gly Ile Gly Ser Glu Ile Ala Ala Gln Ile Met Glu Ser Asp Ala
305                 310                 315                 320

Phe Asp Tyr Leu Asp Ala Pro Val Glu Arg Val Ser Met Ala Asp Val
                325                 330                 335

Pro Met Pro Tyr Ser His Pro Val Glu Ala Ser Val Pro Asn Ala
            340                 345                 350

Asp Val Val Val Ala Ala Ala Lys Lys Cys Leu Tyr Ile Lys
```

<210> SEQ ID NO 102
<211> LENGTH: 80
<212> TYPE: DNA
<213> ORGANISM: artificial sequence
<220> FEATURE:
<223> OTHER INFORMATION: primer

<400> SEQUENCE: 102
cttatggtga tggcacattt ttgcataaac ctagctgtcc tcgttgaaca tagggggaaa    60
tgcttcaaga aggtattgac                                                80

<210> SEQ ID NO 103
<211> LENGTH: 77
<212> TYPE: DNA
<213> ORGANISM: artificial sequence
<220> FEATURE:
<223> OTHER INFORMATION: primer

<400> SEQUENCE: 103
gaagcggacc cagacttaag cctaaccagg ccaattcaac agactgtcgg cgcaagagtt    60
cgaatctctt agcaacc                                                   77

<210> SEQ ID NO 104
<211> LENGTH: 27
<212> TYPE: DNA
<213> ORGANISM: artificial sequence
<220> FEATURE:
<223> OTHER INFORMATION: primer

<400> SEQUENCE: 104
cgccgaagaa gttaagaaaa tccttgc                                        27

<210> SEQ ID NO 105
<211> LENGTH: 26
<212> TYPE: DNA
<213> ORGANISM: artificial sequence
<220> FEATURE:
<223> OTHER INFORMATION: primer

<400> SEQUENCE: 105
ccaggccaat tcaacagact gtcggc                                         26

<210> SEQ ID NO 106
<211> LENGTH: 26
<212> TYPE: DNA
<213> ORGANISM: artificial sequence
<220> FEATURE:
<223> OTHER INFORMATION: primer

<400> SEQUENCE: 106
gacttgaata atgcagcggc gcttgc                                         26

<210> SEQ ID NO 107
<211> LENGTH: 30
<212> TYPE: DNA
<213> ORGANISM: artificial sequence
<220> FEATURE:
<223> OTHER INFORMATION: primer

<400> SEQUENCE: 107
ccaccctctt caattagcta agatcatagc                                     30

```
<210> SEQ ID NO 108
<211> LENGTH: 25
<212> TYPE: DNA
<213> ORGANISM: artificial sequence
<220> FEATURE:
<223> OTHER INFORMATION: primer

<400> SEQUENCE: 108
aaaaattgat tctcatcgta aatgc                                  25

<210> SEQ ID NO 109
<211> LENGTH: 20
<212> TYPE: DNA
<213> ORGANISM: artificial sequence
<220> FEATURE:
<223> OTHER INFORMATION: primer

<400> SEQUENCE: 109
ctgcagcgag gagccgtaat                                        20

<210> SEQ ID NO 110
<211> LENGTH: 77
<212> TYPE: DNA
<213> ORGANISM: artificial sequence
<220> FEATURE:
<223> OTHER INFORMATION: primer

<400> SEQUENCE: 110
aaaagatagt gtagtagtga taaactggtg cttcaatttc ttttatgaa ggctggctta    60 actatgcggc atcagag                                                  77

<210> SEQ ID NO 111
<211> LENGTH: 81
<212> TYPE: DNA
<213> ORGANISM: artificial sequence
<220> FEATURE:
<223> OTHER INFORMATION: primer

<400> SEQUENCE: 111
cccaattggt aaatattcaa caagagacgc gcagtacgta acatgcgaat ccaaactgga    60
acaacactca accctatctc g                                             81

<210> SEQ ID NO 112
<211> LENGTH: 31
<212> TYPE: DNA
<213> ORGANISM: artificial sequence
<220> FEATURE:
<223> OTHER INFORMATION: primer

<400> SEQUENCE: 112
gggtccattg atgaacccat ttgcctcttt c                           31

<210> SEQ ID NO 113
<211> LENGTH: 28
<212> TYPE: DNA
<213> ORGANISM: artificial sequence
<220> FEATURE:
<223> OTHER INFORMATION: primer

<400> SEQUENCE: 113
tcggtttttg caatatgacc tgtgggcc                               28

<210> SEQ ID NO 114
<211> LENGTH: 672
<212> TYPE: DNA
```

<213> ORGANISM: Saccharomyces cerevisiae

<400> SEQUENCE: 114

```
agttcgagtt tatcattatc aatactgcca tttcaaagaa tacgtaaata attaatagta    60
gtgattttcc taactttatt tagtcaaaaa attagccttt taattctgct gtaacccgta   120
catgcccaaa ataggggggcg ggttacacag aatatataac atcgtaggtg tctgggtgaa   180
cagtttattc ctggcatcca ctaaatataa tggagcccgc ttttttaagct ggcatccaga   240
aaaaaaaga atcccagcac caaatatttg ttttcttcac caaccatcag ttcataggtc    300
cattctctta gcgcaactac agagaacagg ggcacaaaca ggcaaaaaac gggcacaacc   360
tcaatggagt gatgcaacct gcctggagta aatgatgaca caaggcaatt gacccacgca   420
tgtatctatc tcattttctt acccttcta ttaccttctg ctctctctga tttggaaaaa    480
gctgaaaaaa aaggttgaaa ccagttccct gaaattattc ccctacttga ctaataagta   540
tataagacg gtaggtattg attgtaattc tgtaaatcta tttcttaaac ttcttaaatt    600
ctactttat agttagtctt ttttttagtt ttaaaacacc aagaacttag tttcgaataa    660
acacacataa ac                                                       672
```

<210> SEQ ID NO 115
<211> LENGTH: 270
<212> TYPE: DNA
<213> ORGANISM: Saccharomyces cerevisiae

<400> SEQUENCE: 115

```
gacctcgagt catgtaatta gttatgtcac gcttacattc acgccctccc cccacatccg    60
ctctaaccga aaaggaagga gttagacaac ctgaagtcta ggtccctatt tattttttta   120
tagttatgtt agtattaaga acgttattta tatttcaaat ttttctttttt tttctgtaca   180
gacgcgtgta cgcatgtaac attatactga aaaccttgct tgagaaggtt ttgggacgct   240
cgaaggcttt aatttgcggc cggtacccaa                                    270
```

<210> SEQ ID NO 116
<211> LENGTH: 643
<212> TYPE: DNA
<213> ORGANISM: Saccharomyces cerevisiae

<400> SEQUENCE: 116

```
gaaatgaata acaatactga cagtactaaa taattgccta cttggcttca catacgttgc    60
atacgtcgat atagataata atgataatga cagcaggatt atcgtaatac gtaatagttg   120
aaaatctcaa aaatgtgtgg gtcattacgt aaataatgat aggaatggga ttcttctatt   180
tttccttttt ccattctagc agccgtcggg aaaacgtggc atcctctctt tcgggctcaa   240
ttggagtcac gctgccgtga gcatcctctc tttccatatc taacaactga gcacgtaacc   300
aatggaaaag catgagctta gcgttgctcc aaaaaagtat tggatggtta ataccatttg   360
tctgttctct tctgactttg actcctcaaa aaaaaaaat ctacaatcaa cagatcgctt   420
caattacgcc ctcacaaaaa ctttttttcct tcttcttcgc ccacgttaaa ttttatccct   480
catgttgtct aacggatttc tgcacttgat ttattataaa aagacaaaga cataatactt   540
ctctatcaat ttcagttatt gttcttcctt gcgttattct tctgttcttc ttttttcttttt   600
gtcatatata accataacca agtaatacat attcaaatct aga                     643
```

<210> SEQ ID NO 117
<211> LENGTH: 20

<212> TYPE: DNA
<213> ORGANISM: artificial sequence
<220> FEATURE:
<223> OTHER INFORMATION: primer

<400> SEQUENCE: 117
cgtgttagtc acatcaggac                                        20

<210> SEQ ID NO 118
<211> LENGTH: 22
<212> TYPE: DNA
<213> ORGANISM: artificial sequence
<220> FEATURE:
<223> OTHER INFORMATION: primer

<400> SEQUENCE: 118
catcgactgc attacgcaac tc                                     22

<210> SEQ ID NO 119
<211> LENGTH: 86
<212> TYPE: DNA
<213> ORGANISM: artificial sequence
<220> FEATURE:
<223> OTHER INFORMATION: primer

<400> SEQUENCE: 119
tggaataatc aatcaattga ggattttatg caaatatcgt ttgaatattt ttccggatct    60
gaaatgaata acaatactga cagtac                                        86

<210> SEQ ID NO 120
<211> LENGTH: 61
<212> TYPE: DNA
<213> ORGANISM: artificial sequence
<220> FEATURE:
<223> OTHER INFORMATION: primer

<400> SEQUENCE: 120
ctcccaattt tcagttgaa aaaggtatat gctctagagc ggccgcccgc aaattaaagc    60
c                                                                   61

<210> SEQ ID NO 121
<211> LENGTH: 61
<212> TYPE: DNA
<213> ORGANISM: artificial sequence
<220> FEATURE:
<223> OTHER INFORMATION: primer

<400> SEQUENCE: 121
ggctttaatt tgcgggcggc cgctctagag catataccct tttcaactga aaaattggga    60
g                                                                   61

<210> SEQ ID NO 122
<211> LENGTH: 84
<212> TYPE: DNA
<213> ORGANISM: artificial sequence
<220> FEATURE:
<223> OTHER INFORMATION: primer

<400> SEQUENCE: 122
ttcgttacat aaaatgcttt ataaaacttt aactaataat tagagattaa atcgcggagc    60
ttgtcaatat taatgttaaa gtgc                                          84

<210> SEQ ID NO 123

```
<211> LENGTH: 55
<212> TYPE: DNA
<213> ORGANISM: artificial sequence
<220> FEATURE:
<223> OTHER INFORMATION: primer

<400> SEQUENCE: 123
agtaatacat attcaaatct agagctgagg atgaatcatt ctgctgaatg cacct        55

<210> SEQ ID NO 124
<211> LENGTH: 55
<212> TYPE: DNA
<213> ORGANISM: artificial sequence
<220> FEATURE:
<223> OTHER INFORMATION: primer

<400> SEQUENCE: 124
atcataagaa attcgcttac tcttaattaa ttaactttct acggaacgga tggcg        55

<210> SEQ ID NO 125
<211> LENGTH: 448
<212> TYPE: DNA
<213> ORGANISM: Saccharomyces cerevisiae

<400> SEQUENCE: 125
cccattaccg acatttgggc gctatacgtg catatgttca tgtatgtatc tgtatttaaa    60 acactttgt attattttc ctcatatatg tgtataggtt tatacggatg atttaattat    120
tacttcacca cccttattt caggctgata tcttagcctt gttactagtt agaaaaagac    180
atttttgctg tcagtcactg tcaagagatt cttttgctgg catttcttct agaagcaaaa    240
agagcgatgc gtcttttccg ctgaaccgtt ccagcaaaaa agactaccaa cgcaatatgg    300
attgtcagaa tcatataaaa gagaagcaaa taactccttg tcttgtatca attgcattat    360
aatatcttct tgttagtgca atatcatata gaagtcatcg aaatagatat taagaaaaac    420
aaactgtaca atcaatcaat caatcatc                                       448

<210> SEQ ID NO 126
<211> LENGTH: 316
<212> TYPE: DNA
<213> ORGANISM: Saccharomyces cerevisiae

<400> SEQUENCE: 126
gagtaagcga atttcttatg atttatgatt tttattatta aataagttat aaaaaaaata    60
agtgtataca aattttaaag tgactcttag gttttaaaac gaaaattctt attcttgagt    120
aactctttcc tgtaggtcag gttgctttct caggtatagc atgaggtcgc tcttattgac    180
cacacctcta ccggcatgcc gagcaaatgc ctgcaaatcg ctccccattt cacccaattg    240
tagatatgct aactccagca atgagttgat gaatctcggt gtgtatttta tgtcctcaga    300
ggacaacacc tgtggt                                                   316

<210> SEQ ID NO 127
<211> LENGTH: 19
<212> TYPE: DNA
<213> ORGANISM: artificial sequence
<220> FEATURE:
<223> OTHER INFORMATION: primer

<400> SEQUENCE: 127
gaaaacgtgg catcctctc                                                 19
```

```
<210> SEQ ID NO 128
<211> LENGTH: 20
<212> TYPE: DNA
<213> ORGANISM: artificial sequence
<220> FEATURE:
<223> OTHER INFORMATION: primer

<400> SEQUENCE: 128
gcatcgagat tatcgggatg                                                   20

<210> SEQ ID NO 129
<211> LENGTH: 55
<212> TYPE: DNA
<213> ORGANISM: artificial sequence
<220> FEATURE:
<223> OTHER INFORMATION: primer

<400> SEQUENCE: 129
agtaatacat attcaaatct agagctgagg atgaaaaaag tcgcacttgt taccg            55

<210> SEQ ID NO 130
<211> LENGTH: 55
<212> TYPE: DNA
<213> ORGANISM: artificial sequence
<220> FEATURE:
<223> OTHER INFORMATION: primer

<400> SEQUENCE: 130
cgtgacataa ctaattacat gattaattaa ttagttaaac accatcccgc cgtcg            55

<210> SEQ ID NO 131
<211> LENGTH: 30
<212> TYPE: DNA
<213> ORGANISM: artificial sequence
<220> FEATURE:
<223> OTHER INFORMATION: primer

<400> SEQUENCE: 131
ggaattcaca catgaaagct ctggtttatc                                        30

<210> SEQ ID NO 132
<211> LENGTH: 28
<212> TYPE: DNA
<213> ORGANISM: artificial sequence
<220> FEATURE:
<223> OTHER INFORMATION: primer

<400> SEQUENCE: 132
gcgtccaggg cgtcaaagat caggcagc                                          28

<210> SEQ ID NO 133
<211> LENGTH: 55
<212> TYPE: DNA
<213> ORGANISM: artificial sequence
<220> FEATURE:
<223> OTHER INFORMATION: primer

<400> SEQUENCE: 133
aaacaaacac acatattaca atagctgagg atgaaagctc tggtttatca cggtg            55

<210> SEQ ID NO 134
<211> LENGTH: 55
<212> TYPE: DNA
<213> ORGANISM: artificial sequence
<220> FEATURE:
<223> OTHER INFORMATION: primer
```

<400> SEQUENCE: 134

```
atcataagaa attcgcttac tcttaattaa tcaggcagcg cctgcgttcg agagg        55
```

<210> SEQ ID NO 135
<211> LENGTH: 753
<212> TYPE: DNA
<213> ORGANISM: Saccharomyces cerevisiae

<400> SEQUENCE: 135

```
gcatgcttgc atttagtcgt gcaatgtatg actttaagat ttgtgagcag gaagaaaagg    60
gagaatcttc taacgataaa cccttgaaaa actgggtaga ctacgctatg ttgagttgct   120
acgcaggctg cacaattaca cgagaatgct cccgcctagg atttaaggct aagggacgtg   180
caatgcagac gacagatcta atgaccgtgt cggtgaagt gttcgccaaa cttttcggtt    240
aacacatgca gtgatgcacg cgcgatggtg ctaagttaca tatatatata tatagccata   300
gtgatgtcta gtaacctttt atggtatatt tcttaatgtg gaaagatact agcgcgcgca   360
cccacacaca agcttcgtct tttcttgaag aaaagaggaa gctcgctaaa tgggattcca   420
ctttccgttc cctgccagct gatggaaaaa ggttagtgga acgatgaaga ataaaaagag   480
agatccactg aggtgaaatt tcagctgaca gcgagtttca tgatcgtgat gaacaatggt   540
aacgagttgt ggctgttgcc agggagggtg gttctcaact tttaatgtat ggccaaatcg   600
ctacttgggt ttgttatata acaaagaaga ataatgaac tgattctctt cctccttctt    660
gtcctttctt aattctgttg taattacctt cctttgtaat ttttttttgta attattcttc   720
ttaataatcc aaacaaacac acatattaca ata                                753
```

<210> SEQ ID NO 136
<211> LENGTH: 28
<212> TYPE: DNA
<213> ORGANISM: artificial sequence
<220> FEATURE:
<223> OTHER INFORMATION: primer

<400> SEQUENCE: 136

```
ggatccgcat gcttgcattt agtcgtgc                                       28
```

<210> SEQ ID NO 137
<211> LENGTH: 20
<212> TYPE: DNA
<213> ORGANISM: artificial sequence
<220> FEATURE:
<223> OTHER INFORMATION: primer

<400> SEQUENCE: 137

```
gggatgcgga cgtattcggc                                                20
```

<210> SEQ ID NO 138
<211> LENGTH: 3378
<212> TYPE: DNA
<213> ORGANISM: artificial sequence
<220> FEATURE:
<223> OTHER INFORMATION: synthesized double coding region

<400> SEQUENCE: 138

```
ggatccgttt aaacaggagg gccaaaatca tgggcaatta cgattcaaca ccgatagcta    60
aaagtgatag gattaaaaga ttggttgatc atttgtatgc taaatgcct gaaattgagg    120
ccgctagagc agagctaatt actgaatcct ttaaggccac cgaaggtcaa cctgttgtta   180
tgagaaaggc tagagctttt gaacatatac taaagaattt gccaattatc ataagaccag   240
```

```
aagaactgat tgttggctca actacaattg cccctagagg ttgccaaacg tatccagaat    300
tctcatacga gtggttagag gctgaatttg aaactgtcga aacgcgttca gctgacccat    360
tttatatttc agaagaaacg aagaaacgtt tgctggctgc cgatgcttat tggaaaggta    420
aaacaacctc agagttggca acttcatata tggccccaga aactctaaga gccatgaagc    480
ataacttctt caccoctgga aactacttct acaatggtgt cggtcatgtc acagttcaat    540
atgaaacagt attagcaatc ggcttgaatg gagtaaaaga gaaggttagg aaagagatgg    600
agaattgtca ttttggtgat gccgattata gtacaaagat gtgtttcttg gagagcattt    660
taatatcgtg tgatgccgta atcacttatg ctaaatagata tgccaagatg gccgaggaaa    720
tggctgaaaa agaaacagat gctgcaagga ggcaagaact attaacaatc gccagggttt    780
gcaaaaacgt tcctgaattc ccagccgaaa gcttccagga ggcctgccaa tccttttggt    840
tcatacaaca agtgcttcaa attgaatcca gtggtcattc aatttcccca ggtagatttg    900
atcaatatat gtatccttat tacgaaaagg atttaaagga aggtagctta actagggaat    960
atgctcagga actgatcgat tgtatctggg ttaagttaaa tgatctgaat aagtgcaggg   1020
atgctgcctc tgctgagggc tttgcaggat attccttatt tcaaaactta atcgttgggg   1080
gccaaacggt tcaaggaagg gacgccacca atgatttgag ttttatgtgt atcacggcat   1140
ctgaacacgt ctttttaccg atgccgtcgt tgtctataag agtttggcat ggtagttcca   1200
aagcactgct tatgagagca gctgaattga ctagaaccgg tataggctta cctgcttatt   1260
acaatgatga agtcatcata ccagcttttg tgcataggg tgctactatg gatgaagcaa   1320
gaaattacaa cataatagga tgtgtcgaac cgcaggttcc tggtaaaact gatggctggc   1380
acgatgcagc attcttaac atgtgcagac ctttggaaat ggtgtttagt aatggttatg   1440
ataacggtga aattgcatct atacaaactg gtaacgtaga atcttttcag agttttgatg   1500
agtttatgga agcttacaga aaacaaatgc tatataacat agaacttatg gtaaatgccg   1560
acaacgcgat agattatgcc cacgcaaagt tggccccatt gccatttgag tcatgtttgg   1620
ttgatgactg tataaagaga ggaatgtccg ctcaggaagg cggcgcaatc tataatttca   1680
ctggtccaca gggctttggt attgcaaacg ttgctgatag cttgtatacg attaagaaat   1740
tggtgttcga ggagaagaga attacgatgg gtgaattaaa gaaagcgttg gaaatgaatt   1800
atggtaaggg tttggatgcc acaaccgctg gtgacatcgc aatgcaggtc gcgaagggac   1860
taaaagatgc cggacaggaa gtgggtcccg acgtgatcgc taatacaatc cgtcaagttc   1920
ttgaaatgga attaccagaa gatgtaagaa agagatatga agagatccat gaaatgatac   1980
ttgagttacc aaagtatggt aatgatatag atgaagttga tgaattagct agagaagcag   2040
cttactttta cacaagacca ttagaaactt ttaagaatcc aaggggtggc atgtatcaag   2100
ccggccttta tcccgtgtcc gctaatgtgc cactaggcgc tcaaacgggg gccacacccg   2160
atggacgttt ggcgcataca cccgtggcgg atggcgttgg tccgacatca ggcttcgata   2220
tatccggacc aacagcttct tgcaattctg tcgccaagtt ggatcatgct atagcctcta   2280
atggtacctt attaatatg aagatgcacc caaccgcaat ggcaggtgaa aagggcttag   2340
aatccttcat atcgttgatc cgtggttatt tcgatcaaca aggtatgcac atgcaattta   2400
acgtagtaga cagggctaca ctgcttgatg cgcaggccca ccctgaaaag tattcaggct   2460
taattgtcag agtggcaggt tattctgccc ttttaccac attgtccaag tcattacaag   2520
atgatataat caaacgtacc gaacaagcag acaatagata ggaaggaaaa acgcgttatg   2580
```

```
aaagaatatc ttaatacttc aggtagaata tttgatatcc agaggtattc tattcacgat    2640
ggccctggtg tgcgtacaat tgtgtttcta aaaggttgtg cccttagatg cagatggtgc    2700
tgtaatcctg aaagccaaag cttcgaagtt gaaacaatga cgattaatgg aaaacctaaa    2760
gtcatgggta aagatgttac agtcgccgag gttatgaaga cggtagaaag agacatgcct    2820
tattaccttc aatcaggtgg tggtatcacc ttatcgggtg gcgaatgtac tttgcaacca    2880
gaattttccc ttggcctatt gagagctgca aaggatttgg gcatatccac ggcaatagag    2940
agcatggcgt acgcaaagta cgaagtaata gaaactcttc ttccgtattt ggatacgtat    3000
ttaatggaca tcaaacatat gaatcctgag aaacataaag aatacactgg tcatgataac    3060
ttgaggatgt tagaaaacgc cttaagagtc gcgcattctg gtcagaccga actgatcatc    3120
agagtacctg tcatcccagg attcaacgca actgagcagg aactactaga tattgcaaaa    3180
ttcgcagata cactgcctgg agttagacaa atacacatct tgccatatca taattttggt    3240
cagggtaaat acgaaggatt gaacagggac tatccgatgg gggacactga gaaaccctct    3300
aatgaacaga tgaaagcttt tcaagaaatg attcaaaaga cacttccct acattgccaa    3360 atcggtggtt aggtcgac                                                  3378

<210> SEQ ID NO 139
<211> LENGTH: 60
<212> TYPE: DNA
<213> ORGANISM: artificial sequence
<220> FEATURE:
<223> OTHER INFORMATION: primer

<400> SEQUENCE: 139
aaccaagtaa tacatattca aatctagagc tgaggatggg caattacgat tcaacaccga      60

<210> SEQ ID NO 140
<211> LENGTH: 60
<212> TYPE: DNA
<213> ORGANISM: Artificial sequence
<220> FEATURE:
<223> OTHER INFORMATION: primer

<400> SEQUENCE: 140
gtaagcgtga cataactaat tacatgatta attaactatc tattgtctgc ttgttcggta      60

<210> SEQ ID NO 141
<211> LENGTH: 60
<212> TYPE: DNA
<213> ORGANISM: Artificial sequence
<220> FEATURE:
<223> OTHER INFORMATION: primer

<400> SEQUENCE: 141
aatccaaaca aacacacata ttacaatagc tgaggatgaa agaatatctt aatacttcag      60

<210> SEQ ID NO 142
<211> LENGTH: 60
<212> TYPE: DNA
<213> ORGANISM: Artificial sequence
<220> FEATURE:
<223> OTHER INFORMATION: primer

<400> SEQUENCE: 142
cataaatcat aagaaattcg cttactctta attaataacc accgatttgg caatgtaggg      60

<210> SEQ ID NO 143
<211> LENGTH: 594
```

```
<212> TYPE: DNA
<213> ORGANISM: Artificial sequence
<220> FEATURE:
<223> OTHER INFORMATION: synthetic double terminator fragment

<400> SEQUENCE: 143
taagagtaag cgaatttctt atgatttatg attttattta ttaaataagt tataaaaaaa    60
ataagtgtat acaaatttta aagtgactct taggttttaa aacgaaaatt cttattcttg   120
agtaactctt tcctgtaggt caggttgctt tctcaggtat agcatgaggt cgctcttatt   180
gaccacacct ctaccggcat gccgagcaaa tgcctgcaaa tcgctcccca tttcacccaa   240
ttgtagatat gctaactcca gcaatgagtt gatgaatctc ggtgtgtatt ttatgtcctc   300
agaggacaac acctgtggta ctagttctag agcggccgcc cgcaaattaa agccttcgag   360
cgtcccaaaa ccttctcaag caaggttttc agtataatgt tacatgcgta cacgcgtctg   420
tacagaaaaa aagaaaaat ttgaaatata ataacgttc ttaatactaa cataactata    480
aaaaaataaa tagggaccta gacttcaggt tgtctaactc cttcctttc ggttagagcg    540 gatgtggggg gagggcgtga atgtaagcgt gacataacta attacatgat taat          594

<210> SEQ ID NO 144
<211> LENGTH: 66
<212> TYPE: DNA
<213> ORGANISM: artificial sequence
<220> FEATURE:
<223> OTHER INFORMATION: primer

<400> SEQUENCE: 144
tataagagct gccattctcg atcgtacgct gcaggtcgac ccgcggatag atctgaaatg    60
aataac                                                              66

<210> SEQ ID NO 145
<211> LENGTH: 60
<212> TYPE: DNA
<213> ORGANISM: artificial sequence
<220> FEATURE:
<223> OTHER INFORMATION: primer

<400> SEQUENCE: 145
cattagaata cgtaatccgc aatgctccgc atgcttgcat ttagtcgtgc aatgtatgac    60

<210> SEQ ID NO 146
<211> LENGTH: 25
<212> TYPE: DNA
<213> ORGANISM: artificial sequence
<220> FEATURE:
<223> OTHER INFORMATION: primer

<400> SEQUENCE: 146
tactgagagt gcaccatacc acagc                                         25

<210> SEQ ID NO 147
<211> LENGTH: 65
<212> TYPE: DNA
<213> ORGANISM: artificial sequence
<220> FEATURE:
<223> OTHER INFORMATION: primer

<400> SEQUENCE: 147
gctaagatca tagctaaagg tacaaaaccg aatacgaaag gattttgccg atttcggcct    60
attgg                                                               65
```

<210> SEQ ID NO 148
<211> LENGTH: 95
<212> TYPE: DNA
<213> ORGANISM: artificial sequence
<220> FEATURE:
<223> OTHER INFORMATION: primer

<400> SEQUENCE: 148
ttctctcccc ttccttttct ttttccagtt ttccctattt tgtccctttt tccgcacaac    60
aagtatcaga tactgagagt gcaccatacc acagc    95

<210> SEQ ID NO 149
<211> LENGTH: 95
<212> TYPE: DNA
<213> ORGANISM: artificial sequence
<220> FEATURE:
<223> OTHER INFORMATION: primer

<400> SEQUENCE: 149
ttatttatat ttatttggtt actaaatttt gtattaattt aataataata agtaatttct    60
aacgtgataa gattttgccg atttcggcct attgg    95

<210> SEQ ID NO 150
<211> LENGTH: 31
<212> TYPE: DNA
<213> ORGANISM: artificial sequence
<220> FEATURE:
<223> OTHER INFORMATION: primer

<400> SEQUENCE: 150
cagcaacagg actaggatga gtagcagcac g    31

<210> SEQ ID NO 151
<211> LENGTH: 26
<212> TYPE: DNA
<213> ORGANISM: artificial sequence
<220> FEATURE:
<223> OTHER INFORMATION: primer

<400> SEQUENCE: 151
gcgccattgt ccctcagaaa caaatc    26

<210> SEQ ID NO 152
<211> LENGTH: 97
<212> TYPE: DNA
<213> ORGANISM: artificial sequence
<220> FEATURE:
<223> OTHER INFORMATION: primer

<400> SEQUENCE: 152
tacggaccta ttgccattgt tattccgatt aatctattgt tcagcagctc ttctctaccc    60
tgtcattcta gatactgaga gtgcaccata ccacagc    97

<210> SEQ ID NO 153
<211> LENGTH: 102
<212> TYPE: DNA
<213> ORGANISM: artificial sequence
<220> FEATURE:
<223> OTHER INFORMATION: primer

<400> SEQUENCE: 153
gtacagggtg tcgtatcttt cattaacggt gatgtgatat gtaaacgata atagcgtgta    60
taatggtagt tataagggat tttgccgatt tcggcctatt gg    102

```
<210> SEQ ID NO 154
<211> LENGTH: 30
<212> TYPE: DNA
<213> ORGANISM: artificial sequence
<220> FEATURE:
<223> OTHER INFORMATION: primer

<400> SEQUENCE: 154
cttagcctct agccatagcc atcatgcaag                                      30

<210> SEQ ID NO 155
<211> LENGTH: 95
<212> TYPE: DNA
<213> ORGANISM: artificial sequence
<220> FEATURE:
<223> OTHER INFORMATION: primer

<400> SEQUENCE: 155
aacatgtgca tgtacacacg taatcgcgcg tgtacatgtc tatatgtgtt acttgaacta     60
tactgttttg tactgagagt gcaccatacc acagc                                95

<210> SEQ ID NO 156
<211> LENGTH: 95
<212> TYPE: DNA
<213> ORGANISM: artificial sequence
<220> FEATURE:
<223> OTHER INFORMATION: primer

<400> SEQUENCE: 156
gctataaaat ggcgcttcca gggaagaata tcatgcgatc acagcactat tattttattt     60
ttccttacga gattttgccg atttcggcct attgg                                95

<210> SEQ ID NO 157
<211> LENGTH: 28
<212> TYPE: DNA
<213> ORGANISM: artificial sequence
<220> FEATURE:
<223> OTHER INFORMATION: primer

<400> SEQUENCE: 157
caacagcagc cacctgctgc cgccgaag                                        28

<210> SEQ ID NO 158
<211> LENGTH: 82
<212> TYPE: DNA
<213> ORGANISM: artificial sequence
<220> FEATURE:
<223> OTHER INFORMATION: primer

<400> SEQUENCE: 158
cttcggaggg ctgtcacccg ctcggcggct tctaatccgt gattttgccg atttcggcct     60
attggttaaa aaatgagctg at                                              82

<210> SEQ ID NO 159
<211> LENGTH: 82
<212> TYPE: DNA
<213> ORGANISM: artificial sequence
<220> FEATURE:
<223> OTHER INFORMATION: primer

<400> SEQUENCE: 159
atcagctcat ttttaaccaa ataggccgaa atcggcaaaa tcacggatta gaagccgccg     60
```

```
agcgggtgac agccctccga ag                                              82
```

<210> SEQ ID NO 160
<211> LENGTH: 97
<212> TYPE: DNA
<213> ORGANISM: artificial sequence
<220> FEATURE:
<223> OTHER INFORMATION: primer

<400> SEQUENCE: 160

```
aacagctcct aacccgcgga ccaattgtga tggttggcgt ttgaatgaag cagcaagcat     60
ttttctcctt gacgttaaag tatagaggta tattaac                              97
```

<210> SEQ ID NO 161
<211> LENGTH: 88
<212> TYPE: DNA
<213> ORGANISM: artificial sequence
<220> FEATURE:
<223> OTHER INFORMATION: primer

<400> SEQUENCE: 161

```
tggaataatc aatcaattga ggattttatg caaatatcgt ttgaatattt ttccgctgag     60
agtgcaccat aaattcccgt tttaagag                                        88
```

<210> SEQ ID NO 162
<211> LENGTH: 70
<212> TYPE: DNA
<213> ORGANISM: artificial sequence
<220> FEATURE:
<223> OTHER INFORMATION: primer

<400> SEQUENCE: 162

```
ttgttctttt gttgcttttg tcaacatcct cagcctttgc cttcgtttat cttgcctgct     60
cattttttag                                                            70
```

<210> SEQ ID NO 163
<211> LENGTH: 70
<212> TYPE: DNA
<213> ORGANISM: artificial sequence
<220> FEATURE:
<223> OTHER INFORMATION: primer

<400> SEQUENCE: 163

```
ctaaaaaatg agcaggcaag ataaacgaag gcaaaggctg aggatgttga caaaagcaac     60
aaaagaacaa                                                            70
```

<210> SEQ ID NO 164
<211> LENGTH: 33
<212> TYPE: DNA
<213> ORGANISM: artificial sequence
<220> FEATURE:
<223> OTHER INFORMATION: primer

<400> SEQUENCE: 164

```
ttcgttacat aaaaatgctt ataaaacttt aac                                  33
```

<210> SEQ ID NO 165
<211> LENGTH: 16387
<212> TYPE: DNA
<213> ORGANISM: artificial sequence
<220> FEATURE:
<223> OTHER INFORMATION: plasmid construct

<400> SEQUENCE: 165

```
tcccattacc gacatttggg cgctatacgt gcatatgttc atgtatgtat ctgtatttaa      60
aacacttttg tattattttt cctcatatat gtgtataggt ttatacggat gatttaatta     120
ttacttcacc acccttttatt tcaggctgat atcttagcct tgttactagt tagaaaaaga    180 cattttgct gtcagtcact gtcaagagat tcttttgctg gcatttcttc tagaagcaaa      240
aagagcgatg cgtctttcc gctgaaccgt tccagcaaaa aagactacca acgcaatatg      300
gattgtcaga atcatataaa agagaagcaa ataactcctt gtcttgtatc aattgcatta     360
taatatcttc ttgttagtgc aatatcatat agaagtcatc gaaatagata ttaagaaaaa     420
caaactgtac aatcaatcaa tcaatcatcg ctgaggatgt tgacaaaagc aacaaaagaa     480
caaaaatccc ttgtgaaaaa cagaggggcg gagcttgttg ttgattgctt agtggagcaa     540
ggtgtcacac atgtatttgg cattccaggt gcaaaaattg atgcggtatt tgacgcttta     600
caagataaag gacctgaaat tatcgttgcc cggcacgaac aaaacgcagc attcatggcc     660
caagcagtcg gccgtttaac tggaaaaccg ggagtcgtgt tagtcacatc aggacccggt     720
gcctctaact tggcaacagg cctgctgaca gcgaacactg aaggagaccc tgtcgttgcg     780
cttgctggaa acgtgatccg tgcagatcgt ttaaaacgga cacatcaatc tttggataat     840
gcggcgctat tccagccgat tacaaaatac agtgtagaag ttcaagatgt aaaaaatata     900
ccggaagctg ttacaaatgc atttaggata gcgtcagcag ggcaggctgg ggccgctttt     960
gtgagctttc gcaagatgt tgtgaatgaa gtcacaaata cgaaaaacgt gcgtgctgtt    1020
gcagcgccaa aactcggtcc tgcagcagat gatgcaatca gtgcggccat agcaaaaatc    1080
caaacagcaa aacttcctgt cgttttggtc ggcatgaaag gcggaagacc ggaagcaatt    1140
aaagcggttc gcaagctttt gaaaaaggtt cagcttccat ttgttgaaac atatcaagct    1200
gccggtaccc tttctagaga tttagaggat caatattttg gccgtatcgg tttgttccgc    1260
aaccagcctg gcgatttact gctagagcag gcagatgttg ttctgacgat cggctatgac    1320
ccgattgaat atgatccgaa attctggaat atcaatggag accggacaat tatccattta    1380
gacgagatta tcgctgacat tgatcatgct taccagcctg atcttgaatt gatcggtgac    1440
attccgtcca cgatcaatca tatcgaacac gatgctgtga aagtggaatt tgcagagcgt    1500
gagcagaaaa tccttttctga tttaaaacaa tatatgcatg aaggtgagca ggtgcctgca    1560
gattggaaat cagacagagc gcaccctctt gaaatcgtta aagagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280 ttatttttttt atagttatgt tagtattaag aacgttattt atatttcaaa ttttttctttt   2340
```

```
ttttctgtac agacgcgtgt acgcatgtaa cattatactg aaaaccttgc ttgagaaggt    2400
tttgggacgc tcgaaggctt taatttgcgg gcggccgctc tagaactagt accacaggtg    2460
ttgtcctctg aggacataaa atacacaccg agattcatca actcattgct ggagttagca    2520
tatctacaat tgggtgaaat ggggagcgat ttgcagcat ttgctcggca tgccggtaga     2580
ggtgtggtca ataagagcga cctcatgcta tacctgagaa agcaacctga cctacaggaa    2640
agagttactc aagaataaga attttcgttt taaaacctaa gagtcacttt aaaatttgta    2700
tacacttatt tttttataa cttatttaat aataaaaatc ataaatcata agaaattcgc     2760
ttactcttaa ttaatcaagc atctaaaaca caaccgttgg aagcgttgga aaccaactta    2820
gcatacttgg atagagtacc tcttgtgtaa cgaggtggag gtgcaaccca actttgttta    2880
cgttgagcca tttccttatc agagactaat aggtcaatct tgttattatc agcatcaatg    2940
ataatctcat cgccgtctct gaccaacccg ataggaccac cttcagcggc ttcgggaaca    3000
atgtggccga ttaagaaccc gtgagaacca ccagagaatc taccatcagt caacaatgca    3060
acatctttac ccaaaccgta acccatcaga gcagaggaag ctttagcat ttcaggcata     3120 cctggtgcac ctcttggacc ttcatatctg ataacaacaa cggttttttc acccttcttg    3180
atttcacctc tttccaaggc ttcaataaag gcaccttcct cttcgaacac acgtgctcta    3240
cccttgaagt aagtaccttc cttaccggta attttaccca cagctccacc tggtgccaat    3300
gaaccgtaca gaatttgcaa gtgaccgttg gccttgattg ggtgggagag tggcttaata    3360
atctcttgtc cttcaggtag gcttggtgct ttctttgcac gttctgccaa agtgtcaccg    3420
gtaacagtca ttgtgttacc gtgcaacatg ttgttttcat atagatactt aatcacagat    3480
tgggtaccac caacgttaat caaatcggcc atgacgtatt taccagaagg tttgaagtca    3540
ccgatcaatg gtgtagtatc actgattctt tggaaatcat ctggtgacaa cttgacaccc    3600
gcagagtgag caacagccac caaatgcaaa acagcattag tggacccacc ggttgcaacg    3660
acataagtaa tggcgttttc aaaagcctct tttgtgagga tatcacgagg taaaataccc    3720
aattccattg tcttcttgat gtattcacca atgttgtcac actcagctaa cttctccttg    3780
gaaacggctg ggaaggaaga ggagtttgga atggtcaaac ctagcacttc agcggcagaa    3840
gccattgtgt tggcagtata cataccacca caagaaccag gacctgggca tgcatgttcc    3900
acaacatctt ctctttcttc ttcagtgaat tgcttggaaa tatattcacc gtaggattgg    3960
aacgcagaga cgatatcgat gttttagag atcctgttaa aacctctagt ggagtagtag     4020
atgtaatcaa tgaagcggaa gccaaaagac cagagtagag gcctatagaa gaaactgcga    4080 tacctttgt gatggctaaa caaacagaca tctttttata tgttttact tctgtatatc       4140 gtgaagtagt aagtgataag cgaatttggc taagaacgtt gtaagtgaac aagggacctc    4200
ttttgccttt caaaaagga ttaaatggag ttaatcattg agatttagtt ttcgttagat      4260
tctgtatccc taaataactc ccttacccga cgggaaggca caaagacttg aataatagc      4320 aaacggccag tagccaagac caaataatac tagagttaac tgatggtctt aaacaggcat    4380
tacgtggtga actccaagac caatatacaa aatatcgata agttattctt gcccaccaat    4440
ttaaggagcc tacatcagga cagtagtacc attcctcaga gaagaggtat acataacaag    4500
aaaatcgcgt gaacaccta tataacttag cccgttattg agctaaaaaa ccttgcaaaa      4560
tttcctatga ataagaatac ttcagacgtg ataaaaattt actttctaac tcttctcacg    4620 ctgccctat ctgttcttcc gctctaccgt gagaaataaa gcatcgagta cggcagttcg      4680
ctgtcactga actaaaacaa taaggctagt tcgaatgatg aacttgcttg ctgtcaaact    4740
```

```
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaattgaa aaattttgta taaaagggat gacctaactt   5040
gactcaatgg cttttacacc cagtattttc cctttccttg tttgttacaa ttatagaagc   5100
aagacaaaaa catatagaca acctattcct aggagttata tttttttacc ctaccagcaa   5160
tataagtaaa aaactagtat gaaggtgttt tacgataaag actgcgatct gagcatcatc   5220
cagggaaaga aggttgctat tataggatat ggttcccaag gacacgcaca agccttgaac   5280
ttgaaagatt ctgggtcga cgtgacagta ggtctgtata aaggtgctgc tgatgcagca   5340
aaggctgaag cacatggctt taaagtcaca gatgttgcag cggctgttgc tggcgctgat   5400
ttagtcatga ttttaattcc agatgaattt caatcgcaat tgtacaaaaa tgaaatagaa   5460
ccaaacatta agaagggcgc taccttggcc ttcagtcatg gatttgccat tcattacaat   5520
caagtagtcc ccagggcaga tttggacgtt attatgattg cacctaaggc tccggggcat   5580
actgttagga gcgaatttgt taagggtggt ggtattccag atttgatcgc tatataccaa   5640
gacgttagcg gaaacgctaa gaatgtagct ttaagctacg cagcaggagt tggtggcggg   5700
agaacgggta atagaaaac cacttttaaa gacgagactg agacagattt atttggagaa   5760
caagcggttc tgtgcggagg aactgttgaa ttggttaaag caggctttga gacgcttgtc   5820
gaagcagggt acgctcccga aatggcatac ttcgaatgtc tacatgaatt gaagttgata   5880
gtagacttaa tgtatgaagg tggtatagct aatatgaact attccatttc aaataatgca   5940
gaatatggtg agtatgtcac cggacctgaa gtcattaacg cagaatcaag acaagccatg   6000
agaaatgcct tgaaacgtat ccaggacggt gaatacgcta agatgttcat aagtgaaggc   6060 gctacggtt acccgagtat gactgctaaa gaagaaaaca atgcagcaca tggtatcgaa   6120
attattggtg aacagttaag gtctatgatg ccctggatcg gtgctaataa gatcgtagac   6180
aaggcgaaaa attaaggccc tgcaggccta tcaagtgctg gaaactttt ctcttggaat   6240 ttttgcaaca tcaagtcata gtcaattgaa ttgacccaat ttcacattta agatttttt   6300 tttttcatcc gacatacatc tgtacactag gaagccctgt ttttctgaag cagcttcaaa   6360
tatatatatt ttttacatat ttattatgat tcaatgaaca atctaattaa atcgaaaaca   6420
agaaccgaaa cgcgaataaa taatttattt agatggtgac aagtgtataa gtcctcatcg   6480
ggacagctac gatttctctt tcggttttgg ctgagctact ggttgctgtg acgcagcggc   6540
attagcgcgg cgttatgagc tacctcgtg gcctgaaaga tggcgggaat aaagcggaac   6600
taaaaattac tgactgagcc atattgaggt caatttgtca actcgtcaag tcacgtttgg   6660
tggacggccc ctttccaacg aatcgtatat actaacatgc gcgcgcttcc tatatacaca   6720
tatacatata tatatatata tatatgtgtg cgtgtatgtg tacacctgta tttaatttcc   6780
ttactcgcgg gttttcttt tttctcaatt cttggcttcc tctttctcga gtatataatt   6840
tttcaggtaa aatttagtac gatagtaaaa tacttctcga actcgtcaca tatacgtgta   6900
cataatgtct gaaccagctc aaaagaaaca aaaggttgct aacaactctc tagagcggcc   6960
gcccgcaaat taaagccttc gagcgtccca aaaccttctc aagcaaggtt ttcagtataa   7020
tgttacatgc gtacacgcgt ctgtacagaa aaaaagaaa aatttgaaat ataaataacg   7080
```

```
ttcttaatac taacataact ataaaaaaat aaatagggac ctagacttca ggttgtctaa    7140
ctccttcctt ttcggttaga gcggatgtgg ggggagggcg tgaatgtaag cgtgacataa    7200
ctaattacat gattaattaa ttattggttt tctggtctca actttctgac ttccttacca    7260
accttccaga tttccatgtt tctgatggtg tctaattcct tttctagctt ttctctgtag    7320
tcaggttgag agttgaattc caaagatctc ttggtttcgg taccgttctt ggtagattcg    7380
tacaagtctt ggaaaacagg cttcaaagca ttcttgaaga ttgggtacca gtccaaagca    7440
cctcttctgg cggtggtgga acaagcatcg tacatgtaat ccataccgta cttaccgatc    7500
aatgggtata gagattgggt agcttcttcg acggtttcgt tgaaagcttc agatggggag    7560
tgaccgtttt ctctcaagac gtcgtattga gccaagaaca taccgtggat accacccatt    7620
aaacaacctc tttcaccgta caagtcagag ttgacttctc tttcgaaagt ggtttggtaa    7680
acgtaaccgg aaccaatggc aacggccaaa gcttgggcct tttcgtgagc cttaccggtg    7740
acatcgttcc agacggcgta agaagagtta ataccacgac cttccttgaa caaagatctg    7800
acagttctac cggaacccct tggagcaacc aagataacat ctaagtcctt tggtggttca    7860
acgtgagtca agtccttgaa gactggggag aaaccgtggg agaagtacaa agtcttaccc    7920
ttggtcaaca atggcttgat agcaggccag gtttctgatt gagcggcatc ggacaacaag    7980
ttcataacgt aactacctct cttgatagca tcttcaacag tgaacaagtt cttgcctgga    8040
acccaaccgt cttcgatggc agccttccaa gaagcaccat ctttacggac accaatgata    8100
acgttcaaac cgttgtctct caagttcaaa ccttgaccgt aaccttggga accgtaaccg    8160
atcaaagcaa aagtgtcgtt cttgaagtag tccaacaact tttctcttgg ccagtcagct    8220
ctttcgtaga cggtttcaac agtaccaccg aagttgattt gcttcaacat cctcagctct    8280
agatttgaat atgtattact tggttatggt tatatatgac aaaagaaaaa gaagaacaga    8340
agaataacgc aaggaagaac aataactgaa attgatagag aagtattatg tctttgtctt    8400
tttataataa atcaagtgca gaaatccgtt agacaacatg agggataaaa tttaacgtgg    8460
gcgaagaaga aggaaaaaag ttttgtgag ggcgtaattg aagcgatctg ttgattgtag    8520
attttttttt tttgaggagt caaagtcaga agagaacaga caaatggtat taaccatcca    8580
atacttttt ggagcaacgc taagctcatg cttttccatt ggttacgtgc tcagttgtta    8640
gatatggaaa gagaggatgc tcacggcagc gtgactccaa ttgagcccga agagaggat    8700
gccacgtttt cccgacggct gctagaatgg aaaaaggaaa aatagaagaa tcccattcct    8760
atcattattt acgtaatgac ccacacattt ttgagatttt caactattac gtattacgat    8820
aatcctgctg tcattatcat tattatctat atcgacgtat gcaacgtatg tgaagccaag    8880
taggcaatta tttagtactg tcagtattgt tattcatttc agatctatcc gcggtggagc    8940
tcgaattcac tggccgtcgt tttacaacgt cgtgactggg aaaaccctgg cgttacccaa    9000
cttaatcgcc ttgcagcaca tccccctttc gccagctggc gtaatagcga agaggcccgc    9060
accgatcgcc cttcccaaca gttgcgcagc ctgaatggcg aatggcgcct gatgcggtat    9120
tttctcctta cgcatctgtg cggtatttca caccgcatac gtcaaagcaa ccatagtacg    9180
cgccctgtag cggcgcatta agcgcggcgg gtgtggtggt tacgcgcagc gtgaccgcta    9240
cacttgccag cgccttagcg cccgctcctt tcgctttctt cccttccttt ctcgccacgt    9300
tcgccggctt tccccgtcaa gctctaaatc ggggcctccc tttagggttc cgatttagtg    9360
ctttacggca cctcgacccc aaaaaacttg atttgggtga tggttcacgt agtgggccat    9420
cgccctgata gacggttttt cgccctttga cgttggagtc cacgttcttt aatagtggac    9480
```

```
tcttgttcca aactggaaca acactcaact ctatctcggg ctattctttt gatttataag    9540
ggattttgcc gatttcggtc tattggttaa aaaatgagct gatttaacaa aaatttaacg    9600
cgaattttaa caaaatatta acgtttacaa ttttatggtg cactctcagt acaatctgct    9660
ctgatgccgc atagttaagc cagccccgac acccgccaac acccgctgac gcgccctgac    9720
gggcttgtct gctcccggca tccgcttaca gacaagctgt gaccgtctcc gggagctgca    9780
tgtgtcagag gttttcaccg tcatcaccga acgcgcgag acgaaaggc ctcgtgatac     9840 gcctattttt ataggttaat gtcatgataa taatggtttc ttagacgtca ggtggcactt    9900
ttcggggaaa tgtgcgcgga acccctattt gtttattttt ctaaatacat tcaaatatgt    9960
atccgctcat gagacaataa ccctgataaa tgcttcaata atattgaaaa aggaagagta   10020
tgagtattca acatttccgt gtcgccctta ttcccttttt tgcggcattt tgccttcctg   10080 ttttgctca cccagaaacg ctggtgaaag taaaagatgc tgaagatcag ttgggtgcac    10140
gagtgggtta catcgaactg gatctcaaca gcggtaagat ccttgagagt tttcgccccg   10200
aagaacgttt tccaatgatg agcactttta aagttctgct atgtggcgcg gtattatccc   10260
gtattgacgc cgggcaagag caactcggtc gccgcataca ctattctcag aatgacttgg   10320
ttgagtactc accagtcaca gaaaagcatc ttacggatgg catgacagta agagaattat   10380
gcagtgctgc cataaccatg agtgataaca ctgcggccaa cttacttctg acaacgatcg   10440
gaggaccgaa ggagctaacc gcttttttgc acaacatggg ggatcatgta actcgccttg   10500
atcgttggga accggagctg aatgaagcca taccaaacga cgagcgtgac accacgatgc   10560
ctgtagcaat ggcaacaacg ttgcgcaaac tattaactgg cgaactactt actctagctt   10620
cccggcaaca attaatagac tggatggagg cggataaagt tgcaggacca cttctgcgct   10680
cggcccttcc ggctggctgg tttattgctg ataaatctgg agccggtgag cgtgggtctc   10740
gcggtatcat tgcagcactg gggccagatg gtaagccctc ccgtatcgta gttatctaca   10800
cgacggggag tcaggcaact atggatgaac gaaatagaca gatcgctgag ataggtgcct   10860
cactgattaa gcattggtaa ctgtcagacc aagtttactc atatatactt tagattgatt   10920
taaaacttca ttttaattt aaaaggatct aggtgaagat cctttttgat aatctcatga   10980
ccaaaatccc ttaacgtgag ttttcgttcc actgagcgtc agaccccgta gaaaagatca   11040
aaggatcttc ttgagatcct tttttctgc gcgtaatctg ctgcttgcaa acaaaaaaac   11100
caccgctacc agcggtggtt tgtttgccgg atcaagagct accaactctt tttccgaagg   11160
taactggctt cagcagagcg cagataccaa atactgttct tctagtgtag ccgtagttag   11220
gccaccactt caagaactct gtagcaccgc ctacatacct cgctctgcta atcctgttac   11280
cagtggctgc tgccagtggc gataagtcgt gtcttaccgg gttggactca agacgatagt   11340
taccggataa ggcgcagcgg tcgggctgaa cggggggttc gtgcacacag cccagcttgg   11400
agcgaacgac ctacaccgaa ctgagatacc tacagcgtga gctatgagaa agcgccacgc   11460
ttcccgaagg gagaaaggcg gacaggtatc cggtaagcgg cagggtcgga acaggagagc   11520
gcacagggga gcttccaggg ggaaacgcct ggtatcttta tagtcctgtc gggtttcgcc   11580
acctctgact tgagcgtcga ttttgtgat gctcgtcagg ggggcggagc ctatggaaaa   11640
acgccagcaa cgcggccttt ttacggttcc tggccttttg ctggccttttg gctcacatgt   11700 tctttcctgc gttatcccct gattctgtgg ataaccgtat taccgccttt gagtgagctg   11760
ataccgctcg ccgcagccga acgaccgagc gcagcgagtc agtgagcgag gaagcggaag   11820
```

```
agcgcccaat acgcaaaccg cctctccccg cgcgttggcc gattcattaa tgcagctggc  11880
acgacaggtt tcccgactgg aaagcgggca gtgagcgcaa cgcaattaat gtgagttagc  11940
tcactcatta ggcacccag gctttacact ttatgcttcc ggctcgtatg ttgtgtggaa  12000
ttgtgagcgg ataacaattt cacacaggaa acagctatga ccatgattac gccaagcttt  12060
ttctttccaa ttttttttt ttcgtcatta taaaaatcat tacgaccgag attcccgggt  12120
aataactgat ataattaaat tgaagctcta atttgtgagt ttagtataca tgcatttact  12180
tataatacag ttttttagtt ttgctggccg catcttctca aatatgcttc ccagcctgct  12240
tttctgtaac gttcaccctc taccttagca tccctccct ttgcaaatag tcctcttcca  12300
acaataataa tgtcagatcc tgtagagacc acatcatcca cggttctata ctgttgaccc  12360
aatgcgtctc ccttgtcatc taaacccaca ccgggtgtca taatcaacca atcgtaacct  12420
tcatctcttc cacccatgtc tctttgagca ataaagccga taacaaaatc tttgtcgctc  12480
ttcgcaatgt caacagtacc cttagtatat tctccagtag ataggagcc cttgcatgac  12540 aattctgcta acatcaaaag gcctctaggt tcctttgtta cttcttctgc cgcctgcttc  12600
aaaccgctaa caatacctgg gcccaccaca ccgtgtgcat tcgtaatgtc tgcccattct  12660
gctattctgt atacacccgc agagtactgc aatttgactg tattaccaat gtcagcaaat  12720
tttctgtctt cgaagagtaa aaaattgtac ttggcggata atgcctttag cggcttaact  12780
gtgccctcca tggaaaaatc agtcaagata tccacatgtg ttttagtaa acaaatttttg  12840 ggacctaatg cttcaactaa ctccagtaat tccttggtgg tacgaacatc caatgaagca  12900
cacaagtttg tttgctttc gtgcatgata ttaaatagct tggcagcaac aggactagga  12960
tgagtagcag cacgttcctt atatgtagct ttcgacatga tttatcttcg tttcctgcag  13020
gtttttgttc tgtgcagttg ggttaagaat actgggcaat ttcatgtttc ttcaacacta  13080
catatgcgta tatataccaa tctaagtctg tgctccttcc ttcgttcttc cttctgttcg  13140
gagattaccg aatcaaaaaa atttcaagga aaccgaaatc aaaaaaaaga ataaaaaaaa  13200
aatgatgaat tgaaaagctt gcatgcctgc aggtcgactc tagtatactc cgtctactgt  13260
acgatacact tccgctcagg tccttgtcct ttaacgaggc cttaccactc ttttgttact  13320
ctattgatcc agctcagcaa aggcagtgtg atctaagatt ctatcttcgc gatgtagtaa  13380
aactagctag accgagaaag agactagaaa tgcaaaaggc acttctacaa tggctgccat  13440
cattattatc cgatgtgacg ctgcattttt tttttttttt tttttttttt tttttttttt  13500
tttttttttt ttttttttgta caaatatcat aaaaaaagag aatctttta agcaaggatt  13560 ttcttaactt cttcggcgac agcatcaccg acttcggtgg tactgttgga accacctaaa  13620
tcaccagttc tgatacctgc atccaaaacc tttttaactg catcttcaat ggctttacct  13680
tcttcaggca agttcaatga caatttcaac atcattgcag cagacaagat agtggcgata  13740
gggttgacct tattctttgg caaatctgga gcggaaccat ggcatggttc gtacaaacca  13800
aatgcggtgt tcttgtctgg caaagaggcc aaggacgcag atggcaacaa acccaaggag  13860
cctgggataa cggaggcttc atcggagatg atatcaccaa acatgttgct ggtgattata  13920
ataccattta ggtgggttgg gttcttaact aggatcatgg cggcagaatc aatcaattga  13980
tgttgaactt tcaatgtagg gaattcgttc ttgatggttt cctccacagt ttttctccat  14040
aatcttgaag aggccaaaac attagcttta tccaaggacc aaataggcaa tggtggctca  14100
tgttgtaggg ccatgaaagc ggccattctt gtgattcttt gcacttctgg aacggttgtat  14160 tgttcactat cccaagcgac accatcacca tcgtcttcct ttctcttacc aaagtaaata  14220
```

```
cctcccacta attctctaac aacaacgaag tcagtacctt tagcaaattg tggcttgatt    14280
ggagataagt ctaaaagaga gtcggatgca aagttacatg gtcttaagtt ggcgtacaat    14340
tgaagttctt tacggatttt tagtaaacct tgttcaggtc taacactacc ggtacccat     14400 ttaggaccac ccacagcacc taacaaaacg gcatcagcct tcttggaggc ttccagcgcc    14460
tcatctggaa gtggaacacc tgtagcatcg atagcagcac caccaattaa atgattttcg    14520
aaatcgaact tgacattgga acgaacatca gaaatagctt taagaacctt aatggcttcg    14580
gctgtgattt cttgaccaac gtggtcacct ggcaaaacga cgatcttctt aggggcagac    14640
attacaatgg tatatccttg aaatatatat aaaaaaaaaa aaaaaaaaaa aaaaaaaaa     14700 tgcagcttct caatgatatt cgaatacgct ttgaggagat acagcctaat atccgacaaa    14760
ctgttttaca gatttacgat cgtacttgtt acccatcatt gaattttgaa catccgaacc    14820
tgggagtttt ccctgaaaca gatagtatat ttgaacctgt ataataatat atagtctagc    14880
gctttacgga agacaatgta tgtatttcgg ttcctggaga aactattgca tctattgcat    14940
aggtaatctt gcacgtcgca tccccggttc attttctgcg tttccatctt gcacttcaat    15000
agcatatctt tgttaacgaa gcatctgtgc ttcattttgt agaacaaaaa tgcaacgcga    15060
gagcgctaat ttttcaaaca aagaatctga gctgcatttt tacagaacag aaatgcaacg    15120
cgaaagcgct attttaccaa cgaagaatct gtgcttcatt tttgtaaaac aaaaatgcaa    15180
cgcgagagcg ctaatttttc aaacaaagaa tctgagctgc atttttacag aacagaaatg    15240
caacgcgaga gcgcttatttt accaacaaag aatctatact tctttttttgt tctacaaaaa   15300 tgcatcccga gagcgctatt tttctaacaa agcatcttag attactttt ttctcctttg     15360 tgcgctctat aatgcagtct cttgataact ttttgcactg taggtccgtt aaggttagaa    15420
gaaggctact ttggtgtcta ttttctcttc cataaaaaaa gcctgactcc acttcccgcg    15480
tttactgatt actagcgaag ctgcgggtgc attttttcaa gataaaggca tccccgatta    15540
tattctatac cgatgtggat tgcgcatact tgtgaacag aaagtgatag cgttgatgat     15600
tcttcattgg tcagaaaatt atgaacggtt tcttctattt tgtctctata tactacgtat    15660
aggaaatgtt tacattttcg tattgttttc gattcactct atgaatagtt cttactacaa    15720 ttttttttgtc taaagagtaa tactagagat aaacataaaa aatgtagagg tcgagtttag    15780
atgcaagttc aaggagcgaa aggtggatgg gtaggttata tagggatata gcacagagat    15840
atatagcaaa gagatacttt tgagcaatgt ttgtggaagc ggtattcgca atattttagt    15900
agctcgttac agtccggtgc gttttttggtt ttttgaaagt gcgtcttcag agcgcttttg    15960
gttttcaaaa gcgctctgaa gttcctatac tttctagaga ataggaactt cggaatagga    16020
acttcaaagc gttccgaaaa cgagcgcttc cgaaaatgc aacgcgagct gcgcacatac     16080
agctcactgt tcacgtcgca cctatatctg cgtgttgcct gtatatatat atacatgaga    16140
agaacggcat agtgcgtgtt tatgcttaaa tgcgtactta tatgcgtcta tttatgtagg    16200
atgaaaggta gtctagtacc tcctgtgata ttatcccatt ccatgcgggg tatcgtatgc    16260
ttccttcagc actacccttt agctgttcta tatgctgcca ctcctcaatt ggattagtct    16320
catccttcaa tgctatcatt tcctttgata ttggatcata tgcatagtac cgagaaacta    16380
gaggatc                                                              16387
```

<210> SEQ ID NO 166
<211> LENGTH: 250
<212> TYPE: DNA

<213> ORGANISM: Saccharomyces cerevisiae

<400> SEQUENCE: 166

| | | |
|---|---|---|
| ccgcaaatta aagccttcga gcgtcccaaa accttctcaa gcaaggtttt cagtataatg | 60 |
| ttacatgcgt acacgcgtct gtacagaaaa aaagaaaaa tttgaaatat aaataacgtt | 120 |
| cttaatacta acataactat aaaaaaataa atagggacct agacttcagg ttgtctaact | 180 |
| ccttcctttt cggttagagc ggatgtgggg ggagggcgtg aatgtaagcg tgacataact | 240 |
| aattacatga | 250 |

<210> SEQ ID NO 167
<211> LENGTH: 1181
<212> TYPE: DNA
<213> ORGANISM: Saccharomyces cerevisiae

<400> SEQUENCE: 167

| | |
|---|---|
| taaaacctct agtggagtag tagatgtaat caatgaagcg gaagccaaaa gaccagagta | 60 |
| gaggcctata gaagaaactg cgatacccttt tgtgatggct aaacaaacag acatcttttt | 120 |
| atatgttttt acttctgtat atcgtgaagt agtaagtgat aagcgaattt ggctaagaac | 180 |
| gttgtaagtg aacaagggac ctcttttgcc tttcaaaaaa ggattaaatg gagttaatca | 240 |
| ttgagattta gttttcgtta gattctgtat ccctaaataa ctcccttacc cgacgggaag | 300 |
| gcacaaaaga cttgaataat agcaaacggc cagtagccaa gaccaaataa tactagagtt | 360 |
| aactgatggt cttaaacagg cattacgtgg tgaactccaa gaccaatata caaaatatcg | 420 |
| ataagttatt cttgcccacc aatttaagga gcctacatca ggacagtagt accattcctc | 480 |
| agagaagagg tatacataac aagaaaatcg cgtgaacacc ttatataact tagcccgtta | 540 |
| ttgagctaaa aaaccttgca aaatttccta tgaataagaa tacttcagac gtgataaaaa | 600 |
| tttactttct aactcttctc acgctgcccc tatctgttct tccgctctac cgtgagaaat | 660 |
| aaagcatcga gtacggcagt tcgctgtcac tgaactaaaa caataaggct agttcgaatg | 720 |
| atgaacttgc ttgctgtcaa acttctgagt tgccgctgat gtgacactgt gacaataaat | 780 |
| tcaaaccggt tatagcggtc tcctccggta ccggttctgc cacctccaat agagctcagt | 840 |
| aggagtcaga acctctgcgg tggctgtcag tgactcatcc gcgtttcgta agttgtgcgc | 900 |
| gtgcacattt cgcccgttcc cgctcatctt gcagcaggcg gaaattttca tcacgctgta | 960 |
| ggacgcaaaa aaaaaataat taatcgtaca agaatcttgg aaaaaaaatt gaaaaatttt | 1020 |
| gtataaaagg gatgacctaa cttgactcaa tggcttttac acccagtatt ttcccttttcc | 1080 |
| ttgtttgtta caattataga agcaagacaa aaacatatag acaacctatt cctaggagtt | 1140 |
| atattttttt accctaccag caatataagt aaaaaactag t | 1181 |

<210> SEQ ID NO 168
<211> LENGTH: 1014
<212> TYPE: DNA
<213> ORGANISM: artificial sequence
<220> FEATURE:
<223> OTHER INFORMATION: Mutant of Pseudomonas fluorescens ilvC coding region

<400> SEQUENCE: 168

| | |
|---|---|
| atgaaggtgt ttacgataaa agactgcgat ctgagcatca tccagggaaa gaaggttgct | 60 |
| attataggat atggttccca aggacacgca caagccttga acttgaaaga ttctggggtc | 120 |
| gacgtgacag taggtctgta taaaggtgct gctgatgcag caaaggctga agcacatggc | 180 |

```
tttaaagtca cagatgttgc agcggctgtt gctggcgctg atttagtcat gattttaatt    240
ccagatgaat ttcaatcgca attgtacaaa aatgaaatag aaccaaacat taagaagggc    300
gctaccttgg ccttcagtca tggatttgcc attcattaca atcaagtagt ccccagggca    360
gatttggacg ttattatgat tgcacctaag gctccggggc atactgttag gagcgaattt    420
gttaagggtg gtggtattcc agatttgatc gctatatacc aagacgttag cggaaacgct    480
aagaatgtag ctttaagcta cgcagcagga gttggtggcg ggagaacggg tataatagaa    540
accactttta aagacgagac tgagacagat ttatttggag aacaagcggt tctgtgcgga    600
ggaactgttg aattggttaa agcaggcttt gagacgcttg tcgaagcagg gtacgctccc    660
gaaatggcat acttcgaatg tctacatgaa ttgaagttga tagtagactt aatgtatgaa    720
ggtggtatag ctaatatgaa ctattccatt tcaaataatg cagaatatgg tgagtatgtc    780
accggacctg aagtcattaa cgcagaatca agacaagcca tgagaaatgc cttgaaacgt    840
atccaggacg tgaatacgc taagatgttc ataagtgaag cgctacggg ttacccgagt    900 atgactgcta aagaagaaa caatgcagca catggtatcg aaattattgg tgaacagtta    960
aggtctatga tgccctggat cggtgctaat aagatcgtag acaaggcgaa aaat          1014
```

<210> SEQ ID NO 169
<211> LENGTH: 338
<212> TYPE: PRT
<213> ORGANISM: artificial sequence
<220> FEATURE:
<223> OTHER INFORMATION: mutant of Pseudomonas fluorescens protein

<400> SEQUENCE: 169

```
Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Ala Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220
```

-continued

```
Phe Glu Cys Leu His Glu Leu Lys Leu Ile Val Asp Leu Met Tyr Glu
225                 230                 235                 240
Gly Gly Ile Ala Asn Met Asn Tyr Ser Ile Ser Asn Asn Ala Glu Tyr
            245                 250                 255
Gly Glu Tyr Val Thr Gly Pro Glu Val Ile Asn Ala Glu Ser Arg Gln
        260                 265                 270
Ala Met Arg Asn Ala Leu Lys Arg Ile Gln Asp Gly Glu Tyr Ala Lys
    275                 280                 285
Met Phe Ile Ser Glu Gly Ala Thr Gly Tyr Pro Ser Met Thr Ala Lys
290                 295                 300
Arg Arg Asn Asn Ala Ala His Gly Ile Glu Ile Ile Gly Glu Gln Leu
305                 310                 315                 320
Arg Ser Met Met Pro Trp Ile Gly Ala Asn Lys Ile Val Asp Lys Ala
                325                 330                 335
Lys Asn
```

<210> SEQ ID NO 170
<211> LENGTH: 759
<212> TYPE: DNA
<213> ORGANISM: Saccharomyces cerevisiae

<400> SEQUENCE: 170

```
ggccctgcag gcctatcaag tgctggaaac ttttttctctt ggaattttg caacatcaag        60
tcatagtcaa ttgaattgac ccaatttcac atttaagatt ttttttttttt catccgacat      120
acatctgtac actaggaagc cctgttttc tgaagcagct tcaaatatat atatttttta        180
catatttatt atgattcaat gaacaatcta attaaatcga aacaagaac cgaaacgcga         240
ataaataatt tatttagatg gtgacaagtg tataagtcct catcgggaca gctacgattt       300
ctctttcggt tttggctgag ctactggttg ctgtgacgca gcggcattag cgcggcgtta       360
tgagctaccc tcgtggcctg aaagatggcg ggaataaagc ggaactaaaa attactgact       420
gagccatatt gaggtcaatt tgtcaactcg tcaagtcacg tttggtggac ggccccttc        480
caacgaatcg tatatactaa catgcgcgcg cttcctatat acacatatac atatatatat      540
atatatatat gtgtgcgtgt atgtgtacac ctgtatttaa tttccttact cgcgggtttt       600
tcttttttct caattcttgg cttcctcttt ctcgagtata taattttca ggtaaaattt        660
agtacgatag taaatactt ctcgaactcg tcacatatac gtgtacataa tgtctgaacc        720
agctcaaaag aaacaaaagg ttgctaacaa ctctctaga                              759
```

<210> SEQ ID NO 171
<211> LENGTH: 15539
<212> TYPE: DNA
<213> ORGANISM: artificial sequence
<220> FEATURE:
<223> OTHER INFORMATION: constructed plasmid

<400> SEQUENCE: 171

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accataaatt cccgttttaa gagcttggtg agcgctagga gtcactgcca ggtatcgttt       240
gaacacggca ttagtcaggg aagtcataac acagtcctt cccgcaattt tctttttcta        300
ttactcttgg cctcctctag tacactctat attttttat gcctcggtaa tgattttcat       360
```

```
tttttttttt ccacctagcg gatgactctt ttttttcctt agcgattggc attatcacat       420
aatgaattat acattatata aagtaatgtg atttcttcga agaatatact aaaaaatgag       480
caggcaagat aaacgaaggc aaagatgaca gagcagaaag ccctagtaaa gcgtattaca       540
aatgaaacca agattcagat tgcgatctct ttaaagggtg gtcccctagc gatagagcac       600
tcgatcttcc cagaaaaaga ggcagaagca gtagcagaac aggccacaca atcgcaagtg       660
attaacgtcc acacaggtat agggtttctg gaccatatga tacatgctct ggccaagcat       720
tccggctggt cgctaatcgt tgagtgcatt ggtgacttac acatagacga ccatcacacc       780
actgaagact gcgggattgc tctcggtcaa gcttttaaag aggccctagg ggccgtgcgt       840
ggagtaaaaa ggtttggatc aggatttgcg ccttttggatg aggcactttc cagagcggtg       900
gtagatcttt cgaacaggcc gtacgcagtt gtcgaacttg gtttgcaaag ggagaaagta       960
ggagatctct cttgcgagat gatcccgcat tttcttgaaa gctttgcaga ggctagcaga      1020
attaccctcc acgttgattg tctgcgaggc aagaatgatc atcaccgtag tgagagtgcg      1080
ttcaaggctc ttgcggttgc cataagagaa gccacctcgc ccaatggtac caacgatgtt      1140
ccctccacca aaggtgttct tatgtagtga caccgattat ttaaagctgc agcatacgat      1200
atatatacat gtgtatatat gtataacctat gaatgtcagt aagtatgtat acgaacagta      1260
tgatactgaa gatgacaagg taatgcatca ttctatacgt gtcattctga acgaggcgcg      1320 cttttccttttt ttcttttttgc ttttttcttt ttttttctctt gaactcgacg gatctatgcg      1380
gtgtgaaata ccgcacagat gcgtaaggag aaaataccgc atcaggaaat tgtaagcgtt      1440
aatattttgt taaaattcgc gttaaatttt tgttaaatca gctcattttt taaccaatag      1500
gccgaaatcg gcaaaatccc ttataaatca aagaataga ccgagatagg gttgagtgtt      1560
gttccagttt ggaacaagag tccactatta agaacgtgg actccaacgt caaagggcga      1620
aaaaccgtct atcagggcga tggcccacta cgtgaaccat ccccctaatc aagttttttg      1680
gggtcgaggt gccgtaaagc actaaatcgg aaccctaaag ggagccccg atttagagct      1740 tgacggggaa agccggcgaa cgtggcgaga aggaaggga agaaagcgaa aggagcgggc      1800
gctagggcgc tggcaagtgt agcggtcacg ctgcgcgtaa ccaccacac cgccgcgctt      1860 aatgcgccgc tacagggcgc gtccattcgc cattcaggct gcgcaactgt tgggaagggc      1920
gcggtgcggg cctcttcgct attacgccag ctggcgaaag gggatgtgc tgcaaggcga      1980 ttaagttggg taacgccagg gttttcccag tcacgacgtt gtaaaacgac ggccagtgag      2040
cgcgcgtaat acgactcact ataggggcgaa ttgggtaccg gccccccct cgaggtcgac      2100 ggcgcgccac tggtagagag cgactttgta tgccccaatt gcgaaacccg cgatatcctt      2160
ctcgattctt tagtacccga ccaggacaag gaaaaggagg tcgaaacgtt tttgaagaaa      2220
caagaggaac tacacggaag ctctaaagat ggcaaccagc cagaaactaa gaaaatgaag      2280
ttgatggatc caactggcac cgctggcttg aacaacaata ccagccttcc aacttctgta      2340
aataacggcg gtacgccagt gccaccagta ccgttacctt tcggtatacc tccttttcccc      2400 atgtttccaa tgcccttcat gcctccaacg gctactatca caatcctca tcaagctgac      2460 gcaagccca agaaatgaat aacaatactg acagtactaa ataattgcct acttggcttc      2520
acatacgttg catacgtcga tatagataat aatgataatg acagcaggat tatcgtaata      2580
cgtaatagct gaaaatctca aaaatgtgtg ggtcattacg taaataatga taggaatggg      2640
attcttctat ttttccttttt tccattctag cagccgtcgg gaaaacgtgg catcctctct      2700
```

```
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa cttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccattttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag ctgcggtgg   3720 tatgtatact gctaacacaa tggcgacagc tattgaagtt ttgggactta gccttccggg   3780
ttcatcttct caccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggg tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca agtttctgg   4320 tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttcccctt tcatcaatga ttgttggtaa   4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttcactttg atatctccga   4680 tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaaatgttg tcctggttgc tgtggttaag cggccgcgtt   4860
aattcaaatt aattgatata gttttttaat gagtattgaa tctgtttaga aataatggaa   4920
tattattttt atttatttat ttatattatt ggtcggctct tttcttctga aggtcaatga   4980
caaaatgata tgaaggaaat aatgatttct aaaattttac aacgtaagat atttttacaa   5040
aagcctagct catctttgt catgcactat tttactcacg cttgaaatta acggccagtc   5100
```

```
cactgcggag tcatttcaaa gtcatcctaa tcgatctatc gttttgata gctcattttg    5160 gagttcgcga ttgtcttctg ttattcacaa ctgttttaat ttttatttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tcttttaact    5340
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg gacgtgtcac tctacttcgc cttttccct actcctttta    5580 gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760 tgattttga tattgtataa aaaaaccaaa tatgtataaa aaagtgaat aaaaaatacc    5820 aagtatggag aaatatatta gaagtctata cgttaaacca cccgggcccc ccctcgaggt    5880
cgacggtatc gataagcttg atatcgaatt cctgcagccc gggggatcca ctagttctag    5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat ttttttata acttatttaa    6240 taataaaaat cataaatcat aagaaattcg cttactctta attaatcaaa aagttaaaat    6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttaatctctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaccctg    6840 tgtaaccttt gcaactttaa ctgcggaacc gtaacggtg gaaaatccgc accctatcaa    6900
gcaaactttt tccagtggtg aagctgcatc gattttagcg acagatatct cgtccaccac    6960
tgtgtattgg gaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc    7380
tttacactta ataactttac cggctgttga catcctcagc tagctattgt aatatgtgtg    7440
```

```
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt ttccatcagc    7740
tggcagggaa cggaaagtgg aatcccattt agcgagcttc ctctttttctt caagaaaaga    7800 cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtcttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atcctttcca    8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagattttta    8640
catttctggt gttgaaggga aagatatgag ctatacagcg gaatttccat atcactcaga    8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt ttttttcatgt agatgatact gactgcacgc aaatataggc atgatttata    8880
ggcatgattt tgatggctgta ccgataggaa cgctaagagt aacttcagaa tcgttatcct    8940
ggcggaaaaa attcatttgt aaactttaaa aaaaaagcc aatatcccca aaattattaa    9000
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta aatgcaagat ttaaagtaaa ttcacggccc    9240
tgcaggcctc agctcttgtt ttgttctgca aataacttac ccatcttttt caaaacttta    9300
ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaagaag tgccttgttc agccacgatc    9780
gtctcattac tttgggtcaa attttcgaca gcttgccaca gtctatcttg tgacaacagc    9840
```

```
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg ttttttcagcc   10380
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agccttttcc gttcttgcgt acccgtcggc catataggag   10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca atacctaccg tctttatata   11040
cttattagtc aagtagggga ataatttcag ggaactggtt tcaacctttt ttttcagctt   11100
tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt ttttttgcctg tttgtgcccc tgttctctgt agttgcgcta agagaatgga   11280
cctatgaact gatggttggt gaagaaaaca atattttggt gctgggattc tttttttttc   11340
tggatgccag cttaaaaagc gggctccatt atatttagtg gatgccagga ataaactgtt   11400
cacccagaca cctacgatgt tatatattct gtgtaacccg ccccctattt tgggcatgta   11460
cgggttacag cagaattaaa aggctaattt tttgactaaa taaagttagg aaaatcacta   11520
ctattaatta tttacgtatt ctttgaaatg gcagtattga taatgataaa ctcgaactga   11580
aaaagcgtgt ttttttattca aaatgattct aactcccctta cgtaatcaag gaatcttttt   11640
gccttggcct ccgcgtcatt aaacttcttg ttgttgacgc taacattcaa cgctagtata   11700
tattcgtttt tttcaggtaa gttctttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
acaaggtcct cgaaaatagg gcgcgcccca ccgcggtgga gctccagctt ttgttcccctt   11940
tagtgagggt taattgcgcg cttggcgtaa tcatggtcat agctgtttcc tgtgtgaaat   12000
tgttatccgc tcacaattcc acacaacata cgagccggaa gcataaagtg taaagcctgg   12060
ggtgcctaat gagtgagcta actcacatta attgcgttgc gctcactgcc cgctttccag   12120
tcgggaaacc tgtcgtgcca gctgcattaa tgaatcggcc aacgcgcggg gagaggcggt   12180
```

-continued

```
ttgcgtattg ggcgctcttc cgcttcctcg ctcactgact cgctgcgctc ggtcgttcgg    12240
ctgcggcgag cggtatcagc tcactcaaag gcggtaatac ggttatccac agaatcaggg    12300
gataacgcag gaaagaacat gtgagcaaaa ggccagcaaa aggccaggaa ccgtaaaaag    12360
gccgcgttgc tggcgttttt ccataggctc cgcccccctg acgagcatca caaaaatcga    12420
cgctcaagtc agaggtggcg aaacccgaca ggactataaa gataccaggc gtttccccct    12480
ggaagctccc tcgtgcgctc tcctgttccg accctgccgc ttaccggata cctgtccgcc    12540
tttctccctt cgggaagcgt ggcgctttct catagctcac gctgtaggta tctcagttcg    12600
gtgtaggtcg ttcgctccaa gctgggctgt gtgcacgaac cccccgttca gcccgaccgc    12660
tgcgccttat ccggtaacta tcgtcttgag tccaacccgg taagacacga cttatcgcca    12720
ctggcagcag ccactggtaa caggattagc agagcgaggt atgtaggcgg tgctacagag    12780
ttcttgaagt ggtggcctaa ctacggctac actagaagaa cagtatttgg tatctgcgct    12840
ctgctgaagc cagttacctt cggaaaaaga gttggtagct cttgatccgg caaacaaacc    12900
accgctggta gcggtggttt ttttgtttgc aagcagcaga ttacgcgcag aaaaaaagga    12960
tctcaagaag atcctttgat cttttctacg gggtctgacg ctcagtggaa cgaaaactca    13020
cgttaaggga ttttggtcat gagattatca aaaaggatct tcacctagat ccttttaaat    13080
taaaaatgaa gttttaaatc aatctaaagt atatatgagt aaacttggtc tgacagttac    13140
caatgcttaa tcagtgaggc acctatctca gcgatctgtc tatttcgttc atccatagtt    13200
gcctgactcc ccgtcgtgta gataactacg atacgggagg gcttaccatc tggccccagt    13260
gctgcaatga taccgcgaga cccacgctca ccggctccag atttatcagc aataaaccag    13320
ccagccggaa gggccgagcg cagaagtggt cctgcaactt tatccgcctc catccagtct    13380
attaattgtt gccgggaagc tagagtaagt agttcgccag ttaatagttt gcgcaacgtt    13440
gttgccattg ctacaggcat cgtggtgtca cgctcgtcgt ttggtatggc ttcattcagc    13500
tccggttccc aacgatcaag gcgagttaca tgatccccca tgttgtgcaa aaaagcggtt    13560
agctccttcg gtcctccgat cgttgtcaga agtaagttgg ccgcagtgtt atcactcatg    13620
gttatggcag cactgcataa ttctcttact gtcatgccat ccgtaagatg cttttctgtg    13680
actggtgagt actcaaccaa gtcattctga gaatagtgta tgcggcgacc gagttgctct    13740
tgcccggcgt caatacggga taataccgcg ccacatagca gaactttaaa agtgctcatc    13800
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttcctttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt ttgtagaaca    14160
aaaatgcaac gcgagagcgc taattttca acaaagaat ctgagctgca tttttacaga    14220
acagaaatgc aacgcgaaag cgctatttta ccaacgaaga atctgtgctt cattttttgta    14280 aaacaaaaat gcaacgcgag agcgctaatt tttcaaacaa agaatctgag ctgcatttttt    14340 acagaacaga aatgcaacgc gagagcgcta ttttaccaac aaagaatcta acttcttttt    14400
ttgttctaca aaaatgcatc ccgagagcgc tattttttcta acaaagcatc ttagattact    14460
ttttttctcc tttgtgcgct ctataatgca gtctcttgat aacttttgc actgtaggtc    14520 cgttaaggtt agaagaaggc tactttggtg tctattttct cttccataaa aaaagcctga    14580
```

| | | | |
|---|---|---|---|
| ctccacttcc | cgcgtttact | gattactagc gaagctgcgg | gtgcattttt tcaagataaa | 14640 |
| ggcatcccg | attatattct | ataccgatgt ggattgcgca | tactttgtga acagaaagtg | 14700 |
| atagcgttga | tgattcttca | ttggtcagaa aattatgaac | ggtttcttct attttgtctc | 14760 |
| tatatactac | gtataggaaa | tgtttacatt ttcgtattgt | tttcgattca ctctatgaat | 14820 |
| agttcttact | acaatttttt | tgtctaaaga gtaatactag | agataaacat aaaaaatgta | 14880 |
| gaggtcgagt | ttagatgcaa | gttcaaggag cgaaaggtgg | atgggtaggt tatataggga | 14940 |
| tatagcacag | agatatatag | caaagagata cttttgagca | atgtttgtgg aagcggtatt | 15000 |
| cgcaatattt | tagtagctcg | ttacagtccg gtgcgttttt | ggttttttga agtgcgtct | 15060 |
| tcagagcgct | tttggttttc | aaaagcgctc tgaagttcct | atactttcta gagaatagga | 15120 |
| acttcggaat | aggaacttca | aagcgtttcc gaaaacgagc | gcttccgaaa atgcaacgcg | 15180 |
| agctgcgcac | atacagctca | ctgttcacgt cgcacctata | tctgcgtgtt gcctgtatat | 15240 |
| atatatacat | gagaagaacg | gcatagtgcg tgtttatgct | taaatgcgta cttatatgcg | 15300 |
| tctatttatg | taggatgaaa | ggtagtctag tacctcctgt | gatattatcc cattccatgc | 15360 |
| ggggtatcgt | atgcttcctt | cagcactacc ctttagctgt | tctatatgct gccactcctc | 15420 |
| aattggatta | gtctcatcct | tcaatgctat catttccttt | gatattggat catactaaga | 15480 |
| aaccattatt | atcatgacat | taacctataa aaataggcgt | atcacgaggc cctttcgtc | 15539 |

<210> SEQ ID NO 172
<211> LENGTH: 1644
<212> TYPE: DNA
<213> ORGANISM: artificial sequence
<220> FEATURE:
<223> OTHER INFORMATION: Bacillus subtilis kivD coding region codon
      optimized for expression is S. cerevisiae

<400> SEQUENCE: 172

| | | | |
|---|---|---|---|
| atgtatacag | taggtgacta | tctgttggac agattacacg | aattaggtat agaagaaata | 60 |
| ttcggagtac | caggtgacta | caatttgcaa tttctagatc | aaattatttc acacaaagat | 120 |
| atgaaatggg | tgggaaatgc | taatgagtta atgcctcct | atatggccga cgggtacgca | 180 |
| agaacgaaaa | aggctgcggc | attcttgact acatttggtg | ttggcgaatt atccgcagtt | 240 |
| aatggcttag | cgggctccta | tgctgagaac ctgcctgttg | ttgagatcgt gggatctcct | 300 |
| acctcgaaag | tgcagaacga | aggtaagttt gttcaccata | cgttggctga tggtgatttc | 360 |
| aagcacttta | tgaagatgca | cgaaccggtt actgctgcca | ggactttatt gacagccgag | 420 |
| aatgcaactg | ttgaaattga | tagtgtgttg tctgccttac | taaaggaaag aaagccggtt | 480 |
| tacatcaatt | tacctgtaga | tgtagctgcc gctaaggctg | aaaaaccatc cttgcctctt | 540 |
| aagaaggaaa | attccacgtc | gaatacatct gatcaagaga | ttctgaacaa atacaggaa | 600 |
| agtctgaaga | atgccaagaa | accaattgta atcacaggcc | atgaaattat atcgttcggc | 660 |
| ctagagaaga | ctgttactca | gtttatttca aagactaagt | tacctattac tactttgaac | 720 |
| tttggtaaat | catctgttga | tgaagcattg ccctcatttt | tggggattta caacggtact | 780 |
| ctgtcagagc | caaacttgaa | ggaatttgtg gaatctgctg | attttattct tatgttgggt | 840 |
| gtaaagctta | ccgattctag | tacgggtgca tttactcacc | atcttaatga aaataaaatg | 900 |
| atttccttga | atatcgatga | aggtaaaatt ttcaacgaaa | gaatccaaaa tttcgacttc | 960 |
| gaatccctga | tatcatctct | tcttgacttg tccgaaattg | aatataaagg caagtacata | 1020 |
| gataaaaagc | aagaagattt | tgtaccttct aacgcgctgt | tgtcacaaga tagactgtgg | 1080 |

```
caagctgtcg aaaatttgac ccaaagtaat gagacgatcg tggctgaaca aggcacttct   1140
ttcttcggtg cctcatctat atttctgaaa tcgaaatcac attttattgg tcaacccttg   1200
tggggatcta taggatacac tttccccgca gctctaggca gccaaattgc agataaagaa   1260
tctagacatt tattgtttat cggagatgga tcattgcaac tgactgtcca agaattagga   1320
ctagccatta gagagaagat aaacccaatc tgctttatca ttaataacga tggttacacg   1380
gttgagaggg aaattcatgg tccgaaccag agttataatg acattcctat gtggaattac   1440
tcaaaactgc agaaagttt cggggcaacg aagacagag ttgtgtccaa aattgtgaga    1500
acagaaaatg aattcgtatc cgtgatgaaa gaagctcaag cagatccaaa taggatgtat   1560
tggatagaac ttattctagc aaaggagggt gcacctaaag ttttgaaaaa gatgggtaag   1620
ttatttgcag aacaaaacaa gagc                                         1644
```

<210> SEQ ID NO 173
<211> LENGTH: 548
<212> TYPE: PRT
<213> ORGANISM: Bacillus subtilis

<400> SEQUENCE: 173

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270
```

```
Ala Asp Phe Ile Leu Met Leu Gly Val Lys Leu Thr Asp Ser Ser Thr
            275                 280                 285
Gly Ala Phe Thr His His Leu Asn Glu Asn Lys Met Ile Ser Leu Asn
        290                 295                 300
Ile Asp Glu Gly Lys Ile Phe Asn Glu Arg Ile Gln Asn Phe Asp Phe
305                 310                 315                 320
Glu Ser Leu Ile Ser Ser Leu Leu Asp Leu Ser Glu Ile Glu Tyr Lys
                325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
        355                 360                 365
Ser Asn Glu Thr Ile Val Ala Glu Gln Gly Thr Ser Phe Phe Gly Ala
    370                 375                 380
Ser Ser Ile Phe Leu Lys Ser Lys Ser His Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ala Ile Arg Glu Lys Ile Asn
        435                 440                 445
Pro Ile Cys Phe Ile Ile Asn Asn Asp Gly Tyr Thr Val Glu Arg Glu
    450                 455                 460
Ile His Gly Pro Asn Gln Ser Tyr Asn Asp Ile Pro Met Trp Asn Tyr
465                 470                 475                 480
Ser Lys Leu Pro Glu Ser Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Pro Asn Arg Met Tyr Trp Ile Glu Leu Ile Leu Ala Lys
        515                 520                 525
Glu Gly Ala Pro Lys Val Leu Lys Lys Met Gly Lys Leu Phe Ala Glu
    530                 535                 540
Gln Asn Lys Ser
545

<210> SEQ ID NO 174
<211> LENGTH: 1125
<212> TYPE: DNA
<213> ORGANISM: artificial sequence
<220> FEATURE:
<223> OTHER INFORMATION: horse ADH coding region codon optimized for
      S. cerevisiae expression

<400> SEQUENCE: 174
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactg tcgtcctggt gataaagtg atcccactgt tcactcctca atgtggtaag     300
tgtagagtct gcaaacatcc tgagggtaat ttctgcctta aaaatgattt gtctatgcct     360
agaggtacta tgcaggatgg tacaagcaga tttacatgca gagggaaacc tatacaccat     420
```

-continued

```
ttccttggta cttctacatt ttcccaatac acagtggtgg acgagatatc tgtcgctaaa      480
atcgatgcag cttcaccact ggaaaaagtt tgcttgatag ggtgcggatt ttccaccggt      540
tacggttccg cagttaaagt tgcaaaggtt acacagggtt cgacttgtgc agtattcggt      600
ttaggaggag taggactaag cgttattatg gggtgtaaag ctgcaggcgc agcgaggatt      660
ataggtgtag acatcaataa ggacaaattt gcaaaagcta aggaggtcgg ggctactgaa      720
tgtgttaacc ctcaagatta taagaaacca atacaagaag tccttactga aatgtcaaac      780
ggtggagttg atttctcttt tgaagttata ggccgtcttg atactatggt aactgcgttg      840
tcctgctgtc aagaggcata tggagtcagt gtgatcgtag gtgttcctcc tgattcacaa      900
aatttgtcga tgaatcctat gctgttgcta agcggtcgta catggaaggg agctatattt      960
ggcggtttta agagcaagga tagtgttcca aaacttgttg ccgactttat ggcgaagaag      1020
tttgctcttg atcctttaat tacacatgta ttgccattcg agaaaatcaa tgaagggttt      1080
gatttgttaa gaagtggtga atctattcgt acaattttaa cttt                      1125
```

<210> SEQ ID NO 175
<211> LENGTH: 375
<212> TYPE: PRT
<213> ORGANISM: Equus caballus

<400> SEQUENCE: 175

```
Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
```

```
                   245                 250                 255
Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375

<210> SEQ ID NO 176
<211> LENGTH: 9089
<212> TYPE: DNA
<213> ORGANISM: artificial sequence
<220> FEATURE:
<223> OTHER INFORMATION: constructed plasmid

<400> SEQUENCE: 176
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataccac agcttttcaa ttcaattcat cattttttt ttattctttt ttttgatttc     240
ggtttctttg aaatttttt gattcggtaa tctccgaaca aaggaagaa cgaaggaagg     300 agcacagact tagattggta tatatacgca tatgtagtgt tgaagaaaca tgaaattgcc     360
cagtattctt aacccaactg cacagaacaa aaacctgcag gaaacgaaga taaatcatgt     420
cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaaacacatg     600
tggatatctt gactgatttt tccatggagg gcacagttaa gccgctaaag gcattatccg     660
ccaagtacaa tttttactc ttcgaagaca gaaaatttgc tgacattggt aatacagtca     720
aattgcagta ctctgcgggt gtatacgaa tagcagaatg gcagacatt acgaatgcac     780 acggtgtggt gggcccaggt attgttagcg gtttgaagca ggcggcagaa gaagtaacaa     840
aggaacctag aggccttttg atgttagcag aattgtcatg caagggctcc ctatctactg     900
gagaatatac taagggtact gttgacattg cgaagagcga caaagatttt gttatcggct     960
ttattgctca agagacatg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaagggaa    1140 gggatgctaa ggtagagggt gaacgttaca gaaaagcagg ctgggaagca tatttgaaa    1200 gatgcggcca gcaaaactaa aaaactgtat tataagtaaa tgcatgtata ctaaactcac    1260
aaattagagc ttcaatttaa ttatatcagt tattacccta tgcggtgtga aataccgcac    1320
```

```
agatgcgtaa ggagaaaata ccgcatcagg aaattgtaaa cgttaatatt ttgttaaaat    1380
tcgcgttaaa tttttgttaa atcagctcat tttttaacca ataggccgaa atcggcaaaa    1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg ggcccccct cgaggtcgac tggccattaa    2040
tctttcccat attagatttc gccaagccat gaaagttcaa gaaaggtctt tagacgaatt    2100
acccttcatt tctcaaactg gcgtcaaggg atcctggtat ggttttatcg ttttatttct    2160
ggttcttata gcatcgtttt ggacttctct gttcccatta ggcggttcag gagccagcgc    2220
agaatcattc tttgaaggat acttatcctt tccaattttg attgtctgtt acgttggaca    2280
taaactgtat actagaaatt ggactttgat ggtgaaacta aagatatgg atcttgatac    2340 cggcagaaaa caagtagatt tgactcttcg tagggaagaa atgaggattg agcgagaaac    2400
attagcaaaa agatccttcg taacaagatt tttacatttc tggtgttgaa gggaaagata    2460
tgagctatac agcggaattt ccatatcact cagattttgt tatctaattt tttccttccc    2520
acgtccgcgg gaatctgtgt atattactgc atctagatat atgttatctt atcttggcgc    2580
gtacatttaa ttttcaacgt attctataag aaattgcggg agttttttc atgtagatga    2640 tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaaga    2880 caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tcttttttccg cgatacaagg aagattgttg tcaaacgaac aaccttcaat    3660
```

```
aatgcttctg ccggccttct cgatatctgc tgtatcgtct acaataaccg gaggattacc    3720
cgcgccagct ccgatggcct ttttaccaga attaagaagg ttttttacca tacccgggcc    3780
acccgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca ctttttggcg catgggtgac cattaaatac    3960
aactgcattc cccgcagcta tcatacctat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt atttcggtga ttattttctc    4260
tctttgttcc tttgtgtagt gtagggaaag aatcttttgt gcatgtactg cagaagaaat    4320
ggcattctca acattttcaa atactccaaa acatgaagag ttatctttgt aattctttaa    4380
gttgatgttt tcaccattag tcttcacttt caagtctttg gtggttggga ttaaggtatc    4440
tttatccatg gtgtttgttt atgtgtgttt attcgaaact aagttcttgg tgttttaaaa    4500
ctaaaaaaaa gactaactat aaaagtagaa tttaagaagt ttaagaaata gatttacaga    4560
attacaatca ataccaccg tctttatata cttattagtc aagtagggga ataatttcag    4620
ggaactggtt tcaacctttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt ttttgcctg tttgtgcccc     4800
tgttctctgt agttgcgcta agagaatgga cctatgaact gatggttggt gaagaaaaca    4860
atattttggt gctgggattc ttttttttc tggatgccag cttaaaaagc gggctccatt     4920
atatttagtg gatgccagga ataaactgtt cacccagaca cctacgatgt tatatattct    4980
gtgtaacccg ccccctattt tgggcatgta cgggttacag cagaattaaa aggctaattt    5040
tttgactaaa taaagttagg aaaatcacta ctattaatta tttacgtatt ctttgaaatg    5100
gcagtattga taatgataaa ctcgaactga aaaagcgtgt ttttattca aaatgattct     5160
aactccctta cgtaatcaag gaatcttttt gccttggcct ccgcgtcatt aaacttcttg    5220
ttgttgacgc taacattcaa cgctagtata tattcgtttt tttcaggtaa gttcttttca    5280
acgggtctta ctgatgaggc agtcgcgtct gaacctgtta agaggtcaaa tatgtcttct    5340
tgaccgtacg tgtcttgcat gttattagct ttgggaattt gcatcaagtc ataggaaaat    5400
ttaaatcttg gctctcttgg gctcaaggtg acaaggtcct cgaaaatagg gcgcgcccca    5460
ccgcggtgga gctccagctt ttgttccctt tagtgagggt taattgcgcg cttggcgtaa    5520
tcatggtcat agctgtttcc tgtgtgaaat tgttatccgc tcacaattcc acacaacata    5580
ggagccggaa gcataaagtg taaagcctgg ggtgcctaat gagtgaggta actcacatta    5640
attgcgttgc gctcactgcc cgcttttcag tcgggaaacc tgtcgtgcca gctgcattaa    5700
tgaatcggcc aacgcgcggg gagaggcggt ttgcgtattg ggcgctcttc cgcttcctcg    5760
ctcactgact cgctgcgctc ggtcgttcgg ctgcggcgag cggtatcagc tcactcaaag    5820
gcggtaatac ggttatccac agaatcaggg gataacgcag gaaagaacat gtgagcaaaa    5880
ggccagcaaa aggccaggaa ccgtaaaaag gccgcgttgc tggcgttttt ccataggctc    5940
cgcccccctg acgagcatca caaaaatcga cgctcaagtc agaggtggcg aaacccgaca    6000
ggactataaa gataccaggc gtttccccct ggaagctccc tcgtgcgctc tcctgttccg    6060
```

```
accctgccgc ttaccggata cctgtccgcc tttctccctt cgggaagcgt ggcgctttct    6120
catagctcac gctgtaggta tctcagttcg gtgtaggtcg ttcgctccaa gctgggctgt    6180
gtgcacgaac cccccgttca gcccgaccgc tgcgccttat ccggtaacta tcgtcttgag    6240
tccaacccgg taagacacga cttatcgcca ctggcagcag ccactggtaa caggattagc    6300
agagcgaggt atgtaggcgg tgctacagag ttcttgaagt ggtggcctaa ctacggctac    6360
actagaagga cagtatttgg tatctgcgct ctgctgaagc cagttacctt cggaaaaaga    6420
gttggtagct cttgatccgg caaacaaacc accgctggta gcggtggttt ttttgtttgc    6480
aagcagcaga ttacgcgcag aaaaaaagga tctcaagaag atcctttgat cttttctacg    6540
gggtctgacg ctcagtggaa cgaaaactca cgttaaggga ttttggtcat gagattatca    6600
aaaaggatct tcacctagat ccttttaaat taaaaatgaa gttttaaatc aatctaaagt    6660
atatatgagt aaacttggtc tgacagttac caatgcttaa tcagtgaggc acctatctca    6720
gcgatctgtc tatttcgttc atccatagtt gcctgactcc ccgtcgtgta gataactacg    6780
atacgggagg gcttaccatc tggccccagt gctgcaatga taccgcgaga cccacgctca    6840
ccggctccag atttatcagc aataaaccag ccagccggaa gggccgagcg cagaagtggt    6900
cctgcaactt tatccgcctc catccagtct attaattgtt gccgggaagc tagagtaagt    6960
agttcgccag ttaatagttt gcgcaacgtt gttgccattg ctacaggcat cgtggtgtca    7020
cgctcgtcgt ttggtatggc ttcattcagc tccggttccc aacgatcaag gcgagttaca    7080
tgatccccca tgttgtgcaa aaaagcggtt agctccttcg gtcctccgat cgttgtcaga    7140
agtaagttgg ccgcagtgtt atcactcatg gttatggcag cactgcataa ttctcttact    7200
gtcatgccat ccgtaagatg cttttctgtg actggtgagt actcaaccaa gtcattctga    7260
gaatagtgta tgcggcgacc gagttgctct tgcccggcgt caatacggga taataccgcg    7320
ccacatagca gaactttaaa agtgctcatc attggaaaac gttcttcggg gcgaaaactc    7380
tcaaggatct taccgctgtt gagatccagt tcgatgtaac ccactcgtgc acccaactga    7440
tcttcagcat cttttacttt caccagcgtt tctgggtgag caaaaacagg aaggcaaaat    7500
gccgcaaaaa agggaataag ggcgacacgg aaatgttgaa tactcatact cttcctttt    7560 caatattatt gaagcattta tcagggttat tgtctcatga gcggatacat atttgaatgt    7620
atttagaaaa ataaacaaat aggggttccg cgcacatttc cccgaaaagt gccacctgaa    7680
cgaagcatct gtgcttcatt tgtagaaca aaaatgcaac gcgagagcgc taattttca    7740 aacaaagaat ctgagctgca tttttacaga acagaaatgc aacgcgaaag cgctatttta    7800
ccaacgaaga atctgtgctt cattttgta aaacaaaaat gcaacgcgag agcgctaatt    7860
tttcaaacaa agaatctgag ctgcattttt acagaacaga atgcaacgc gagagcgcta    7920 ttttaccaac aaagaatcta tacttctttt tgttctaca aaatgcatc ccgagagcgc    7980 tattttctca caaagcatc ttagattact tttttctcc tttgtgcgct ctataatgca    8040
gtctcttgat aacttttgc actgtaggtc cgttaaggtt agaagaaggc tactttggtg    8100
tctattttct cttccataaa aaagcctga ctccacttcc cgcgtttact gattactagc    8160
gaagctgcgg gtgcatttt tcaagataaa ggcatcccg attatattct ataccgatgt    8220
ggattgcgca tactttgtga acagaaagtg atagcgttga tgattcttca ttggtcagaa    8280
aattatgaac ggtttcttct attttgtctc tatatactac gtataggaaa tgtttacatt    8340
ttcgtattgt tttcgattca ctctatgaat agttcttact acaattttt tgtctaaaga    8400
```

-continued

```
gtaatactag agataaacat aaaaaatgta gaggtcgagt ttagatgcaa gttcaaggag    8460
cgaaaggtgg atgggtaggt tatataggga tatagcacag agatatatag caaagagata    8520
cttttgagca atgtttgtgg aagcggtatt cgcaatattt tagtagctcg ttacagtccg    8580
gtgcgttttt ggttttttga aagtgcgtct tcagagcgct tttggttttc aaaagcgctc    8640
tgaagttcct atactttcta gagaatagga acttcggaat aggaacttca aagcgtttcc    8700
gaaaacgagc gcttccgaaa atgcaacgcg agctgcgcac atacagctca ctgttcacgt    8760
cgcacctata tctgcgtgtt gcctgtatat atatatacat gagaagaacg gcatagtgcg    8820
tgtttatgct aaatgcgta cttatatgcg tctatttatg taggatgaaa ggtagtctag    8880
tacctcctgt gatattatcc cattccatgc ggggtatcgt atgcttcctt cagcactacc    8940
ctttagctgt tctatatgct gccactcctc aattggatta gtctcatcct tcaatgctat    9000
catttccttt gatattggat catactaaga aaccattatt atcatgacat taacctataa    9060
aaataggcgt atcacgaggc cctttcgtc                                      9089
```

<210> SEQ ID NO 177
<211> LENGTH: 1023
<212> TYPE: DNA
<213> ORGANISM: Saccharomyces cerevisiae

<400> SEQUENCE: 177

```
caccgcggtg gggcgcgccc tattttcgag gaccttgtca ccttgagccc aagagagcca      60
agatttaaat tttcctatga cttgatgcaa attcccaaag ctaataacat gcaagacacg     120
tacggtcaag aagacatatt tgacctctta acaggttcag acgcgactgc ctcatcagta     180
agacccgttg aaaagaactt acctgaaaaa acgaatata tactagcgtt gaatgttagc      240
gtcaacaaca agaagtttaa tgacgcggag gccaaggcaa aaagattcct tgattacgta     300
agggagttag aatcattttg aataaaaaac acgcttttc agttcgagtt tatcattatc      360
aatactgcca tttcaaagaa tacgtaaata attaatagta gtgattttcc taactttatt    420
tagtcaaaaa attagccttt taattctgct gtaacccgta catgcccaaa ataggggggcg    480
ggttacacag aatatataac atcgtaggtg tctgggtgaa cagtttattc ctggcatcca    540
ctaaatataa tggagcccgc ttttaagct ggcatccaga aaaaaaaga atcccagcac     600
caaaatattg ttttcttcac caaccatcag ttcataggtc cattctctta gcgcaactac    660
agagaacagg ggcacaaaca ggcaaaaaac gggcacaacc tcaatggagt gatgcaacct    720
gcctggagta aatgatgaca caaggcaatt gacccacgca tgtatctatc tcattttctt    780
acaccttcta ttaccttctg ctctctctga tttggaaaaa gctgaaaaaa aaggttgaaa    840
ccagttccct gaaattattc ccctacttga ctaataagta tataaagacg gtaggtattg    900
attgtaattc tgtaaatcta tttcttaaac ttcttaaatt ctacttttat agttagtctt    960
tttttagtt taaaacacc aagaacttag tttcgaataa acacacataa actagtaaac   1020
aaa                                                                 1023
```

<210> SEQ ID NO 178
<211> LENGTH: 21
<212> TYPE: DNA
<213> ORGANISM: artificial sequence
<220> FEATURE:
<223> OTHER INFORMATION: primer

<400> SEQUENCE: 178

```
caaaagctga gctccaccgc g                                              21
```

<210> SEQ ID NO 179
<211> LENGTH: 44
<212> TYPE: DNA
<213> ORGANISM: artificial sequence
<220> FEATURE:
<223> OTHER INFORMATION: primer

<400> SEQUENCE: 179

| | |
|---|---|
| gtttactagt ttatgtgtgt ttattcgaaa ctaagttctt ggtg | 44 |

<210> SEQ ID NO 180
<211> LENGTH: 8994
<212> TYPE: DNA
<213> ORGANISM: artificial sequence
<220> FEATURE:
<223> OTHER INFORMATION: constructed plasmid

<400> SEQUENCE: 180

| | |
|---|---|
| ctagttctag agcggccgcc accgcggtgg agctccagct tttgttccct ttagtgaggg | 60 |
| ttaattgcgc gcttggcgta atcatggtca tagctgtttc ctgtgtgaaa ttgttatccg | 120 |
| ctcacaattc cacacaacat aggagccgga agcataaagt gtaaagcctg gggtgcctaa | 180 |
| tgagtgaggt aactcacatt aattgcgttg cgctcactgc ccgctttcca gtcgggaaac | 240 |
| ctgtcgtgcc agctgcatta atgaatcggc caacgcgcgg ggagaggcgg tttgcgtatt | 300 |
| gggcgctctt ccgcttcctc gctcactgac tcgctgcgct cggtcgttcg ctgcggcga | 360 |
| gcggtatcag ctcactcaaa ggcggtaata cggttatcca cagaatcagg ggataacgca | 420 |
| ggaaagaaca tgtgagcaaa aggccagcaa aaggccagga accgtaaaaa ggccgcgttg | 480 |
| ctggcgtttt tccataggct ccgcccccct gacgagcatc acaaaaatcg acgctcaagt | 540 |
| cagaggtggc gaaacccgac aggactataa agataccagg cgtttccccc tggaagctcc | 600 |
| ctcgtgcgct ctcctgttcc gaccctgccg cttaccggat acctgtccgc ctttctccct | 660 |
| tcgggaagcg tggcgctttc tcatagctca cgctgtaggt atctcagttc ggtgtaggtc | 720 |
| gttcgctcca agctgggctg tgtgcacgaa ccccccgttc agcccgaccg ctgcgcctta | 780 |
| tccggtaact atcgtcttga gtccaacccg gtaagacacg acttatcgcc actggcagca | 840 |
| gccactggta acaggattag cagagcgagg tatgtaggcg gtgctacaga gttcttgaag | 900 |
| tggtggccta actacggcta cactagaagg acagtatttg gtatctgcgc tctgctgaag | 960 |
| ccagttacct tcggaaaaag agttggtagc tcttgatccg gcaaacaaac caccgctggt | 1020 |
| agcggtggtt tttttgtttg caagcagcag attacgcgca gaaaaaaagg atctcaagaa | 1080 |
| gatcctttga tcttttctac ggggtctgac gctcagtgga acgaaaactc acgttaaggg | 1140 |
| attttggtca tgagattatc aaaaaggatc ttcacctaga tccttttaaa ttaaaaatga | 1200 |
| agttttaaat caatctaaag tatatatgag taaacttggt ctgacagtta ccaatgctta | 1260 |
| atcagtgagg cacctatctc agcgatctgt ctatttcgtt catccatagt tgcctgactc | 1320 |
| cccgtcgtgt agataactac gatacgggag ggcttaccat ctggccccag tgctgcaatg | 1380 |
| ataccgcgag acccacgctc accggctcca gatttatcag caataaacca gccagccgga | 1440 |
| agggccgagc gcagaagtgg tcctgcaact ttatccgcct ccatccagtc tattaattgt | 1500 |
| tgccgggaag ctagagtaag tagttcgcca gttaatagtt tgcgcaacgt tgttgccatt | 1560 |
| gctacaggca tcgtggtgtc acgctcgtcg tttggtatgg cttcattcag ctccggttcc | 1620 |
| caacgatcaa ggcgagttac atgatccccc atgttgtgca aaaaagcggt tagctccttc | 1680 |

```
ggtcctccga tcgttgtcag aagtaagttg gccgcagtgt tatcactcat ggttatggca    1740
gcactgcata attctcttac tgtcatgcca tccgtaagat gcttttctgt gactggtgag    1800
tactcaacca agtcattctg agaatagtgt atgcggcgac cgagttgctc ttgcccggcg    1860
tcaatacggg ataataccgc gccacatagc agaactttaa aagtgctcat cattggaaaa    1920
cgttcttcgg ggcgaaaact ctcaaggatc ttaccgctgt tgagatccag ttcgatgtaa    1980
cccactcgtg cacccaactg atcttcagca tcttttactt tcaccagcgt ttctgggtga    2040
gcaaaaacag gaaggcaaaa tgccgcaaaa aagggaataa gggcgacacg gaaatgttga    2100
atactcatac tcttcctttt tcaatattat tgaagcattt atcagggtta ttgtctcatg    2160
agcggataca tatttgaatg tatttagaaa aataaacaaa taggggttcc gcgcacattt    2220
ccccgaaaag tgccacctga acgaagcatc tgtgcttcat tttgtagaac aaaaatgcaa    2280
cgcgagagcg ctaattttc aaacaaagaa tctgagctgc attttacag aacagaaatg    2340 caacgcgaaa gcgctatttt accaacgaag aatctgtgct tcattttgt aaaacaaaaa    2400 tgcaacgcga gagcgctaat ttttcaaaca agaatctga gctgcatttt tacagaacag    2460 aaaatgcaacg cgagagcgct attttaccaa caaagaatct atacttcttt tttgttctac    2520
aaaaatgcat cccgagagcg ctattttct aacaaagcat cttagattac ttttttctc    2580 ctttgtgcgc tctataatgc agtctcttga taacttttg cactgtaggt ccgttaaggt    2640
tagaagaagg ctactttggt gtctattttc tcttccataa aaaagcctg actccacttc    2700 ccgcgtttac tgattactag cgaagctgcg ggtgcatttt ttcaagataa aggcatcccc    2760
gattatattc tataccgatg tggattgcgc atacttgtg aacagaaagt gatagcgttg    2820
atgattcttc attggtcaga aaattatgaa cggtttcttc tattttgtct ctatatacta    2880
cgtataggaa atgtttacat tttcgtattg ttttcgattc actctatgaa tagttcttac    2940
tacaattttt ttgtctaaag agtaatacta gagataaaca taaaaaatgt agaggtcgag    3000
tttagatgca agttcaagga gcgaaaggtg gatgggtagg ttatataggg atatagcaca    3060
gagatatata gcaaagagat acttttgagc aatgtttgtg gaagcggtat tcgcaatatt    3120
ttagtagctc gttacagtcc ggtgcgtttt tggttttttg aaagtgcgtc ttcagagcgc    3180
ttttggtttt caaaagcgct ctgaagttcc tatactttct agagaatagg aacttcggaa    3240
taggaacttc aaagcgtttc cgaaaacgag cgcttccgaa aatgcaacgc gagctgcgca    3300
catacagctc actgttcacg tcgcacctat atctgcgtgt tgcctgtata tatatataca    3360
tgagaagaac ggcatagtgc gtgtttatgc ttaaatgcgt acttatatgc gtctatttat    3420
gtaggatgaa aggtagtcta gtacctcctg tgatattatc ccattccatg cggggtatcg    3480
tatgcttcct tcagcactac cctttagctg ttctatatgc tgccactcct caattggatt    3540
agtctcatcc ttcaatgcta tcatttcctt tgatattgga tcatactaag aaaccattat    3600
tatcatgaca ttaacctata aaataggcg tatcacgagg ccctttcgtc tcgcgcgttt    3660
cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggctgg cttaactatg cggcatcaga gcagattgta ctgagagtgc accatatcga    3840
ctacgtcgta aggccgtttc tgacagagta aaattcttga gggaactttc accattatgg    3900
gaaatgcttc aagaaggtat tgacttaaac tccatcaaat ggtcaggtca ttgagtgttt    3960
tttatttgtt gtatttttt tttttagag aaaatcctcc aatatcaaat taggaatcgt    4020
agtttcatga ttttctgtta cacctaactt tttgtgtggt gccctcctcc ttgtcaatat    4080
```

-continued

```
taatgttaaa gtgcaattct ttttccttat cacgttgagc cattagtatc aatttgctta   4140
cctgtattcc tttactatcc tccttttcct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg attttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgt ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca ttttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaattttgt taaatcagct   6180
cattttttaa ccaataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
```

```
gcccccgatt tagagcttga cggggaaagc cggcgaacgt ggcgagaaag gaagggaaga    6480
aagcgaaagg agcgggcgct agggcgctgg caagtgtagc ggtcacgctg cgcgtaacca    6540
ccacacccgc cgcgcttaat gcgccgctac agggcgcgtc gcgccattcg ccattcaggc    6600
tgcgcaactt ttgggaaggg cgatcggtgc gggcctcttc gctattacgc cagctggcga    6660
aaggggatg tgctgcaagg cgattaagtt gggtaacgcc agggttttcc cagtcacgac     6720
gttgtaaaac gacggccagt gagcgcgcgt aatacgactc actataggc gaattgggta     6780
ccgggccccc cctcgaggtc gacggtatcg ataagcttga tatcgaattc ctgcagcccg    6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
tatatatata tagccatagt gatgtctaag taacctttat ggtatatttc ttaatgtgga    7200
aagatactag cgcgcgcacc cacacacaag cttcgtctt tcttgaagaa aagaggaagc     7260
tcgctaaatg ggattccact ttccgttccc tgccagctga tggaaaaagg ttagtggaac    7320
gatgaagaat aaaagagag atccactgag gtgaaatttc agctgacagc gagtttcatg     7380
atcgtgatga acaatggtaa cgagttgtgg ctgttgccag ggagggtggt tctcaacttt    7440
taatgtatgg ccaaatcgct acttgggttt gttatataac aaagaagaaa taatgaactg    7500
attctcttcc tccttcttgt cctttcttaa ttctgttgta attaccttcc tttgtaatt     7560
tttttgtaat tattcttctt aataatccaa acaaacacac atattacaat agctagctga    7620
ggatgaaggc attagtttat catggggatc acaaatttc gttagaagac aaaccaaaac     7680
ccactctgca gaaaccaaca gacgttgtgg ttagggtgtt gaaaacaaca atttgcggta    7740
ctgacttggg aatatacaaa ggtaagaatc ctgaagtggc agatggcaga atcctgggtc    7800
atgagggcgt tggcgtcatt gaagaagtgg gcgaatccgt gacacaattc aaaaagggg     7860
ataaagtttt aatctcctgc gttactagct gtggatcgtg tgattattgc aagaagcaac    7920
tgtattcaca ctgtagagac ggtggctgga ttttaggtta catgatcgac ggtgtccaag    7980
ccgaatacgt cagaatacca catgctgaca attcattgta taagatcccg caaactatcg    8040
atgatgaaat tgcagtacta ctgtccgata ttttacctac tggacatgaa attggtgttc    8100
aatatggtaa cgttcaacca ggcgatgctg tagcaattgt aggagcaggt cctgttggaa    8160
tgtcagtttt gttaactgct caattttact cgcctagtac cattattgtt atcgacatgg    8220
acgaaaaccg tttacaatta gcgaaggagc ttggggccac acacactatt aactccggta    8280
ctgaaaatgt tgtcgaagct gtgcatcgta tagcagccga aggagtggat gtagcaatag    8340
aagctgttgg tataccccgca acctgggaca tctgtcagga aattgtaaaa cccggcgctc    8400
atattgccaa cgtgggagtt catggtgtta aggtggactt tgaaattcaa aagttgtgga    8460
ttaagaatct aaccatcacc actggtttgg ttaacactaa tactacccca atgttgatga    8520
aggtagcctc tactgataaa ttgccttaa agaaaatgat tactcacagg tttgagttag     8580
ctgaaatcga acacgcatat caggttttct tgaatggcgc taaagaaaaa gctatgaaga    8640
ttattctatc taatgcaggt gccgcctaat taattaagag taagcgaatt tcttatgatt    8700
tatgattttt attattaaat aagttataaa aaaataagt gtatacaaat tttaaagtga    8760
ctcttaggtt ttaaaacgaa aattcttatt cttgagtaac tctttcctgt aggtcaggtt    8820
```

```
gctttctcag gtatagcatg aggtcgctct tattgaccac acctctaccg gcatgccgag    8880
caaatgcctg caaatcgctc cccatttcac ccaattgtag atatgctaac tccagcaatg    8940
agttgatgaa tctcggtgtg tattttatgt cctcagagga caacacctgt ggta          8994

<210> SEQ ID NO 181
<211> LENGTH: 39
<212> TYPE: DNA
<213> ORGANISM: artificial sequence
<220> FEATURE:
<223> OTHER INFORMATION: primer

<400> SEQUENCE: 181
cacacatatt acaatagcta gctgaggatg aaagctctg                             39

<210> SEQ ID NO 182
<211> LENGTH: 39
<212> TYPE: DNA
<213> ORGANISM: artificial sequence
<220> FEATURE:
<223> OTHER INFORMATION: primer

<400> SEQUENCE: 182
cagagctttc atcctcagct agctattgta atatgtgtg                             39

<210> SEQ ID NO 183
<211> LENGTH: 9491
<212> TYPE: DNA
<213> ORGANISM: artificial sequence
<220> FEATURE:
<223> OTHER INFORMATION: constructed plasmid

<400> SEQUENCE: 183
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat attttttttat gcctcggtaa tgattttcat    360
tttttttttt ccctagcgg atgactcttt ttttttctta gcgattggca ttatcacata     420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga     660
ttaacgtcca cacaggtata gggtttctgg accatatgat acatgctctg gccaagcatt     720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
```

```
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320
ccttttttct ttttgctttt tctttttttt tctcttgaac tcgacggatc tatgcggtgt    1380
gaaataccgc acagatgcgt aaggagaaaa taccgcatca ggaaattgta aacgttaata    1440
ttttgttaaa attcgcgtta aattttttgtt aaatcagctc attttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt tttttggggt    1680
cgaggtgccg taaagcacta aatcggaacc ctaaagggag cccccgattt agagcttgac    1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggggatgt gctgcaaggc    1980 gattaagttg ggtaacgcca gggttttccc agtcacgacg ttgtaaaacg acggccagtg    2040
agcgcgcgta atacgactca ctataggccg aattgggtac cgggccccccc ctcgaggtcg    2100 acggcgcgcc actggtagag agcgactttg tatgccccaa ttgcgaaacc cgcgatatcc    2160
ttctcgattc tttagtaccc gaccaggaca aggaaaagga ggtcgaaacg ttttttgaaga    2220 aacaagagga actacacgga agctctaaag atggcaacca gccagaaact aagaaaatga    2280
agttgatgga tccaactggc accgctggct tgaacaacaa taccagcctt ccaacttctg    2340
taaataacgg cggtacgcca gtgccaccag taccgttacc tttcggtata cctccttttcc    2400 ccatgtttcc aatgcccttc atgcctccaa cggctactat cacaaatcct catcaagctg    2460
acgcaagccc taagaaatga ataacaatac tgacagtact aaataattgc ctacttggct    2520
tcacatacgt tgcatacgtc gatatagata ataatgataa tgacagcagg attatcgtaa    2580
tacgtaatag ttgaaaatct caaaaatgtg tgggtcatta cgtaaataat gataggaatg    2640
ggattcttct attttttcctt tttccattct agcagccgtc gggaaaacgt ggcatcctct    2700 cttcgggct caattggagt cacgctgccg tgagcatcct ctctttccat atctaacaac    2760
tgagcacgta accaatggaa aagcatgagc ttagcgttgc tccaaaaaag tattggatgg    2820
ttaataccat ttgtctgttc tcttctgact ttgactcctc aaaaaaaaaa aatctacaat    2880
caacagatcg cttcaattac gccctcacaa aaactttttt ccttcttctt cgcccacgtt    2940
aaattttatc cctcatgttg tctaacggat ttctgcactt gatttattat aaaaagacaa    3000
agacataata cttctctatc aatttcagtt attgttcttc cttgcgttat tcttctgttc    3060 ttcttttttct tttgtcatat ataaccataa ccaagtaata catattcaaa ctagtatgac    3120
tgacaaaaaa actcttaaag acttaagaaa tcgtagttct gtttacgatt caatggttaa    3180
atcacctaat cgtgctatgt tgcgtgcaac tggtatgcaa gatgaagact ttgaaaaacc    3240
tatcgtcggt gtcatttcaa cttgggctga aacacacct tgtaatatcc acttacatga    3300
ctttggtaaa ctagccaaag tcggtgttaa ggaagctggt gcttggccag ttcagttcgg    3360
aacaatcacg gttctgatg gaatcgccat gggaacccaa ggaatgcgtt tctccttgac    3420
atctcgtgat attattgcag attctattga agcagccatg ggaggtcata atgcggatgc    3480
ttttgtagcc attggcggtt gtgataaaaa catgcccggt tctgttatcg ctatggctaa    3540
```

```
catggatatc ccagccattt ttgcttacgg cggaacaatt gcacctggta atttagacgg    3600
caaagatatc gatttagtct ctgtctttga aggtgtcggc cattggaacc acggcgatat    3660
gaccaaagaa gaagttaaag cttttggaatg taatgcttgt cccggtcctg gaggctgcgg    3720
tggtatgtat actgctaaca caatggcgac agctattgaa gttttgggac ttagccttcc    3780
gggttcatct tctcacccgg ctgaatccgc agaaagaaa gcagatattg aagaagctgg    3840
tcgcgctgtt gtcaaaatgc tcgaaatggg cttaaaacct tctgacattt taacgcgtga    3900
agcttttgaa gatgctatta ctgtaactat ggctctggga ggttcaacca actcaaccct    3960
tcacctctta gctattgccc atgctgctaa tgtggaattg acacttgatg atttcaatac    4020
tttccaagaa aaagttcctc atttggctga tttgaaacct tctggtcaat atgtattcca    4080
agacctttac aaggtcggag gggtaccagc agttatgaaa tatctcctta aaaatggctt    4140
ccttcatggt gaccgtatca cttgtactgg caaaacagtc gctgaaaatt tgaaggcttt    4200
tgatgattta acacctggtc aaaaggttat tatgccgctt gaaaatccta acgtgaaga    4260
tggtccgctc attattctcc atggtaactt ggctccagac ggtgccgttg ccaaagtttc    4320
tggtgtaaaa gtgcgtcgtc atgtcggtcc tgctaaggtc tttaattctg aagaagaagc    4380
cattgaagct gtcttgaatg atgatattgt tgatggtgat gttgttgtcg tacgttttgt    4440
aggaccaaag gcggtcctg gtatgcctga aatgctttc ctttcatcaa tgattgttgg    4500
taaagggcaa ggtgaaaaag ttgcccttct gacagatggc cgcttctcag gtggtactta    4560
tggtcttgtc gtgggtcata tcgctcctga agcacaagat ggcggtccaa tcgcctacct    4620
gcaaacagga gacatagtca ctattgacca agacactaag gaattacact tgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagtttttt aatgagtatt gaatctgttt agaaataatg    4920
gaatattatt tttatttatt tatttatat attggtcggc tcttttcttc tgaaggtcaa    4980
tgacaaaatg atatgaagga ataatgatt tctaaaattt tacaacgtaa gatattttta    5040
caaaagccta gctcatcttt tgtcatgcac tattttactc acgcttgaaa ttaacggcca    5100
gtccactgcg gagtcattc aaagtcatcc taatcgatct atcgttttg atagctcatt    5160
ttggagttcg cgattgtctt ctgttattca caactgtttt aatttttatt tcattctgga    5220
actcttcgag ttctttgtaa agtctttcat agtagcttac tttatcctcc aacatattta    5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgttttgtt ctcccatcac aatttaatat acctgatgga    5520
ttcttatgaa gcgctgggta atggacgtgt cactctactt cgccttttc cctactcctt    5580
ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaaatata ttagaagtct atacgttaaa ccaccgcggt ggagctccag    5880
```

```
cttttgttcc ctttagtgag ggttaattgc gcgcttggcg taatcatggt catagctgtt    5940
tcctgtgtga aattgttatc cgctcacaat tccacacaac ataggagccg gaagcataaa    6000
gtgtaaagcc tggggtgcct aatgagtgag gtaactcaca ttaattgcgt tgcgctcact    6060
gcccgctttc cagtcgggaa acctgtcgtg ccagctgcat taatgaatcg gccaacgcgc    6120
ggggagaggc ggtttgcgta ttgggcgctc ttccgcttcc tcgctcactg actcgctgcg    6180
ctcggtcgtt cggctgcggc gagcggtatc agctcactca aaggcggtaa tacggttatc    6240
cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
ggcgtttccc cctggaagct ccctcgtgcg ctctcctgtt ccgaccctgc cgcttaccgg    6480
atacctgtcc gcctttctcc cttcgggaag cgtggcgctt tctcatagct cacgctgtag    6540
gtatctcagt tcggtgtagg tcgttcgctc caagctgggc tgtgtgcacg aaccccccgt    6600
tcagcccgac cgctgcgcct tatccggtaa ctatcgtctt gagtccaacc cggtaagaca    6660
cgacttatcg ccactggcag cagccactgg taacaggatt agcagagcga ggtatgtagg    6720
cggtgctaca gagttcttga agtggtggcc taactacggc tacactagaa ggacagtatt    6780
tggtatctgc gctctgctga agccagttac cttcggaaaa agagttggta gctcttgatc    6840
cggcaaacaa accaccgctg gtagcggtgg ttttttttgtt tgcaagcagc agattacgcg    6900
cagaaaaaaa ggatctcaag aagatccttt gatcttttct acggggtctg acgctcagtg    6960
gaacgaaaac tcacgttaag ggattttggt catgagatta tcaaaaagga tcttcaccta    7020 gatccttttaa aattaaaaat gaagttttaa atcaatctaa agtatatatg agtaaacttg    7080
gtctgacagt taccaatgct taatcagtga ggcacctatc tcagcgatct gtctatttcg    7140
ttcatccata gttgcctgac tccccgtcgt gtagataact acgatacggg agggcttacc    7200
atctggcccc agtgctgcaa tgataccgcg agacccacgc tcaccggctc cagatttatc    7260
agcaataaac cagccagccg gaagggccga gcgcagaagt ggtcctgcaa ctttatccgc    7320
ctccatccag tctattaatt gttgccggga agctagagta agtagttcgc cagttaatag    7380
tttgcgcaac gttgttgcca ttgctacagg catcgtggtg tcacgctcgt cgtttggtat    7440
ggcttcattc agctccggtt cccaacgatc aaggcgagtt acatgatccc ccatgttgtg    7500
caaaaaagcg gttagctcct tcggtcctcc gatcgttgtc agaagtaagt tggccgcagt    7560
gttatcactc atggttatgg cagcactgca taattctctt actgtcatgc catccgtaag    7620
atgcttttct gtgactggtg agtactcaac caagtcattc tgagaatagt gtatgcggcg    7680
accgagttgc tcttgcccgg cgtcaatacg ggataatacc gcgccacata gcagaacttt    7740
aaaagtgctc atcattggaa aacgttcttc ggggcgaaaa ctctcaagga tcttaccgct    7800
gttgagatcc agttcgatgt aacccactcg tgcacccaac tgatcttcag catcttttac    7860
tttcaccagc gtttctgggt gagcaaaaac aggaaggcaa aatgccgcaa aaaagggaat    7920
aagggcgaca cggaaatgtt gaatactcat actcttcctt tttcaatatt attgaagcat    7980
ttatcagggt tattgtctca tgagcggata catatttgaa tgtatttaga aaataaaca    8040 aataggggtt ccgcgcacat ttccccgaaa agtgccacct gaacgaagca tctgtgcttc    8100
attttgtaga acaaaaatgc aacgcgagag cgctaatttt tcaaacaaag aatctgagct    8160
gcatttttac agaacagaaa tgcaacgcga aagcgctatt ttaccaacga agaatctgtg    8220
cttcattttt gtaaaacaaa aatgcaacgc gagagcgcta attttttcaaa caagaatct    8280
```

```
gagctgcatt tttacagaac agaaatgcaa cgcgagagcg ctattttacc aacaaagaat      8340
ctatacttct tttttgttct acaaaaatgc atcccgagag cgctatttt ctaacaaagc       8400 atcttagatt actttttttc tcctttgtgc gctctataat gcagtctctt gataaacttt      8460
tgcactgtag gtccgttaag gttagaagaa ggctactttg tgtctatttt tctcttccat     8520
aaaaaaagcc tgactccact tcccgcgttt actgattact agcgaagctg cgggtgcatt     8580
ttttcaagat aaaggcatcc ccgattatat tctataccga tgtggattgc gcatactttg     8640
tgaacagaaa gtgatagcgt tgatgattct tcattggtca gaaaattatg aacggtttct      8700
tctattttgt ctctatatac tacgtatagg aaatgtttac attttcgtat tgttttcgat      8760
tcactctatg aatagttctt actacaattt ttttgtctaa agagtaatac tagagataaa      8820
cataaaaaat gtagaggtcg agtttagatg caagttcaag gagcgaaagg tggatgggta     8880
ggttatatag ggatatagca cagagatata tagcaaagag atacttttga gcaatgtttg     8940
tggaagcggt attcgcaata ttttagtagc tcgttacagt ccggtgcgtt tttggttttt     9000
tgaaagtgcg tcttcagagc gcttttggtt ttcaaaagcg ctctgaagtt cctatacttt     9060
ctagagaata ggaacttcgg aataggaact tcaaagcgtt tccgaaaacg agcgcttccg     9120
aaaatgcaac gcgagctgcg cacatacagc tcactgttca cgtcgcacct atatctgcgt     9180
gttgcctgta tatatata catgagaaga acggcatagt gcgtgtttat gcttaaatgc       9240
gtacttatat gcgtctattt atgtaggatg aaaggtagtc tagtacctcc tgtgatatta     9300
tcccattcca tgcggggtat cgtatgcttc cttcagcact acccttagc tgttctatat      9360 gctgccactc ctcaattgga ttagtctcat ccttcaatgc tatcatttcc tttgatattg    9420
gatcatctaa gaaaccatta ttatcatgac attaacctat aaaaataggc gtatcacgag     9480
gccctttcgt c                                                         9491

<210> SEQ ID NO 184
<211> LENGTH: 1000
<212> TYPE: DNA
<213> ORGANISM: Saccharymoces cerevisiae

<400> SEQUENCE: 184
gttaattcaa attaattgat atagttttttt aatgagtatt gaatctgttt agaaataatg       60
gaatattatt tttatttatt tatttatatt attggtcggc tcttttcttc tgaaggtcaa      120
tgacaaaatg atatgaagga ataatgatt tctaaaattt tacaacgtaa gatatttta      180 caaaagccta gctcatcttt tgtcatgcac tattttactc acgcttgaaa ttaacggcca      240
gtccactgcg gagtcatttc aaagtcatcc taatcgatct atcgttttttg atagctcatt     300 ttggagttcg cgattgtctt ctgttattca caactgtttt aattttttatt tcattctgga    360 actcttcgag ttctttgtaa agtctttcat agtagcttac tttatcctcc aacatattta      420
acttcatgtc aatttcggct cttaaatttt ccacatcatc aagttcaaca tcatctttta      480
acttgaattt attctctagc tcttccaacc aagcctcatt gctccttgat ttactggtga      540
aaagtgatac actttgcgcg caatccaggt caaaactttc ctgcaaagaa ttcaccaatt      600
tctcgacatc atagtacaat ttgttttgtt ctcccatcac aatttaatat acctgatgga      660
ttcttatgaa gcgctgggta atggacgtgt cactctactt cgccttttc cctactcctt       720 ttagtacgga agacaatgct aataaataag agggtaataa taatattatt aatcggcaaa     780
aaagattaaa cgccaagcgt ttaattatca gaaagcaaac gtcgtaccaa tccttgaatg      840
```

```
cttcccaatt gtatattaag agtcatcaca gcaacatatt cttgttatta aattaattat      900
tattgatttt tgatattgta taaaaaaacc aaatatgtat aaaaaaagtg aataaaaaat      960
accaagtatg gagaaatata ttagaagtct atacgttaaa                          1000
```

<210> SEQ ID NO 185
<211> LENGTH: 1713
<212> TYPE: DNA
<213> ORGANISM: Streptococcus mutans

<400> SEQUENCE: 185

```
atgactgaca aaaaaactct taaagactta agaaatcgta gttctgttta cgattcaatg       60
gttaaatcac ctaatcgtgc tatgttgcgt gcaactggta tgcaagatga agactttgaa      120
aaacctatcg tcggtgtcat ttcaacttgg gctgaaaaca caccttgtaa tatccactta      180
catgactttg gtaaactagc caaagtcggt gttaaggaag ctggtgcttg gccagttcag      240
ttcggaacaa tcacggtttc tgatggaatc gccatgggaa cccaaggaat gcgtttctcc      300
ttgacatctc gtgatattat tgcagattct attgaagcag ccatgggagg tcataatgcg      360
gatgcttttg tagccattgg cggttgtgat aaaaacatgc ccggttctgt tatcgctatg      420
gctaacatgg atatcccagc catttttgct tacggcggaa caattgcacc tggtaattta      480
gacggcaaag atatcgattt agtctctgtc tttgaaggtg tcggccattg gaaccacggc      540
gatatgacca agaagaagt taaagctttg gaatgtaatg cttgtcccgg tcctggaggc      600
tgcggtggta tgtatactgc taacacaatg gcgacagcta ttgaagtttt gggacttagc      660
cttccgggtt catcttctca cccggctgaa tccgcagaaa agaaagcaga tattgaagaa      720
gctggtcgcg ctgttgtcaa aatgctcgaa atgggcttaa aaccttctga cattttaacg      780
cgtgaagctt tgaagatgc tattactgta actatggctc tgggaggttc aaccaactca      840
acccttcacc tcttagctat tgcccatgct gctaatgtgg aattgacact tgatgatttc      900
aatactttcc aagaaaaagt tcctcatttg gctgatttga aaccttctgg tcaatatgta      960
ttccaagacc tttacaaggt cggaggggta ccagcagtta tgaaatatct ccttaaaaat     1020
ggcttccttc atggtgaccg tatcacttgt actggcaaaa cagtcgctga aaatttgaag     1080
gcttttgatg attttaacacc tggtcaaaag gttattatgc cgcttgaaaa tcctaaacgt     1140
gaagatggtc cgctcattat tctccatggt aacttggctc cagacggtgc cgttgccaaa     1200
gtttctggtg taaaagtgcg tcgtcatgtc ggtcctgcta aggtctttaa ttctgaagaa     1260
gaagccattg aagctgtctt gaatgatgat attgttgatg gtgatgttgt tgtcgtacgt     1320
tttgtaggac caaagggcgg tcctggtatg cctgaaatgc tttcccttc atcaatgatt     1380 gttggtaaag ggcaaggtga aaagttgcc cttctgacag atggccgctt ctcaggtggt     1440
acttatggtc ttgtcgtggg tcatatcgct cctgaagcac aagatggcgg tccaatcgcc     1500
tacctgcaaa caggagacat agtcactatt gaccaagaca ctaaggaatt acactttgat     1560
atctccgatg aagagttaaa acatcgtcaa gagaccattg aattgccacc gctctattca     1620
cgcggtatcc ttggtaaaata tgctcacatc gtttcgtctg cttctagggg agccgtaaca     1680
gacttttgga agcctgaaga aactggcaaa aaa                                  1713
```

<210> SEQ ID NO 186
<211> LENGTH: 571
<212> TYPE: PRT
<213> ORGANISM: Streptococcus mutans

<400> SEQUENCE: 186

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
                20                  25                  30

Gly Met Gln Asp Glu Asp Phe Glu Lys Pro Ile Val Gly Val Ile Ser
            35                  40                  45

Thr Trp Ala Glu Asn Thr Pro Cys Asn Ile His Leu His Asp Phe Gly
        50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
                100                 105                 110

Ala Ala Met Gly Gly His Asn Ala Asp Ala Phe Val Ala Ile Gly Gly
            115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
                180                 185                 190

Asn Ala Cys Pro Gly Pro Gly Gly Cys Gly Gly Met Tyr Thr Ala Asn
            195                 200                 205

Thr Met Ala Thr Ala Ile Glu Val Leu Gly Leu Ser Leu Pro Gly Ser
210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
            245                 250                 255

Asp Ile Leu Thr Arg Glu Ala Phe Glu Asp Ala Ile Thr Val Thr Met
                260                 265                 270

Ala Leu Gly Gly Ser Thr Asn Ser Thr Leu His Leu Leu Ala Ile Ala
            275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
            405                 410                 415
```

Asn Ser Glu Glu Ala Ile Glu Ala Val Leu Asn Asp Asp Ile Val
        420                 425                 430

Asp Gly Asp Val Val Val Arg Phe Val Gly Pro Lys Gly Gly Pro
        435                 440                 445

Gly Met Pro Glu Met Leu Ser Leu Ser Ser Met Ile Val Gly Lys Gly
        450                 455                 460

Gln Gly Glu Lys Val Ala Leu Leu Thr Asp Gly Arg Phe Ser Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
        500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
        530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570

<210> SEQ ID NO 187
<211> LENGTH: 2145
<212> TYPE: DNA
<213> ORGANISM: artificial sequence
<220> FEATURE:
<223> OTHER INFORMATION: constructed chimeric gene

<400> SEQUENCE: 187

| | | |
|---|---|---|
| gcatgcttgc atttagtcgt gcaatgtatg actttaagat tgtgagcag gaagaaaagg | 60 |
| gagaatcttc taacgataaa cccttgaaaa actgggtaga ctacgctatg ttgagttgct | 120 |
| acgcaggctg cacaattaca cgagaatgct cccgcctagg atttaaggct aagggacgtg | 180 |
| caatgcagac gacagatcta aatgaccgtg tcggtgaagt gttcgccaaa cttttcggtt | 240 |
| aacacatgca gtgatgcacg cgcgatggtg ctaagttaca tatatatata tatatatata | 300 |
| tatagccata gtgatgtcta agtaaccttt atggtatatt tcttaatgtg aaagatact | 360 |
| agcgcgcgca cccacacaca agcttcgtct tttcttgaag aaaagaggaa gctcgctaaa | 420 |
| tgggattcca ctttccgttc cctgccagct gatggaaaaa ggttagtgga acgatgaaga | 480 |
| ataaaagag agatccactg aggtgaaatt tcagctgaca gcgagtttca tgatcgtgat | 540 |
| gaacaatggt aacgagttgt ggctgttgcc agggagggtg gttctcaact tttaatgtat | 600 |
| ggccaaatcg ctacttgggt tgttatata caaagaagaa ataatgaac tgattctctt | 660 |
| cctccttctt gtcctttctt aattctgttg taattacctt cctttgtaat ttttttttgta | 720 |
| attattcttc ttaataatcc aaacaaacac acatattaca atagctagct gaggatgaag | 780 |
| gcattagttt atcatgggga tcacaaaatt tcgttagaag acaaaccaaa acccactctg | 840 |
| cagaaaccaa cagacgttgt ggttaggtg ttgaaaacaa caatttgcgg tactgacttg | 900 |
| ggaatataca aagtaagaa tcctgaagtg cagatggca gaatcctggg tcatgagggc | 960 |
| gttggcgtca ttgaagaagt gggcgaatcc gtgacacaat tcaaaaaggg ggataaagtt | 1020 |
| ttaatctcct gcgttactag ctgtggatcg tgtgattatt gcaagaagca actgtattca | 1080 |
| cactgtagag acgttgctg gatttttaggt tacatgatcg acggtgtcca agccgaatac | 1140 |
| gtcagaatac cacatgctga caattcattg tataagatcc cgcaaactat cgatgatgaa | 1200 |

-continued

```
attgcagtac tactgtccga tattttacct actggacatg aaattggtgt tcaatatggt    1260
aacgttcaac caggcgatgc tgtagcaatt gtaggagcag gtcctgttgg aatgtcagtt    1320
ttgttaactg ctcaatttta ctcgcctagt accattattg ttatcgacat ggacgaaaac    1380
cgtttacaat tagcgaagga gcttgggccc acacacacta ttaactccgg tactgaaaat    1440
gttgtcgaag ctgtgcatcg tatagcagcc gaaggagtgg atgtagcaat agaagctgtt    1500
ggtatacccg caacctggga catctgtcag gaaattgtaa acccggcgc tcatattgcc    1560 aacgtgggag ttcatggtgt taaggtggac tttgaaattc aaaagttgtg gattaagaat    1620
ctaaccatca ccactggttt ggttaacact aatactaccc caatgttgat gaaggtagcc    1680
tctactgata aattgccttt aaagaaaatg attactcaca ggtttgagtt agctgaaatc    1740
gaacacgcat atcaggtttt cttgaatggc gctaaagaaa aagctatgaa gattattcta    1800
tctaatgcag gtgccgccta attaattaag agtaagcgaa tttcttatga tttatgattt    1860
ttattattaa ataagttata aaaaaaataa gtgtatacaa attttaaagt gactcttagg    1920
ttttaaaacg aaaattctta ttcttgagta actctttcct gtaggtcagg ttgctttctc    1980
aggtatagca tgaggtcgct cttattgacc acacctctac cggcatgccg agcaaatgcc    2040
tgcaaatcgc tccccatttc acccaattgt agatatgcta actccagcaa tgagttgatg    2100
aatctcggtg tgtattttat gtcctcagag gacaacacct gtggt                    2145
```

<210> SEQ ID NO 188
<211> LENGTH: 4280
<212> TYPE: DNA
<213> ORGANISM: artificial sequence
<220> FEATURE:
<223> OTHER INFORMATION: vector

<400> SEQUENCE: 188

```
ggggatcctc tagagtcgac ctgcaggcat gcaagcttgg cgtaatcatg gtcatagctg      60
tttcctgtgt gaaattgtta tccgctcaca attccacaca acatacgagc cggaagcata     120
aagtgtaaag cctggggtgc ctaatgagtg agctaactca cattaattgc gttgcgctca     180
ctgcccgctt tccagtcggg aaacctgtcg tgccagctgc attaatgaat cggccaacgc     240
gcggggagag gcggtttgcg tattgggcgc tcttccgctt cctcgctcac tgactcgctg     300
cgctcggtcg ttcggctgcg gcgagcggta tcagctcact caaaggcggt aatacggtta     360
tccacagaat caggggataa cgcaggaaag aacatgtgag caaaaggcca gcaaaaggcc     420
aggaaccgta aaaaggccgc gttgctggcg tttttccata ggctccgccc ccctgacgag     480
catcacaaaa atcgacgctc aagtcagagg tggcgaaacc cgacaggact ataaagatac     540
caggcgtttc ccctggaag ctccctcgtg cgctctcctg ttccgaccct gccgcttacc      600
ggatacctgt ccgcctttct cccttcggga agcgtggcgc tttctcatag ctcacgctgt     660
aggtatctca gttcggtgta ggtcgttcgc tccaagctgg gctgtgtgca cgaacccccc     720
gttcagcccg accgctgcgc cttatccggt aactatcgtc ttgagtccaa cccggtaaga    780
cacgacttat cgccactggc agcagccact ggtaacagga ttagcagagc gaggtatgta     840
ggcggtgcta cagagttctt gaagtggtgg cctaactacg gctacactag aaggacagta     900
tttggtatct gcgctctgct gaagccagtt accttcggaa aaagagttgg tagctcttga     960
tccggcaaac aaaccaccgc tggtagcggt ggtttttttg tttgcaagca gcagattacg    1020
cgcagaaaaa aaggatctca agaagatcct ttgatctttt ctacggggtc tgacgctcag    1080
```

```
tggaacgaaa actcacgtta agggattttg gtcatgagat tatcaaaaag gatcttcacc    1140
tagatccttt taaattaaaa atgaagtttt aaatcaatct aaagtatata tgagtaaact    1200
tggtctgaca gttaccaatg cttaatcagt gaggcaccta tctcagcgat ctgtctattt    1260
cgttcatcca tagttgcctg actcccgtc gtgtagataa ctacgatacg ggagggctta     1320
ccatctggcc ccagtgctgc aatgataccg cgagacccac gctcaccggc tccagattta    1380
tcagcaataa accagccagc cggaagggcc gagcgcagaa gtggtcctgc aactttatcc    1440
gcctccatcc agtctattaa ttgttgccgg gaagctagag taagtagttc gccagttaat    1500
agtttgcgca acgttgttgc cattgctaca ggcatcgtgg tgtcacgctc gtcgtttggt    1560
atggcttcat tcagctccgg ttcccaacga tcaaggcgag ttacatgatc ccccatgttg    1620
tgcaaaaaag cggttagctc cttcggtcct ccgatcgttg tcagaagtaa gttggccgca    1680
gtgttatcac tcatggttat ggcagcactg cataattctc ttactgtcat gccatccgta    1740
agatgctttt ctgtgactgg tgagtactca accaagtcat tctgagaata gtgtatgcgg    1800
cgaccgagtt gctcttgccc ggcgtcaata cgggataata ccgcgccaca tagcagaact    1860
ttaaaagtgc tcatcattgg aaaacgttct cggggcgaaa actctcaag gatcttaccg     1920 ctgttgagat ccagttcgat gtaacccact cgtgcaccca actgatcttc agcatctttt    1980
actttcacca gcgtttctgg gtgagcaaaa acaggaaggc aaaatgccgc aaaaaaggga    2040
ataagggcga cacggaaatg ttgaatactc atactcttcc ttttcaata ttattgaagc     2100 atttatcagg gttattgtct catgagcgga tacatatttg aatgtattta gaaaaataaa    2160
caaatagggg ttccgcgcac atttccccga aaagtgccac ctgacgtcta agaaaccatt    2220
attatcatga cattaaccta taaaaatagg cgtatcacga ggccctttcg tctcgcgcgt    2280
ttcggtgatg acggtgaaaa cctctgacac atgcagctcc cggagacggt cacagcttgt    2340
ctgtaagcgg atgccgggag cagacaagcc cgtcagggcg cgtcagcggg tgttggcggg    2400
tgtcggggct ggcttaacta tgcggcatca gagcagattg tactgagagt gcaccatatg    2460
cggtgtgaaa taccgcacag atgcgtaagg agaaaatacc gcatcaggcg ccattcgcca    2520
ttcaggctgc gcaactgttg ggaagggcga tcggtgcggg cctcttcgct attacgccag    2580
ctggcgaaag ggggatgtgc tgcaaggcga ttaagttggg taacgccagg gttttcccag    2640
tcacgacgtt gtaaaacgac ggccagtgaa ttcgagctcg gtaccccggg ctctgagaca    2700
gtagtaggtt agtcatcgct ctaccgacgc gcaggaaaag aaagaagcat tgcggattac    2760
gtattctaat gttcagcccg cggaacgcca gcaaatcacc acccatgcgc atgatactga    2820
gtcttgtaca cgctgggctt ccagtgtact gagagtgcac cataccacag cttttcaatt    2880
caattcatca ttttttttt attcttttt ttgatttcgg tttctttgaa attttttga      2940 ttcggtaatc tccgaacaga aggaagaacg aaggaaggag cacagactta gattggtata    3000
tatacgcata tgtagtgttg aagaaacatg aaattgccca gtattcttaa cccaactgca    3060
cagaacaaaa acctgcagga aacgaagata aatcatgtcg aaagctacat ataaggaacg    3120
tgctgctact catcctagtc ctgttgctgc caagctattt aatatcatgc acgaaaagca    3180
aacaaacttg tgtgcttcat tggatgttcg taccaccaag gaattactgg agttagttga    3240
agcattaggt cccaaaattt gtttactaaa aacacatgtg gatatcttga ctgatttttc    3300
catggagggc acagttaagc cgctaaaggc attatccgcc aagtacaatt ttttactctt    3360
cgaagacaga aaatttgctg acattggtaa tacagtcaaa ttgcagtact ctgcgggtgt    3420
atacagaata gcagaatggg cagacattac gaatgcacac ggtgtggtgg gcccaggtat    3480
```

```
tgttagcggt ttgaagcagg cggcagaaga agtaacaaag gaacctagag gccttttgat    3540
gttagcagaa ttgtcatgca agggctccct atctactgga gaatatacta agggtactgt    3600
tgacattgcg aagagcgaca aagatttttgt tatcggcttt attgctcaaa gagacatggg   3660
tggaagagat gaaggttacg attggttgat tatgacaccc ggtgtgggtt tagatgacaa    3720
gggagacgca ttgggtcaac agtatagaac cgtggatgat gtggtctcta caggatctga    3780
cattattatt gttggaagag gactatttgc aaagggaagg gatgctaagg tagagggtga    3840
acgttacaga aaagcaggct gggaagcata tttgagaaga tgcggccagc aaaactaaaa    3900
aactgtatta taagtaaatg catgtatact aaactcacaa attagagctt caatttaatt    3960
atatcagtta ttaccctatg cggtgtgaaa taccgcacag atgcgtaagg agaaaatacc    4020
gcatcaggaa attgtaaacg ttaatatttt gttaaaattc gcgttaaatt tttgttaaat    4080
cagctcattt tttaaccaat aggccgaaat cggcaaaatc ttcagcccgc ggaacgccag    4140
caaatcacca cccatgcgca tgatactgag tcttgtacac gctgggcttc cagtgatgat    4200
acaacgagtt agccaaggtg agcacggatg tctaaattag aattacgttt taatatcttt    4260
ttttccatat ctagggctag                                                4280

<210> SEQ ID NO 189
<211> LENGTH: 30
<212> TYPE: DNA
<213> ORGANISM: artificial sequence
<220> FEATURE:
<223> OTHER INFORMATION: primer

<400> SEQUENCE: 189
gcatgcttgc atttagtcgt gcaatgtatg                                      30

<210> SEQ ID NO 190
<211> LENGTH: 54
<212> TYPE: DNA
<213> ORGANISM: artificial sequence
<220> FEATURE:
<223> OTHER INFORMATION: primer

<400> SEQUENCE: 190
gaacattaga atacgtaatc cgcaatgcac tagtaccaca ggtgttgtcc tctg           54

<210> SEQ ID NO 191
<211> LENGTH: 54
<212> TYPE: DNA
<213> ORGANISM: artificial sequence
<220> FEATURE:
<223> OTHER INFORMATION: primer

<400> SEQUENCE: 191
cagaggacaa cacctgtggt actagtgcat tgcggattac gtattctaat gttc           54

<210> SEQ ID NO 192
<211> LENGTH: 28
<212> TYPE: DNA
<213> ORGANISM: artificial sequence
<220> FEATURE:
<223> OTHER INFORMATION: primer

<400> SEQUENCE: 192
caccttggct aactcgttgt atcatcac                                        28

<210> SEQ ID NO 193
```

```
<211> LENGTH: 100
<212> TYPE: DNA
<213> ORGANISM: artificial sequence
<220> FEATURE:
<223> OTHER INFORMATION: primer

<400> SEQUENCE: 193
ttttaagccg aatgagtgac agaaaaagcc cacaacttat caagtgatat tgaacaaagg    60
gcgaaacttc gcatgcttgc atttagtcgt gcaatgtatg                         100

<210> SEQ ID NO 194
<211> LENGTH: 98
<212> TYPE: DNA
<213> ORGANISM: artificial sequence
<220> FEATURE:
<223> OTHER INFORMATION: primer

<400> SEQUENCE: 194
cccaattggt aaatattcaa caagagacgc gcagtacgta acatgcgaat tgcgtaattc    60
acggcgataa caccttggct aactcgttgt atcatcac                            98

<210> SEQ ID NO 195
<211> LENGTH: 29
<212> TYPE: DNA
<213> ORGANISM: artificial sequence
<220> FEATURE:
<223> OTHER INFORMATION: primer

<400> SEQUENCE: 195
caaaagccca tgtcccacac caaaggatg                                      29

<210> SEQ ID NO 196
<211> LENGTH: 26
<212> TYPE: DNA
<213> ORGANISM: artificial sequence
<220> FEATURE:
<223> OTHER INFORMATION: primer

<400> SEQUENCE: 196
caccatcgcg cgtgcatcac tgcatg                                         26

<210> SEQ ID NO 197
<211> LENGTH: 22
<212> TYPE: DNA
<213> ORGANISM: artificial sequence
<220> FEATURE:
<223> OTHER INFORMATION: primer

<400> SEQUENCE: 197
gagaagatgc ggccagcaaa ac                                             22

<210> SEQ ID NO 198
<211> LENGTH: 2745
<212> TYPE: DNA
<213> ORGANISM: artificial sequence
<220> FEATURE:
<223> OTHER INFORMATION: constructed coding region-terminator segment

<400> SEQUENCE: 198
atgactgaca aaaaaactct taagacttta agaaatcgta gttctgttta cgattcaatg    60
gttaaatcac ctaatcgtgc tatgttgcgt gcaactggta tgcaagatga agactttgaa   120
aaacctatcg tcggtgtcat ttcaacttgg gctgaaaaca cacttgtaa tatccactta   180 catgactttg gtaaactagc caaagtcggt gttaaggaag ctggtgcttg gccagttcag   240
```

```
ttcggaacaa tcacggtttc tgatggaatc gccatgggaa cccaaggaat gcgtttctcc    300
ttgacatctc gtgatattat tgcagattct attgaagcag ccatgggagg tcataatgcg    360
gatgcttttg tagccattgg cggttgtgat aaaaacatgc ccggttctgt tatcgctatg    420
gctaacatgg atatcccagc cattttgct tacggcggaa caattgcacc tggtaattta    480
gacggcaaag atatcgattt agtctctgtc tttgaaggtg tcggccattg gaaccacggc    540
gatatgacca agaagaagt taaagctttg gaatgtaatg cttgtcccgg tcctggaggc    600
tgcggtggta tgtatactgc taacacaatg gcgacagcta ttgaagtttt gggacttagc    660
cttccgggtt catcttctca cccgctgaa tccgcagaaa agaaagcaga tattgaagaa    720
gctggtcgcg ctgttgtcaa atgctcgaa atgggcttaa aaccttctga cattttaacg    780
cgtgaagctt tgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga accttctgg tcaatatgta    960 ttccaagacc tttacaaggt cggagggta ccagcagtta tgaaatatct ccttaaaaat    1020
ggcttccttc atggtgaccg tatcacttgt actggcaaaa cagtcgctga aaatttgaag    1080
gcttttgatg atttaacacc tggtcaaaag gttattatgc cgcttgaaaa tcctaaacgt    1140
gaagatggtc cgctcattat tctccatggt aacttggctc cagacggtgc cgttgccaaa    1200
gtttctggtg taaaagtgcg tcgtcatgtc ggtcctgcta aggtctttaa ttctgaagaa    1260
gaagccattg aagctgtctt gaatgatgat attgttgatg gtgatgttgt tgtcgtacgt    1320
tttgtaggac caaagggcgg tcctggtatg cctgaaatgc tttccctttc atcaatgatt    1380
gttggtaaag gcaaggtga aaaagttgcc cttctgacag atggccgctt ctcaggtggt    1440
acttatggtc ttgtcgtggg tcatatcgct cctgaagcac aagatggcgg tccaatcgcc    1500
tacctgcaaa caggagacat agtcactatt gaccaagaca ctaaggaatt acactttgat    1560
atctccgatg aagagttaaa acatcgtcaa gagaccattg aattgccacc gctctattca    1620
cgcggtatcc ttggtaaata tgctcacatc gtttcgtctg cttctagggg agccgtaaca    1680
gacttttgga agcctgaaga aactggcaaa aaatgttgtc ctggttgctg tggttaagcg    1740
gccgcgttaa ttcaaattaa ttgatatagt ttttaatga gtattgaatc tgtttagaaa    1800
taatggaata ttatttttat ttatttattt atattattgg tcggctcttt tcttctgaag    1860
gtcaatgaca aaatgatatg aaggaaataa tgatttctaa aattttacaa cgtaagatat    1920
ttttacaaaa gcctagctca tcttttgtca tgcactattt tactcacgct tgaaattaac    1980
ggccagtcca ctgcggagtc atttcaaagt catcctaatc gatctatcgt ttttgatagc    2040
tcattttgga gttcgcgatt gtcttctgtt attcacaact gttttaattt ttatttcatt    2100
ctggaactct tcgagttctt tgtaaagtct ttcatagtag cttactttat cctccaacat    2160
atttaacttc atgtcaattt cggctcttaa attttccaca tcatcaagtt caacatcatc    2220
ttttaacttg aatttattct ctagctcttc caaccaagcc tcattgctcc ttgatttact    2280
ggtgaaaagt gatacacttt gcgcgcaatc caggtcaaaa ctttcctgca agaattcac    2340 caatttctcg acatcatagt acaatttgtt ttgttctccc atcacaattt aatatacctg    2400
atggattctt atgaagcgct gggtaatgga cgtgtcactc tacttcgcct ttttccctac    2460
tccttttagt acgaagacaa atgctaataa ataagagggt aataataata ttattaatcg    2520
gcaaaaaaga ttaaacgcca agcgtttaat tatcagaaag caaacgtcgt accaatcctt    2580
```

```
gaatgcttcc caattgtata ttaagagtca tcacagcaac atattcttgt tattaaatta    2640
attattattg atttttgata ttgtataaaa aaaccaaata tgtataaaaa aagtgaataa    2700
aaaataccaa gtatggagaa atatattaga agtctatacg ttaaa                   2745
```

<210> SEQ ID NO 199
<211> LENGTH: 99
<212> TYPE: DNA
<213> ORGANISM: artificial sequence
<220> FEATURE:
<223> OTHER INFORMATION: primer

<400> SEQUENCE: 199

```
tcctttctca attattattt tctactcata acctcacgca aaataacaca gtcaaatcaa    60
tcaaagtatg actgacaaaa aaactcttaa agacttaag                          99
```

<210> SEQ ID NO 200
<211> LENGTH: 77
<212> TYPE: DNA
<213> ORGANISM: artificial sequence
<220> FEATURE:
<223> OTHER INFORMATION: primer

<400> SEQUENCE: 200

```
gaacattaga atacgtaatc cgcaatgctt ctttcttttc cgtttaacgt atagacttct    60
aatatatttc tccatac                                                  77
```

<210> SEQ ID NO 201
<211> LENGTH: 45
<212> TYPE: DNA
<213> ORGANISM: artificial sequence
<220> FEATURE:
<223> OTHER INFORMATION: primer

<400> SEQUENCE: 201

```
aaacggaaaa gaaagaagca ttgcggatta cgtattctaa tgttc                   45
```

<210> SEQ ID NO 202
<211> LENGTH: 88
<212> TYPE: DNA
<213> ORGANISM: artificial sequence
<220> FEATURE:
<223> OTHER INFORMATION: primer

<400> SEQUENCE: 202

```
tattttcgt tacataaaaa tgcttataaa actttaacta ataattagag attaaatcgc     60
caccttggct aactcgttgt atcatcac                                      88
```

<210> SEQ ID NO 203
<211> LENGTH: 27
<212> TYPE: DNA
<213> ORGANISM: artificial sequence
<220> FEATURE:
<223> OTHER INFORMATION: primer

<400> SEQUENCE: 203

```
gactttgga agcctgaaga aactggc                                        27
```

<210> SEQ ID NO 204
<211> LENGTH: 20
<212> TYPE: DNA
<213> ORGANISM: artificial sequence
<220> FEATURE:
<223> OTHER INFORMATION: primer

<400> SEQUENCE: 204
cttggcagca acaggactag    20

<210> SEQ ID NO 205
<211> LENGTH: 26
<212> TYPE: DNA
<213> ORGANISM: artificial sequence
<220> FEATURE:
<223> OTHER INFORMATION: primer

<400> SEQUENCE: 205
ccaggccaat tcaacagact gtcggc    26

<210> SEQ ID NO 206
<211> LENGTH: 2347
<212> TYPE: DNA
<213> ORGANISM: artificial sequence
<220> FEATURE:
<223> OTHER INFORMATION: constructed URA3 marker with flanking
      homologous repeat sequences for HIS gene replacement and marker
      excision

<400> SEQUENCE: 206
gcattgcgga ttacgtattc taatgttcag gtgctggaag aagagctgct taaccgccgc    60
gcccagggtg aagatccacg ctactttacc ctgcgtcgtc tggatttcgg cggctgtcgt    120
ctttcgctgg caacgccggt tgatgaagcc tgggacggtc cgctctcctt aaacggtaaa    180
cgtatcgcca cctcttatcc tcacctgctc aagcgttatc tcgaccagaa aggcatctct    240
tttaaatcct gcttactgaa cggttctgtt gaagtcgccc cgcgtgccgg actggcggat    300
gcgatttgcg atctggtttc caccggtgcc acgctggaag ctaacggcct gcgcgaagtc    360
gaagttatct atcgctcgaa agcctgcctg attcaacgcg atggcgaaat ggaagaatcc    420
aaacagcaac tgatcgacaa actgctgacc cgtattcagg gtgtgatcca ggcgcgcgaa    480
tcaaaataca tcatgatgca cgcaccgacc gaacgtctgg atgaagtcat ggtacctact    540
gagagtgcac ataccacag cttttcaatt caattcatca ttttttttt attcttttt    600 ttgatttcgg tttctttgaa attttttga ttcggtaatc tccgaacaga aggaagaacg    660
aaggaaggag cacagactta gattggtata tatacgcata tgtagtgttg aagaaacatg    720
aaattgccca gtattcttaa cccaactgca cagaacaaaa acctgcagga aacgaagata    780
aatcatgtcg aaagctacat ataaggaacg tgctgctact catcctagtc ctgttgctgc    840
caagctattt aatatcatgc acgaaaagca aacaaacttg tgtgcttcat ggatgttcg    900 taccaccaag gaattactgg agttagttga agcattaggt cccaaaattt gtttactaaa    960
aacacatgtg gatatcttga ctgatttttc catggagggc acagttaagc cgctaaaggc    1020
attatccgcc aagtacaatt ttttactctt cgaagacaga aaatttgctg acattggtaa    1080
tacagtcaaa ttgcagtact ctgcgggtgt atacagaata gcagaatggg cagacattac    1140
gaatgcacac ggtgtggtgg gcccaggtat tgttagcggt ttgaagcagg cggcagaaga    1200
agtaacaaag gaacctagag gccttttgat gttagcagaa ttgtcatgca agggctccct    1260
atctactgga gaatatacta agggtactgt tgacattgcg aagagcgaca agatttttgt    1320
tatcggcttt attgctcaaa gagacatggg tggaagagat gaaggttacg attggttgat    1380
tatgacaccc ggtgtgggtt tagatgacaa gggagacgca ttgggtcaac agtatagaac    1440
cgtggatgat gtggtctcta caggatctga cattattatt gttggaagag gactatttgc    1500

```
aaagggaagg gatgctaagg tagagggtga acgttacaga aaagcaggct gggaagcata    1560
tttgagaaga tgcggccagc aaaactaaaa aactgtatta taagtaaatg catgtatact    1620
aaactcacaa attagagctt caatttaatt atatcagtta ttaccctatg cggtgtgaaa    1680
taccgcacag atgcgtaagg agaaaatacc gcatcaggaa attgtaaacg ttaatatttt    1740
gttaaaattc gcgttaaatt tttgttaaat cagctcattt tttaaccaat aggccgaaat    1800
cggcaaaatc tctagagtgc tggaagaaga gctgcttaac cgccgcgccc agggtgaaga    1860
tccacgctac tttaccctgc gtcgtctgga tttcggcggc tgtcgtcttt cgctggcaac    1920
gccggttgat gaagcctggg acggtccgct ctccttaaac ggtaaacgta tcgccacctc    1980
ttatcctcac ctgctcaagc gttatctcga ccagaaaggc atctctttta aatcctgctt    2040
actgaacggt tctgttgaag tcgccccgcg tgccggactg gcggatgcga tttgcgatct    2100
ggtttccacc ggtgccacgc tggaagctaa cggcctgcgc gaagtcgaag ttatctatcg    2160
ctcgaaagcc tgcctgattc aacgcgatgg cgaaatggaa gaatccaaac agcaactgat    2220
cgacaaactg ctgacccgta ttcagggtgt gatccaggcg cgcgaatcaa aatacatcat    2280
gatgcacgca ccgaccgaac gtctggatga agtcatccag tgatgataca acgagttagc    2340
caaggtg                                                              2347

<210> SEQ ID NO 207
<211> LENGTH: 80
<212> TYPE: DNA
<213> ORGANISM: artificial sequence
<220> FEATURE:
<223> OTHER INFORMATION: primer

<400> SEQUENCE: 207
cttcgaagaa tatactaaaa aatgagcagg caagataaac gaaggcaaag gcattgcgga    60
ttacgtattc taatgttcag                                                80

<210> SEQ ID NO 208
<211> LENGTH: 80
<212> TYPE: DNA
<213> ORGANISM: artificial sequence
<220> FEATURE:
<223> OTHER INFORMATION: primer

<400> SEQUENCE: 208
cttcgaagaa tatactaaaa aatgagcagg caagataaac gaaggcaaag gcattgcgga    60
ttacgtattc taatgttcag                                                80
```

ENHANCED PYRUVATE TO ACETOLACTATE CONVERSION IN YEAST

CROSS REFERENCE TO RELATED APPLICATIONS

This application claims the benefit of priority of U.S. Provisional Application No. 61/058,970, filed Jun. 5, 2008.

FIELD OF THE INVENTION

The invention relates to the field of industrial microbiology and the metabolism of yeast. More specifically, engineering yeast for a high flux through an acetolactate intermediate allows increased production of compounds in pathways including acetolactate as an upstream substrate.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase. 2-Butanone, also referred to as methyl ethyl ketone (MEK), is a widely used solvent and is the most important commercially produced ketone, after acetone. It is used as a solvent for paints, resins, and adhesives, as well as a selective extractant, activator of oxidative reactions, and it can be chemically converted to 2-butanol by reacting with hydrogen in the presence of a catalyst (Nystrom, R. F. and Brown, W. G. (J. Am. Chem. Soc. (1947) 69:1198). 2,3-butanediol may be used in the chemical synthesis of butene and butadiene, important industrial chemicals currently obtained from cracked petroleum, and esters of 2,3-butanediol may be used as plasticizers (Voloch et al. Fermentation Derived 2,3-Butanediol, in Comprehensive Biotechnology, Pergamon Press Ltd, England Vol 2, Section 3:933-947 (1986)).

Microorganisms may be engineered for expression of biosynthetic pathways for production of 2,3-butanediol, 2-butanone, 2-butanol and isobutanol. Commonly owned and co-pending U.S. Patent Application publication U.S. 20070092957 A1 discloses the engineering of recombinant microorganisms for production of isobutanol. Commonly owned and co-pending U.S. Patent Application publications U.S. 20070259410A1 and U.S. 20070292927A1 disclose the engineering of recombinant microorganisms for production of 2-butanone or 2-butanol. Multiple pathways are disclosed for biosynthesis of isobutanol and 2-butanol, all of which initiate with cellular pyruvate. Butanediol is an intermediate in the 2-butanol pathway disclosed in commonly owned and co-pending U.S. Patent Application publication U.S. 20070292927A1.

Production of 2,3-butanediol, 2-butanone, 2-butanol and isobutanol in recombinant yeasts is limited by availability of substrate flow from natural yeast metabolic pathways into engineered biosynthetic pathways producing these compounds. Since the biosynthetic pathways for isobutanol, 2,3-butanediol, 2-butanol, and 2-butanone draw from host cell production of pyruvate, this substrate may be a limitation in product formation. The first step in these engineered pathways is conversion of pyruvate to acetolactate, which is catalyzed by acetolactate synthase.

Pyruvate metabolism has been altered in yeast for production of lactic acid and glycerol. U.S.20070031950 discloses a yeast strain with a disruption of one or more pyruvate decarboxylase or pyruvate dehydrogenase genes and expression of a D-lactate dehydrogenase gene, which is used for production of D-lactic acid. Ishida et al. (Biosci. Biotech. and Biochem. 70:1148-1153 (2006)) describe *Saccharomyces cerevisiae* with disrupted pyruvate dehydrogenase genes and expression of lactate dehydrogenase. U.S.2005/0059136 discloses glucose tolerant $C_2$ carbon source-independent (GCSI) yeast strains with no pyruvate decarboxylase activity, which may have an exogenous lactate dehydrogenase gene. Nevoigt and Stahl (Yeast 12:1331-1337 (1996)) describe the impact of reduced pyruvate decarboxylase and increased NAD-dependent glycerol-3-phosphate dehydrogenase in *Saccharomyces cerevisiae* on glycerol yield.

To improve the production of isobutanol, 2,3-butanediol, 2-butanol or 2-butanone in yeast, the problem remaining to be solved is to increase the conversion of pyruvate to acetolactate, which then flows into engineered biosynthetic pathways to produce these compounds.

SUMMARY OF THE INVENTION

The invention describers the finding that that by combining expression of acetolactate synthase enzyme activity in the yeast cytosol with reduced pyruvate decarboxylase activity, a surprisingly high flux from pyruvate to acetolactate can be achieved. The invention provides yeast cells that are engineered to have high conversion of endogenous pyruvate to acetolactate in the cytoplasm due to suppression of competing metabolic pathways in the presence of cytosolic acetolactate synthase activity. The yeast cells may also have an engineered complete biosynthetic pathway for production of isobutanol, 2,3-butanediol, 2-butanone or 2-butanol. The engineered yeast may be used for production of isobutanol, 2,3-butanediol, 2-butanone or 2-butanol, or other products derived from acetolactate such as valine, isoleucine and isoamyl alcohol.

Accordingly the invention provides a recombinant yeast cell comprising at least one gene encoding a cytosol-localized polypeptide having acetolactate synthase activity wherein the yeast cell is substantially free of an enzyme having pyruvate decarboxylase activity, and wherein the cell converts pyruvate to acetolactate. Preferred recombinant yeast cells of the invention are those having disruptions in genes encoding pyruvate decarboxylases, pyruvate dehydrogenases and NAD-dependent glycerol-3-phosphate dehydrogenases.

In other embodiments the invention provides recombinant yeast cells having the ability to produce 2,3-butanedidol, isobutanol, 2-butanone or 2-butanol comprising at least one gene encoding a cytosol-localized polypeptide having acetolactate synthase activity wherein the yeast cell is substantially free of an enzyme having pyruvate decarboxylase activity, and wherein the cell converts pyruvate to acetolactate with at least about 60% of theoretical yield.

In another embodiment the invention provides methods for the production of 2,3-butanediol, isobutanol, 2-butanone or 2-butanol comprising growing the recombinant yeast cells of the invention under conditions wherein 2,3-butanediol, isobutanol, 2-butanone or 2-butanol is produced and optionally recovering the 2,3-butanediol, isobutanol, 2-butanone or 2-butanol.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

FIGS. 4A-4D show sequence relationships of acetolactate synthase (als) coding regions that were retrieved by BLAST analysis using the sequence of *B. subtilis* AlsS, limiting to the 100 closest neighbors. The als encoding sequence is identified by its source organism.

Figure 1:
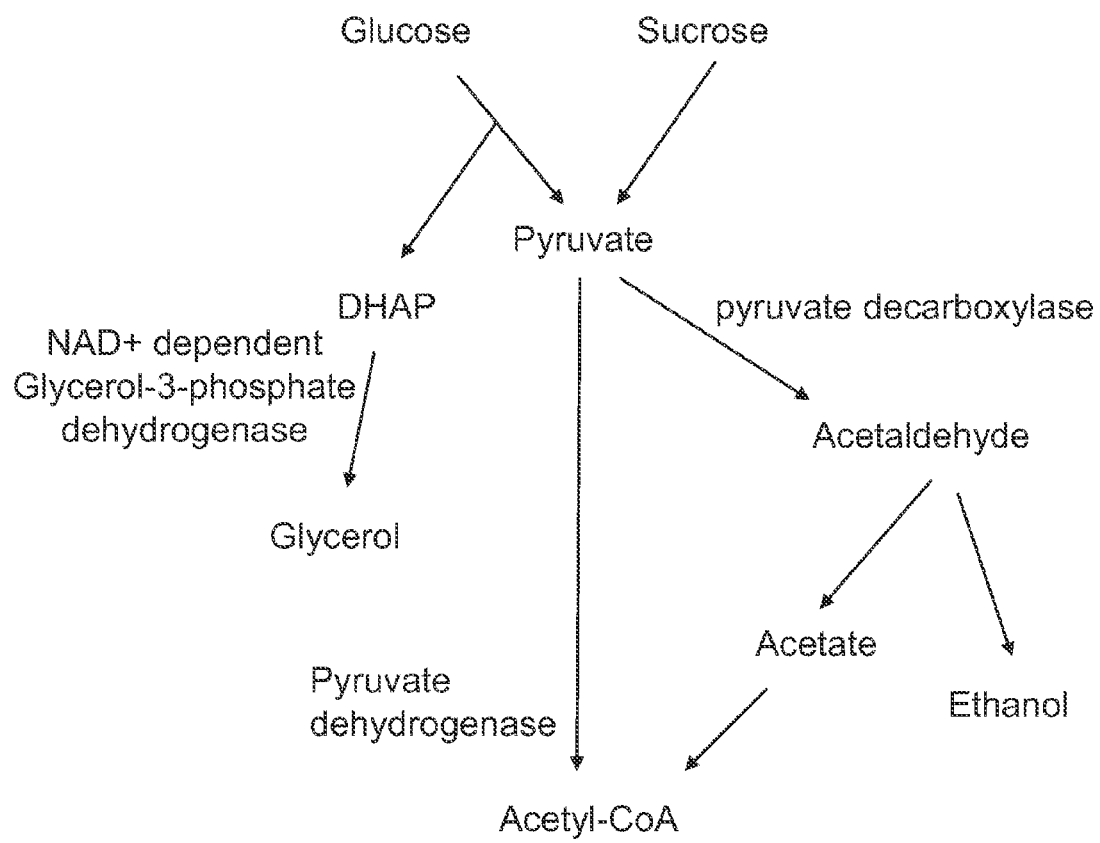
FIG. 1 shows pathways and enzymes for pyruvate utilization.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID Numbers of Expression Coding Regions and Proteins

| Description | SEQ ID NO: Nucleic acid | SEQ ID NO: Amino acid |
|---|---|---|
| *Klebsiella pneumoniae* budB (acetolactate synthase) | 1 | 2 |
| *Bacillus subtilis* alsS (acetolactate synthase) | 3 | 4 |
| *Lactococcus lactis* als (acetolactate synthase) | 5 | 6 |
| Als *Staphylococcus aureus* | 7 | 8 |
| Als *Listeria monocytogenes* | 9 | 10 |
| Als *Streptococcus mutans* | 11 | 12 |
| Als *Streptococcus thermophilus* | 13 | 14 |
| Als *Vibrio angustum* | 15 | 16 |
| Als *Bacillus cereus* | 17 | 18 |
| budA, acetolactate decarboxylase from *Klebsiella pneumoniae* ATCC 25955 | 19 | 20 |
| alsD, acetolactate decarboxylase from *Bacillus subtilis* | 21 | 22 |
| budA, acetolactate decarboxylase from *Klebsiella terrigena* | 23 | 24 |
| budC, butanediol dehydrogenase from *Klebsiella pneumoniae* IAM1063 | 25 | 26 |
| butanediol dehydrogenase from *Bacillus cereus* | 27 | 28 |
| butB, butanediol dehydrogenase from *Lactococcus lactis* | 29 | 30 |
| RdhtA, B12-indep diol dehydratase from *Roseburia inulinivorans* | 31 | 32 |
| RdhtB, B12-indep diol dehydratase reactivase from *Roseburia inulinivorans* | 33 | 34 |
| sadB, butanol dehydrogenase from *Achromobacter xylosoxidans* | 35 | 36 |
| *S. cerevisiae* ILV5 (acetohydroxy acid reductoisomerase) | 37 | 38 |
| *Vibrio cholerae* ketol-acid reductoisomerase | 39 | 40 |
| *Pseudomonas aeruginosa* ketol-acid reductoisomerase | 41 | 42 |
| *Pseudomonas fluorescens* ketol-acid reductoisomerase | 43 | 44 |
| *S. cerevisiae* ILV3 (Dihydroxyacid dehydratase; DHAD) | 45 | 46 |

TABLE 1-continued

SEQ ID Numbers of Expression Coding Regions and Proteins

| Description | SEQ ID NO: Nucleic acid | SEQ ID NO: Amino acid |
|---|---|---|
| *Lactococcus lactis* kivD (branched-chain α-keto acid decarboxylase), codon optimized | 47 | 48 |
| *Lactococcus lactis* kivD (branched-chain α-keto acid decarboxylase) | 49 | 48* |
| Pf5.IlvC-Z4B8 mutant *Pseudomonas fluorescens* acetohydroxy acid reductoisomerase | 168 | 169 |
| *Bacillis subtilis* kivD codon optimized for *S. cerevisiae* expression | 172 | 173 |
| *Equus caballus* alcohol dehydrogenase codon optimized for *S. cerevisiae* expression | 174 | 175 |
| *Streptococcus mutans* ilvD (DHAD) | 185 | 186 |

*The same amino acid sequence is encoded by SEQ ID NOs: 47 and 49.

TABLE 2

SEQ ID Numbers of Disruption target Gene coding regions and Proteins

| Description | SEQ ID NO: Nucleic acid | SEQ ID NO: Amino acid |
|---|---|---|
| PDC1 pyruvate decarboxylase from *Saccharomyces cerevisiae* | 50 | 51 |
| PDC5 pyruvate decarboxylase from *Saccharomyces cerevisiae* | 52 | 53 |
| PDC6 pyruvate decarboxylase from *Saccharomyces cerevisiae* | 54 | 55 |
| pyruvate decarboxylase from *Candida glabrata* | 56 | 57 |
| PDC1 pyruvate decarboxylase from *Pichia stipitis* | 58 | 59 |
| PDC2 pyruvate decarboxylase from *Pichia stipitis* | 60 | 61 |
| pyruvate decarboxylase from *Kluyveromyces lactis* | 62 | 63 |
| pyruvate decarboxylase from *Yarrowia lipolytica* | 64 | 65 |
| pyruvate decarboxylase from *Schizosaccharomyces pombe* | 66 | 67 |
| GPD1 NAD-dependent glycerol-3-phosphate dehydrogenase from *Saccharomyces cerevisiae* | 68 | 69 |
| GPD2 NAD-dependent glycerol-3-phosphate dehydrogenase from *Saccharomyces cerevisiae* | 70 | 71 |
| GPD1 NAD-dependent glycerol-3-phosphate dehydrogenase from *Pichia stipitis* | 72 | 73 |
| GPD2 NAD-dependent glycerol-3-phosphate dehydrogenase from *Pichia stipitis* | 74 | 75 |
| NAD-dependent glycerol-3-phosphate dehydrogenase from *Kluyveromyces thermotolerans* | 76 | 77 |
| GPD1 NAD-dependent glycerol-3-phosphate dehydrogenase from *Schizosaccharomyces pombe* | 78 | 79 |
| GPD2 NAD-dependent glycerol-3-phosphate dehydrogenase from *Schizosaccharomyces pombe* | 80 | 81 |
| PDA1, Pyruvate dehydrogenase from *Saccharomyces cerevisiae* | 82 | 83 |
| PDB1, Pyruvate dehydrogenase from *Saccharomyces cerevisiae* | 84 | 85 |
| Lat1 pyruvate dehydrogenase complex from *Saccharomyces cerevisiae* | 86 | 87 |
| Lpd1 pyruvate dehydrogenase complex from *Saccharomyces cerevisiae* | 88 | 89 |

TABLE 2-continued

SEQ ID Numbers of Disruption target Gene coding regions and Proteins

| Description | SEQ ID NO: Nucleic acid | SEQ ID NO: Amino acid |
|---|---|---|
| Pdx1 pyruvate dehydrogenase complex from *Saccharomyces cerevisiae* | 90 | 91 |
| PDA1, Pyruvate dehydrogenase from *Pichia stipitis* | 92 | 93 |
| PDB1, Pyruvate dehydrogenase from *Pichia stipitis* | 94 | 95 |
| Pyruvate dehydrogenase from *Kluyveromyces lactis* | 96 | 97 |
| PDA1, Pyruvate dehydrogenase from *Schizosacharomyces pombe* | 98 | 99 |
| PDB1, Pyruvate dehydrogenase from *Schizosacharomyces pombe* | 100 | 101 |

SEQ ID NOs:102-113, 117-134, 127-134, 136, 137, 139-164, 178, 179, 181, 182, 189-197, 199-205 and 207-208 are sequencing and PCR primers used and described in the Examples.

SEQ ID NO:114 is the *S. cerevisiae* GPD1 promoter.
SEQ ID NO:115 is the *S. cerevisiae* CYC1 terminator.
SEQ ID NO:116 is the *S. cerevisiae* FBA promoter.
SEQ ID NO:125 is the *S. cerevisiae* CUP1 promoter.
SEQ ID NO:126 is the *S. cerevisiae* ADH1 terminator.
SEQ ID NO:135 is the *S. cerevisiae* GPM1 promoter.
SEQ ID NO:138 is the sequence of a synthetic fragment containing coding regions for *Roseburia inulinivorans* $B_{12}$-independent diol dehydratase and reactivase.
SEQ ID NO:143 is the dual terminator.
SEQ ID NO:165 is the sequence of the pLH475-Z4B8 vector.
SEQ ID NO:166 is the *S. cerevisiae* CYC1-2 terminator.
SEQ ID NO:167 is the *S. cerevisiae* ILV5 promoter.
SEQ ID NO:170 is the *S. cerevisiae* ILV5 terminator.
SEQ ID NO:171 is the sequence of the pLH468 vector.
SEQ ID NO:176 is the sequence of the pNY8 vector.
SEQ ID NO:177 is the *S. cerevisiae* GPD1-2 promoter.
SEQ ID NO:180 is the sequence of the pRS425::GPM-sadB vector.
SEQ ID NO:183 is the sequence of the pRS423 FBA ilvD (Strep) vector.
SEQ ID NO:184 is the *S. cerevisiae* FBA terminator.
SEQ ID NO:187 is the sequence of the GPM-sadB-ADHt fragment.
SEQ ID NO:188 is the sequence of the pUC19-URA3r vector.
SEQ ID NO: 198 is the sequence of the ilvD-FBA1t fragment.
SEQ ID NO:206 is the sequence of the URA3r2 marker template DNA.

DETAILED DESCRIPTION OF THE INVENTION

The present invention relates to recombinant yeast cells engineered for improved production of acetolactate and compounds having acetolactate as an upstream intermediate including isobutanol, 2,3-butanediol, 2-butanone and 2-butanol. In addition, the present invention relates to methods of producing these compounds using the present engineered yeast cells. Isobutanol, 2,3-butanediol, 2-butanone and 2-butanol are important compounds for use in replacing fossil fuels either directly or as intermediates for further chemical synthesis, in addition to applications as solvents and/or extractants.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 2-butanol, 1-butanol, isobutanol, or mixtures thereof.

The term "isobutanol biosynthetic pathway" refers to an enzyme pathway to produce isobutanol from pyruvate.

The term "2-butanol biosynthetic pathway" refers to an enzyme pathway to produce 2-butanol from pyruvate.

The term "2-butanone biosynthetic pathway" refers to an enzyme pathway to produce 2-butanone from pyruvate.

The terms "acetolactate synthase" and "acetolactate synthetase" are used intechangeably herein to refer to an enzyme that catalyzes the conversion of pyruvate to acetolactate and $CO_2$. Preferred acetolactate synthases are known by the EC number 2.2.1.6 (*Enzyme Nomenclature* 1992, Academic Press, San Diego). These enzymes are available from a number of sources, including, but not limited to, *Bacillus subtilis* (DNA: SEQ ID NO:3; protein: SEQ ID NO:4), *Klebsiella pneumoniae* (DNA: SEQ ID NO:1; protein:SEQ ID NO:2), and *Lactococcus lactis* (DNA: SEQ ID NO:5; protein: SEQ ID NO:6).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (DNA: SEQ ID NO:21, Protein: SEQ ID NO:22), *Klebsiella terrigena* (DNA: SEQ ID NO:23, Protein: SEQ ID NO:24) and *Klebsiella pneumoniae* (DNA: SEQ ID NO:19, protein: SEQ ID NO:20).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (DNA: SEQ ID NO:25, protein: SEQ ID NO:26). (R)-specific butanediol dehydrogenases are known as EC 1.1.1.4 and are available, for example, from *Bacillus cereus* (DNA: SEQ ID NO:27, protein: SEQ ID NO:28), and *Lactococcus lactis* (DNA: SEQ ID NO:29, protein: SEQ ID NO:30).

The term "substantially free" when used in reference to the presence or absence of enzyme activities (pyruvate decarboxylase, pyruvate dehydrogenase, NAD-dependent glycerol-3-phosphate dehydrogenase) in carbon pathways that compete with the present isobutanol pathway means that the level of the enzyme is substantially less than that of the same enzyme in the wildtype host, where less than about 20% of the wildtype level is preferred and less than about 10% of the wildtype level is more preferred. The activity may be less than about 5% or 1% of wildtype activity.

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, and polysaccharides. The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA). Expression may also refer to translation of mRNA into a polypeptide.

As used herein the term "transformation" refers to the transfer of a nucleic acid molecule into a host cell, which may be maintained as a plasmid or integrated into the genome. Host cells containing the transformed nucleic acid molecules are referred to as "transgenic" or "recombinant" or "transformed" cells.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without effecting the amino acid sequence of an encoded polypeptide. The skilled artisan is well aware of the "cod.

The term "codon-optimized" as it refers to coding regions of nucleic acid molecules for transformation of various hosts, refers to the alteration of codons in the coding regions of the nucleic acid molecules to reflect the typical codon usage of the host organism without altering the polypeptide encoded by the DNA. on-bias" exhibited by a specific host cell in usage of nucleotide codons to specify a given amino acid. Therefore, when synthesizing a coding region for improved expression in a host cell, it is desirable to design the coding region such that its frequency of codon usage approaches the frequency of preferred codon usage of the host cell.

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2$^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Man iatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

Production Through Acetolactate from Endogenous Pyruvate

Figure 2:
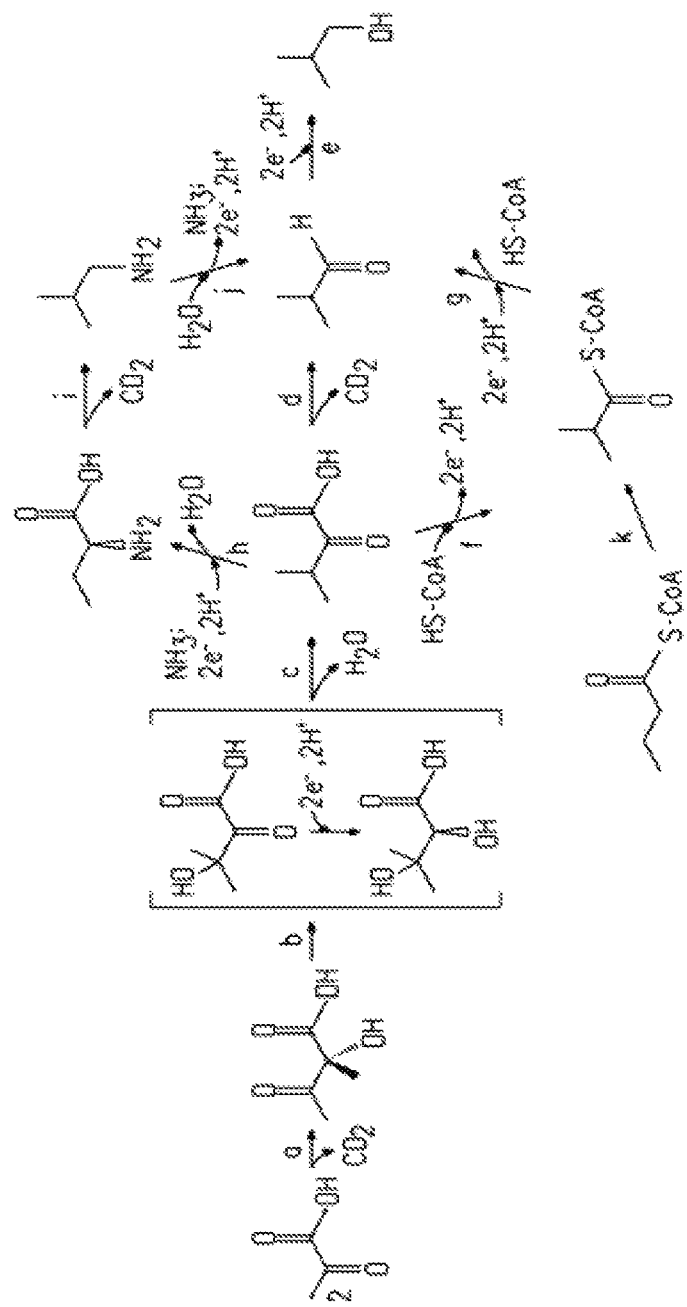
FIG. 2 shows three different isobutanol biosynthetic pathways.
Figure 3:
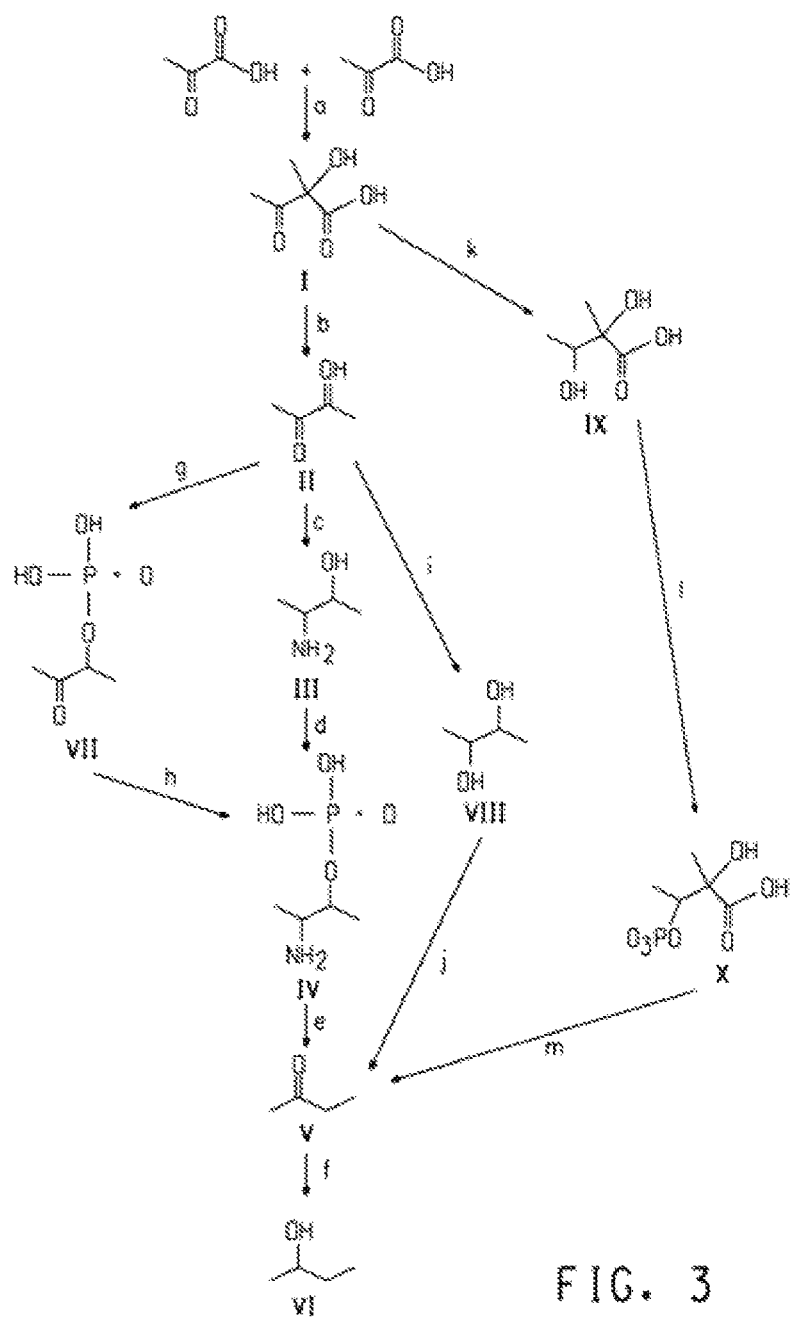
FIG. 3 shows four different 2-butanol biosynthetic pathways.

Yeast cells produce pyruvate from sugars, which is then utilized in a number of pathways of cellular metabolism including those shown in FIG. 1. Yeast cells can be engineered to produce a number of desirable products with the initial biosynthetic pathway step being conversion of endogenous pyruvate to acetolactate. Engineered biosynthetic pathways for synthesis of isobutanol (see FIG. 2) are described in commonly owned and co-pending U.S. Patent Application Publication U.S.20070092957, which is herein incorporated by reference, and for synthesis of 2-butanol and 2-butanone (see FIG. 3) are described in commonly owned and co-pending U.S. Patent Application Publications U.S.20070259410 and U.S. 20070292927, which are herein incorporated by reference. The product 2,3-butanediol is an intermediate in the biosynthetic pathway described in U.S. 20070292927. Each of these pathways has the initial step of converting pyruvate to acetolactate by acetolactate synthase. Therefore product yield from these biosynthetic pathways will in part depend upon the amount of acetolactate that can be produced from pyruvate and the amount of pyruvate that is available.

Applicants have discovered that by combining expression of acetolactate synthase enzyme activity in the yeast cytosol with reduced pyruvate decarboxylase activity, a surprisingly high flux from pyruvate to acetolactate can be achieved. Flux from pyruvate to acetolactate may be measured by conversion of glucose or sucrose to 2,3-butanediol. Pyruvate is produced from glucose or sucrose. Synthesis of 2,3-butanediol requires two additional steps: conversion of acetolactate to acetoin by acetolactate decarboxylase, and conversion of acetoin to 2,3-butanediol by butanediol dehydrogenase. Thus at least as much flux from pyruvate to acetolactate must occur as the measured flux from glucose or sucrose to 2,3-butanediol, and potentially more since the two enzymatic steps following acetolactate are likely to be less than 100% efficient.

Applicants found that about 86% of the theoretical yield of sucrose conversion to 2,3-butanediol was achieved in the presence of an electron sink, as shown in Example 4 herein. About 90% of the theoretical yield of glucose conversion to 2,3-butanediol was achieved in the presence of an electron sink. The theoretical yield of glucose to 2,3-butanediol is calculated to be 0.5 g of 2,3-butanediol per 1 g of glucose. An electron sink is required for redox balance in the biosynthetic pathway to 2,3-butanediol. Complete 2-butanol and isobutanol biosynthetic pathways that are disclosed in U.S. Patent Publications U.S.20070092957, U.S.20070259410, and U.S. 20070292927, are in themselves redox balanced and require no additional electron sink to reach maximal product formation.

Glucose conversion to 2,3-butanediol without an added electron sink was found herein to be about 60% of theoretical yield (0.3 g of 2,3-butanediol per 1 g of glucose), and conversion was about 68% from sucrose. Thus the conversion of pyruvate to acetolactate achieved was at least about 60%. Therefore by combining expression of acetolactate synthase enzyme activity in the yeast cytosol with reducing pyruvate decarboxylase activity, without balance of redox equivalents, conversion of pyruvate to acetolactate may achieve at least about 60% of theoretical yield. By combining expression of acetolactate synthase enzyme activity in the yeast cytosol with reducing pyruvate decarboxylase activity, and with balance of redox equivalents, conversion of pyruvate to acetolactate may achieve at least about 86% of theoretical yield.

Expression of Acetolactate Synthase in the Yeast Cytosol

Endogenous acetolactate synthase in yeast is encoded in the mitochondrial genome and expressed in the mitochondria. To prepare a recombinant yeast strain of the present invention a genetic modification is made that provides cytosolic expression of acetolactate synthase. Acetolactate synthase is expressed from the nucleus and no mitochondrial targeting signal is included so that the enzyme remains in the cytosol (cytosol-localized).

Acetolactate synthase enzymes, which also may be called acetohydroxy acid synthase, belong to EC 2.2.1.6 (switched from 4.1.3.18 in 2002), are well-known, and they participate in the biosynthetic pathway for the proteinogenic amino acids leucine and valine, as well as in the pathway for fermentative production of 2,3-butanediol and acetoin in a number of organisms.

The skilled person will appreciate that polypeptides having acetolactate synthase activity isolated from a variety of sources will be useful in the present invention independent of sequence homology. Some examples of suitable acetolactate synthase enzymes are available from a number of sources, as described in the definitions above. Acetolactate synthase enzyme activities that have substrate preference for pyruvate over ketobutyrate are of particular utility, such as those encoded by alsS of *Bacillus* and budB of *Klebsiella* (Gollop et al., *J. Bacteriol.* 172(6):3444-3449 (1990); Holtzclaw et al., *J. Bacteriol.* 121(3):917-922 (1975)).

Because acetolactate synthases are well known, and because of the prevalence of genomic sequencing, suitable acetolactate synthases may be readily identified by one skilled in the art on the basis of sequence similarity using bioinformatics approaches. Typically BLAST (described above) searching of publicly available databases with known acetolactate synthase amino acid sequences, such as those provided herein, is used to identify acetolactate synthases, and their encoding sequences, that may be used in the present strains. For example, acetolactate synthases that are the 100 closest neighbors of the *B. subtilis* AlsS sequence are depicted in a phylogenetic tree in FIG. 4. The homology relationships between the sequences identified are shown in this tree. Among these sequences are those having 40% identity, yet these have been verified as acetolactate synthases. A representative sequence from each bracket is given in Table 2. Acetolactate synthase proteins having at least about 70-75%, 75%-80%, 80-85%, 85%-90%, 90%-95% or at least about 98% sequence identity to any of the acetolactate synthase proteins in Table 1 (SEQ ID NOs:2, 4, 6, 8, 10, 12, 14, 16, and 18), or any of the acetolactate synthase proteins represented in FIG. 4 may be used in the present strains. Identities are based on the Clustal W method of alignment using the default parameters of GAP PENALTY=10, GAP LENGTH PENALTY=0.1, and Gonnet 250 series of protein weight matrix.

Figure 4A:
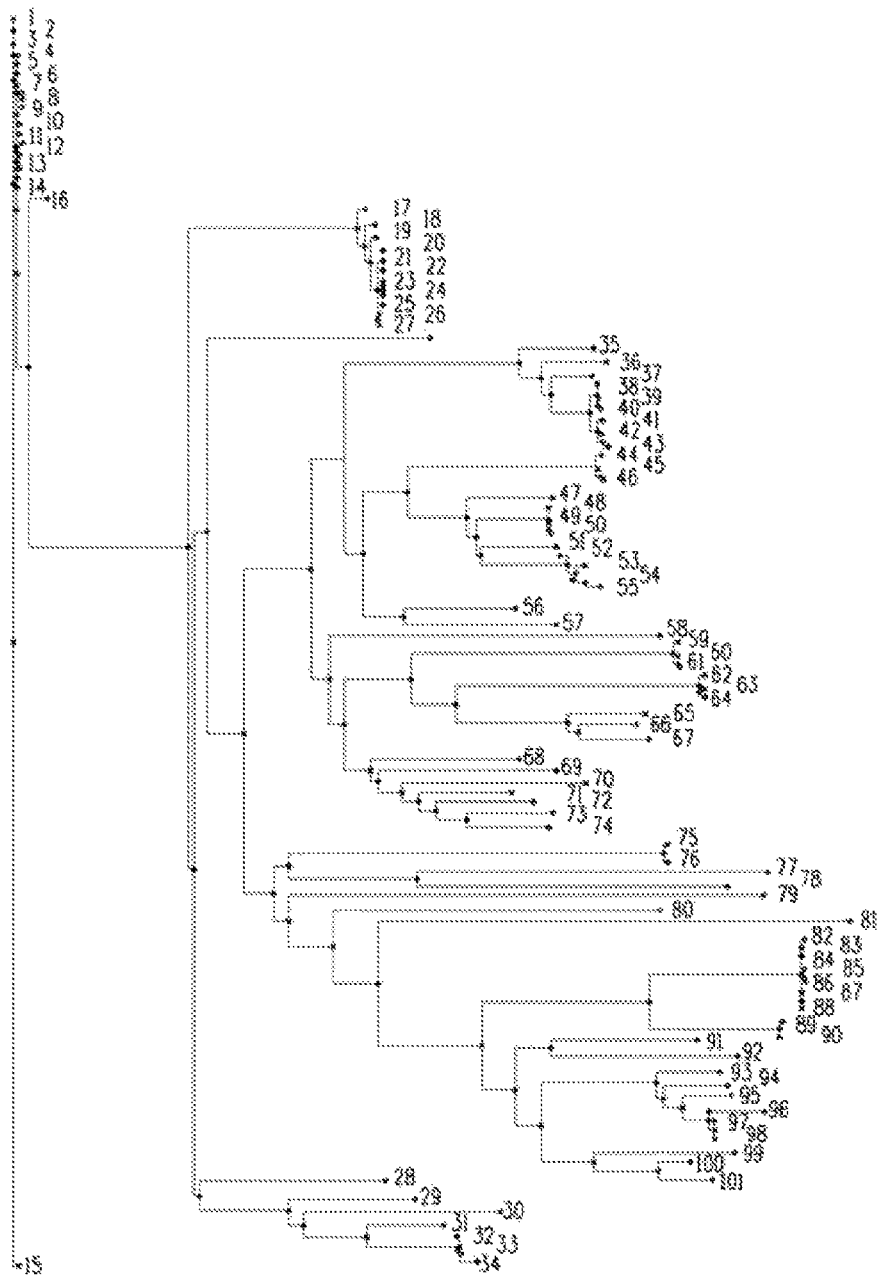

Examples of sequences encoding acetolactate synthase which may be used to provide cytosolic expression of acetolactate synthase activity are listed in Table 1 (SEQ ID NOs:1, 3, 5, 7, 9,11,13,15,17). Additional acetolactate synthase encoding sequences that may be used for yeast cytosolic expression may be identified in the literature and in bioinformatics databases well known to the skilled person, and some coding regions for als proteins are represented in FIG. 4 by the source organism. Any Als having EC number 2.2.1.6 may be identified by one skilled in the art and may be used in the present strains.

Additionally, the sequences described herein or those recited in the art may be used to identify other homologs in nature. For example each of the acetolactate synthase encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. U.S.A* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the acetolactate synthase encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS U.S.A* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., PNAS U.S.A 86:5673 (1989); Loh et al., *Science* 243:217 (1989)).

Alternatively, the described acetolactate synthase encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Cytosolic expression of acetolactate synthase is achieved by transforming with a gene comprising a sequence encoding an acetolactate synthase protein, with no mitochondrial targeting signal sequence. Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, operably linked to a coding region of interest, and a transcriptional terminator. A number of yeast promoters can be used in constructing expression cassettes for genes encoding an acetolactate synthase, including, but not limited to constitutive promoters FBA, GPD1, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1.

Suitable promoters, transcriptional terminators, and acetolactate synthase coding regions may be cloned into *E. coli*-yeast shuttle vectors, and transformed into yeast cells as described in Examples 2-4. These vectors allow strain propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with a chimeric gene encoding an acetolactate synthase may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a≥21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an E. coli strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding regionX-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

Reduced Pyruvate Decarboxylase Activity

Endogenous pyruvate decarboxylase activity in yeast converts pyruvate to acetaldehyde, which is then converted to ethanol or to acetyl-CoA via acetate (see FIG. 1). Yeasts may have one or more genes encoding pyruvate decarboylase. For example, there is one gene encoding pyruvate decarboxylase in Kluyveromyces lactis, while there are three isozymes of pyruvate decarboxylase encoded by the PDC1, PCD5, and PDC6 genes in Saccharomyces cerevisiae, as well as a pyruvate decarboxylase regulatory gene PDC2. Expression of pyruvate decarboxylase from PDC6 is minimal. In the present yeast strains the pyruvate decarboxylase activity is reduced by disrupting at least one gene encoding a pyruvate decarboxylase, or a gene regulating pyruvate decarboxylase gene expression. For example, in S. cerevisiae the PDC1 and PDC5 genes, or all three genes, are disrupted. In addition, pyruvate decarboxylase activity may be reduced by disrupting the PDC2 regulatory gene in S. cerevisiae. In other yeasts, genes encoding pyruvate decarboxylase proteins such as those having at least about 80-85%, 85%-90%, 90%-95%, or at least about 98% sequence identity to PDC1 or PDC5 may be disrupted.

Examples of yeast strains with reduced pyruvate decarboxylase activity due to disruption of pyruvate decarboxylase encoding genes have been reported such as for Saccharomyces in Flikweert et al. (Yeast (1996) 12:247-257), for Kluyveromyces in Bianchi et al. (Mol. Microbiol. (1996) 19(1):27-36), and disruption of the regulatory gene in Hohmann, (Mol Gen Genet. (1993) 241:657-666). Saccharomyces strains having no pyruvate decarboxylase activity are available from the ATCC with Accession #200027 and #200028.

Expression of pyruvate decarboxylase genes may be reduced in any yeast strain that is also engineered with cytosolic acetolactate synthase expression and other biosynthetic pathway enzyme encoding genes for production of a compound derived from acetolactate. Examples of yeast pyruvate decarboxylase genes that may be targeted for disruption are listed in Table 2 (SEQ ID NOs:50, 52, 54, 56, 58, 60, 62, 64, 66). Other target genes, such as those encoding pyruvate decarboxylase proteins having at least about 80-85%, 85%-90%, 90%-95%, or at least about 98% sequence identity to the pyruvate decarboxylases listed in Table 2 (SEQ ID NOs:51, 53, 55, 57, 59, 61, 63, 65, 67) may be identified in the literature and in bioinformatics databases well known to the skilled person. Additionally, the sequences described herein or those recited in the art may be used to identify homologs in other yeast strains, as described above for identification of acetolactate synthase encoding genes.

Alternatively, because pyruvate decarboxylase encoding sequences are well known, and because sequencing of the genomes of yeasts is prevalent, suitable pyruvate decarboxylase gene targets may be identified on the basis of sequence similarity using bioinformatics approaches. Genomes have been completely sequenced and annotated and are publicly available for the following yeast strains: Ashbya gossypii ATCC 10895, Candida glabrata CBS 138, Kluyveromyces lactis NRRL Y-1140, Pichia stipitis CBS 6054, Saccharomyces cerevisiae S288c, Schizosaccharomyces pombe 972h-, and Yarrowia lipolytica CLIB122. Typically BLAST (described above) searching of publicly available databases with known pyruvate decarboxylase encoding sequences or pyruvate decarboxylase amino acid sequences, such as those provided herein, is used to identify pyruvate decarboxylase encoding sequences of other yeasts.

Accordingly it is within the scope of the invention to provide pyruvate decarboxylase proteins having at least about 70-75%, 75%-80%, 80-85%, 85%-90%, 90%-95% or at least about 98% sequence identity to any of the pyruvate decarboxylase proteins disclosed herein (SEQ ID NO:51, 53, 55, 57, 59, 61, 63, 65, and 67) Identities are based on the Clustal W method of alignment using the default parameters of GAP PENALTY=10, GAP LENGTH PENALTY=0.1, and Gonnet 250 series of protein weight matrix.

Genes encoding pyruvate decarboxylase may be disrupted in any yeast cell using genetic modification. Many methods for genetic modification of target genes are known to one skilled in the art and may be used to create the present yeast strains. Modifications that may be used to reduce or eliminate expression of a target protein are disruptions that include, but are not limited to, deletion of the entire gene or a portion of the gene encoding a pyruvate decarboxylase, inserting a DNA fragment into a pyruvate decarboxylase encoding gene (in either the promoter or coding region) so that the protein is not expressed or expressed at lower levels, introducing a mutation into a pyruvate decarboxylase coding region which adds a stop codon or frame shift such that a functional protein is not expressed, and introducing one or more mutations into a pyruvate decarboxylase coding region to alter amino acids so that a non-functional or a less enzymatically active protein is expressed. In addition, expression of a pyruvate decarboxylase gene may be blocked by expression of an antisense RNA or an interfering RNA, and constructs may be introduced that result in cosuppression. Moreover, a pyruvate decarboxylase encoding gene may be synthesized whose expression is low because rare codons are substituted for plentiful ones, and this gene substituted for the endogenous corresponding pyruvate decarboxylase encoding gene. Such a gene will produce the same polypeptide but at a lower rate. In addition, the synthesis or stability of the transcript may be lessened by mutation. Similarly the efficiency by which a protein is translated from mRNA may be modulated by mutation. All of these methods may be readily practiced by one skilled in the art making use of the known or identified sequences encoding pyruvate decarboxylase proteins.

DNA sequences surrounding a pyruvate decarboxylase coding sequence are also useful in some modification procedures and are available for yeasts such as for *Saccharomycse cerevisiae* in the complete genome sequence coordinated by Genome Project ID9518 of Genome Projects coordinated by NCBI (National Center for Biotechnology Information) with identifying GOPID #13838. Additional examples of yeast genomic sequences include that of *Yarrowia lipolytica*, GOPIC #13837, and of *Candida albicans*, which is included in GPID #10771, #10701 and #16373. Other yeast genomic sequences can be readily found by one of skill in the art in publicly available databases.

In particular, DNA sequences surrounding a pyruvate decarboxylase coding sequence are useful for modification methods using homologous recombination. For example, in this method pyruvate decarboxylase gene flanking sequences are placed bounding a selectable marker gene to mediate homologous recombination whereby the marker gene replaces the pyruvate decarboxylase gene. Also partial pyruvate decarboxylase gene sequences and pyruvate decarboxylase gene flanking sequences bounding a selectable marker gene may be used to mediate homologous recombination whereby the marker gene replaces a portion of the target pyruvate decarboxylase gene. In addition, the selectable marker may be bounded by site-specific recombination sites, so that following expression of the corresponding site-specific recombinase, the resistance gene is excised from the pyruvate decarboxylase gene without reactivating the latter. The site-specific recombination leaves behind a recombination site which disrupts expression of the pyruvate decarboxylase protein. The homologous recombination vector may be constructed to also leave a deletion in the pyruvate decarboxylase gene following excision of the selectable marker, as is well known to one skilled in the art.

Deletions may be made using mitotic recombination as described in Wach et al. ((1994) Yeast 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence (as described in Methods in Enzymology, v 194, pp 281-301 (1991)).

Moreover, promoter replacement methods may be used to exchange the endogenous transcriptional control elements allowing another means to modulate expression such as described in Mnaimneh et al. ((2004) Cell 118(1):31-44) and in Example 12 herein.

In addition, pyruvate decarboxylase activity in any yeast cell may be disrupted using random mutagenesis, which is followed by screening to identify strains with reduced pyruvate decarboxylase activity. Using this type of method, the DNA sequence of the pyruvate decarboxylase encoding region, or any other region of the genome affecting expression of pyruvate carboxylase activity, need not be known.

Methods for creating genetic mutations are common and well known in the art and may be applied to the exercise of creating rmutants. Commonly used random genetic modification methods (reviewed in Methods in Yeast Genetics, 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of yeast commonly involves treatment of yeast cells with one of the following DNA mutagens: ethyl methanesulfonate (EMS), nitrous acid, diethyl sulfate, or N-methyl-N'-nitro-N-nitroso-guanidine (MNNG). These methods of mutagenesis have been reviewed in Spencer et al (Mutagenesis in Yeast, 1996, *Yeast Protocols: Methods in Cell and Molecular Biology*. Humana Press, Totowa, N.J.). Chemical mutagenesis with EMS may be performed as described in Methods in Yeast Genetics, 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al (Mutagenesis in Yeast, 1996, *Yeast Protocols: Methods in Cell and Molecular Biology*. Humana Press, Totowa, N.J.). Introduction of a mutator phenotype can also be used to generate random chromosomal mutations in yeast. Common mutator phenotypes can be obtained through disruption of one or more of the following genes: PMS1, MAG1, RAD18 or RAD51. Restoration of the non-mutator phenotype can be easily obtained by insertion of the wildtype allele. Collections of modified cells produced from any of these or other known random mutagenesis processes may be screened for reduced pyruvate decarboxylase activity.

Reduced Pyruvate Dehydrogenase Activity

Endogenous pyruvate dehydrogenase activity is in the yeast mitochondrion and catalyzes oxidative decarboxylation of pyruvate to form acetyl-CoA. Acetyl-CoA is used in the TCA cycle and in fatty acid biosynthesis. The pyruvate dehydrogenase enzyme is one enzyme of a multienzyme pyruvate dehydrogenase complex. Pyruvate dehydrogenase (EC 1.2.4.1) itself has alpha and beta subunits: PDA1 and PDB1, respectively, forming the E1 component. The complex includes an E2 core which has dihydrolipoamide acetyltransferase activity (EC 2.3.1.12) and E3 which has dihydrolipoamide dehydrogenase activity (EC1.8.1.4). E2 may be encoded by lat1 and E3 by lpd1. An additional complex protein is encoded by pdx1. Thus the pyruvate dehydrogenase complex may include PDA1, PDB1, Lat1, Lpd1, and Pdx1, or homologous proteins encoded by genes which may have alternative names in various yeasts.

Any of the genes encoding pyruvate dehydrogenase complex enzymes of yeast may be disrupted to reduce pyruvate dehydrogenase activity in a yeast cell to prepare a strain of one embodiment of the invention. Examples of yeast pyruvate dehydrogenase complex protein encoding genes that may be targeted for disruption are listed in Table 2 (SEQ ID NOs:82, 84, 86, 88, 90, 92, 94, 96, 98, 100). Other target genes, such as those encoding pyruvate dehydrogenase proteins having at least about 80-85%, 85%-9090%-95%, or at least about 98% sequence identity to the pyruvate dehydrogenases listed in Table 2 (SEQ ID NOs:83, 85, 87, 89, 91, 93, 95, 97, 99, 101) may be identified in the literature and in bioinformatics databases well known to the skilled person as described abpve. Additionally, the sequences described herein or those recited in the art may be used to identify other homologs in nature as described above for acetolactate synthase encoding sequences.

Accordingly it is within the scope of the invention to provide pyruvate dehydrogenase complex proteins having at least about 70-75%, 75%-80%, 80-85%, 85%-90%, 90%-95% or at least about 98% sequence identity to any of the pyruvate dehydrogenase complex proteins disclosed herein (SEQ ID NO: 83, 85, 87, 89, 91, 93, 95, 97, 99, 101). Identities are based on the Clustal W method of alignment using the default parameters of GAP PENALTY=10, GAP LENGTH PENALTY=0.1, and Gonnet 250 series of protein weight matrix.

Genes encoding pyruvate dehydrogenase complex proteins may be disrupted in any yeast cell using genetic modification. Many methods for genetic modification of target genes are known to one skilled in the art and may be used to create the present yeast strains. Examples of methods that may be used are as described above for disruption of pyruvate decarboxylase encoding genes. In addition, pyruvate dehydrogenase activity in any yeast cell may be disrupted using random mutagenesis, which is followed by screening to identify strains with reduced pyruvate dehydrogenase activity. Using this type of method, the DNA sequence of the pyruvate dehydrogenase encoding region, or any other region of the genome affecting expression of pyruvate dehydrogenase activity, need not be known. Examples of methods are as described above for random mutagenesis of pyruvate decarboxylase.

Reduced glycerol-3-phosphate Dehydrogenase Activity

Endogenous NAD-dependent glycerol-3-phosphate dehydrogenase is a key enzyme in glycerol synthesis, converting dihydroxyacetone phosphate (DHAP) to glycerol-3-phosphate. playing a major role in cellular oxidation of NADH. Yeast strains may have one or more genes encoding NAD-dependent glycerol-3-phosphate dehydrogenase (GPD). In some yeasts, such as *S. cerevisiae, S. pombe*, and *P. stipitis*, GPD1 and GPD2 are functional homologs for NAD-dependent glycerol-3-phosphate dehydrogenase. Any of the genes encoding NAD-dependent glycerol-3-phosphate dehydrogenase enzymes of yeast may be disrupted to reduce NAD-dependent glycerol-3-phosphate dehydrogenase activity in a yeast cell to prepare a strain of one embodiment of the invention. Examples of coding regions of yeast NAD-dependent glycerol-3-phosphate dehydrogenase protein encoding genes that may be targeted for disruption are listed in Table 2 (SEQ ID NOs:68, 70, 72, 74, 76, 80). Other target genes, such as those encoding NAD-dependent glycerol-3-phosphate dehydrogenase proteins having at least about 80-85%, 85%-90%, 90%-95%, or at least about 98% sequence identity to the NAD-dependent glycerol-3-phosphate dehydrogenases listed in Table 2 (SEQ ID NOs:69, 71, 73, 75, 77, 79, 81) may be identified in the literature and in bioinformatics databases well known to the skilled person. Additionally, the sequences described herein or those recited in the art may be used to identify other homologs in nature as described above for acetolactate synthase encoding sequences.

Accordingly it is within the scope of the invention to provide NAD-dependent glycerol-3-phosphate dehydrogenase proteins having at least about 70-75%, 75%-80%, 80-85%, 85%-90%, 90%-95% or at least about 98% sequence identity to any of the NAD-dependent glycerol-3-phosphate dehydrogenase proteins disclosed herein (SEQ ID NO: 69, 71, 73, 75, 77, 79, 81). Identities are based on the Clustal W method of alignment using the default parameters of GAP PENALTY=10, GAP LENGTH PENALTY=0.1, and Gonnet 250 series of protein weight matrix.

Genes encoding NAD-dependent glycerol-3-phosphate dehydrogenases may be disrupted in any yeast cell using genetic modification. Many methods for genetic modification of target genes are known to one skilled in the art and may be used to create the present yeast strains. In addition, random mutagenesis and screening may be used to disrupt expression of NAD-dependent glycerol-3-phosphate dehydrogenases. Examples of genetic modification and random mutagenesis methods that may be used are as described above for disruption of pyruvate decarboxylase encoding genes.

Yeast Cells with Enhanced Pyruvate Conversion to Acetolactate

The characteristics of the yeast strains disclosed herein may be made in any yeast host that is amenable to genetic manipulation. Examples include yeasts of *Saccharomyces, Schizosaccharomyces, Hansenula, Candida, Kluyveromyces, Yarrowia* and *Pichia*. Suitable strains include, but are not limited to, *Saccharomyces cerevisiae, Schizosaccharomyces pombe, Kluyveromyces lactis, Kluyveromyces thermotolerans, Candida glabrata, Candida albicans, Pichia stipitis* and *Yarrowia lipolytica*. Most suitable is *Saccharomyces cerevisiae*.

For maximal production of some products such as 2,3-butanediol, isobutanol, 2-butanone, or 2-butanol the yeast strains used as production hosts preferably have enhanced tolerance to the produced chemical, and have a high rate of carbohydrate utilization. These characteristics may be conferred by mutagenesis and selection, genetic engineering, or may be natural.

Product Biosynthesis in Enhanced Pyruvate to Acetolactate Conversion Strain

Any product that has acetolatate as a pathway intermediate may be produced with greater effectiveness in a yeast strain disclosed herein having enhanced conversion of pyruvate to acetolactate. A list of such products includes, but is not limited to, valine, leucine, isoamyl alcohol, 2,3-butanediol, 2-butanone, 2-butanol, and isobutanol.

Biosynthesis of valine includes steps of acetolactate conversion to 2,3-dihydroxy-isovalerate by acetohydroxyacid reductoisomerase (ILV5), conversion of 2,3-dihydroxy-isovalerate to 2-keto-isovalerate by dihydroxy-acid dehydratase (ILV3), and conversion of 2-keto-isovalerate to valine by branched-chain amino acid transaminase (BAT2) and branched-chain animo acid aminotransferase (BAT1). Biosynthesis of leucine includes the same steps to 2-keto-isovalerate, followed by conversion of 2-keto-isovalerate to alpha-isopropylmalate by alpha-isopropylmalate synthase (LEU9, LEU4), conversion of alpha-isopropylmalate to beta-isopropylmalate by isopropylmalate isomerase (LEU1), conversion of beta-isopropylmalate to alpha-ketoisocaproate by beta-IPM dehydrogenase (LEU2), and finally conversion of alpha-ketoisocaproate to leucine by branched-chain amino acid transaminase (BAT2) and branched-chain amino acid aminotransferase (BAT1). Increased conversion of pyruvate to acetolactate will increase flow to these pathways, particularly if one or more enzymes of the pathway is overexpressed to pull acetolactate into the pathway. Thus it is desired for production of valine or leucine to overexpress at least one of the enzymes in these described pathways.

Biosynthesis of isoamyl alcohol includes steps of leucine conversion to alpha-ketoisocaproate by branched-chain amino acid transaminase (BAT2) and branched-chain amino acid aminotransferase (BAT1), conversion of alpha-ketoisocaproate to 3-methylbutanal by ketoisocaproate decarboxylase (THI3) or decarboxylase ARO10, and finally conversion of 3-methylbutanal to isoamyl alcohol by an alcohol dehydrogenase such as ADH1 or SFA1. Thus further production of isoamyl alcohol benefits from increased production of leucine or the alpha-ketoisocaproate intermediate by overexpression of one or more enzymes in biosynthetic pathways for these chemicals. In addition, one or both enzymes for the final two steps may be overexpressed.

Biosynthetic pathways starting with a step of converting pyruvate to acetolactate for synthesis of isobutanol are disclosed in commonly owned and co-pending U.S. Patent Application publication U.S. 20070092957 A1, which is herein incorporated by reference. A diagram of the disclosed isobutanol biosynthetic pathways is provided in FIG. 2. Production of isobutanol in a strain disclosed herein benefits from increased availability of acetolactate. As described in U.S. 20070092957 A1, steps in an example isobutanol biosynthetic pathway using acetolactate include conversion of:

- acetolactate to 2,3-dihydroxyisovalerate (FIG. 2 pathway step b) as catalyzed for example by acetohydroxy acid isomeroreductase;
- 2,3-dihydroxyisovalerate to α-ketoisovalerate (FIG. 2 pathway step c) as catalyzed for example by acetohydroxy acid dehydratase;
- α-ketoisovalerate to isobutyraldehyde (FIG. 2 pathway step d) as catalyzed for example by branched-chain α-keto acid decarboxylase; and
- isobutyraldehyde to isobutanol (FIG. 2 pathway step e) as catalyzed for example by branched-chain alcohol dehydrogenase.

Genes that may be used for expression of these enzymes, as well as those for two additional isobutanol pathways, are described in U.S. 20070092957 A1, and additional genes that may be used can be identified by one skilled in the art. The preferred use in all three pathways of ketol-acid reductoisomerase (KARI) enzymes with particularly high activities are disclosed in commonly owned and co-pending U.S. Patent Application Publication #20080261230. Examples of high activity KARIs disclosed therein are those from *Vibrio cholerae* (DNA: SEQ ID NO:39; protein SEQ ID NO:40), *Pseudomonas aeruginosa* PAO1, (DNA: SEQ ID NO:41; protein SEQ ID NO:42), and *Pseudomonas fluorescens* PF5 (DNA: SEQ ID NO:43; protein SEQ ID NO:44).

Useful for the last step of converting isobutyraldehyde to isobutanol is a new butanol dehydrogenase isolated from an environmental isolate of a bacterium identified as *Achromobacter xylosoxidans* that is disclosed in commonly owned and co-pending U.S. patent application Ser. No. 12/430,356 (DNA: SEQ ID NO:35, protein SEQ ID NO:36).

Additionally described in U.S. 20070092957 A1 are construction of chimeric genes and genetic engineering of yeast, exemplified by *Saccharomyces cerevisiae*, for isobutanol production using the disclosed biosynthetic pathways.

Biosynthetic pathways starting with a step of converting pyruvate to acetolactate for synthesis of 2-butanone and 2-butanol are disclosed in commonly owned and co-pending U.S. Patent Application publications U.S. 20070259410A1 and U.S. 20070292927A1, which are herein incorporated by reference. A diagram of the disclosed 2-butanone and 2-butanol biosynthetic pathways is provided in FIG. 3. 2-Butanone is the product made when the last depicted step of converting 2-butanone to 2-butanol is omitted. Production of 2-butanone or 2-butanol in a strain disclosed herein benefits from increased availability of acetolactate. As described in U.S. 20070292927A1, steps in an example biosynthetic pathway using acetolactate include conversion of:

- acetolactate to acetoin (FIG. 3 step b) as catalyzed for example by acetolactate decarboxylase;
- acetoin to 2,3-butanediol (FIG. 3 step i) as catalyzed for example by butanediol dehydrogenase;
- 2,3-butanediol to 2-butanone (FIG. 3 step j) as catalyzed for example by diol dehydratase or glycerol dehydratase; and
- 2-butanone to 2-butanol (FIG. 3 step f) as catalyzed for example by butanol dehydrogenase.

Genes that may be used for expression of these enzymes are described in U.S. 20070292927A1. The use in this pathway in yeast of the butanediol dehydratase from *Roseburia inulinivorans*, RdhtA, (protein SEQ ID NO:32, coding region SEQ ID NO:31) is disclosed in commonly owed and co-pending U.S. patent application Ser. No. 12/111,359. This enzyme is used in conjunction with the butanediol dehydratase reactivase from *Roseburia inulinivorans*, RdhtB, (protein SEQ ID NO:34, coding region SEQ ID NO:33). This butanediol dehydratase is desired in many hosts because it does not require coenzyme $B_{12}$.

Useful for the last step of converting 2-butanone to 2-butanol is a new butanol dehydrogenase isolated from an environmental isolate of a bacterium indetified as *Achromobacter xylosoxidans* that is disclosed in commonly owned and co-pending U.S. patent application Ser. No. 12/430,356 (DNA: SEQ ID NO:35, protein SEQ ID NO:36).

Additionally described in U.S. Patent Application 12/111359 are construction of chimeric genes and genetic engineering of yeast for 2-butanol production using the U.S. 20070292927A1 disclosed biosynthetic pathway. 2,3-butanediol is an intermediate in this 2-butanol pathway and the steps in its synthesis are also described above.

Fermentation Media

Yeasts disclosed herein may be grown in fermentation media for production of a product having acetolactate as an intermediate. Fermentation media must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for production of the desired product.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1-butanol production.

Methods for Butanol Isolation from the Fermentation Medium

Bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245,199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987), and by *Methods in Yeast Genetics,* 2005, Cold Spring Harbor Laboratory Press, Cold Spring Harbor, N.Y.

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of microbial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Microbial strains were obtained from The American Type Culture Collection (ATCC), Manassas, Va., unless otherwise noted. The oligonucleotide primers used in the following Examples are given in Table 3. All the oligonucleotide primers were synthesized by Sigma-Genosys (Woodlands, Tex.) or Integrated DNA Technologies (Coralsville, Iowa).

Synthetic complete medium is described in Amberg, Burke and Strathern, 2005, Methods in Yeast Genetics, Cold Spring Harbor Laboratory Press, Cold Spring Harbor, N.Y.

GC Method

The GC method utilized an HP-InnoWax column (30 m×0.32 mm ID, 0.25 μm film) from Agilent Technologies (Santa Clara, Calif.). The carrier gas was helium at a flow rate of 1 ml/min measured at 150° C. with constant head pressure; injector split was 1:10 at 200° C.; oven temperature was 45° C. for 1 min, 45° C. to 230° C. at 10° C./min, and 230° C. for 30 sec. FID detection was used at 260° C. with 40 ml/min helium makeup gas. Culture broth samples were filtered through 0.2 μM spin filters before injection. Depending on analytical sensitivity desired, either 0.1 μl or 0.5 μl injection volumes were used. Calibrated standard curves were generated for the following compounds: ethanol, isobutanol, acetoin, meso-2,3-butanediol, and (2S,3S)-2,3-butanediol. Analytical standards were also utilized to identify retention times for isobutryaldehyde, isobutyric acid, and isoamyl alcohol.

HPLC

Analysis for fermentation by-product composition is well known to those skilled in the art. For example, one high performance liquid chromatography (HPLC) method utilizes a Shodex SH-1011 column with a Shodex SH-G guard column (both available from Waters Corporation, Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol retention time is 47.6 minutes.

For Example 15, isobutanol concentration in the aqueous phase was measured by HPLC (Waters Alliance Model, Milford, Mass. or Agilent 1100 Series, Santa Clara, Calif.) using a Shodex sugar SH1011 column, 8.0 mm×300 mm, (Showa Denko K. K., Kanagawa, Japan (through Thompson Instruments, Clear Brook, Va.)) using 0.01 N aqueous sulfuric acid, isocratic, as the eluant. The sample was passed through a 0.2 μm syringe filter (PALL GHP membrane) into an HPLC vial. The HPLC run conditions were as follows:

Injection volume: 10 μL
Flow rate: 0.80 mL/minute
Run time: 32 minutes
Column Temperature: 50° C.
Detector: refractive index
Detector temperature: 40° C.

UV detection: 210 nm, 4 nm bandwidth After the run, concentration in the sample was determined from a standard curves for isobutanol. The retention time was 27.0 minutes.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "wt %" means percent by weight, "HPLC" means high performance liquid chromatography, and "GC" means gas chromatography. The term "molar selectivity" is the number of moles of product produced per mole of sugar substrate consumed and is reported as a percent.

Example 1

Disruption of Pyruvate Decarboxylase Genes

The purpose of this example is to describe disruption of pyruvate decarboxylase genes in *S. cerevisiae* by chromosomal deletion of genes encoding the three major isozymes: PDC1, PDC5, and PDC6.

The PDC1 gene, encoding a first isozyme of pyruvate decarboxylase, was disrupted by insertion of a LEU2 marker cassette by homologous recombination, which completely removed the endogenous PDC1 coding sequence. The LEU2 marker in pRS425 (ATCC No. 77106) was PCR-amplified from plasmid DNA using Phusion DNA polymerase (New England Biolabs Inc., Beverly, Mass.; catalog no. F-540S) using primers PDC1::LEU2-F and PDC1::LEU2-R, given as SEQ ID NOs:102 and 103, which generated a 2.0 kb PCR product. The PDC1 portion of each primer was derived from the 5' region upstream of the PDC1 promoter and 3' region downstream of the transcriptional terminator, such that integration of the LEU2 marker results in replacement of the pdc1 coding region. The PCR product was transformed into S. cerevisiae BY4741 (ATCC #201388) using standard genetic techniques (Methods in Yeast Genetics, 2005, Cold Spring Harbor Laboratory Press, Cold Spring Harbor, N.Y., pp.201-202) and transformants were selected on synthetic complete media lacking leucine and supplemented with 2% glucose at 30° C. Transformants were screened by PCR using primers 112590-30E and 112590-30F, given as SEQ ID NOs:104 and 105, to verify integration at the PDC1 chromosomal locus with replacement of the PDC1 coding region. The identified correct transformants have the genotype: BY4741 pdc1::LEU2.

The PDC5 locus encoding a second isozyme of pyruvate decarboxylase was deleted by gene disruption. A pdc5::kanMX4 cassette was PCR-amplified from strain YLR134W chromosomal DNA (ATCC No. 4034091) using Phusion DNA polymerase and primers PDC5::KanMXF and PDC5::KanMXR, given as SEQ ID NOs:106 and 107, which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into BY4741 pdc1::LEU2 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 µg/ml) at 30° C. Transformants were screened by PCR to verify correct integration at the PDC locus with replacement of the PDC5 coding region using primers PDC5kofor and N175, given as SEQ ID NOs:108 and 109, respectively. The identified correct transformants have the genotype: BY4741 pdc1::LEU2 pdc5::kanMX4.

The PDC6 locus encoding a third isozyme of pyruvate decarboxylase was disrupted by insertion of a MET15 marker. The MET15 marker was PCR-amplified from plasmid pRS421 (ATCC No. 87475) using Phusion DNA polymerase and primers 112590-46A and 112590-46B, given as SEQ ID NOs: 110 and 111, respectively. The PDC6 portion of each primer was derived from the 5' region upstream of the PDC6 promoter and 3' region downstream of the coding region, such that integration of the MET15 marker results in replacement of the PDC6 coding region. The PCR product was transformed into BY4741 pdc1::LEU2 pdc5::kanMX4 using standard genetic techniques (Methods in Yeast Genetics, 2005, Cold Spring Harbor Laboratory Press, Cold Spring Harbor, N.Y., pp.201-202) and transformants were selected on synthetic complete media lacking methionine and supplemented with 1% ethanol at 30° C. Transformants were screened by PCR to verify correct chromosomal integration at the PDC6 locus with replacement of the PDC6 coding region using primers 112590-34E and 112590-34F, given as SEQ ID NOs:112 and 113, respectively. The identified correct transformants have the genotype: BY4741 pdc1::LEU2 pdc5::kanMX4 pdc6::MET15.

Example 2

Engineering S. cerevisiae Strains for Cytosolic Expression of Acetolactate Synthase and Deletion of Pyruvate Decarboxylase Genes The purpose of this example is to describe the construction and introduction of acetolactate synthase genes for expression in the cytosol of a yeast strain that also has deletions of pyruvate decarboxylase genes PDC1 and PDC5. Two yeast promoters were independently used to control alsS gene expression—the glycolytic FBA promoter from the S. cerevisiae fructose 1,6-bisphosphate aldolase or the HIS3 promoter from the S. cerevisiae imidazoleglycerol-phosphate dehydratase gene.

Expression plasmid pRS426-FBAp-alsS was constructed via the following steps. The 1.7 kb alsS coding region fragment of pRS426::GPD::alsS::CYC was isolated by gel purification following BbvCI and PacI digestion. This plasmid has a chimeric gene containing the GPD1 promoter (SEQ ID NO:114), the alsS coding region from Bacillus subtilis (SEQ ID NO:3), and the CYC1 terminator (SEQ ID NO:115]) and was described in commonly owned and co-pending U.S. Patent Publication # U.S.20070092957 A1, Example 17 which is herein incorporated by reference. The ILV5 fragment from plasmid pRS426::FBA::ILV5::CYC, also described in U.S.20070092957 A1, Example 17, was removed by restriction digestion with BbvCI and PacI and the remaining 6.6 kb vector fragment was gel purified. This vector has a chimeric gene containing the FBA promoter (SEQ ID NO:116) and CYC1 terminator bounding the coding region of the ILV5 gene of S. cerevisiae (SEQ ID NO:37). These two purified fragments were ligated overnight at 16° C. and transformed into E. coli TOP10 chemically competent cells (Invitrogen). Transformants were obtained by plating cells on LB Amp100 medium. Insertion of alsS into the vector was confirmed by restriction digestion pattern and PCR (primers N98SeqF1 and N99SeqR2, SEQ ID NOs:117 and 118).

A pdc1::FBAp-alsS-LEU2 disruption cassette was created by joining the FBAp-a/sS segment from pRS426-FBAp-alsS to the LEU2 gene from pRS425 (ATCC No. 77106) by SOE PCR (as described by Horton et al. (1989) Gene 77:61-68) using as template pRS426-FBAp-alsS and pRS425 plasmid DNAs, with Phusion DNA polymerase (New England Biolabs Inc., Beverly, Mass.; catalog no. F-540S) and primers 112590-48A and 11 2590-30B through D, given as SEQ ID NOs:119, SEQ ID NOs:120-122. The outer primers for the SOE PCR (112590-48A and 11 2590-30D) contained 5' and 3' 50 bp regions homologous to regions upstream and downstream of the PDC1 promoter and terminator. The completed cassette PCR fragment was transformed into BY4741 (ATCC No. 201388) and transformants were maintained on synthetic complete media lacking leucine and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-30E and 112590-30F, given as SEQ ID NOs:104 and 105, to verify integration at the PDC1 locus with deletion of the PDC1 coding region. The correct transformants have the genotype: BY4741 pdc1::FBAp-alsS-LEU2.

A pdc1::HIS3p-alsS-LEU2 disruption cassette was created by amplifying the HIS3 promoter from pRS423 (ATCC No. 77104) with Phusion DNA polymerase and joining it to a PCR-amplified alsS-LEU2 cassette from strain BY4741 pdc1::FBAp-alsS-LEU2. Primers utilized for the PCR, 112590-48B through 112590-48D and 112590-45B, are given as SEQ ID NOs:161-163 and 164. The outer primers for the SOE PCR contained 5' and 3' 50 bp regions homologous to the regions upstream and downstream of the PDC1 promoter and terminator. The completed pdc1::HIS3p-alsS-LEU2 cassette was transformed into BY4741 and transformants were maintained on synthetic complete media lacking leucine and supplemented with 2% glucose at 30° C. (*Methods in Yeast Genetics,* 2005, Cold Spring Harbor Laboratory Press, Cold Spring Harbor, N.Y., pp. 201-202). Transformants were screened by PCR using external primers 112590-30E and 112590-30F, given as SEQ ID NOs:104 and 105, to verify integration at the PDC1 locus with deletion of the PDC1 coding region. The correct transformants have the genotype: BY4741 pdc1::HIS3p-alsS-LEU2.

The PDC5 locus encoding the second isozyme of pyruvate decarboxylase was deleted by gene disruption. The pdc5::kanMX4 cassette was PCR-amplified using Phusion DNA polymerase from strain YLR134W chromosomal DNA (ATCC No. 4034091) using primers PDC5::KanMXF and PDC5::KanMXR, given as SEQ ID NOs:106 and 107, which generated a ~2.2 kb PCR product. The PDC5 portion of each primer was derived from the 5' region upstream of the PDC5 promoter and 3' region downstream of the coding region, such that integration of the kanMX4 marker results in replacement of the PDC5 coding region. The PCR product was transformed into BY4741 pdc1::FBAp-alsS-LEU2 and BY4741 pdc1::HIS3p-alsS-LEU2 using standard genetic techniques (*Methods in Yeast Genetics,* 2005, Cold Spring Harbor Laboratory Press, Cold Spring Harbor, N.Y., pp. 201-202) with selection on YP media supplemented with 1% ethanol and geneticin (200 µg/ml) at 30° C. Transformants were screened by PCR to verify correct chromosomal integration using primers PDC5kofor and N175, given as SEQ ID NOs:108 and 109, respectively. The correct transformants have the genotype: BY4741 pdc1::FBAp-alsS-LEU2 pdc5::kanMX4 or BY4741 pdc1::HIS3p-alsS-LEU2 pdc5::kanMX4.

Example 3

Vector Construction for the Production of Butanediol

The purpose of this example is to describe the construction of vectors for the expression of acetolactate decarboxylase, butanediol dehydrogenase, and, optionally, acetolactate synthase and/or secondary alcohol dehydrogenase activity in the cytosol of yeast.

Construction of pRS423::CUP1-alsS+FBA-budA

The budA gene, encoding acetolactate decarboxylase, was amplified from genomic DNA prepared from *Klebsiella pneumonia* (ATCC #25955) using Phusion™ Hot Start High-Fidelity DNA Polymerase (New England Biolabs, Inc.). The primers used (N579 and N580, provided as SEQ ID NOs:123 and 124) added sequence upstream of the start codon that was homologous to the yeast FBA promoter and sequence downstream of the stop codon that was homologous to the yeast ADH terminator. Plasmid pRS423::CUP1-alsS+FBA-ILV3, which has a chimeric gene containing the CUP1 promoter (SEQ ID NO:125), alsS coding region from *Bacillus subtilis* (SEQ ID NO:3), and CYC1 terminator (SEQ ID NO:115) as well as a chimeric gene containing the FBA promoter (SEQ ID NO:116), ILV3 coding region from *S. cerevisiae* (SEQ ID NO:45), and ADH1 terminator (SEQ ID NO:126) (described in commonly owned and co-pending U.S. Patent Publication # U.S.20070092957 A1, Example 17) was restriction digested with NcoI and PmII to remove the ILV3 coding region. The 11.1 kb vector band was gel purified. Approximately 1 µg of cut vector DNA was combined with 1 µg of the budA PCR product and transformed into *S. cerevisiae* strain BY4741. The insert and vector were combined by homologous recombination in vivo to form a circular vector (also known as "gap repair cloning"; described in Ma et al. (1987) Genetics 58:201-216) that allows retention of the selectable marker (in this case, HIS3). Transformants were selected on synthetic complete medium lacking histidine. Colonies were patched to a new plate and cells from these patches were used to prepare plasmid DNA (Zymoprep™ Yeast Plasmid Miniprep Kit, Zymo Research). PCR was used to screen plasmids for the presence of alsS (primers N98SeqF1 and N99SeqR2, SEQ ID NOs: 117 and 118) and for proper insertion of budA (N160SeqF1 and N84SeqR2, SEQ ID NOs:127 and 128).

Construction of pRS426::FBA-budC

The budC coding region for butanediol dehydrogenase was amplified from genomic DNA prepared from *Klebsiella pneumonia* (ATCC #25955) using Phusion™ Hot Start High-Fidelity DNA Polymerase (New England Biolabs, Inc.). The primers used (N581 and N582, provided as SEQ ID NOs:129 and 130) added sequence upstream of the start codon that was homologous to the yeast FBA promoter and sequence downstream of the stop codon that was homologous to the yeast CYC1 terminator. The plasmid pRS426::FBA::alsS (described in Example 2, also called pRS426-FBAp-a/sS) was digested with BbvCI and PacI to release an alsS fragment. The remaining linear vector was gel purified. Approximately 1 µg of vector was combined with 1 µg of budC PCR product and transformed into BY4741 to obtained gap repair clones (see above). Transformants were selected on synthetic complete medium lacking uracil. Plasmids were prepared from patches of 5 transformant colonies. The presence of FBA-budC was screened using PCR with primers N160SeqF1 and N582 (SEQ ID NOs:127 and 130).

Construction of pRS423::FBA-budC+FBA-budA

The pRS423::CUP1-alsS+FBA-budA vector described above was digested with SacII and MluI to remove CUP1-alsS. SacII/MluI digestion was also used to isolate FBA-budC from pRS426::FBA-budC (see above). The appropriate fragments (7.6 kb vector fragment and 1.6 kb FBA-budC fragment) were gel purified, ligated and transformed into *E. coli* TOP10 competent cells (Invitrogen). Transformant colonies were screened by PCR to confirm incorporation of the budC fragment using primers N581 and N582 (SEQ ID NOs:129 and 130).

Construction of pRS425::GPM-sadB

A DNA fragment encoding a butanol dehydrogenase (protein of SEQ ID NO:36) from *Achromobacter xylosoxidans* (disclosed in commonly owned and co-pending U.S. Patent Application CL3926) was cloned. The coding region of this gene called sadB for secondary alcohol dehydrogenase (SEQ ID NO:35) was amplified using standard conditions from *A. xylosoxidans* genomic DNA, prepared using a Gentra Puregene kit (Gentra Systems, Inc., Minneapolis, Minn.; catalog number D-5500A) following the recommended protocol for gram negative organisms using forward and reverse primers N473 and N469 (SEQ ID NOs:131 and 132), respectively. The PCR product was TOPO-Blunt cloned into pCR4 BLUNT (Invitrogen) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH terminator (N583 and N584, provided as SEQ ID NOs:133 and 134). The PCR product was then cloned using "gap repair" methodology in *Saccharomyces cerevisiae* (Ma et al. ibid) as follows. The yeast-*E. coli* shuttle vector pRS425::GPM::kivD::ADH which contains the GPM promoter (SEQ ID NO:135), kivD coding region from *Lactococcus lactis* (SEQ D NO:47), and ADH1 terminator (SEQ ID NO:126) (described in commonly owned and co-pending U.S. Patent Publication # U.S.20070092957A1, Example 17) was digested with BbvCI and PacI restriction enzymes to release the kivD coding region. Approximately 1 µg of the remaining vector fragment was transformed into *S. cerevisiae* strain BY4741 along with 1 µg of sadB PCR product. Transformants were selected on synthetic complete medium lacking leucine. The proper recombination event, generating pRS425::GPM-sadB, was confirmed by PCR using primers N142 and N459 (SEQ ID NOs:136 and 137).

Construction of pRS426::FBA-budC+GPM-sadB

The GPM-sadB-ADH promoter-gene-terminator cassette was transferred to pRS426 (ATCC No. 77107), a yeast-*E. coli* shuttle vector carrying the URA3 selection marker, by gap repair cloning. The cassette was isolated from pRS425::GPM-sadB by digestion with SalI and SacII, and the pRS426 vector was linearized with BamHI prior to ligation. The resulting vector, pRS426::GPM-sadB was confirmed by PCR using primers N142 and N459 (SEQ ID NOs:136 and 137). In order to add the budC gene encoding acetoin reductase from *Klebsiella pneumonia* to this vector, a fragment containing budC was excised from pRS423::FBA-budC+FBA-budA using SphI and SapI.

For construction of pRS423::FBA-budC+FBA-budA, the pRS423::CUP1-alsS+FBA-budA vector described above was digested with SacI and MluI to remove CUP1-alsS. SacII/MluI digestion was also used to isolate FBA-budC from pRS426::FBA-budC (described above). The appropriate fragments (7.6 kb vector fragment and 1.6 kb FBA-budC fragment) were gel purified, ligated and transformed into *E. coli* TOP10 competent cells (Invitrogen). Transformant colonies were screened by PCR to confirm incorporation of the budC fragment using primers N581 and N582 (SEQ ID NOs: 129 and 130).

The SphI-SapI budC fragment from pRS423::FBA-budC+FBA-budA carries portions of the vector upstream of the FBA promoter as well as part of the ADH terminator to allow for cloning by gap repair cloning into the pRS426::GPM-sadB vector that was linearized with SacII. Transformants resulting from this cloning were plated on medium lacking uracil to select for recombination of the two linear sequences. The resulting vector, pRS426::FBA-budC+GPM-sadB was confirmed by PCR using primers N581 and N582 (SEQ ID NOs: 129 and 130).

Example 4

Production of Butanediol

The purpose of this example is to describe the production of butanediol in a yeast strain. The yeast strain comprises deletions of PDC1 and PDC5, genes encoding two isozymes of pyruvate decarboxylase, and constructs for heterologous expression of AlsS (acetolactate synthase), BudA (acetolactate decarboxylase), and BudC (butanediol dehydrogenase). Optionally, the yeast strain further comprises a construct for heterologous expression of SadB (secondary alcohol dehydrogenase).

Strain Construction

Plasmids pRS423::CUP1-alsS+FBA-budA and pRS426::FBA-budC were introduced into BY4741 Δpdc1::FBA-alsS Δpdc5::kanMX4 and into BY4741 Δpdc1::HIS3-alsS Δpdc5::kanMX4 by standard PEG/lithium acetate-mediated transformation methods. Plasmids pRS423::CUP1-alsS+FBA-budA and pRS426::FBA-budC+GPM-sadB were introduced into BY4741 Δpdc1::HIS3-alsS Δpdc5::kanMX4. In all cases, transformants were selected on synthetic complete medium lacking glucose, histidine and uracil. Ethanol (1% v/v) was used as the carbon source. After three days, transformants were patched to synthetic complete medium lacking histidine and uracil. This medium contained both 2% glucose and 1% ethanol as carbon sources. The resulting strains were further examined, as described below.

Production of BDO from Glucose in Shake Flasks

The strains BY4741 Apdc1::FBA-alsS Δpdc5::kanMX4/pRS423::CUP1-alsS+FBA-budA/pRS426::FBA-budC (Strain 1 in Table 3) and BY4741 Δpdc1::HIS3-alsS Δpdc5::kanMX4/pRS423::CUP1-alsS+FBA-budA/ pRS426::FBA-budC (Strain 2 in Table 3) were grown in synthetic complete medium without uracil or histidine, supplemented with 0.5% (v/v) ethanol. The strains were grown in vented flasks or sealed vials as listed in Table 3, with agitation (225 rpm) at 30° C. After 48 hours filtered culture medium was analyzed by HPLC using the sugar column method described in General Methods.

TABLE 3

Butanediol (BDO) production in engineered yeast strains

| Strain | Culture Condition | BDO* Titer, mM | BDO Molar Selectivity | Glycerol Molar Selectivity |
|---|---|---|---|---|
| 1 | 75 ml culture in 125 ml vented flask | 76 | 0.64 | 0.47 |
| 1 | 40 ml culture in 50 ml sealed vial | 29 | 0.58 | 0.54 |
| 2 | 40 ml culture in 50 ml sealed vial | 52 | 0.64 | 0.51 |

*Butanediol (BDO) refers to the sum of meso-2,3-butanediol, (2S,3S)-(+)-2,3-butanediol and (2R,3R)-(−)-2,3-butanediol. The latter two forms are also referred to as ±-butanediol. Molar selectivity is moles product/moles glucose consumed.

Production of BDO from Glucose in Fermenters

The strain BY4741 Δpdc1::FBA-alsS Δpdc5::kanMX4/pRS423::CUP1-alsS+FBA-budA/pRS426::FBA-budC (Strain 1 in Table 3) was grown in 2 L baffled shake flasks containing 0.4 L medium at 30° C. with shaking at 200 RPM. The medium contained per L: 6.7 g yeast nitrogen base without amino acids (DIFCO, product #291940); 0.1 g L-leucine; 0.02 g L-tryptophan; 1.4 g yeast synthetic drop-out medium supplements without histidine, leucine, tryptophan and uracil (Sigma, product #Y2001); 20 g D-glucose; and 10 mL ethanol. When the cells in the flask reached an $OD_{600}$ of 2.9, 60 mL aliquots were used to inoculate fermenters.

One liter fermenters were prepared with 540 mL of medium containing (per L): 6.7 g yeast nitrogen base without amino acids (DIFCO, product #291940); 0.2 g L-leucine; 0.04 g L-tryptophan; 2.8 g yeast synthetic drop-out medium supplements without histidine, leucine, tryptophan and uracil (Sigma, product #Y2001); and 10 mL ethanol. D-glucose (50% w/w) was added fed-batch so that concentration, initially at 30 g/L, varied between 30 and 5 g/L. Temperature was controlled at 30° C. and pH was maintained at pH 5.5 with the addition of either 50% (w/w) NaOH or 20% (w/v) H₃PO₄. Air was sparged at 0.3 standard liters per min without back pressure and the minimum stir speed was set to 100 rpm. dO was 100% initially and rpm was programmed to control dO at 30%, however, oxygen demand was low and the dO of all fermenters (Runs #1-3 in Table 5) remained in the 90% range throughout the phase of air sparging. In two fermenters (duplicate Runs #2-3), nitrogen sparge replaced air sparge at 35 hrs into the run. Over the course of the fermentations, samples were withdrawn for cell mass ($OD_{600}$), substrate utilization and by-product distribution measurements. Substrate and by-product concentrations were determined from HPLC analysis. The results are summarized in Table 4, below. Despite the difference in gas sparging between the fermenters, the results were not significantly different. Butanediol (BDO, sum of meso-butanediol and ±-butanediol) was produced at an average concentration of 229 mM with a molar selectivitiy of 0.63 (mole butanediol produced/moles glucose consumed). The molar selectivity obtained in shake flasks was identical to that obtained in fermenters.

TABLE 4

Fermentative production of butanediol (BDO) using *E. coli* strain BY4741 Δpdc1::FBA-alsS Δpdc5::kanMX4/pRS423::CUP1-alsS + FBA-budA/pRS426::FBA-budC.

| Run # | Time, hr | $OD_{600}$ | Glucose consumed, mM | meso-Butanediol, mM | ±-Butanediol, mM | Glycerol, mM | Butanediol Molar Selectivity |
|---|---|---|---|---|---|---|---|
| Run #1 | 0 | 0.0 | 0 | 0 | 0 | 0 | 0.00 |
| " | 4 | 0.3 | 20 | 7 | 2 | 9 | 0.47 |
| " | 12 | 0.6 | 30 | 12 | 4 | 17 | 0.54 |
| " | 20 | 1.0 | 53 | 23 | 7 | 33 | 0.56 |
| " | 28 | 2.2 | 98 | 45 | 15 | 65 | 0.61 |
| " | 36 | 3.1 | 164 | 69 | 23 | 100 | 0.56 |
| " | 44 | 4.4 | 217 | 106 | 34 | 154 | 0.65 |
| " | 52 | 5.1 | 307 | 148 | 43 | 212 | 0.62 |
| " | 60 | 5.4 | 343 | 175 | 48 | 249 | 0.65 |
| " | 68 | 6.1 | 412 | 207 | 55 | 295 | 0.63 |
| " | 72 | 6.5 | 447 | 224 | 57 | 319 | 0.63 |
| Run #2 | 0 | 0.0 | 0 | 0 | 0 | 0 | 0.00 |
| " | 4 | 0.3 | 19 | 7 | 2 | 10 | 0.52 |
| " | 12 | 0.6 | 32 | 12 | 4 | 17 | 0.50 |
| " | 20 | 1.0 | 58 | 22 | 7 | 32 | 0.50 |
| " | 28 | 2.3 | 106 | 44 | 15 | 64 | 0.56 |
| " | 36 | 3.5 | 170 | 70 | 23 | 101 | 0.55 |
| " | 44 | 4.7 | 234 | 109 | 34 | 157 | 0.61 |
| " | 52 | 5.9 | 327 | 154 | 44 | 217 | 0.61 |
| " | 60 | 5.9 | 367 | 184 | 50 | 258 | 0.64 |
| " | 68 | 6.8 | 441 | 219 | 57 | 304 | 0.63 |
| " | 72 | 7.2 | 467 | 237 | 60 | 328 | 0.64 |
| Run #3 | 0 | 0.0 | 0 | 0 | 0 | 2 | 0.00 |
| " | 4 | 0.3 | 19 | 7 | 2 | 12 | 0.51 |
| " | 12 | 0.6 | 33 | 12 | 4 | 19 | 0.49 |
| " | 20 | 1.1 | 58 | 23 | 7 | 36 | 0.52 |
| " | 28 | 2.2 | 109 | 45 | 15 | 67 | 0.55 |
| " | 36 | 3.4 | 173 | 73 | 24 | 107 | 0.56 |
| " | 44 | 4.4 | 234 | 112 | 35 | 164 | 0.63 |
| " | 52 | 6.3 | 326 | 153 | 44 | 220 | 0.61 |
| " | 60 | 5.9 | 371 | 183 | 50 | 260 | 0.63 |
| " | 68 | 6.7 | 445 | 218 | 57 | 307 | 0.62 |
| " | 72 | 7.6 | 454 | 226 | 58 | 317 | 0.63 |

Coproduction of BDO and 2-butanol from Sugar (Glucose or Sucrose) in the Presence of absence of 2-butanone The strain BY4741 Δpdc1::HIS3-alsS Δpdc5::kanMX4/pRS423::CUP1-alsS+FBA-budA/pRS426::FBA-budC+GPM-sadB was grown in 50 ml culture medium in 125-ml vented flasks with agitation (225 rpm) at 30° C. Culture medium was synthetic complete medium without uracil or histidine, supplemented with 0.5% (v/v) ethanol with and without 2-butanone. When using 2-butanone, cultures were inoculated into serum vials (50 ml) containing 40 ml of aerobic medium (same medium as above but also containing 83 mM 2-butanone). Vials were then sealed with stoppers and crimps. Vials were also incubated at 30° C. with agitation. After 48 hours filtered culture medium was analyzed by HPLC (sugar column method).

The added 2-butanone serves as a substrate for production of 2-butanol by the sadB encoded secondary alcohol dehydrogenase, This reaction is used to balance reducing equivalents during BDO synthesis as follows:

The formation of BDO from glucose requires the concomitant production of a reducing equivalent (e.g. NADH):

Glucose→BDO+NADH

In the absence of 2-butanone, the reducing equivalent is absorbed by the production of a compound more reduced than glucose, e.g glycerol:

0.5 Glucose+1 NADH→1 Glycerol

In the presence of 2-butanone, the reducing equivalent is absorbed by the production of a more reduced derivative of 2-butanone, which acts as an electron sink:

2-Butanone+NADH→2-Butanol

Thus, higher yield from glucose is obtained in the presence of the 2-butanone electron sink. Moreover, the capacity of *S. cerevesiae*, comprising Δpdc1::HIS3-alsS Δpdc5/pRS423::

CUP1-alsS, to provide ≥0.86 C6 equivalents (from glucose or sucrose) to a product downstream of acetolactate was demonstrated, as given in Table 5.

TABLE 5

Production of butanediol and 2-butanol by engineered yeast strain.

| Carbon source | Electron sink | BDO titer (mM) | BDO molar yield | Glycerol Molar Yield | 2-butanol titer (mM) | % of theoretical yield BDO |
|---|---|---|---|---|---|---|
| Glucose | None | 73 | 0.62 | 0.25 | — | 62 |
| Glucose | 2-butanone | 102 | 0.90 | 0.11 | 78 | 90 |
| Sucrose | None | 87 | 0.68 | 0.14 | — | 68 |
| Sucrose | 2-butanone | 101 | 0.86 | 0.08 | 82 | 86 |

Data are averages of duplicate experiments.
Selectivity from sucrose is normalized to mol C6 sugar.

The strain BY4741 Δpdc1::LEU2 Δpdc5::kanMX4 (described in Example 1) was transformed with plasmids pRS423::CUP1-alsS+FBA-budA and pRS426::FBA-budC+GPM-sadB (both plasmids described in Example 3) to produce the strain BY4741 Δpdc1::LEU2 Δpdc5::kanMX4/ pRS423: :CUP1-alsS+FBA-budA/ pRS426::FBA-budC+GPM-sadB. This strain (Strain 4 in Table 6) contains alsS only on a plasmid, but is otherwise isogenic with Strain 3 of Table 6 which contains both chromosomal and plasmid copies of alsS. Strain 3 in Table 6 is BY4741 Δpdc1::HIS3-alsS Δpdc5::kanMX4/pRS423::CUP1-alsS+FBA-budA/ pRS426::FBA-budC+GPM-sadB (described previously in Example 4). Strain 3 and two isolates of Strain 4 were grown in the presence of glucose and 2-butanone (MEK) as described above. The BDO molar yield is indistinguishable between strains.

TABLE 6

Production of butanediol and 2-butanol by engineered yeast strains.

| Strain | Carbon source | Electron sink | BDO titer (mM) | BDO molar yield | Glycerol Molar Yield | 2-butanol titer (mM) | % of theoretical yield BDO |
|---|---|---|---|---|---|---|---|
| Strain 3 | Glucose | MEK | 102 | 0.90 | 0.18 | 75 | 90 |
| Strain 4, isolate 1 | Glucose | MEK | 100 | 0.88 | 0.19 | 74 | 88 |
| Strain 4, isolate 2 | Glucose | MEK | 101 | 0.90 | 0.19 | 75 | 90 |

Example 5

Prophetic

Production of 2-butanol by Recombinant *S. cerevisiae* Strain Additionally Expressing $B_{12}$-Independent Diol Dehydratase A $B_{12}$-independent (S-adenosylmethionine (SAM)-dependent) butanediol dehydratase (SEQ ID NO:32) and its associated reactivase (SEQ ID NO:34) from the bacterium *Roseburia inulinivorans* are the topic of commonly owned and co-pending U.S. Patent Application CL3893CIP. The sequences encoding these proteins (SEQ ID NOs:31 and 33, respectively), hereafter referred to as rdhtA and rdhtB, respectively, were synthesized as one DNA fragment (SEQ ID NO:138) by standard methods and cloned into an *E. coli* vector (by DNA2.0, Inc., Menlo Park, Calif.). The resulting clone was named pJ206::rdhtAB. The synthetic DNA fragment also contained a consensus ribosome binding site 5' of the rdhtA coding region and terminal restriction sites recognized by BamHI (5' end) and SalI (3' end).

pJ206::rdhtAB was used as a PCR template to prepare separate RdhtA and RdhtB coding region fragments. The RdhtA coding region for the diol dehydratase was amplified by PCR using primers N695 and N696 (SEQ ID NOs:130 and 140). The RdhtB coding region for the diol dehydratase activase, was amplified by PCR using primers N697 and N698 (SEQ ID NOs:141 and 142). The two DNA fragments were combined with a dual terminator DNA fragment (SEQ ID NO:143) that has an ADH terminator (SEQ ID NO:126) and a CYCL terminator (SEQ ID NO:115) adjacent to each other in opposing orientation using SOE PCR (Horton et al. (1989) Gene 77:61-68). The dual terminator fragment was isolated as a 0.6 kb fragment following Pacd digestion of pRS426:: FBA-ILV5+GPM-kivD (described in commonly owned and co-pending U.S. Patent Publication # 20070092957 A1, Example 17). The resulting 4 kb DNA fragment had the rdhtA and rdhtB coding regions in opposing orientation on either side of the dual terminator, with the 3' end of each coding region adjacent to the dual terminator sequence. This DNA fragment was then cloned by gap repair methodology (Ma et al. (1987) Genetics 58:201-216) into the yeast shuttle vector pRS426::FBA-ILV5+GPM-kivD that was prepared by digestion with BbvCI to remove the ILV5 and kivD coding regions and dual terminator sequence between their 3' ends.

pRS426::FBA-ILV5+GPM-kivD was described in commonly owned and co-pending U.S. Patent Publication # 20070092957 A1, Example 17. It contains in order: the FBA promoter (SEQ ID NO:116), the coding region of the ILV5 gene of *S. cerevisiae* (SEQ ID NO:37), the dual terminator fragment (SEQ ID NO:143), the kivD coding region from *Lactococcus lactis* (SEQ D NO:47), and the GPM promoter (SEQ ID NO:135), with the ILV5 and kivD coding regions in opposite orientation.

The resulting plasmid, pRS426::RdhtAB, contained the rdhtA gene under the control of the FBA promoter (SEQ ID NO:116) and the rdhtB gene under control of the GPM promoter (SEQ ID NO:1 35). The activity of the diol dehydratase in several of the yeast clones was confirmed by growing the yeast cells anaerobically in the presence of 1,2-propanediol and analyzing culture supernatants for the presence of propanol by GC or HPLC (as described in General Methods).

The FBA-RdhtA+GPM-RdhtB portion of pRS426:: RdhtAB is then integrated into the yeast genome by homologous recombination, as follows. The region is amplified from the plasmid construct using primers N742 and N743 (SEQ ID NOs:144 and 145). Similarly, the URA3 marker is amplified from pRS426 (ATCC No. 77107) using primers N744a and N745a (SEQ ID NOs:146 and 147). These two DNA fragments are then combined using SOE PCR (Horton et al. (1989) Gene 77:61-68). The linear product is transformed into the BY4741 pdc1::HIS3p-alsS-LEU2 pdc5::kanMX strain that was described in Example 2.

Transformants are obtained on medium lacking uracil. Integration at the former PDC5 locus (replacing the kanMX4 marker) is confirmed by PCR and by screening for geneticin sensitivity. Clones are tested for diol dehydratase activity as described above. The URA3 marker is recycled by passaging the clones in the presence of 5-fluorotic acid using standard yeast methods (*Methods in Yeast Genetics*, 2005, Cold Spring Harbor Laboratory Press, Cold Spring Harbor, N.Y). PCR is used to confirm that the integrated RdhtA and RdhtB genes have been undisturbed by marker recycling.

The resulting strain, BY4741 pdc1::HIS3p-alsS pdc5::RdhtAB is then transformed with butanediol pathway plasmids pRS423::CUP1-alsS+FBA-budA and pRS426::FBA-budC+GPM-sadB, that were described in Example 3. BDO and/or 2-butanol production is confirmed in the resulting transformants by HPLC or GC as described in General Methods. It is expected that cells grown with vigorous aeration on glucose produce only BDO and that cells grown under more anaerobic conditions convert some BDO to 2-butanol. Repeated passaging of the strains under anaerobic conditions may enhance production of 2-butanol, since the complete pathway does not result in net accumulation of NADH and therefore does not require loss of energy and carbon to glycerol formation.

Example 6

Prophetic

Production of Isobutanol in Recombinant *S. cerevisiae* [BY4741 pdc1::FBAP-alsS-LEU2 pdc5::kanMX4]

The purpose of this prophetic example is to describe how to obtain isobutanol production in a yeast strain that is disrupted for pyruvate decarboxylase activities, and expresses cytosolic acetolactate synthase.

Construction of vectors pRS423::CUP1p-alsS+FBAp-ILV3 and pHR81::FBAp-ILV5-GPMp-kivD is described in U.S. Patent Publication # U.S.20070092957 A1, Example 17. pRS423::CUP1p-alsS+FBAp-ILV3 has a chimeric gene containing the CUP1 promoter (SEQ ID NO:125), the alsS coding region from *Bacillus subtilis* (SEQ ID NO:3), and CYC1 terminator (SEQ ID NO:115) as well as a chimeric gene containing the FBA promoter (SEQ ID NO:116), the coding region of the ILV3 gene of *S. cerevisiae* (SEQ ID NO:45), and the ADH1 terminator (SEQ ID NO:126). pHR81::FBAp-ILV5+GPMp-kivD is the pHR81 vector (ATCC #87541) with a chimeric gene containing the FBA promoter, the coding region of the ILV5 gene of *S. cerevisiae* (SEQ ID NO:37), and the CYC1 terminator as well as a chimeric gene containing the GPM promoter (SEQ ID NO:135), the coding region from kivD gene of *Lactococcus lactis* (SEQ ID NO:47), and the ADH1 terminator. pHR81 has URA3 and leu2-d selection markers.

The PDC6 locus encoding a third isozyme of pyruvate decarboxylase is disrupted by insertion of a MET15 marker in BY4741 pdc1::FBAp-alsS-LEU2 pdc5::kanMX4 (described in Example 2) using the method described in Example 1. The correct transformants are identified as having the genotype: BY4741 pdc1::LEU2 pdc5::kanMX4 pdc6::MET15.

Plasmid vectors pRS423::CUP1p-alsS+FBAp-ILV3 and pHR81::FBAp-ILV5+GPMp-kivD are transformed into strain BY4741 pdc1::FBAp-alsS-LEU2 pdc5::kanMX4 or BY4741 pdc1::LEU2 pdc5::kanMX4 pdc6::MET15 using standard genetic techniques (*Methods in Yeast Genetics*, 2005, Cold Spring Harbor Laboratory Press, Cold Spring Harbor, N.Y.) and maintained on synthetic complete media lacking histidine and uracil, and supplemented with 1% ethanol. Aerobic cultures are grown in 250 ml flasks containing 50 ml synthetic complete media lacking histidine and uracil, and supplemented with 2% glucose and 0.5% ethanol in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection and GC (HP-Innowax, 0.32 mm×0.25 μm×30 m (Agilent Technologies, Inc., Santa Clara, Calif.) with flame ionization detection (FID) for isobutanol content. Isobutanol is detected.

Example 7

Prophetic

Disruption of Glycerol Formation in a *S. cerevisiae* Strain with Deleted Genes Encoding Pyruvate Decarboxylase and Cytosolic Expression of Acetolactate Synthase The purpose of this prophetic example is to describe how to disrupt glycerol formation in a yeast strain that is also disrupted in pyruvate decarboxylase genes, and contains a cassette for expression of cytosolic acetolactate synthase.

GPD1 encodes an NAD-dependent glycerol-3-phosphate dehydrogenase which is a key enzyme in glycerol synthesis and plays a major role in cellular oxidation of NADH. A gpd1::URA3 disruption cassette is constructed by PCR amplification of the URA3 marker from pRS426 (ATCC No. 77107) with primers 112590-T8 and 112590-T9, given as SEQ ID NOs:148 and 149. These primers create a 1.4 kb URA3 PCR product that contains 70 bp 5' and 3' extensions identical to sequences upstream and downstream of the GPD1 chromosomal locus for homologous recombination. The PCR product is transformed into BY4741 pdc1::FBAp-alsS-LEU2 pdc5::kanMX4 or BY4741 pdc1::HIS3p-alsS-LEU2 pdc5::kanMX4 using standard genetic techniques (*Methods in Yeast Genetics*, 2005, Cold Spring Harbor Laboratory Press, Cold Spring Harbor, N.Y., pp. 201-202) with selection on synthetic complete media lacking uracil and supplemented with 1% ethanol at 30° C. Transformants are screened by PCR using primers 112590-T4 and 112590-T10, given as SEQ ID NOs:150 and 151, to verify integration at the correct site and disruption of GPD1. The correct transformants have the genotype: BY4741 pdc1::FBAp-alsS-LEU2 pdc5::kanMX4 gpd1::URA3 or BY4741 pdc1::HIS3p-alsS-LEU2 pdc5::kanMX4 gpd1::URA3. The URA3 marker is disrupted if desired by plating on 5-fluorootic acid (5FOA; Zymo Research, Orange, Calif.) using standard yeast techniques (*Methods in Yeast Genetics*, 2005, Cold Spring Harbor Laboratory Press, Cold Spring Harbor, N.Y.) producing strains BY4741 pdc1::FBAp-alsS-LEU2 pdc5::kanMX4 Δgpd1 and BY4741 pdc1::HIS3p-alsS-LEU2 pdc5::kanMX4 Δgpd1.

GPD2 encodes an NAD-dependent glycerol-3-phosphate dehydrogenase and is a functional homolog of GPD1. A gpd2::URA3 disruption cassette is constructed by PCR amplification of the URA3 marker from pRS426 (ATCC No. 77107) with primers 112590-T11 and 112590-T12, given as SEQ ID NOs:152 and 153. These primers create a 1.4 kb URA3 PCR product that contains 70 bp 5' and 3' extensions identical to sequences upstream and downstream of the GPD2 chromosomal locus for homologous recombination. The PCR product is transformed into BY4741 pdc1::FBAp-alsS-LEU2 pdc5::kanMX4 Δgpd1 or BY4741 pdc1::HIS3p-alsS-LEU2 pdc5::kanMX4 Δgpd1 using standard genetic techniques (*Methods in Yeast Genetics*, 2005, Cold Spring Harbor Laboratory Press, Cold Spring Harbor, N.Y., pp. 201-202) with selection on synthetic complete media lacking uracil and supplemented with 1% ethanol at 30° C. Transformants are screened by PCR using primers 112590-T13 and 112590-T4, given as SEQ ID NOs:154 and 150, to verify integration at the correct site and disruption of GPD2. The correct transformants have the genotype: BY4741 pdc1::FBAp-alsS-LEU2 pdc5::kanMX4 Δgpd1 gpd2::URA3 or BY4741 pdc1:: HIS3p-alsS-LEU2 pdc5::kanMX4 Δgpd1 gpd2::URA3. The URA3 marker is disrupted by plating on 5-fluorootic acid (5FOA; Zymo Research, Orange, Calif.) using standard yeast techniques (*Methods in Yeast Genetics*, 2005, Cold Spring Harbor Laboratory Press, Cold Spring Harbor, N.Y.) producing strains BY4741 pdc1::FBAp-alsS-LEU2 pdc5::kanMX4 Δgpd1Δgpd2 and BY4741 pdc1::HIS3p-alsS-LEU2 pdc5:: kanMX4 Δgpd1 Δgpd2.

Example 8

Prophetic

Production of Isobutanol in Recombinant *S. cerevisiae* [BY4741 pdc1::FBAp-alsS-LEU2 pdc5::kanMX4 Δgpd1Δgpd2]

The purpose of this prophetic example is to describe how to obtain isobutanol production in a yeast strain that is disrupted for pyruvate decarboxylase and glycerol-3-phosphate dehydrogenase activities, and expresses cytosolic acetolactate synthase.

Plasmid vectors pRS423::CUP1p-alsS+FBAp-ILV3 and pHR81::FBAp-ILV5+GPMp-kivD (see Example 6) are transformed into strain BY4741 pdc1::FBAp-alsS-LEU2 pdc5::kanMX4 Δgpd1Δgpd2 (described in Example 7) using standard genetic techniques (*Methods in Yeast Genetics*, 2005, Cold Spring Harbor Laboratory Press, Cold Spring Harbor, N.Y.) and maintained on synthetic complete media lacking histidine and uracil, and supplemented with 1% ethanol. Aerobic cultures are grown in 250 ml flasks containing 50 ml synthetic complete media lacking histidine and uracil, and supplemented with 2% glucose and 0.5% ethanol in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection) and GC (HP-Innowax, 0.32 mm×0.25 μm×30 m (Agilent Technologies, Inc., Santa Clara, Calif.) with flame ionization detection (FID) for isobutanol content. Isobutanol is detected.

Example 9

Prophetic

Increasing Pyruvate Accessibility by Disruption of Pyruvate Dehydrogenase in a *S. cerevisiae* Strain with Deleted Genes Encoding Pyruvate Decarboxylase and Cytosolic Expression of Acetolactate Synthase The purpose of this prophetic example is to describe how to increase pyruvate accessibility by disrupting pyruvate dehydrogenase in a yeast strain that is also disrupted for pyruvate decarboxylase and glycerol-3-phosphate dehydrogenase, and contains a cassette for expression of cytosolic acetolactate synthase.

PDA1 encodes the alpha subunit of pyruvate dehydrogenase. Pyruvate dehydrogenase, consisting of alpha (Pda1p) and beta (Pdb1p) subunits, is the E1 component of the large multienzyme pyruvate dehydrogenase complex. Cells lacking PDA1 are viable but lack pyruvate dehydrogenase activity, show slower growth on glucose, and exhibit increased formation of petites that lack mitochondrial DNA. A pda1:: URA3 disruption cassette is constructed by PCR amplification of the URA3 marker from pRS426 (ATCC No. 77107) with primers 112590-T1 and 112590-T2, given as SEQ ID NOs:155 and 156. These primers create a 1.4 kb URA3 PCR product that contains 70 bp 5' and 3' extensions identical to sequences upstream and downstream of the PDA1 chromosomal locus for homologous recombination. The PCR product is transformed into BY4741 pdc1::FBAp-alsS-LEU2 pdc5::kanMX4 Δgpd1 Δgpd2 or BY4741 pdc1::HIS3p-alsS-LEU2 pdc5::kanMX4 Δgpd1Δgpd2 using standard genetic techniques (*Methods in Yeast Genetics*, 2005, Cold Spring Harbor Laboratory Press, Cold Spring Harbor, N.Y., pp. 201-202) and maintained on synthetic complete media lacking uracil and supplemented with 1% ethanol at 30° C. Transformants are screened by PCR using primers 112590-T3 and 112590-T4, given as SEQ ID NOs:157 and 150, to verify integration at the correct site and disruption of PDA1. The absence of pyruvate dehydrogenase activity could also be confirmed by measuring enzyme activity as described by Neveling et al. (*J. Bacteriol.* 180(6):1540-8). The correct transformants have the genotype: BY4741 pdc1::FBAp-alsS-LEU2 pdc5::kanMX4 Δgpd1 Δgpd2 pda1::URA3 or BY4741 pdc1::HIS3p-alsS-LEU2 pdc5::kanMX4 Δgpd1 Δgpd2 pda1::URA3. The URA3 marker is disrupted if desired by plating on 5-fluorootic acid (5FOA; Zymo Research, Orange, Calif.) using standard yeast techniques (*Methods in Yeast Genetics*, 2005, Cold Spring Harbor Laboratory Press, Cold Spring Harbor, N.Y.) producing strains BY4741 pdc1:: FBAp-alsS-LEU2 pdc5::kanMX4 Δgpd1 Δgpd2 Δpda1 or BY4741 pdc1::HIS3p-alsS-LEU2 pdc5::kanMX4 Δgpd1 Δgpd2 Δpda1.

Example 10

Prophetic

Production of Isobutanol in Recombinant *S. cerevisiae* [BY4741 pdc1::FBAp-alsS-LEU2 pdc5::kanMX4 Δgpd1 Δgdp2 Δgdp1]

The purpose of this prophetic example is to describe how to obtain isobutanol production in a yeast strain that is disrupted for pyruvate decarboxylase, glycerol-3-phosphate dehydrogenase, and pyruvate dehydrogenase activities, and also expresses cytosolic acetolactate synthase.

Plasmid vectors pRS423::CUP1p-a/sS+FBAp-ILV3 and pHR81 ::FBAp-ILV5+GPMp-kivD (see Example 6) are transformed into strain BY4741 pdc1::FBAp-alsS-LEU2 pdc5::kanMX4 Δgpd1 Δgpd2 Δpda1 (see Example 9) using standard genetic techniques (Methods in Yeast Genetics, 2005, Cold Spring Harbor Laboratory Press, Cold Spring Harbor, N.Y.) and maintained on synthetic complete media lacking histidine and uracil, and supplemented with 1% ethanol. Aerobic cultures are grown in 250 ml flasks containing 50 ml synthetic complete media (minus histidine and uracil) supplemented with 2% glucose and 0.5% ethanol in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection) and GC (HP-Innowax, 0.25 mm×0.2 μm×25 m (Agilent Technologies, Inc., Santa Clara, Calif.) with flame ionization detection (FID) for isobutanol content.

Example 11

Prophetic

Increasing Pyruvate Accessibility by Suppression of Pyruvate Dehydrogenase in a S. cerevisiae Strain with Deleted Genes Encoding Pyruvate Decarboxylase and glycerol-3-phosphate Dehydrogenase, and Cytosolic Expression of Acetolactate Synthase The purpose of this prophetic example is to describe how to increase pyruvate accessibility by disrupting pyruvate dehydrogenase in a yeast strain that is also disrupted for pyruvate decarboxylase and glycerol-3-phosphate dehydrogenase, and contains a cassette for overexpression of acetolactate synthase.

PDA1 encodes the alpha subunit of pyruvate dehydrogenase. Pyruvate dehydrogenase, consisting of alpha (Pda1p) and beta (Pdb1p) subunits, is the E1 component of the large multienzyme pyruvate dehydrogenase complex. Cells lacking PDA1 are viable but lack pyruvate dehydrogenase activity, show slower growth on glucose, and exhibit increased formation of petites that lack mitochondrial DNA. To suppress expression of PDA1, we will substitute the endogenous PDA1 promoter with the GAL1 promoter which is repressed when glucose is present in the media.

A URA3::GAL1p-PDA1 integration cassette is constructed by SOE PCR. The URA3 marker is amplified from pRS426 (ATCC No. 77107) with primers 112590-T1 and 112590-T5, given as SEQ ID NOs:155 and 158. The GAL1 promoter is PCR-amplified from plasmid pYES2 (Invitrogen, Carlsbad, Calif.) with primers 112590-T6 and 112590-T7, given as SEQ ID NOs:159 and 160. The two PCR products are fused together by SOE PCR and amplified with external primers 112590-T1 and 112590-T7, yielding a 1.8 kb PCR product. These primers add 5' and 3' extensions identical to sequences upstream of the PDA1 locus and to the coding sequence of PDA1 for homologous recombination. The PCR product is transformed into BY4741 pdc1::FBAp-alsS-LEU2 pdc5::kanMX4 Δgpd1 Δgpd2 or BY4741 pdc1::HIS3p-alsS-LEU2 pdc5::kanMX4 Δgpd1 Δgpd2 using standard genetic techniques (Methods in Yeast Genetics, 2005, Cold Spring Harbor Laboratory Press, Cold Spring Harbor, N.Y., pp. 201-202) and maintained on synthetic complete media lacking uracil and supplemented with 1% ethanol at 30° C. Transformants are screened by PCR using primers 112590-T3 and 112590-T4, given as SEQ ID NOs:157 and 150, to verify integration at the correct site and disruption of PDA1. The suppression of pyruvate dehydrogenase activity is confirmed by measuring enzyme activity as described by Neveling, et al. [J. Bacteriol. 180(6):1540-8]. The correct transformants have the genotype: BY4741 pdc1::FBAp-alsS-LEU2 pdc5::kanMX4 Δgpd1 Δgpd2 URA3::GAL1p-PDA1 or BY4741 pdc1::HIS3p-alsS-LEU2 pdc5::kanMX4 Δgpd1 Δgpd2 URA3::GAL1p-PDA1. The URA3 is disrupted if desired by plating on 5-fluorootic acid (5FOA; Zymo Research, Orange, Calif.) using standard yeast techniques (Methods in Yeast Genetics, 2005, Cold Spring Harbor Laboratory Press, Cold Spring Harbor, N.Y.).

Example 12

Prophetic

Production of Isobutanol in Recombinant S. cerevisiae [BY4741 pdc1::FBAP-alsS-LEU2 pdc5::kanMX4 Δgpd1 Δgpd2 GAL1 p-PDA1]

The purpose of this prophetic example is to describe how to obtain isobutanol production in a yeast strain that is disrupted for pyruvate decarboxylase and glycerol-3-phosphate dehydrogenase activities, has suppression of pyruvate dehydrogenase activity through use of the galactose promoter, and expresses cytosolic acetolactate synthase.

Plasmid vectors pRS423::CUP1p-a/sS+FBAp-ILV3 and pHR81 ::FBAp-ILV5+GPMp-kivD (see Example 6) are transformed into strain BY4741 pdc1::FBAp-alsS-LEU2 pdc5::kanMX4 Δgpd1 Δgpd2 GAL1p-PDA1 (Example 11) using standard genetic techniques (Methods in Yeast Genetics, 2005, Cold Spring Harbor Laboratory Press, Cold Spring Harbor, N.Y.) and maintained on synthetic complete media lacking histidine and uracil, and supplemented with 1% ethanol. Aerobic cultures are grown in 250 ml flasks containing 50 ml synthetic complete media (minus histidine and uracil) supplemented with 2% glucose and 0.5% ethanol in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection) and GC (HP-Innowax, 0.25 mm×0.2 μm×25 m (Agilent Technologies, Inc., Santa Clara, Calif.) with flame ionization detection (FID) for isobutanol content. Isobutanol is detected.

Example 13

Construction of Expression Vectors for Isobutanol Pathway Gene Expression in S. cerevisiae pLH475-Z4B8 Construction The pLH475-Z4B8 plasmid (SEQ ID NO:165) was constructed for expression of ALS and KARI in yeast. pLH475-Z4B8 is a pHR81 vector (ATCC #87541) containing the following chimeric genes:
1) the CUP1 promoter (SEQ ID NO: 125), acetolactate synthase coding region from Bacillus subtilis (AlsS; SEQ ID NO:3; protein SEQ ID NO:4) and CYC1 terminator (CYC1-2; SEQ ID NO:166);
2) an ILV5 promoter (SEQ ID NO:167), Pf5.llvC-Z4B8 coding region (SEQ ID NO:168; protein SEQ ID NO:169) and ILV5 terminator (SEQ ID NO:170); and 3) the FBA1 promoter (SEQ ID NO: 116), S. cerevisiae KARI coding region (ILV5; SEQ ID NO: 37; protein SEQ ID NO:38) and CYC1 terminator.

The Pf5.llvC-Z4B8 coding region is a sequence encoding KARI derived from *Pseudomonas fluorescens* but containing mutations, that was described in commonly owned and co-pending U.S. patent application Ser. No. 12/337,736, which is herein incorporated by reference. The Pf5.llvC-Z4B8 encoded KARI (SEQ ID NO:169) has the following amino acid changes as compared to the natural *Pseudomonas fluorescens* KARI:

C33L: cysteine at position 33 changed to leucine,
R47Y: arginine at position 47 changed to tyrosine,
S50A: serine at position 50 changed to alanine,
T52D: threonine at position 52 changed to asparagine,
V53A: valine at position 53 changed to alanine,
L61F: leucine at position 61 changed to phenylalanine,
T80I: threonine at position 80 changed to isoleucine,
A156V: alanine at position 156 changed to threonine, and
G170A: glycine at position 170 changed to alanine.

The Pf5.llvC-Z4B8 coding region was was synthesized by DNA 2.0 (Palo Alto, Calif.; SEQ ID NO:6) based on codons that were optimized for expression in *Saccharomyces cerevisiae*.

Expression Vector pLH468

The pLH468 plasmid (SEQ ID NO:171) was constructed for expression of DHAD, KivD and HADH in yeast.

Coding regions for *B. subtilis* ketoisovalerate decarboxylase (KivD) and Horse liver alcohol dehydrogenase (HADH) were synthesized by DNA2.0 based on codons that were optimized for expression in *Saccharomyces cerevisiae* (SEQ ID NO:172 and 174, respectively) and provided in plasmids pKivD-DNA2.0 and pHadhy-DNA2.0. The encoded proteins are SEQ ID NOs 173 and 175, respectively. Individual expression vectors for KivD and HADH were constructed. To assemble pLH467 (pRS426::$P_{GPD1}$-kivDy-GPD1t), vector pNY8 (SEQ ID NO:176; also named pRS426.GPD-ald-GPDt, described in commonly owned and co-pending U.S. Patent App. Pub. U.S.2008/0182308, Example 17, which is herein incorporated by reference) was digested with AscI and SfiI enzymes, thus excising the GPD1 promoter SEQ ID NO: 114, and the ald coding region. A GPD1 promoter fragment (GPD1-2; SEQ ID NO:177) from pNY8 was PCR amplified to add an AscI site at the 5' end, and an SpeI site at the 3' end, using 5' primer OT1068 and 3' primer OT1067 (SEQ ID NOs:178 and 179). The AscI/SfiI digested pNY8 vector fragment was ligated with the GPD1 promoter PCR product digested with AscI and SpeI, and the SpeI-SfiI fragment containing the codon optimized kivD coding region isolated from the vector pKivD-DNA2.0. The triple ligation generated vector pLH467 (pRS426::$P_{GPD1}$-kivDy-GPD1t). pLH467 was verified by restriction mapping and sequencing.

pLH435 (pRS425::$P_{GPM1}$-Hadhy-ADH1t) was derived from vector pRS425::GPM-sadB (SEQ ID NO:180) which is described in commonly owned and co-pending U.S. Patent App. No. 61/058,970, Example 3, which is herein incorporated by reference. pRS425::GPM-sadB is the pRS425 vector (ATCC #77106) with a chimeric gene containing the GPM1 promoter (SEQ ID NO:135), coding region from a butanol dehydrogenase of *Achromobacter xylosoxidans* (sadB; SEQ ID NO: 35; protein SEQ ID NO:36: disclosed in commonly owned and co-pending U.S. Patent App. No. 61/048291), and ADH1 terminator (SEQ ID NO:126). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NO:181 and 182) to generate vector pRS425-GPMp-sadB-NheI, which was verified by sequencing. pRS425::$P_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC #87474) was digested with SacI and NotI, and ligated with the SacI-SalI fragment from pLH467 that contains the $P_{GPD1}$-kivDy-GPD1t cassette together with the SalI-NotI fragment from pLH435 that contains the $P_{GPM1}$-Hadhy-ADH1t cassette in a triple ligation reaction. This yielded the vector pRS411:: $P_{GPD1}$-kivDy-$P_{GPM1}$-Hadhy (pLH441), which was verified by restriction mapping.

In order to generate a co-expression vector for all three genes in the lower isobutanol pathway: ilvD, kivDy and Hadhy, we used pRS423 FBA ilvD(Strep) (SEQ ID NO:183), which is described in commonly owned and co-pending U.S. Patent Application No. 61/100792, as the source of the IlvD gene. This shuttle vector contains an F1 origin of replication (nt 1423 to 1879) for maintenance in *E. coli* and a 2 micron origin (nt 8082 to 9426) for replication in yeast. The vector has an FBA promoter (nt 2111 to 3108; SEQ ID NO:10;) and FBA terminator (nt 4861 to 5860; SEQ ID NO:184). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO:185; protein SEQ ID NO:186) from *Streptococcus mutans* UA159 (ATCC #700610) is between the FBA promoter and FBA terminator forming a chimeric gene for expression. In addition there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD (*Streptococcus mutans*)-Lumio. This generated vector pLH468 (pRS423::$P_{FBA1}$-ilvD(Strep)Lumio-FBA1t-$P_{GPD1}$-kivDy-GPD1t-$P_{GPM1}$-hadhy-ADH1t), which was confirmed by restriction mapping and sequencing.

Example 14

Pyruvate Decarboxylase Gene Inactivation

This example describes insertion-inactivation of endogenous PDC1, PDC5, and PDC6 genes of *S. cerevisiae*. PDC1, PDC5, and PDC6 genes encode the three major isozymes of pyruvate decarboxylase. The resulting PDC inactivation strain was used as a host for expression vectors pLH475-Z4B8 and pLH468 that were described in Example 13.

Construction of pdc6::GPMp1-sadB Integration Cassette and PDC6 Deletion:

A pdc6::GPM1p-sadB-ADH1t-URA3r integration cassette was made by joining the GPM-sadB-ADHt segment (SEQ ID NO:187) from pRS425::GPM-sadB (described above) to the URA3r gene from pUC19-URA3r. pUC19-URA3r (SEQ ID NO:188) contains the URA3 marker from pRS426 (ATCC #77107) flanked by 75 bp homologous repeat sequences to allow homologous recombination in vivo and removal of the URA3 marker. The two DNA segments were joined by SOE PCR (as described by Horton et al. (1989) Gene 77:61-68) using as template pRS425::GPM-sadB and pUC19-URA3r plasmid DNAs, with Phusion DNA polymerase (New England Biolabs Inc., Beverly, Mass.; catalog no. F-540S) and primers 114117-11A through 114117-11D (SEQ ID NOs:189, 190, 191 and 192), and 114117-13A and 114117-13B (SEQ ID NOs:193 and 194).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 112590-34G and 112590-34H (SEQ ID NOs:195 and 196), and 112590-34F and 112590-49E (SEQ ID NOs: 113 and 197) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::$P_{GPM1}$-sadB-ADH1t.

Construction of pdc1::PDC1-ilvD Integration Cassette and PDC1 Deletion:

A pdc1::PDC1p-ilvD-FBA1t-URA3r integration cassette was made by joining the i/vD-FBA1t segment (SEQ ID NO:198) from pLH468 (described above) to the URA3r gene from pUC19-URA3r by SOE PCR (as described by Horton et al. (1989) Gene 77:61-68) using as template pLH468 and pUC19-URA3r plasmid DNAs, with Phusion DNA polymerase (New England Biolabs Inc., Beverly, Mass.; catalog no. F-540S) and primers 114117-27A through 114117-27D (SEQ ID NOs:199, 200, 201 and 202).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::$P_{GPM1}$-sadB-ADH1t and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 114117-36D and 135 (SEQ ID NOs 203 and 204), and primers 112590-49E and 112590-30F (SEQ ID NOs 197 and 205) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::GPM1p-sadB-ADH1t pdc1::PDC1p-ilvD-FBA1t.

HIS3 Deletion

To delete the endogenous HIS3 coding region, a his3::URA3r2 cassette was PCR-amplified from URA3r2 template DNA (SEQ ID NO;206). URA3r2 contains the URA3 marker from pRS426 (ATCC #77107) flanked by 500 bp homologous repeat sequences to allow homologous recombination in vivo and removal of the URA3 marker. PCR was done using Phusion DNA polymerase and primers 114117-45A and 114117-45B (SEQ ID NOs:207 and 208) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA73" has the genotype: BY4700 pdc6::GPM1p-sadB-ADH1t pdc1::PDC1p-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion DNA polymerase and primers PDC5::KanMXF and PDC5::KanMXR (SEQ ID NOs:106 and 107) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (*Methods in Yeast Genetics,* 2005, Cold Spring Harbor Laboratory Press, Cold Spring Harbor, N.Y., pp. 201-202) and transformants were selected on YP media supplemented with 1% ethanol and geneticin (200 μg/ml) at 30° C. Transformants were screened by PCR to verify correct integration at the PDC locus with replacement of the PDC5 coding region using primers PDC5kofor and N175 (SEQ ID NOs: 108 and 109). The identified correct transformants have the genotype: BY4700 pdc6::GPM1p-sadB-ADH1t pdc1::PDC1p-ilvD-FBA1t Δhis3 pdc5::kanMX4.

Plasmid vectors pLH468 and pLH475-Z4B8 were simultaneously transformed into strain BY4700 pdc6::GPM1p-sadB-ADH1t pdc1::PDC1p-ilvD-FBA1t Δhis3 pdc5::kanMX4 using standard genetic techniques (*Methods in Yeast Genetics,* 2005, Cold Spring Harbor Laboratory Press, Cold Spring Harbor, N.Y.) and the resulting strain was maintained on synthetic complete media lacking histidine and uracil, and supplemented with 1% ethanol at 30° C. The resulting strain was named NGI-049.

Example 15

Production of Isobutanol by *Saccharomyces cerevisiae* Strain NGI-049

A seed culture of NGI-049 for inoculum preparation was grown in Yeast Nitrogen Base (YNB) without amino acids medium (6.7 g/L), supplemented with amino acid dropout mix (1.4 g/L), leucine (100 mg/L) and tryptophan (20 mg/L). Ethanol at 1% (v/v) was used as the sole carbon source for seed cultures. The fermentation medium was a semi-synthetic medium, the composition of which is given in Table 7.

TABLE 7

Fermentation Medium Composition

| Ingredient | Amount/L |
| --- | --- |
| 1. YNB w/o amino acids[a] | 6.7 g |
| 2. Sigma Dropout Mix (Y2001)[b] | 2.8 g |
| 3. Leucine (10 g/L) | 20 mL |
| 4. Tryptophan (10 g/L) | 4 mL |
| 5. Ethanol | 10 mL |
| 6. Glucose 50 wt % stock | 4 g |

[a] Obtained from BD Diagnostic Systems, Sparks, MD
[b] Obtained from Sigma-Aldrich, St. Louis, MO Ingredients 1-4 from Table 7 were added to water at the prescribed concentration to make a final volume of 0.54 L in the fermentor. The contents of the fermentor were sterilized by autoclaving. Components 5 and 6 were mixed, filter sterilized and added to the fermentor after the autoclaved medium had cooled. The total final volume of the fermentation medium (the aqueous phase) was about 0.54 L.

The fermentation was done using a 1 L autoclavable bioreactor, Bio Console ADI 1025 (Applikon, Inc, Holland) with a working volume of 900 mL. The temperature was maintained at 30° C. during the entire fermentation and the pH was maintained at 5.5 using sodium hydroxide. Following inoculation of the sterile fermentation medium with seed culture (10 vol %), the fermentor was operated aerobically at a 30% dissolved oxygen (DO) set point with 0.3 vvm of air flow by automatic control of the agitation rate (rpm). Once the initial batched glucose of 2 g/L was consumed, glucose was fed using a pump at an exponential rate such that glucose never accumulated above 0.2 g/L in the fermentor. Once the desired optical density ($OD_{600}$) was reached (i.e., $OD_{600}$=6), the culture was induced to isobutanol production phase by feeding glucose such that excess glucose (>2 g/L) was maintained at all times during fermentation. Two hours post glucose excess, 60 mL of filter sterilized 10× Yeast Extract Peptone stock solution (10× YEP=100 g/L of yeast extract and 200 g/L of peptone) was added. Glucose was fed (50 wt % stock solution) to the fermentor to keep levels of glucose greater than 2 g/L.

Because efficient production of isobutanol requires microaerobic conditions to enable redox balance in the biosynthetic pathway, air was continuously supplied to the fermentor at 0.3 vvm. Continuous aeration led to significant stripping of isobutanol from the aqueous phase of the fermentor. To quantify the loss of isobutanol due to stripping, the off-gas from the fermentor was directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 were monitored continuously to quantify the amount of isobutanol in the gas stream.

Glucose and organic acids in the aqueous phase were monitored during the fermentation using HPLC. Glucose was also monitored quickly using a glucose analyzer (YSI, Inc., Yellow Springs, Ohio). Isobutanol in the aqueous phase was quantified by HPLC as described in the General Methods Section herein above after the aqueous phase was removed periodically from the fermentor. For isobutanol production, the effective titer, the effective rate, and the effective yield, all corrected for the isobutanol lost due to stripping, were 3 g/L, 0.04 g/L/h, and 0.16 g/g, respectively.

What is claimed is:

1. A recombinant yeast cell comprising a 2-butanone or 2-butanol biosynthetic pathway, said pathway comprising cytosol-localized polypeptide having acetolactate synthase activity, said cytosol-localized polypeptide having acetolactate synthase activity for conversion of pyruvate to acetolactate and comprising an amino acid sequence having at least 98% identity to SEQ ID NO:2, based on the Clustal W method of alignment using the default parameters of GAP PENALTY=10, GAP LENGTH PENALTY=0.1, and Gonnet 250 series of protein weight matrix; and, wherein the yeast cell is substantially free of an enzyme having pyruvate decarboxylase activity, and wherein the cell converts pyruvate to acetolactate, wherein the conversion of pyruvate to acetolactate is at least about 60% of theoretical yield.

2. The recombinant yeast cell of claim 1 further comprising a balance in reducing equivalents wherein the conversion of pyruvate to acetolactate is at least about 86% of theoretical yield.

3. The recombinant yeast cell of claim 1 comprising disruption in at least one gene encoding a polypeptide having pyruvate decarboxylase activity or a disruption in at least one gene encoding a regulatory element controlling pyruvate decarboxylase gene expression.

4. The recombinant yeast cell of claim 1 wherein the yeast is selected from the group consisting of *Saccharomyces, Schizosaccharomyces, Hansenula, Candida, Kluyveromyces, Yarrowia*, and *Pichia*.

5. The recombinant yeast cell of claim 3 wherein the polypeptide having pyruvate decarboxylase activity is selected from the group consisting of PDC1, PDC2, PDC5 and PDC6.

6. The recombinant yeast cell of claim 5 wherein PDC1 is encoded by a gene encoding a polypeptide having at least 80% identity to SEQ ID NO:51, wherein the 80% identity is based on the Clustal W method of alignment using the default parameters of GAP PENALTY=10, GAP LENGTH PENALTY=0.1, and Gonnet 250 series of protein weight matrix.

7. The recombinant yeast cell of claim 3 wherein at least one gene encoding a polypeptide having pyruvate decarboxylase activity encodes a polypeptide having at least 80% identity to the amino acid sequence selected from the group consisting of SEQ ID NO:63, 65 and 67, wherein the 80% identity is based on the Clustal W method of alignment using the default parameters of GAP PENALTY=10, GAP LENGTH PENALTY=0.1, and Gannet 250 series of protein weight matrix.

8. The recombinant yeast cell of claim 1 wherein the polypeptide having acetolactate synthase activity is defined by the Enzyme Commission Number EC 2.2.1.6.

9. The recombinant yeast cell of claim 1 substantially free of an enzyme complex having pyruvate dehydrogenase activity.

10. The recombinant yeast cell of claim 9 wherein the enzyme complex having pyruvate dehydrogenase activity is defined by the Enzyme Commission Number, EC 1.2.4.1.

11. The recombinant yeast cell of claim 10 comprising disruption in at least one gene encoding a protein of a multi-enzyme pyruvate dehydrogenase complex comprising the following proteins: PDA1, PDB1, Lat1, Lpd1, and Pdx1.

12. The recombinant yeast cell of claim 10 comprising a disruption in a gene encoding a polypeptide selected from the group consisting of:
   a) a PDA 1 polypeptide having at least 80% identity to a sequence selected from the group consisting of: SEQ ID NO:83; SEQ ID NO:93; and SEQ ID NO:99;
   b) a PDAB1 polypeptide having at least 80% identity to a sequence selected from the group consisting of: SEQ ID NO:85; SEQ ID NO:95; and SEQ ID NO:101;
   c) an LAT1 polypeptide having at least 80% identity to SEQ ID NO:87;
   d) an LPD1 polypeptide having at least 80% identity to SEQ ID NO:89;
   e) a PDX1 polypeptide having at least 80% identity to SEQ ID NO:91;
wherein the 80% identity is based on the Clustal W method of alignment using the default parameters of GAP PENALTY=10, GAP LENGTH PENALTY=0.1, and Gonnet 250 series of protein weight matrix.

13. The recombinant yeast cell of claim 10 comprising a disruption in a gene encoding a polypeptide having at least 80% identity to a sequence as set forth in SEQ ID NO:97, based on the Clustal W method of alignment using the default parameters of GAP PENALTY=10, GAP LENGTH PENALTY=0.1, and Gonnet 250 series of protein weight matrix.

14. The recombinant yeast cell of claim 1 substantially free of an enzyme having NAD-dependent glycerol-3-phosphate dehydrogenase activity.

15. The recombinant yeast cell of claim 14 comprising disruption in at least one gene encoding a NAD-dependent glycerol-3-phosphate dehydrogenase comprising the following proteins: GPD1, and GPD2.

16. The recombinant yeast cell of claim 15 comprising a disruption in a gene encoding a polypeptide selected from the group consisting of:
   a) a GPD1 polypeptide having at least 80% identity to a sequence selected from the group consisting of: SEQ ID NO:69; 73; and 79;
   b) a GPD2 polypeptide having at least 80% identity to a sequence selected from the group consisting of: SEQ ID NO:71; 75; and 81;
wherein the 80% identity is based on the Clustal W method of alignment using the default parameters of GAP PENALTY=10, GAP LENGTH PENALTY=0.1, and Gonnet 250 series of protein weight matrix.

17. The recombinant yeast cell of claim 14 comprising a disruption in a gene encoding a polypeptide having at least 80% identity to a sequence as set forth in SEQ ID NO:77, based on the Clustal W method of alignment using the default parameters of GAP PENALTY=10, GAP LENGTH PENALTY=0.1, and Gonnet 250 series of protein weight matrix.

18. The recombinant yeast cell of claim 1 wherein the yeast produces 2-butanol or 2-butanone and wherein conversion of pyruvate to acetolactate is at least about 60% of theoretical yield.

19. A method for the production of 2-butanol or 2-butanone comprising growing the recombinant yeast cell of claim 18 under conditions wherein the product is produced and optionally recovering the product.

20. The recombinant yeast of claim 18 further comprising reduced pyruvate dehydrogenase activity.

21. The recombinant yeast cell of claim 1 wherein the 2-butanone or 2-butanol biosynthetic pathway further comprises the following substrate to product conversions:
   a) acetolactate to acetoin;
   b) acetoin to 2,3-butanediol;
   c) 2,3-butanediol to 2-butanone.

22. The recombinant yeast cell of claim 21, wherein the recombinant yeast cell further comprises the substrate to product conversion 2-butanone to 2-butanol.

* * * * *